(12) United States Patent
Djukanovic et al.

(10) Patent No.: US 10,676,754 B2
(45) Date of Patent: Jun. 9, 2020

(54) COMPOSITIONS AND METHODS FOR PRODUCING PLANTS RESISTANT TO GLYPHOSATE HERBICIDE

(71) Applicants: E I DU PONT DE NEMOURS AND COMPANY, Wilmington, DE (US); PIONEER HI-BRED INTERNATIONAL, INC., Johnston, IA (US)

(72) Inventors: Vesna Djukanovic, Johnston, IA (US); Spencer Charles Jones, Des Moines, IA (US); Zhan-Bin Liu, West Chester, PA (US); Michael Lassner, Urbandale, IA (US); Leszek Aleksander Lyznik, Johnston, IA (US)

(73) Assignees: E I DU PONT DE NEMOURS AND COMPANY, Wilmington, DE (US); PIONEER HI-BRED INTERNATIONAL, INC. IA (US)

( * ) Notice: Subject to any disclaimer, the term of this patent is extended or adjusted under 35 U.S.C. 154(b) by 204 days.

(21) Appl. No.: 15/325,116

(22) PCT Filed: Jul. 1, 2015

(86) PCT No.: PCT/US2015/038767
§ 371 (c)(1),
(2) Date: Jan. 10, 2017

(87) PCT Pub. No.: WO2016/007347
PCT Pub. Date: Jan. 14, 2016

(65) Prior Publication Data
US 2017/0306349 A1 Oct. 26, 2017

Related U.S. Application Data

(60) Provisional application No. 62/023,246, filed on Jul. 11, 2014.

(51) Int. Cl.
*C12N 15/82* (2006.01)
*A01H 1/02* (2006.01)
*A01H 4/00* (2006.01)

(52) U.S. Cl.
CPC .......... *C12N 15/8275* (2013.01); *A01H 1/02* (2013.01); *A01H 4/008* (2013.01); *C12N 15/8213* (2013.01); *C12N 15/8241* (2013.01); *C12Y 301/00* (2013.01); *C12N 2310/20* (2017.05)

(58) Field of Classification Search
CPC ............ C12N 2310/20; C12N 15/8275; C12N 15/8213
See application file for complete search history.

(56) References Cited

U.S. PATENT DOCUMENTS

| | | | |
|---|---|---|---|
| 5,196,525 A | 3/1993 | McPherson et al. | |
| 5,310,667 A | 5/1994 | Eichholtz et al. | |
| 5,837,850 A | 11/1998 | Huffman | |
| 5,866,775 A | 2/1999 | Eichholtz et al. | |
| 6,040,497 A * | 3/2000 | Spencer ............... | C12N 9/1092 536/24.1 |
| 6,225,114 B1 | 5/2001 | Eichholtz et al. | |
| 6,248,876 B1 | 6/2001 | Barry et al. | |
| 6,867,293 B2 | 3/2005 | Andrews et al. | |
| 7,169,970 B2 | 1/2007 | Warner et al. | |
| 7,626,077 B2 | 12/2009 | Held et al. | |
| 8,436,159 B2 | 5/2013 | Alibhai et al. | |
| 8,586,361 B2 | 11/2013 | Tao et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang | |
| 8,871,445 B2 | 10/2014 | Cong et al. | |

(Continued)

FOREIGN PATENT DOCUMENTS

| | | |
|---|---|---|
| WO | 2005/049842 A2 | 6/2005 |
| WO | 2007/025097 A2 | 3/2007 |

(Continued)

OTHER PUBLICATIONS

Xu, Junwang, et al. "The first intron of rice EPSP synthase enhances expression of foreign gene." Science in China Series C: Life Sciences 46.6 (2003): 561 (Year: 2003).*
Shan, Qiwei, et al. "Targeted genome modification of crop plants using a CRISPR-Cas system." Nature biotechnology31.8 (2013): 686 (Year: 2013).*
Li, Jian-Feng, et al. "Multiplex and homologous recombination-mediated genome editing in *Arabidopsis* and Nicotiana benthamiana using guide RNA and Cas9." Nature biotechnology 31.8 (2013): 688. (Year: 2013).*

(Continued)

*Primary Examiner* — Weihua Fan

(57) ABSTRACT

The present disclosure includes the production of a mutant plant resistant to an herbicide of the phosphonomethylglycine family, e.g. glyphosate. Compositions and methods are provided for editing a nucleotide sequence of interest in a cell employing a guide polynucleotide/Cas endonuclease system, wherein the Cas endonuclease is guided by a guide polynucleotide to recognize and optionally introduce a double strand break at a specific target site into the genome of a cell. The nucleotide sequence of interest to be edited can be located within or outside the target site that is recognized by a Cas endonuclease. More specifically, compositions and methods are provided for editing an enolpyruvylshikimate-3-phosphate synthase (EPSPS) nucleotide sequence in a cell. The methods and compositions employ a guide polynucleotide/Cas endonuclease system to provide for an effective system for editing EPSPS nucleotide sequences of within the genome of a cell. Also provided are compositions and methods for the production of glyphosate tolerant plant cells, plants explants, seeds and grain.

9 Claims, 20 Drawing Sheets

Specification includes a Sequence Listing.

(56) References Cited

U.S. PATENT DOCUMENTS

| | | |
|---|---|---|
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,163,284 B2 | 10/2015 | Liu et al. |
| 9,493,782 B2 | 11/2016 | Cigan et al. |
| 9,840,713 B2 | 12/2017 | Zhang |
| 9,885,033 B2 | 11/2018 | Joung et al. |
| 2007/0178593 A1 | 8/2007 | Miller et al. |
| 2009/0104700 A1 | 4/2009 | Samuel et al. |
| 2009/0133152 A1 | 5/2009 | Lyznik |
| 2010/0076057 A1 | 3/2010 | Sontheimer et al. |
| 2010/0159598 A1 | 6/2010 | Jayakumar et al. |
| 2010/0311168 A1 | 12/2010 | Samuel et al. |
| 2011/0035836 A1 | 2/2011 | Eudes et al. |
| 2011/0247100 A1 | 10/2011 | Samboju et al. |
| 2013/0145503 A1* | 6/2013 | Gupta ............... C12N 15/8213 800/298 |
| 2013/0198888 A1 | 8/2013 | Falco et al. |
| 2013/0263324 A1 | 10/2013 | Lassner et al. |
| 2014/0020131 A1 | 1/2014 | Bidney et al. |
| 2014/0068797 A1 | 3/2014 | Doudna et al. |
| 2014/0096284 A1 | 4/2014 | Martin-Ortigosa et al. |
| 2014/0173783 A1* | 6/2014 | Ainley ............... C12N 15/8213 800/320.1 |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0242702 A1 | 8/2014 | Chen et al. |
| 2014/0273235 A1 | 9/2014 | Voytas |
| 2014/0342456 A1 | 11/2014 | Mali et al. |
| 2015/0067922 A1 | 3/2015 | Yang et al. |
| 2015/0167000 A1 | 6/2015 | Voytas et al. |
| 2015/0167009 A1 | 6/2015 | D'Halluin |

FOREIGN PATENT DOCUMENTS

| | | |
|---|---|---|
| WO | 2009/042164 A1 | 4/2009 |
| WO | 2010/011961 A3 | 1/2010 |
| WO | 2010077319 | 7/2010 |
| WO | 2011143124 | 11/2011 |
| WO | 2011/156535 A1 | 12/2011 |
| WO | 2012/129373 A2 | 9/2012 |
| WO | 2013066423 | 5/2013 |
| WO | 2013068845 | 5/2013 |
| WO | 2013/098244 A1 | 7/2013 |
| WO | 2013112686 | 8/2013 |
| WO | 2013/142578 A1 | 9/2013 |
| WO | 2013141680 | 9/2013 |
| WO | WO-2013160230 A1 * | 10/2013 ......... C12N 15/8213 |
| WO | 2013176772 | 11/2013 |
| WO | 2014018423 | 1/2014 |
| WO | 2014/065596 A1 | 5/2014 |
| WO | 2014071006 | 5/2014 |
| WO | 2014/093479 A1 | 6/2014 |
| WO | 2014/093635 A1 | 6/2014 |
| WO | 2014093635 | 6/2014 |
| WO | 2014093694 | 6/2014 |
| WO | 2014093712 | 6/2014 |
| WO | 2014093768 | 6/2014 |
| WO | 2014/144155 A1 | 9/2014 |
| WO | 2014/164775 A1 | 10/2014 |
| WO | 2014/186686 A2 | 11/2014 |
| WO | 2015/026883 A1 | 2/2015 |
| WO | 2015/026885 A1 | 2/2015 |
| WO | 2015/026886 A1 | 2/2015 |

OTHER PUBLICATIONS

Jiang, Wenzhi, et al. "Demonstration of CRISPR/Cas9/sgRNA-mediated targeted gene modification in *Arabidopsis*, tobacco, sorghum and rice." Nucleic acids research 41.20 (2013): e188-e188. (Year: 2013).*

Voytas, Daniel F., and Caixia Gao. "Precision genome engineering and agriculture: opportunities and regulatory challenges." PLoS biology 12.6 (2014): e1001877. (Year: 2014).*

Jiang, Wenzhi, et al. "Demonstration of CRISPR/Cas9/sgRNA-mediated targeted gene modification in Arabidopsis, tobacco, sorghum and rice."Nucleic acids research 41.20 (2013): e188-e188. (Year: 2013).*

Rodolphe Barrangou et al., CRISPR PRovides Acquired Resistance Against Viruses in Prokaryotes, Science, 2007, pp. 1709-1712, vol. 315.

Rodolphe Barrangou et al., RNA-mediated programmable DNA cleavage, Nature Biotechnology, Sep. 2012, pp. 836-838, vol. 30, No. 9.

Rodolphe Barrangou et al., CRISPR-Cas sytems and RNA-guided interference, WIREs RNA, 2013, pp. 267-278, vol. 4.

Khaoula Belhaj et al., Plant genome editing made easy: targeted mutagenesis in model and crop plants using the CRISPR/Cas system, Plant Methods, 2013, pp. 39-48, vol. 9.

Nannan Chang et al., Genome editing with RNA-guided Cas9 nuclease in Zebrafish embryos, Cell Research, 2013, pp. 465-472, vol. 23.

Seung Woo Cho et al., Targeted genome engineering in human cells with the Cas9 RNA-guided endonuclease, Nature Biotechnology, Mar. 2013, pp. 230-232, vol. 31, No. 3.

Krzysztof Chylinski et al., The tracrRNA and Cas9 families of type II CRISPR-Cas immunity systems, RNA Biology, May 2013, pp. 726-737, vol. 10, No. 10.

Le Cong et al., Multiplex Genome Engineering Using CRISPR/Cas Systems, Sciencexpress Reports, Jan. 3, 2013, pp. 1-7, vol. 1.

Elitza Deltcheva et al., CRISPR RNA maturation by trans-encoded small RNA and host factor RNase III, Nature, Mar. 31, 2011, pp. 602-607, vol. 471.

Kathleen D'Halluin et al., Targeted molecular trait stacking in cotton through targeted double-strand break induction, Plant Biotechnology Journal, pp. 933-941, vol. 11.

James E. Dicarlo et al., Genome engineering in *Saccharomyces cerevisiae* using CRISPR-Cas systems, Nucleic Acids Research, Mar. 4, 2013, pp. 4336-4343, vol. 41, No. 7.

Zhengyan Feng et al., Efficient genome editing in plants using a CRISPR/Cas system, Cell Research, 2013, pp. 1229-1232, vol. 23.

Yanfang Fu et al., Improving CRISPR-Cas nuclease specificity using truncated guide RNAs, Nature Biotechnology, Mar. 2014, vol. 32, No. 3.

Todd Funke et al., Structural Basis of Glyphosate Resistance Resulting from the Double Mutation Thr[97] Ile and Pro[101] Ser in 5-Enolpyruvylshikimate-e-phosphate Synthase from *Escherichia coli*, Journal of Biological Chemistry, Apr. 10, 2009, pp. 9864-9860, vol. 284, No. 15.

Thomas Gaj et al., ZFN, TALEN and CRISPR/Cas-based methods for genome engineering, Trends Biotechnology, Jul. 2013, pp. 397-405, vol. 31(7).

Josiane E. Garneau et al., The CRISPR/Cas bacterial immune system cleaves bacteriophase and plasmid DNA, Nature, 2010, pp. 67-71, vol. 468.

Giedrius Gasiunas et al., Cas9-crRNA ribonucleoprotein complex mediates specific DNA cleavage for adaptive immunity in bacteria, PNAS, Sep. 4, 2012, e2579-2586.

Luke A Gilbert et al., CRISPR-Mediated Modular RNA-Guided Regulation of Transcription in Eukaryotes, Cell, Jul. 18, 2013, pp. 442-451, vol. 154(2).

Scott J. Gratz et al., Genome Engineering of *Drosophila* with the CRISPR RNA-Guided Cas9 Nuclease, Aug. 2013, Genetics, pp. 1029-1035, vol. 194.

(56) References Cited

OTHER PUBLICATIONS

Daniel H. Haft et al., A Guild of 45 CRISPR-Associated (Cas) Protein Families and Multiple CRISPR/Cas Subtypes Exist in Prokaryotic Genomes, PLoS Computational Biology, Nov. 2005, pp. 474-483, vol. 1, Issue 6.

Caryn R. Hale et al. , RNA-Guided RNA Cleavage by a CRISPR RNA-Cas Protein Complex, Cell, Nov. 25, 2009, pp. 945-956, vol. 139.

Rachel E. Haurwitz et al., Sequence- and Structure-Specific RNA Processing by a CRISPR Endonuclease, Science, Sep. 10, 2010, pp. 1355-1358, vol. 329.

Philippe Horvath et al., Diversity, Activity, and Evolution of CRISPR Loci in *Streptococcus thermophilus*, Journal of Bacteriology, Feb. 2008, pp. 1401-1412, vol. 190, No. 4.

Philippe Horvath et al., CRISPR/Cas, the Immune System of Bacteria and Archaea, Science, Jan. 8, 2010, pp. 167-170, vol. 327.

Zhonggang Hou et al., Efficient genome engineering in human pluripotent stem cells using Cas9 from Neisseria meningitides, PNAS, Sep. 24, 2013, pp. 15644-15649, vol. 110, No. 39.

Patrick D. Hsu et al., DNA targeting specificity of RNA-guided Cas9 nucleases, Nature Biotechnology, Sep. 2013, pp. 827-834, vol. 31, No. 9.

Woong Y. Hwang et al., Efficient In Vivo Genome Editing Using RNA-Guided Nucleases, Nature Biotech, Mar. 2013, pp. 227-229, vol. 31, No. 3.

Kyle Jacoby et al., Expanding LAGLIDADG endonuclease scaffold diversity by rapidly surveying evolutionary sequence space, Nucleic Acids Research, Feb. 2012, pp. 4954-4964, vol. 40, No. 11.

Martin Jinek et al., A Programmable Dual-RNA-Guided DNA Endonuclease in Adaptive Bacterial Immunity, Science, Aug. 17, 2012, pp. 816-821, vol. 337.

Martin Jinek et al., RNA-programmed genome editing in human cells, eLife, 2013, e00471, pp. 1-9.

Ross A. Johnson et al., A rapid assay to quantify the cleavage efficiency of custom-designed nucleases in planta, Plant Mol Biol, 2013, pp. 207-221, vol. 82.

Eugene V. Koonin et al., CRISPR-CAS Evolution of an RNA-based adaptive immunity system in prokaryotes, RNA Biology, May 2013, pp. 679-686, vol. 10:5.

Jian-Feng Li et al., Multiplex and homologous recombination-mediated genome editing in *Arabidopsis* and *Nicotiana benthamiana* using guide RNA and Cas9, Nature Biotechnology, Aug. 2013, pp. 688-691, vol. 31, No. 8.

Michael R. Lieber et al., The Mechanism of Double-Strand DNA Break Repair by the Nonhomologous DNA End Joining Pathway, Annu Rev Biochem, 2010, pp. 181-211, vol. 79.

Ming Ma et al., A Guide RNA Sequence Design Platform for the CRISPR/Cas9 System for Model Organism Genomes, BioMed Research International, 2013, 4 pages, Article ID 270805.

Morgan L. Maeder et al., CRISPR RNA-guided activation of endogenous human genes, Nature Methods, Oct. 2013, pp. 977-979, vol. 10, No. 10.

Kira S. Makarova et al., Evolution and classification of the CRISPR-Cas systems, Nat Rev Microbiol, Jun. 2011, pp. 467-477, vol. 9(6).

Prashant Mali et al., RNA-Guided Human Genome Engineering via Cas9, Sciencexpress, Feb. 15, 2013, pp. 823-826, vol. 15, 339(6121).

Yanfei Mao et al., Application of the CRISPR-Cas System for Efficient Genome Engineering in Plants, Molecular Plant, Nov. 2013, pp. 2008-2011, vol. 6, No. 6.

Luciano A. Marraffini et al., CRISPR Interference Limits Horizontal Gene Transfer in Staphylococci by Targeting DNA, Science, Dec. 19, 2008, pp. 1843-1845, vol. 322(5909).

Luciano A. Marraffini et al., CRISPR interference: RNA-directed adaptive immunity in bacteria and archaea, Nat Rev Genet, Mar. 2010, pp. 181-190, vol. 11(3).

Jin Miao et al., Targeted mutagenesis in rice using CRISPR-Cas System, Cell Research, 2013, pp. 1233-1236, vol. 23.

Jeffrey C. Miller et al., A TALE nuclease architecture for efficient genome editing, Nature Biotechnology, Feb. 2011, pp. 143-148, vol. 29.

F. J. Mojica et al., Biological significance of a family of regularly spaced repeats in the genomes of Archaea, Bacteria and mitochondria, Molecular Microbiology, May 2000, pp. 244-246, vol. 36.

Vladimir Nekrasov et al., Targeted mutagenesis in the model plant *Nicotiana benthamiana* using Cas9 RNA-guided endonuclease, Nature Biotechnology, pp. 691-693, vol. 31, No. 8.

Nancy Podevin et al., Site-directed nucleases: a paradigm shift in predictable, knowledge-based plant breeding, Trends in Biotechnology, Jun. 2013, pp. 375-383, vol. 31, No. 6.

Lei S. Qi et al., Repurposing CRISPR as an RNA-Guided Platform for Sequence-Specific Control of Gene Expression, Cell, Feb. 28, 2013, pp. 1173-1183, vol. 152(5).

Sivaprakash Ramalingam et al., A CRISPR way to engineer the human genome, Genome Biology, 2013, 4 pages, vol. 14:107.

Paul D. Sadowski, Site-specific genetic recombination: hops, flips, and flops, FASEB, 1993, pp. 760-767, vol. 7.

Neville E. Sanjana et al., A Transcription Activator-Like Effector (TALE) Toolbox for Genome Engineering, Nat. Protoc, 2012, pp. 171-192, vol. 7(1).

Rimantas Sapranauskas et al., The *Streptococcus thermophilus* CRISPR/Cas system provides immunity in *Escherichia coli* Nucleic Acids Research, Aug. 2011, pp. 9275-9282, vol. 39, No. 21.

Brian Sauer, Site-specific recombination: developments and applications, Current Opinion in Biotechnology, 1994, pp. 521-527, vol. 5.

Qiwei Shan et al., Targeted genome modification of crop plants using a CRISPR-Cas system, Nature Biotechnology, Aug. 2013, pp. 686-688, vol. 31, No. 8.

Bin Shen et al., Generation of gene-modified mice via Cas9/RNA-mediated gene targeting, Cell Research, May 2013, pp. 720-723, vol. 23, No. 5.

Bruno Tinland et al., The T-DNA-linked VirD2 protein contains two distinct functional nuclear localization signals, Proc. Natl. Acad. Sci, Aug. 1992, pp. 7442-7446, vol. 89.

John Van Der Oost, New Tool for Genome Surgery, Science, Feb. 15, 2013, pp. 768-770, vol. 339.

Daniel F. Voytas, Plant Genome Engineering with Sequence-Specific Nucleases, Annual Review of Plant Biology, pp. 327-350, vol. 64.

Daniel F. Voytas et al., Precision Genome Engineering and Agriculture: Opportunities and Regulatory Challenges, PLOS Biology, Jun. 2014, vol. 12, Issue 6, e1001877.

Jianbin Wang et al., Targeted gene addition to a predetermined site in the human genome using a ZFN-based nicking enzyme, Genome Research, 2012, pp. 1316-1326.

Haoyi Wang et al., One-Step Generation of Mice Carrying Mutations in Multiple Genes by CRISPR/Cas-Mediated Genome Engineering, Cell, May 9, 2013, pp. 910-918, vol. 153(4).

Blake Wiedenheft et al., RNA-guided genetic silencing systems in bacteria and archaea, Nature, Feb. 16, 2012, pp. 331-338, vol. 482.

Kabin Xie et al., RNA-Guided Genome Editing in Plants Using a CRISPR-Cas System, Nov. 2013, Molecular Plant, pp. 1975-1983, vol. 6, No. 6.

Peter R. Beetham, A tool for functional plant genomics: Chimeric RNA/DNA oligonucleotides cause in vivo gene-specific mutations, Proc. Natl., Acad. Sci USA, Plant Biology, Jul. 1999, pp. 8774-8778, vol. 96.

Prashant Mali et al., CAS9 transcriptional activators for target specificity screening and paired nickases for cooperative genome engineering, Nat. Biotechnol., Sep. 2013, pp. 833-838, vol. 31(9).

Scott R. Baerson et al., Glyphosate-Resistant Goosegrass. Identification of a Mutation in the Target Enzyme 5-Enolpyruvylshikimate-e-Phosphate Synthase, Plant Physiology, 2002, pp. 1265-1275, vol. 129(3).

Peter K. Busk et al., Regulation of abscisic acid-induced transcription, Plant Molecular Biology, 1998, pp. 425-435, vol. 37.

Le Cong et al., Multiplex Genome Engineering Using CRISPR/Cas Systems, Science, Feb. 15, 2013, pp. 819-823, vol. 339.

Kazuko Yamaguchi-Shinozaki et al., A Novel cis-Acting Element in an *Arabidopsis* Gene Is Involved in Responsiveness to Drought, Low-Temperature, or High-Salt Stress, The Plant Cell, Feb. 1994, pp. 251-264, vol. 6.

(56) References Cited

OTHER PUBLICATIONS

Min Zhou et al., Identification of a Glyphosate-Resistant Mutant of Rice 5-Enolpyruvylshikimate e-Phosphate Synthase Using a Directed Evolution Strategy, Plant Physiology, Jan. 2006, pp. 184-195, vol. 140.
L. A. Lyznik et al., Double-strand break-induced targeted mutagenesis in plants, Transgenic Plants: Methods and Protocols, Springer, 2012, Chapter 32, pp. 399-416.
U.S. Appl. No. 13/800,447, filed Mar. 13, 2013.
International Search Report and Written Opinion—PCT/US2014/051778—dated Dec. 3, 2014.
International Search Report and Written Opinion—PCT/US2014/051780—dated Dec. 9, 2014.
International Search Report and Written Opinion—PCT/US2015/038767—dated Aug. 27, 2015.
Grissa I et al: "CRISPRFinder: a web tool to identify clustered regularly interspaced short palindromic repeats", Nucleic Acids Research, Information Retrieval Ltd, GB, May 31, 2007, pp. W52-W57, vol. 35.
Zhiyong Mao et al., Comparison of nonhomologous end joining and homologous recombination in human cells, DNA Repair, 2008, 7:1765-1771.
Kevin M Esvelt et al: "Orthogonal Cas9 proteins for RNA-guided gene regulation and editing", Nature Methods, Sep. 29, 2013, pp. 1116-1121, vol. 10 No. 11.
Wenyan Jiang et al., RNA-guided editing of bacterial genomes using CRISPR-Cas systems, Nature Biotechnology, Mar. 2013, pp. 233, vol. 31, No. 3.
Shiraz A Shah et al: "Protospacer recognition motifs", RNA Biology, May 1, 2013, pp. 1547-6286, vol. 10 No. 5.
Strauss, "Zinc Fingers, TAL Effectors, or Cas9-Based DNA Binding Proteins: What's Best for Targeting Desired Genome Loci?", MolecularPlant, Sep. 2013, vol. 6 No. 5 pp. 1384-1387.
Liang Zhen et al: "Targeted mutagenesis in *Zea mays* using TALENs and the CRISPR/Cas system", Journal of Genetics and Genomics, Dec. 14, 2013, pp. 63-68, vol. 41, No. 2.
Barrangou & Marraffini, "CRISPR-Cas systems: prokaryotes upgrade to adaptive immunity", Mol Cell 54:234-44 (Apr. 2014).
Joseph Bondy-Denomy et al: "To acquire or resist: the complex biological effects of CRISPR-Cas systems", Trends in Microbiology, vol. 22 No. 4, Feb. 26, 2014, pp. 218-225.
Fichtner et al: "Precision genetic modifications: a new era in molecular biology and crop improvement", Planta 239:921-39 (2014).
Guilinger et al.: "Fusion of catalytically inactive Cas9 to Fok1 nuclease improves the specificity of genome modification", Nat Biotech 32(6):577-83 (2014).
Wenzhi Jiang et al., "Efficient CRISPR/Cas9-mediated gene edigin in *Arabidopsis thalian* and inheritance of modified genes in the T2 and T3 generations", PLOS ONE, vol. 9 No. 6, Jun. 11, 2014, p. e99225, XP055219594.
Zhang et al., "The CRISPR/Cas9 system produces specific and homozygous targeted gene editing in rice in one generation", Plant Biotech J, 2014, vol. 12 No. 6, pp. 797-807.
Li et al., "In vivo genome editing restores hemostasis in a mouse model of hemophilia", Nature, 2011, pp. 217-221, vol. 475 No. 7355.
Sinkunas Tomas et al: "Cas3 is a single-stranded DNA nuclease and ATP-dependent helicase in the CRISPR/Cas immune system", EMBO, vol. 30 No. 7, Apr. 2011, pp. 1335-1342.
Li et al. High-efficiency TALEN-based gene editing produces disease-resistant rice. Nat Biotechnol. May 7, 2012, pp. 390-392, vol. 30 No. 5.
Peng et al, "A Synthetic arabinose-inducible promoter confers high levels of recombinant protein expression in hyperthermophilic Archaeon sulfolobus islandicus", Appl Environ Microbiol, Aug. 2012,pp. 5630-5637, vol. 78 No. 16.
Westra et al: "CRISPR immunity relies on the consecutive binding and degradation of negatively supercoiled invader DNA by Cascade and Cas3", Mol Cell, Apr. 19, 2012,pp. 595-605, vol. 46 No. 5.
William Ainley et al: "Trait stacking via targeted genome editing", Plant Biotechnology Journal, Aug. 19, 2013, pp. 1126-1134, vol. 11, No. 9.
Beurdeley et al: "Compact designer TALENs for efficient genome engineering", Nat Commun, Apr. 23, 2013, pp. 1-8, vol. 4, No. 1762.
Anonymous: "cas9-CRISPR-associated endonuclease CAs9—Bacillus cereus VD131—cas9 gene & protein", UniProt database entry: R8LDU5 (2013).
Anonymous: hypothetical protein [Lactobacillus reuteri]: NCBI Reference Sequence WP_019251774.1 (2015).
Vesna Djukanovic et al: "Male-sterile maize plants produced by targeted mutagenesis of the cytochrome P450-like gene (MS26) using a re-designed I-CreI homing endonuclease", The Plant Journal, Nov. 5, 2013, pp. 888-899, vol. 76, No. 5.
Zhang, "Transcription Activator-Like Effector Nucleases Enable Efficient Plant Genome Engineering",Plant Physiology, 2013, vol. 161, pp. 20-27.
Doudna & Charpentier, "The new frontier of genome engineering with CRISPR-Cas9", Sci 346(6213):1258096 (2014).
Kim Goon-Bo et al: "Isolation and characterization of Medicago truncatula U6 promoters for construction of small hairpin RNA-mediated gene silencing vevctors", Plant Molecular Biology Reporter, vol. 31 No. 3, Jun. 2013, pp. 581-593.
Sojung Kim et al: Highly efficient RNA-guided genome editing in human cells via delivery of purified Cas9 ribonucleoproteins, Genome Res, vol. 24, Apr. 2, 2014, pp. 1012-1019.
Vinay Kumar et al: "The CRISPR_Cas system for plant genome editing: advances and opportunities", Journal of Experimental Botany, vol. 66, No. 1, Nov. 4, 2014, pp. 47-57, figure 3, table 3.
Susana Martin-Ortigosa et al: "Mesoporous silica nanoparticle-mediated intracellular Cre protein delivery for maize genome editing via loxP sigte excision", Plant Physio, vol. 164, Issue 2, Feb. 2014, pp. 537-547.
Ramakrishna et al: "Gene disruption by cell-penetrating peptide-mediated delivery of Cas9 protein and guide RNA", Genome Res 24:1020-27 (Apr. 2014).
Xing e al., "A CRISPR/Cas9 toolkit for multiplex genome editing in plants", BMC Plant Biol, 2014, vol. 14 No. 1, pp. 327-338.
Kun Xu et al: Efficient genome engineering in eukaryotes using Cas9 from *Streptococcus thermophilus*, Cellular and Molecular Life Sciences, vol. 72 No. 2, Jul. 20, 2014, pp. 383-399 (and Supplemental).
John A Zuris, et al: "Cationic lipid-mediated delivery of proteins enables efficient protein-based genome editing in vitro and in vivo", Nature Biotech, vol. 33 No. 1, Oct. 30, 2014, pp. 73-80.
J.-H. Oh et al: "CRISPR-Cas9-assisted recombineering in Lactobacillus reuteri", Nucleic Acids Research, vol. 42 No. 17, Sep. 29, 2014, p. e131 (and Supplemental).

* cited by examiner

FIGURE 4
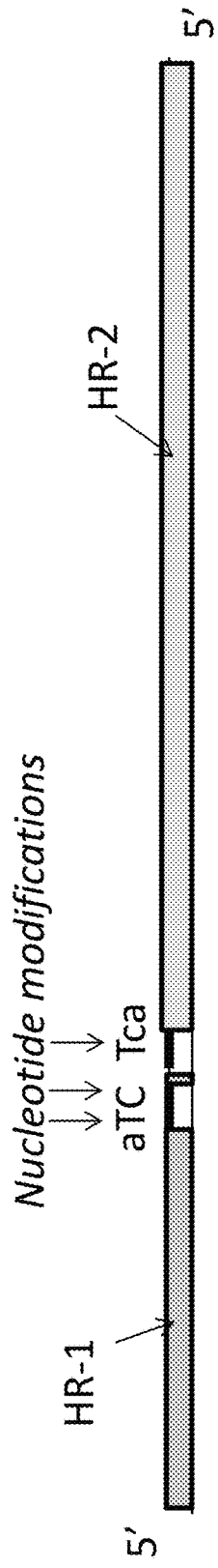
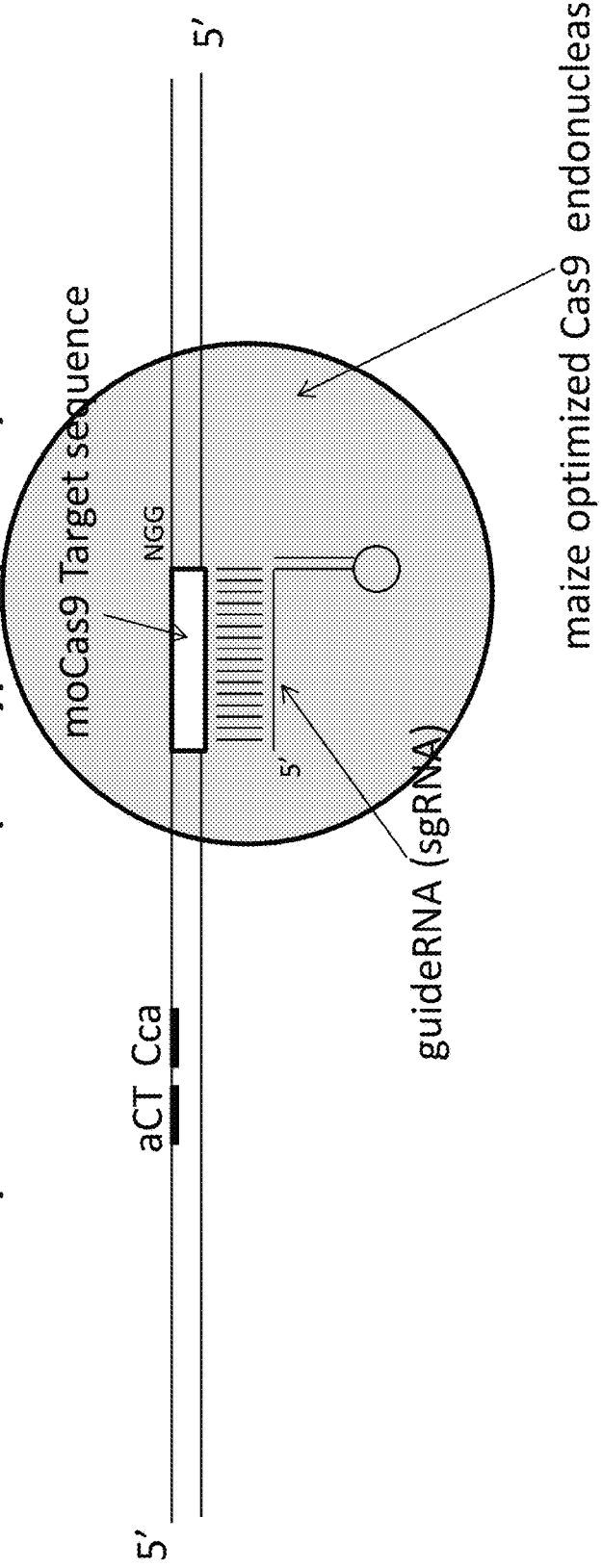

FIGURE 6

*Events with intact moCas target sequence (underlined)*

SEQ ID NO: 35  GGGGAATGCTGGAACTGCAATGCGGGCCATTGACACAGCAGCTGTTACTGCTGCTGGTGGAAATGC

*Events with mutagenized moCas target sequences (underlined)*

SEQ ID NO: 36  GGGGAATGCTGGAACTGCAATGCGGGCCATTG------GCAGCTGTTACTGCTGCTGGTGGAAATGC
SEQ ID NO: 37  GGGGAATGCTGGAACTGCA-----------------CAGCAGCTGTTACTGCTGCTGGTGGAAATGC
SEQ ID NO: 38  GGGGAATGCTG-------------------------------TTACTGCTGCTGGTGGAAATGC

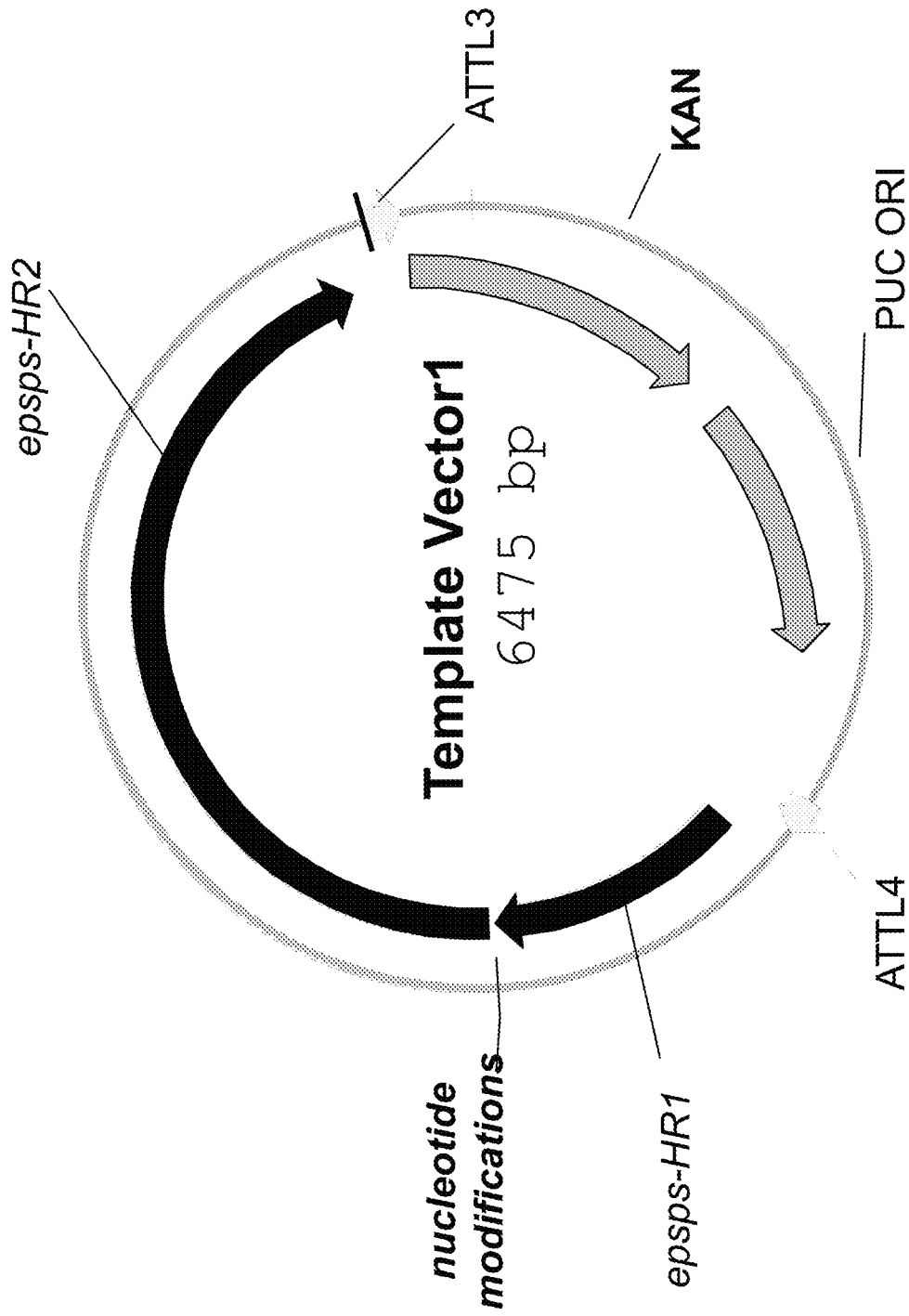

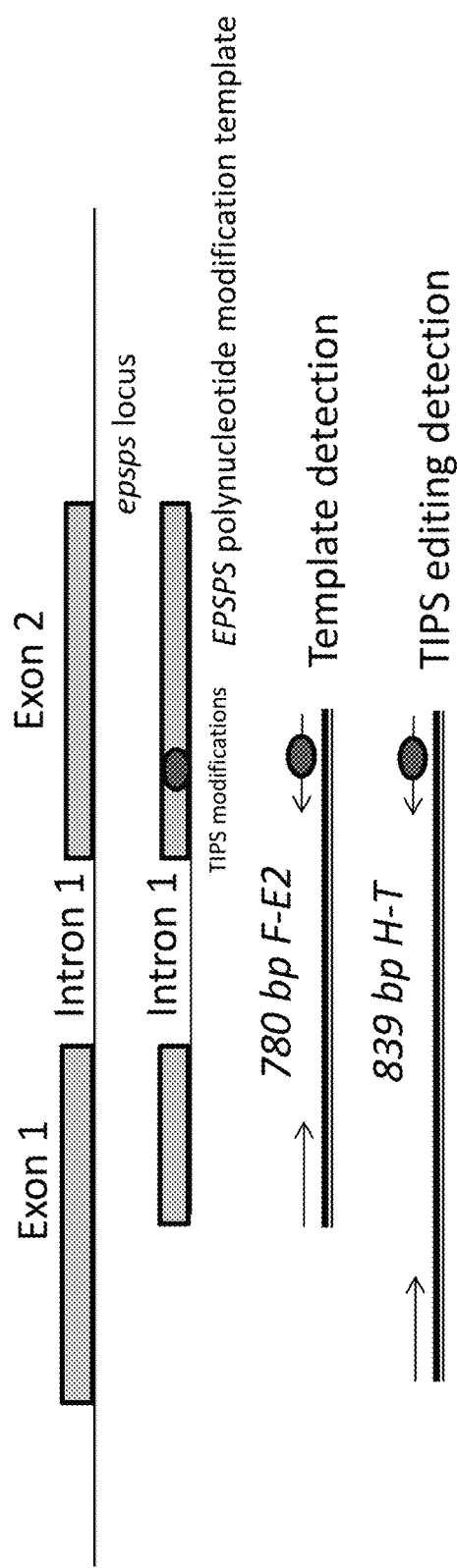
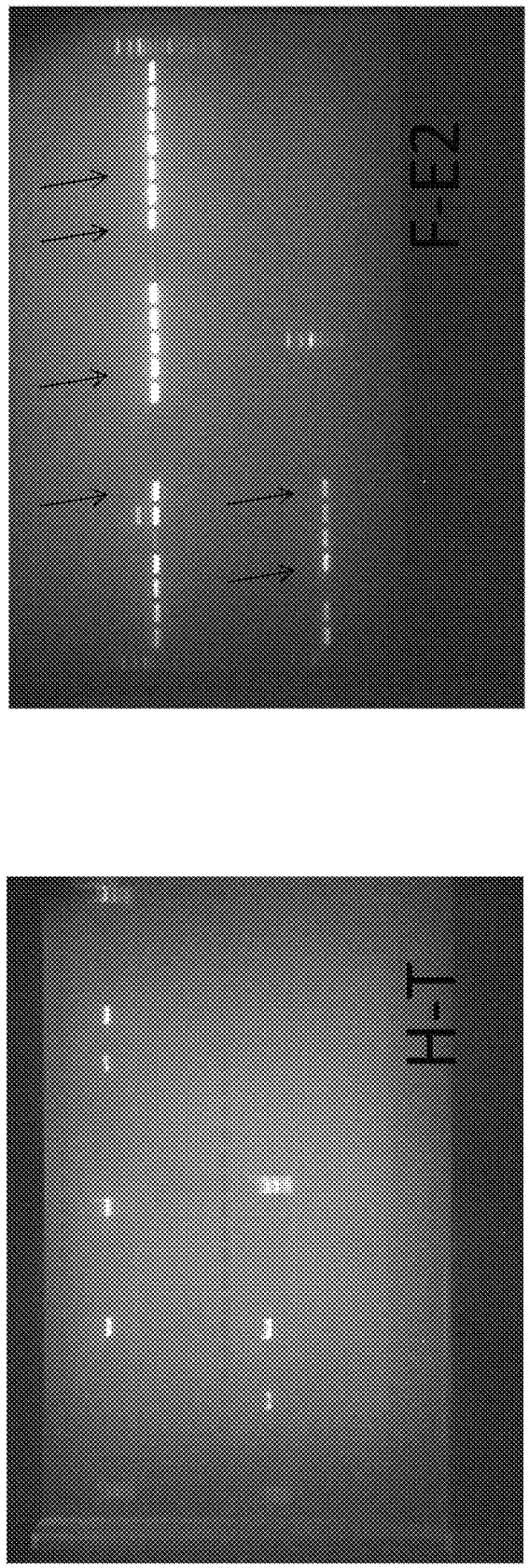
FIGURE 8

Figure 13 A

| VEDAKEEV | Maize |
|---|---|
| GKESKEEI | Petunia |
| GKKSEEEI | Tomato |
| EKDAKEEV | Sorghum |
| VEDSKEEV | Rice |
| GKDGKEEI | Amaranthus |

Figure 13 B

```
         K                                                    T                            P   moCas9 target sequence
GCTAAAGAGGAAGTGCAGCTCTTCTTGGGAATGCTGGAACTGCAATGCGGCCATTGACAGCAGCTGTACTGCTGCTGG
```

Figure 13 C

```
         R                                                    I                            S   moCas9 target sequence
GCTAGAGAGGAAGTGCAGCTCTTCTTGGGAATGCTGGAATGCGCAATGCGGGTCATTGACAGCAGCTGTTACTGCTGCTGG
```

Figure 14 A

CATATCTG

Figure 14 B

CATCTC...ACGATCAGAT..GCACCGCATGTCGCATGCCTA

Figure 14 C

CATATCTGCACGATCAGATATGCACCGCATGTCGCATATCTG

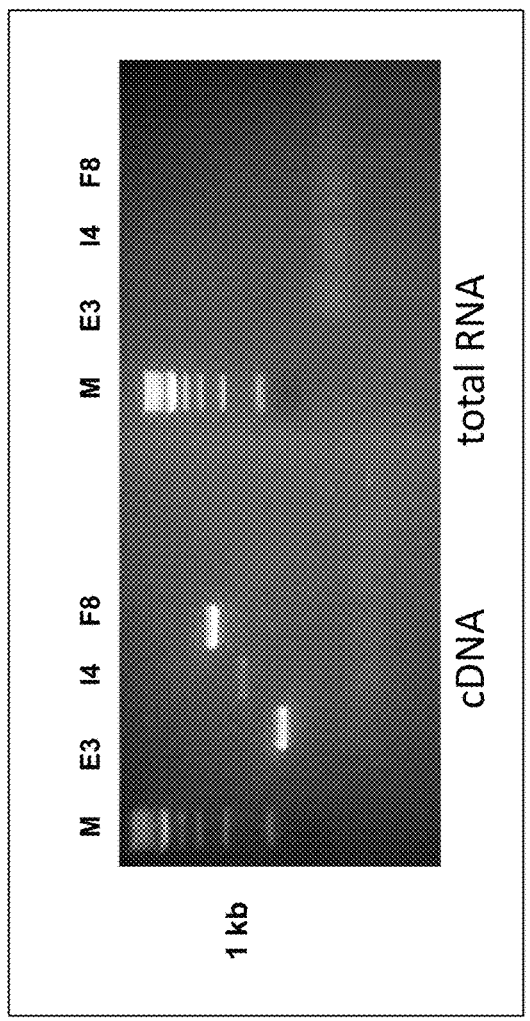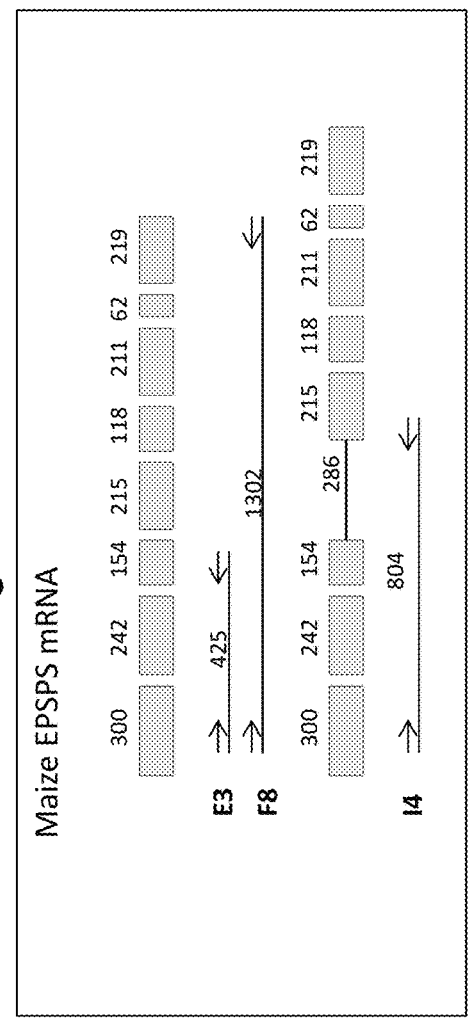
Figure 15 A
Figure 15 B

COMPOSITIONS AND METHODS FOR PRODUCING PLANTS RESISTANT TO GLYPHOSATE HERBICIDE

This application claims the benefit of U.S. Provisional Application No. 62/023,246, filed Jul. 11, 2014, which is incorporated herein in its entirety by reference.

FIELD

The disclosure relates to the field of molecular biology, in particular, to methods for editing the genome of a cell for herbicide resistance.

REFERENCE TO SEQUENCE LISTING SUBMITTED ELECTRONICALLY

The official copy of the sequence listing is submitted electronically via EFS-Web as an ASCII formatted sequence listing with a file named 20150617_BB2366PCT_SeqLst_ST25.txt created on Jun. 17, 2015 and having a size 220 kilobytes and is filed concurrently with the specification. The sequence listing contained in this ASCII formatted document is part of the specification and is herein incorporated by reference in its entirety.

BACKGROUND

Herbicide resistant plants may reduce the need for tillage to control weeds thereby effectively reducing costs to the growers. Development of crops with increased herbicide resistance has been a major breakthrough in current agriculture practices as it has provided farmers with new weed control options.

One herbicide which is the subject of much investigation in this regard is N-phosphonomethylglycine, commonly referred to as glyphosate. Glyphosate inhibits the shikimic acid pathway which leads to the biosynthesis of aromatic compounds including amino acids, hormones and vitamins. Specifically, glyphosate curbs the conversion of phosphoenolpyruvic acid (PEP) and 3-phosphoshikimic acid to 5-enolpyravyl-3-phosphoshikimic acid by inhibiting the enzyme 5-enolpyruvylshikimate-3-phosphate synthase (referred to as EPSPS). Plant genetic engineering methods have been used to modify EPSP synthase DNA and the encoded proteins, and to transfer these molecules into plants of agronomic importance. Variants of class I EPSPS have been isolated (Pro-Ser, U.S. Pat. No. 4,769,061; Gly-Ala, U.S. Pat. No. 4,971,908; Gly-Ala, Gly-Asp, U.S. Pat. No. 5,310,667; Gly-Ala, Ala-Thr, U.S. Pat. No. 5,866,775) that cause resistance to glyphosate. However, many EPSPS variants are not effective enzymes for use in plants (Padgette et. Al., in "Herbicide-resistant Crops", Chapter 4 pp. 53-83. ed. Stephen Duke, Lewis Pub, CRC Press Boca Raton, Fla. 1996). One class I EPSPS variant, T-102-I/P-106-S(TIPS) that is operably linked to a heterologous promoter has been shown to provide glyphosate (N-phosphonomethylglycine) resistance to transgenic maize plants (U.S. Pat. No. 6,040,497).

There remains a need for the development of herbicide-resistant crops and for glyphosate resistant crops in particular. There is also a need to develop herbicide-resistant plants of agronomic value that contain mutated genes obtained through gene editing wherein the mutation of the gene results in herbicide resistance.

Compositions and methods for producing mutant plants that exhibit herbicide resistance, and glyphosate resistance specifically, are provided.

BRIEF SUMMARY

The present disclosure includes the production of a mutant plant resistant to an herbicide of the phosphonomethylglycine family, e.g. glyphosate. Compositions and methods are provided for editing a nucleotide sequence of interest in a cell employing a guide polynucleotide/Cas endonuclease system, wherein the Cas endonuclease is guided by a guide polynucleotide to recognize and optionally introduce a double strand break at a specific target site into the genome of a cell. The nucleotide sequence of interest to be edited can be located within or outside the target site that is recognized by a Cas endonuclease. More specifically, compositions and methods are provided for editing an enolpyruvylshikimate-3-phosphate synthase (EPSPS) nucleotide sequence in a cell. The methods and compositions employ a guide polynucleotide/Cas endonuclease system to provide for an effective system for editing EPSPS nucleotide sequences of within the genome of a cell. The nucleotide sequence to be edited can be located within or outside a target site that is recognized by a Cas endonuclease. Cells include, but are not limited to plant cells. Also provided are compositions and methods for the production of glyphosate tolerant or resistant plant cells, plants explants, seeds and grain.

Thus in a first embodiment of the disclosure, the method comprises a method for editing an enolpyruvylshikimate-3-phosphate synthase (EPSPS) nucleotide sequence in a cell, the method comprising introducing a guide RNA, a polynucleotide modification template, and a Cas endonuclease into said cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence. The polynucleotide modification template can further comprise a non-functional fragment of the EPSPS gene.

In another embodiment, the method comprises a method for producing an enolpyruvylshikimate-3-phosphate synthase (EPSPS) mutant cell, the method comprising: a) introducing into a cell comprising an EPSPS nucleotide sequence, a guide RNA, a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence; and, b) identifying at least one cell of (a) that has at least one nucleotide modification at said EPSPS nucleotide sequence, wherein the modification includes at least one deletion, insertion or substitution of one or more nucleotides in said EPSPS nucleotide sequence. The guide RNA can be introduced into the cell directly by know methods in the art, or by expressing a recombinant DNA construct capable of expressing the guide RNA. The Cas endonuclease can be introduced into the cell directly by know methods in the art, or by expressing a recombinant DNA construct capable of expressing the Cas endonuclease. The polynucleotide modification template (EPSPS polynucleotide modification template) can include a partial fragment of the EPSPS gene (and therefore does not encode a fully functional EPSPS polypeptide by itself).

In other embodiments, the methods comprises a method for duplicating an enolpyruvylshikimate-3-phosphate synthase (EPSPS) gene fragment in a cell a method for replacing a enolpyruvylshikimate-3-phosphate synthase (EPSPS) promoter sequence in a cell a method for inserting a promoter or a regulatory element in an enolpyruvylshikimate-3-phosphate synthase (EPSPS) nucleotide sequence in a cell, a method for editing intron elements of an enolpyruvylshikimate-3-phosphate synthase (EPSPS) nucleotide sequence in a cell, the methods comprising introducing a guide RNA, a polynucleotide modification template and a Cas endonuclease into said cell. Cells can be, but are not limited to, any plant cells.

In another embodiment, the method comprises a method for producing an enolpyruvylshikimate-3-phosphate synthase (EPSPS) mutant plant, the method comprising: a) providing a guide RNA, a polynucleotide modification template, and a Cas endonuclease to a plant cell comprising a EPSPS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said EPSPS nucleotide sequence; b) obtaining a plant from the plant cell of (a); c) evaluating the plant of (b) for the presence of said at least one nucleotide modification; d) selecting a progeny plant that shows resistance to glyphosate.

In another embodiment, the method comprises a method for producing an enolpyruvylshikimate-3-phosphate synthase (EPSPS) mutant plant, the method comprising: a) providing a guide RNA, a polynucleotide modification template, and a Cas endonuclease to a plant cell comprising a EPSPS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said EPSPS nucleotide sequence; b) obtaining a plant from the plant cell of (a); c) evaluating the plant of (b) for the presence of said at least one nucleotide modification; and, d) screening a progeny plant of (c) that is void of said guide RNA and Cas endonuclease.

The invention provides plants, plant parts, plant cells, and seeds comprising an edited gene of interest (such as but not limited to a enolpyruvylshikimate-3-phosphate synthase (EPSPS) gene sequence), wherein these mutated plants, plant parts, plant cells, and seeds comprising the edited gene of interest shows resistance to an herbicide.

Additional embodiments of the methods and compositions of the present invention are disclosed herein.

BRIEF DESCRIPTION OF THE DRAWINGS AND THE SEQUENCE LISTING

The invention can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1A shows a duplex guide polynucleotide containing a double molecule comprising a first nucleotide sequence domain (referred to as Variable Targeting domain, or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the duplex guide polynucleotide comprises two separate molecules that are hybridized along a region of complementarity. The two separate molecules can be RNA, DNA, and/or RNA-DNA-combination sequences. The first molecule of the duplex guide polynucleotide comprising a VT domain linked to a CER domain (shown as crNucleotide) is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The second molecule of the duplex guide polynucleotide comprising a CER domain (shown as tracrNucleotide) is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides).

FIG. 1B shows a single guide polynucleotide comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequences. The single guide polynucleotide comprises a crNucleotide (comprising a VT domain linked to a CER domain) linked to a tracrNucleotide (comprising a CER domain) with a linker nucleotide sequence (shown as a loop). The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides).

FIG. 2A-2C show expression cassettes for Cas9, crRNA and tracrRNA expression. FIG. 2A shows a maize codon optimized Cas9 gene (encoding a Cas9 endonuclease) containing a potato ST-LS1 intron, a SV40 amino terminal nuclear localization sequence (SV40 NLS), and a VirD2 carboxyl terminal NLS (VirD2 NLS), operably linked to a plant ubiquitin promoter (UBI Pro) (such as for example, but not limited to SEQ ID NO: 5). The maize optimized Cas9 gene (just Cas9 coding sequence, no NLSs) corresponds to nucleotide positions 2037-2411 and 2601-6329 of SEQ ID NO: 5 with the potato intron residing at positions 2412-2600 of SEQ ID NO: 5.SV40 NLS is at positions 2010-2036 of SEQ ID NO: 5. VirD2 NLS is at positions 6330-6386 of SEQ ID NO: 5. FIG. 2B shows a maize U6 polymerase III promoter operably linked to a nucleotide sequence encoding a crRNA molecule operably linked to a maize U6 terminator. FIG. 2C shows a maize U6 polymerase III promoter operably linked to a nucleotide sequence encoding a tracrRNA molecule operably linked to a maize U6 PoIIII terminator. FIG. 2 D shows a single guide polynucleotide (guide RNA) operably linked to a maize U6 polymerase III promoter terminating with a maize U6 terminator. FIG. 2E shows the maize optimized Cas9 and single guide RNA expression cassettes combined on a single vector DNA.

FIG. 3 shows a single guide RNA/Cas9 endonuclease complex interacting with the genomic LIGCas-3 target site relative to the appropriately oriented PAM sequence (AGG) at the maize genomic LIGCas-3 target site (SEQ ID NO: 14, Table 1). The single guide RNA (light gray background, SEQ ID NO: 8) is a fusion between a crRNA and tracrRNA and comprises a variable targeting domain that is complementary to one DNA strand of the double strand DNA genomic target site. The Cas9 endonuclease is shown in dark gray. Triangles point towards the expected site of DNA cleavage on both sense and anti-sense DNA strands.

FIG. 4 A-B shows a schematic representation of the single guide RNA/Cas endonuclease system used for editing a nucleotide sequence of interest. To enable specific nucleotide editing, a polynucleotide modification template that includes at least one nucleotide modification (when compared to the nucleotide sequence to be edited) is introduced into a cell together with the single guide RNA and Cas endonuclease expression cassettes. For example, as shown herein, the nucleotide sequence to be edited is an endogenous wild type enolpyruvylshikimate-3-phosphate synthase (EPSPS) gene in maize cells. The Cas endonuclease (shaded circle) is a maize optimized Cas9 endonuclease that cleaves a moCas9 target sequence within the epsps genomic locus using a guide RNA such as SEQ ID NO:24. FIG. 4-A shows a polynucleotide modification template that includes three nucleotide modifications (when compared to the wild type epsps locus depicted in FIG. 4-B) flanked by two EPSPS gene homology regions HR-1 and HR-2. FIG. 4-B shows the guide RNA/maize optimized Cas9 endonuclease complex interacting with the epsps locus. The original amino acid codons of the EPSPS gene that needed to be edited are show as aCT and Cca (FIG. 4-B). The nucleotide codons with modified nucleotides (shown in capitals) are shown as aTC and Tca (FIG. 4-B). No full-length DNA molecule encoding a functional maize EPSPS protein was used in the Examples involving the modification of the endogenous EPSPS gene.

FIG. 5 shows two versions of the Cas9 expression cassette used for the EPSPS gene editing in maize (see also SEQ ID NO: 5 and SEQ ID NO: 23).

FIG. 6 shows some examples of the moCas9 target sequence (underlined), located on EPSPS DNA fragments, mutagenized by the introduction of double-strand breaks at the cleavage site of the moCas9 endonuclease (thick arrow) in maize cells. In SEQ ID NO: 206, three nucleotides were deleted (dashes) next to the moCas9 cleavage site. SEQ ID NOs: 207-208 indicate that the nucleotide deletion can expand beyond the moCAs9 cleavage site FIG. 7 depicts an EPSPS template vector used for delivery of the EPSPS polynucleotide modification template containing the three TIPS nucleotide modifications. The EPSP polynucleotide modification template includes a partial fragment of the EPSPS gene. The vector was 6,475 basepairs (bp) in length and consisted of two homology regions to the epsps locus (epsps-HR1 and epsps-HR2). Two Gateway cloning sites (ATTL4 and ATTL3), an antibiotic resistance gene (KAN), and the pUC origin of replication (PUC ORI) completed synthesis of the EPSPS template vector.

FIG. 8 illustrates the PCR-based screening strategy for the identification of maize events with TIPS nucleotide modifications in maize cells. Two pairs of PCR primers were used to amplify the genomic fragments of the epsps locus (upper section). Both of them contained the TIPS specific primers (an arrow with a dot indicating the site of the three TIPS modifications). The shorter fragment (780 bp F-E2) was produced by amplification of the EPSPS polynucleotide modification template fragment (template detection). The amplified EPSPS polynucleotide modification template fragment was found in all but 4 analyzed events (panel F-E2). The longer fragment (839 bp H-T) was produced by amplification of the genomic EPSPS sequence providing that the epsps locus contained the three nucleotide modifications responsible for the TIPS modifications. Six events were identified as containing the three nucleotide modifications (panel H-T). The white arrows point to events that contain both the amplified EPSPS polynucleotide modification template and the nucleotide modifications responsible for the TIPS modification. No full-length fragment coding for a functional EPSPS was amplified.

FIG. 9A shows a schematic diagram of the PCR protocol used to identify edited EPSPS DNA fragments in selected events. A partial genomic fragment, comprising parts of Exon1, Intron 1 and Exon2 of the epsps locus, was amplified regardless of the editing product (panel A, 1050 bp. F-E3). The amplification products, representing only partial EPSPS gene sequences having one or more mutations, were cloned and sequenced. FIG. 9B shows 2 examples of sequenced amplification products. In some amplification products, the EPSPS nucleotides and the moCas9 target sequence (underlined) were unchanged indicating that one EPSPS allele was not edited (wild type allele; SEQ ID NO: 40). In other amplification products, three specific nucleotide substitutions (representing the TIPS modifications) were identified with no mutations at the moCas9 target sequence (underlined) (SEQ ID NO: 39).

FIG. 10 illustrates an experimental design to replace the EPSPS1 promoter/5'UTR with the soybean ubiquitin promoter/5'UTR/Intron1.

FIG. 11 shows a schematic representing the genetic elements of the EPSP duplication polynucleotide modification template FIG. 12 shows a schematic representing the EPSPS polynucleotide maize ubiquitin promoter template (such as SEQ ID NO: 55) designed to allow for editing of the epsps locus to contain the maize ubiquitin promoter (Ubi promoter+Ubi intron) placed in front of the epsps-TIPS coding sequence (TIPS).

FIG. 13A-13C. Modification of a maize EPSPS polyubiquitination site. (A) The selected putative maize EPSPS polyubiquitination site (Maize) is compared to the analogous sites of other plant species (*Petunia*, Tomato, Sorghum, Rice and *Amaranthus*) (SEQ ID NOS: 111-116, respectively). (B) The nucleotides to be edited in the maize EPSPS coding sequence (underlined, encoded amino acid shown in bold) (SEQ ID NO: 117). (C) The edited EPSPS coding sequence identified in the selected T0 plant (SEQ ID NO: 118).

FIG. 14A-14C. The intron mediated enhanced element (A). The 5' section of the first intron of the EPSPS gene (editing: substitutions underlined and deletions represented by dots) (B) and its edited version conferring three IMEs elements (underlined) (SEQ ID NO: 119) as found in the selected maize T0 plants. The edited nucleotides are shown in bold (C) (SEQ ID NO: 120).

FIG. 15A-15B. Alternatively spliced EPSPS mRNA in maize cells. (A) left panel represents analysis of EPSPS cDNA. The lane 14 in FIG. 36A shows amplification of the EPSPS pre-mRNA containing the 3rd intron unspliced (the 804 bp diagnostic fragment as shown in FIG. 36 B indicates an alternate splicing event). Lanes E3 and F8 show the EPSPS PCR amplified fragments with spliced introns. These diagnostic fragments are not amplified unless cDNA is synthesized (as is evident by the absence of bands in lanes E3, 14, and F8 comprising total RNA (shown in the total RNA panel on right of FIG. 36A). The grey boxes in FIG. 36 B represent the eight EPSPS exons (their sizes are indicated above each of them).

FIG. 16 shows the splicing site at the junction between the second EPSPS intron and the third exon (bolded) (SEQ ID NO: 121). The nucleotide to be edited is underlined. The epsps-TIPS allele containing (SEQ ID NO: 122) the edited $2^{nd}$ intron-$3^{rd}$ exon splicing site as found in the selected maize T0 plants is listed as SEQ ID NO: 83.

SEQUENCES

Figure 1A:
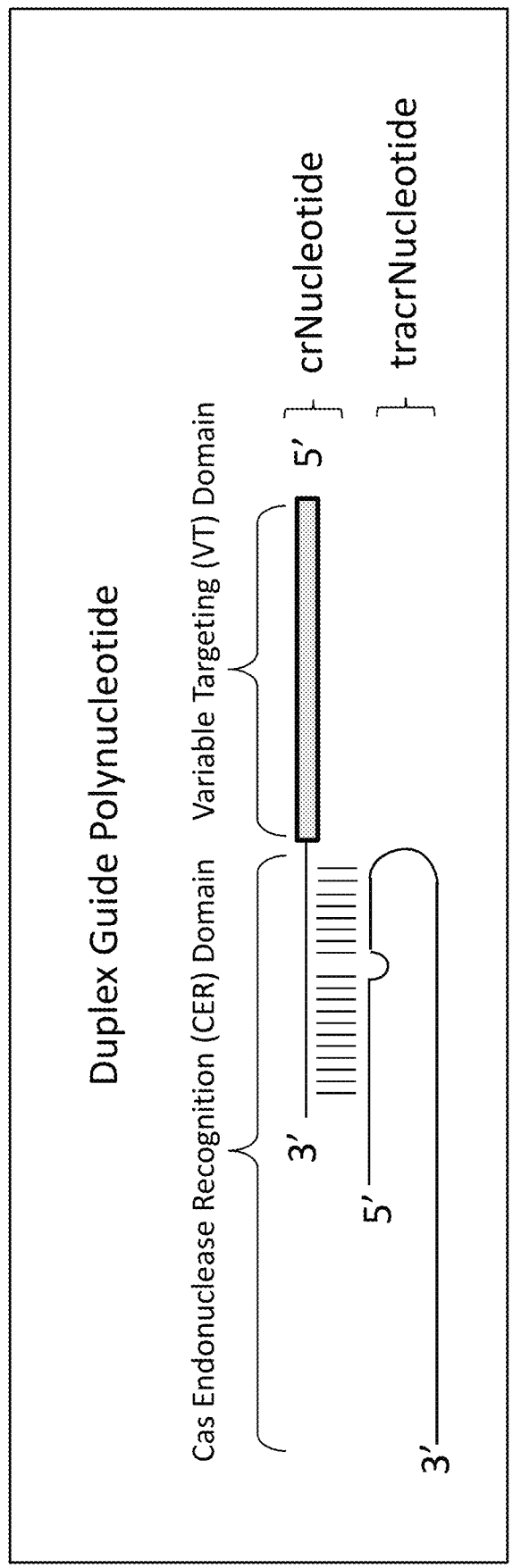

SEQ ID NO: 1 is the nucleotide sequence of the Cas9 gene from Streptococcus pyogenes M1 GAS (SF370).

SEQ ID NO: 2 is the nucleotide sequence of the potato ST-LS1 intron.

SEQ ID NO: 3 is the amino acid sequence of SV40 amino N-terminal.

SEQ ID NO: 4 is the amino acid sequence of Agrobacterium tumefaciens bipartite VirD2 T-DNA border endonuclease carboxyl terminal.

SEQ ID NO: 5 is the nucleotide sequence of an expression cassette expressing the maize optimized Cas9.

SEQ ID NO: 6 is the nucleotide sequence of a crRNA containing the LIGCas-3 target sequence in the variable targeting domain.

SEQ ID NO: 7 is the nucleotide sequence of a tracrRNA from Streptococcus pyogenes M1 GAS (SF370)>

SEQ ID NO: 8 is the nucleotide sequence of a single guide RNA containing the LIGCas-3 target sequence in the variable targeting domain.

SEQ ID NO: 9 is the nucleotide sequence of the maize U6 polymerase III promoter.

SEQ ID NO: 10 is the nucleotide sequence of two copies of the maize U6 polymerase III terminator.

SEQ ID NO: 11 is the nucleotide sequence of a maize optimized single long guide RNA expression cassette containing the LIGCas-3 variable targeting domain.

SEQ ID NO: 12 is the nucleotide sequence of the maize genomic target site LIGCas-1 plus PAM sequence.

SEQ ID NO: 13 is the nucleotide sequence of the maize genomic target site

LIGCas-2 plus PAM sequence.

SEQ ID NO: 14 is the nucleotide sequence of the maize genomic target site LIGCas-3 plus PAM sequence.

SEQ ID NOs: 15-21, 27-34 and 41-52 are nucleotide sequences of PCR primers and probes.

SEQ ID NO: 22 is the amino acid sequence of the maize optimized moCAS9 endonuclease.

SEQ ID NO: 23 is the nucleotide sequence of the maize optimized moCAS9 endonuclease.

SEQ ID NO: 24 is the nucleotide sequence of the DNA version of guide RNA EPSPS sgRNA.

SEQ ID NO: 25 is the nucleotide sequence of the EPSPS polynucleotide template.

SEQ ID NO: 26 is the nucleotide sequence of a DNA fragment comprising the TIPS nucleotide modifications.

SEQ ID NO: 35 is the nucleotide sequence of a DNA fragment with intact Cas target sequence.

SEQ ID NOs: 36-38 are the nucleotide sequence of a DNA fragment with mutated Cas target sequence.

SEQ ID NO: 39 is the nucleotide sequence of a TIPS edited EPSPS nucleotide sequence fragment.

SEQ ID NO: 40 is the nucleotide sequence of a Wild-type epsps nucleotide sequence fragment.

SEQ ID NO: 53 is the nucleotide sequence of the WOL1006, Reverse_primer.

SEQ ID NO: 54 is the nucleotide sequence of the EPSPS-duplication polynucleotide template.

SEQ ID NO: 55 is the nucleotide sequence of the EPSPS-maize ubiquitin promoter polynucleotide template.

SEQ ID NO: 56 is the nucleotide sequence of the EPSPS-K90R polynucleotide template.

SEQ ID NO: 57 is the nucleotide sequence of the EPSPS-IME polynucleotide template.

SEQ ID NO: 58 is the nucleotide sequence of the EPSPS-Tspliced polynucleotide template.

SEQ ID NO: 59 is the nucleotide sequence of the EPSPS-synthetic polynucleotide template.

maize GOS2 5'-UTR1 and intron1 and 5'-UTR2.

SEQ ID NOs: 60-61, 83-84, 96-97 are the nucleotide sequence of the soybean genomic Cas endonuclease target sequences soy EPSPS-CR1, soy EPSPS-CR2, soy EPSPS-CR4, soy EPSPS-CR5, soy EPSPS-CR6, soy EPSPS-CR7, respectively SEQ ID NO: 62 is the nucleotide sequence of the soybean U6 small nuclear RNA promoter GM-U6-13.1.

SEQ ID NOs: 63 and 64 are the nucleotide sequences of the QC868, QC879 plasmids, respectively.

SEQ ID NOs: 65, 66, 85, 86, 87, 98, 99 and 100 are the nucleotide sequences of the RTW1013A, RTW1012A, RTW1199, RTW1200, RTW1190A, RTW1201, RTW1202, RTW1192A respectively.

SEQ ID NOs: 67-81, 88-95, 101-104 are the nucleotide sequences of primers and probes.

SEQ ID NO: 82 is the nucleotide sequence of the soybean codon optimized Cas9.

SEQ ID NO: 105 is the nucleotide sequence of a maize optimized moCAS9 endonuclease.

SEQ ID NO: 106 is the nucleotide sequence of a Cas9 endonuclease, genbank CS571758.1, from S. thermophiles.

SEQ ID NO: 107 is the nucleotide sequence of a Cas9 endonuclease, genbank CS571770.1 from S. thermophiles.

SEQ ID NO: 108 is the nucleotide sequence of a Cas9 endonuclease, genbank CS571785.1, from S. agalactiae.

SEQ ID NO: 109 is the nucleotide sequence of a Cas9 endonuclease genbank CS571790.1, from S. agalactiae.

SEQ ID NO: 110 is the nucleotide sequence of a Cas9 endonuclease, genbank CS571790.1 from S. mutans.

DETAILED DESCRIPTION

The present disclosure includes the production of a mutant plant resistant to an herbicide of the phosphonomethylglycine family, e.g. glyphosate. Compositions and methods are provided for editing a nucleotide sequence of interest in a cell employing a guide polynucleotide/Cas endonuclease system, wherein the Cas endonuclease is guided by a guide polynucleotide to recognize a nucleotide sequence of interest and introduce a double strand break at a specific target site in the genome of a cell. The nucleotide sequence of interest to be edited can be located within or outside the target site that is recognized by a Cas endonuclease. Also, compositions and methods are provided for genome modification of a target site in the genome of a cell and for inserting a polynucleotide sequence of interest into the genome of a cell, employing a guide polynucleotide/Cas endonuclease system.

More specifically, compositions and methods are provided for editing an enolpyruvylshikimate-3-phosphate synthase (EPSPS) nucleotide sequence in a cell. The methods and compositions employ a guide polynucleotide/Cas endonuclease system to provide for an effective system for editing EPSPS nucleotide sequences within the genome of a cell. The nucleotide sequence to be edited can be located within or outside a target site that is recognized by a Cas endonuclease. Cells include, but are not limited to plant cells. Also provided are compositions and methods for the production of glyphosate tolerant or resistant plant cells, plants explants, seeds and grain.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times-also referred to as CRISPR-repeats) which are partially palindromic. The repeated sequences (usually specific to a species) are interspaced by variable sequences of constant length (typically 20 to 58 by depending on the CRISPR locus (WO2007/025097published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060.

As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Figure 3:
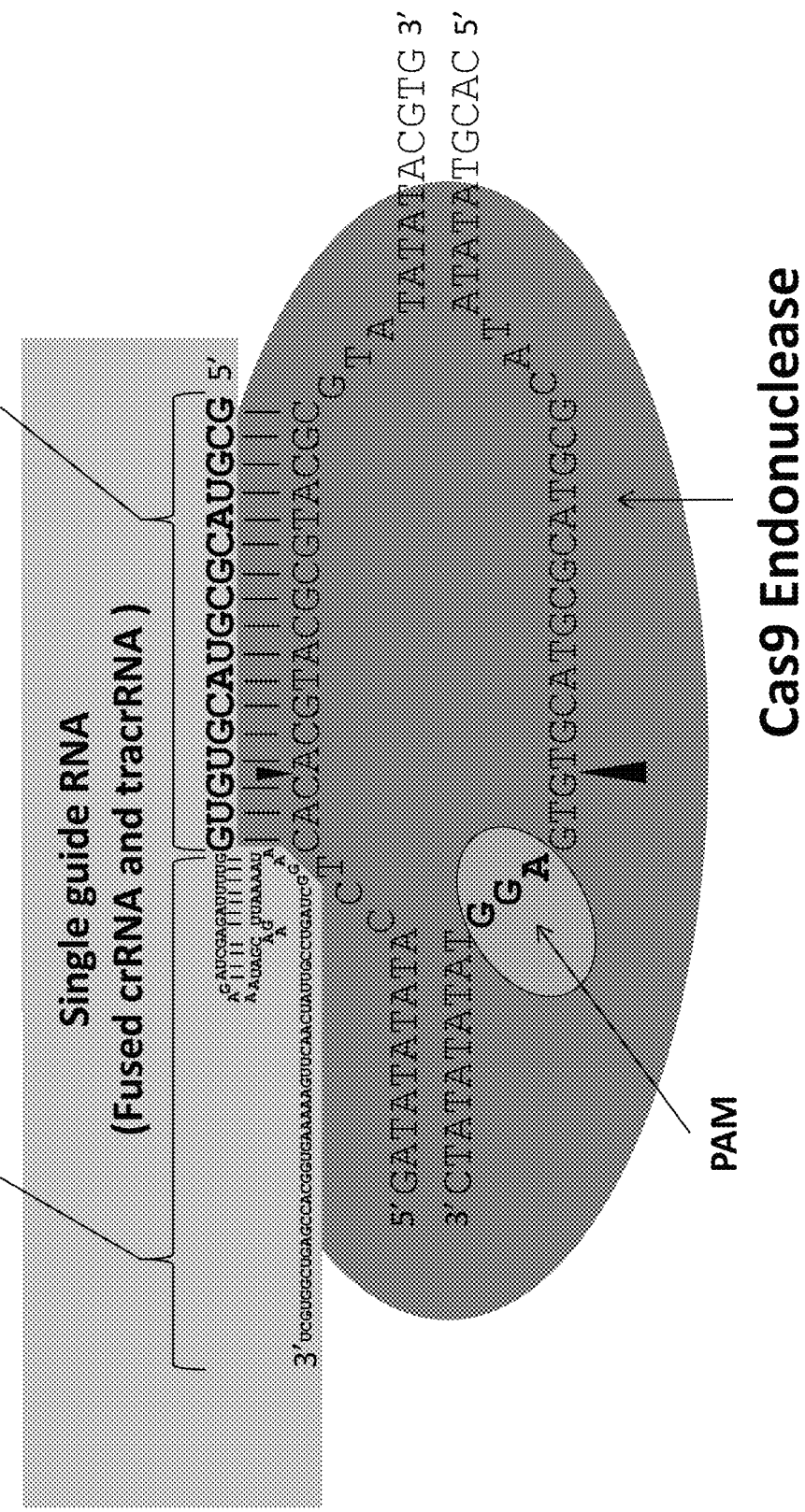

Cas endonuclease relates to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell. As used herein, the tem "guide polynucleotide/Cas endonuclease system" refers to a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide polynucleotide, but only if the correct protospacer-adjacent motif (PAM) is approximately oriented at the 3' end of the target sequence (FIG. 3).

In one embodiment, the Cas endonuclease is a Cas9 endonuclease that is capable of introducing a double strand break at a DNA target site, wherein the DNA cleavage at a specific location is enabled by a) base-pairing complementary between the DNA target site and the variable targeting domain of the guide polynucleotide, and b) the presence of a short protospacer adjacent motif (PAM) immediately adjacent to the DNA target site.

In one embodiment, the Cas endonuclease gene is a Cas9 endonuclease, such as but not limited to, Cas9 genes listed in SEQ ID NOs: 462, 474, 489, 494, 499, 505, and 518 of WO2007/025097published Mar. 1, 2007, and incorporated herein by reference. In another embodiment, the Cas endonuclease gene is plant, maize or soybean optimized Cas9 endonuclease (FIG. 1 A). In another embodiment, the Cas endonuclease gene is operably linked to a SV40 nuclear targeting signal upstream of the Cas codon region.

In one embodiment, the Cas endonuclease gene is a Cas9 endonuclease gene of SEQ ID NO: 105-110, or any functional fragment or variant thereof.

The terms "functional fragment", "fragment that is functionally equivalent" and "functionally equivalent fragment" are used interchangeably herein. These terms refer to a portion or subsequence of a Cas endonuclease sequence in which the ability to create a double-strand break is retained.

The terms "functional variant", "Variant that is functionally equivalent" and "functionally equivalent variant" are used interchangeably herein. These terms refer to a variant of the Cas endonuclease in which the ability create a double-strand break is retained. Fragments and variants can be obtained via methods such as site-directed mutagenesis and synthetic construction.

In one embodiment, the Cas endonuclease gene is a plant codon optimized *Streptococcus pyogenes* Cas9 gene that can recognize any genomic sequence of the form N(12-30)NGG.

In one embodiment, the Cas endonuclease is introduced directly into a cell by any method known in the art, for example, but not limited to transfection and topical application.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more. (patent application WO-PCT PCT/US12/30061 filed on Mar. 22, 2012) Meganucleases have been classified into four families based on conserved sequence motifs (Belfort M, and Perlman P S J. Biol. Chem. 1995; 270:30237-30240). These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr. Op. Biotechnol. 5:521-7; and Sadowski (1993) FASEB 7:760-7. In some examples the recombinase is from the Integrase or Resolvase families.

TAL effector nucleases are a new class of sequence-specific nucleases that can be used to make double-strand breaks at specific target sequences in the genome of a plant or other organism. (Miller et al. (2011) *Nature Biotechnology* 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence.

In one embodiment of the disclosure, the composition comprises a plant or seed comprising a guide polynucleotide and a Cas9 endonuclease, wherein said Cas9 endonuclease and guide polynucleotide are capable of forming a complex and creating a double strand break in a genomic target site of said plant.

Bacteria and Archaea have evolved adaptive immune defenses termed Clustered Regularly Interspaced Short Palindromic Repeats (CRISPR)/CRISPR-associated (Cas) systems that use short RNA to direct degradation of foreign nucleic acids (WO2007/025097published Mar. 1, 2007) The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target.

As used herein, the term "guide polynucleotide", refers to a polynucleotide sequence that can form a complex with a Cas endonuclease and enables the Cas endonuclease to recognize and optionally cleave a DNA target site. The guide polynucleotide can include a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. In some embodiment of this disclosure, the guide polynucleotide does not solely comprise ribonucleic acids (RNAs). A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide (FIG. 1A). The CER domain of the double molecule guide polynucleotide comprises two separate molecules that are hybridized along a region of complementarity (FIG. 1A). The two separate molecules can be RNA, DNA, and/or RNA-DNA-combination sequences. In some embodiments, the first molecule of the duplex guide polynucleotide comprising a VT domain linked to a CER domain (shown as "crNucleotide" in FIG. 1A) is referred to as "crRNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. In one embodiment, the size of the fragment of the crRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain (shown as tracrNucleotide in FIG. 1A) is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

Figure 1B:
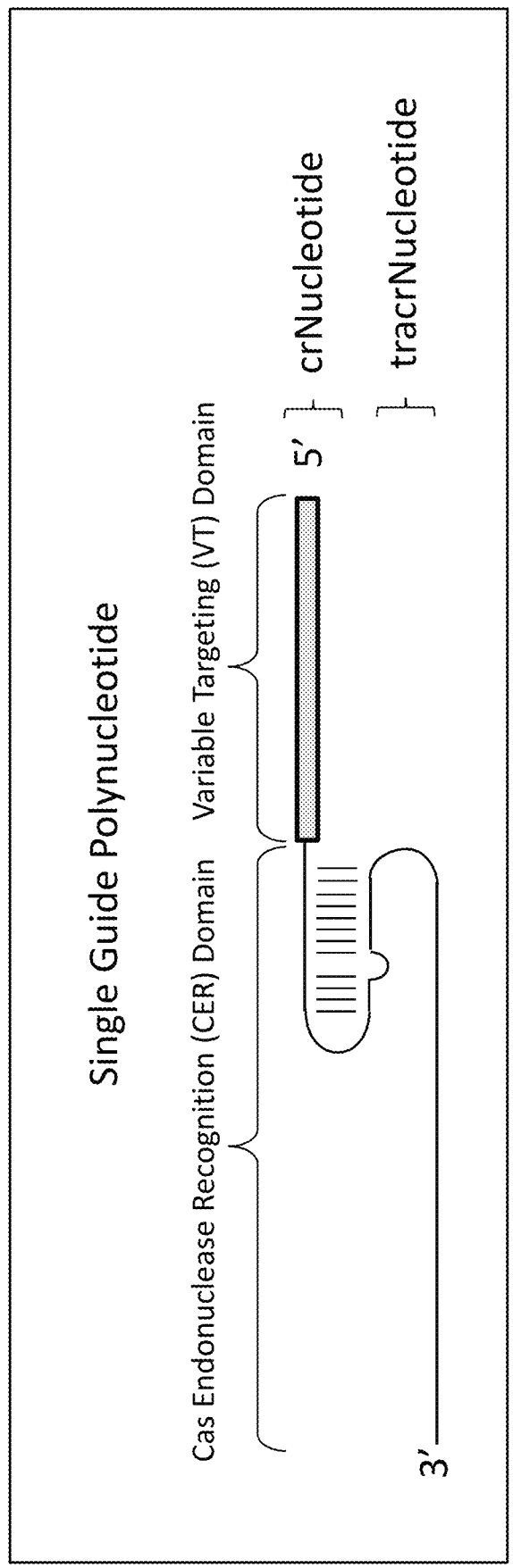

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide (FIG. 1 B). By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence (FIG. 1B). The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

One aspect of using a single guide polynucleotide versus a duplex guide polynucleotide is that only one expression cassette needs to be made to express the single guide polynucleotide.

The term "variable targeting domain" or "VT domain" is used interchangeably herein and refers to a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence (see for example modifications described herein), or any combination thereof.

The term "Cas endonuclease recognition domain" or "CER domain" of a guide polynucleotide is used interchangeably herein and refers to a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In one embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In one embodiment of the disclosure, the composition comprises a guide polynucleotide comprising: (i) a first nucleotide sequence domain (VT domain) that is complementary to a nucleotide sequence in a target DNA; and, (ii) a second nucleotide sequence domain (CER domain) that interacts with a Cas endonuclease, wherein the first nucleotide sequence domain and the second nucleotide sequence domain are composed of deoxyribonucleic acids (DNA), ribonucleic acids (RNA), or a combination thereof. The % complementation between the first nucleotide sequence domain (Variable Targeting domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In one embodiment of the disclosure, the first nucleotide sequence domain (VT domain) and the second nucleotide sequence domain (CER domain) of the guide polynucleotide are located on a single molecule. In another embodiment, the second nucleotide sequence domain (Cas Endonuclease Recognition domain) comprises two separate molecules that are capable of hybridizing along a region of complementarity.

In one embodiment, the composition comprises a guide polynucleotide, wherein the first nucleotide sequence domain (VT domain) is a DNA sequence and the second nucleotide sequence domain (CER domain) is selected from the group consisting of a DNA sequence, a RNA sequence, and a combination thereof.

In one embodiment the guide polynucleotide can be introduce into the plant cell directly using any method known to one skilled in the art, such as for example, but not limited to, particle bombardment or topical applications.

When the guide polynucleotide comprises solely of RNA sequences (also referred to as "guide RNA") it can be introduced indirectly by introducing a recombinant DNA molecule comprising the corresponding guide DNA sequence operably linked to a plant specific promoter that is capable of transcribing the guide polynucleotide in said plant cell. The term "corresponding guide DNA" refers to a DNA molecule that is identical to the RNA molecule but has a "T" substituted for each "U" of the RNA molecule.

In some embodiments, the guide polynucleotide is introduced via particle bombardment or *Agrobacterium* transformation of a recombinant DNA construct comprising the corresponding guide DNA operably linked to a plant U6 polymerase III promoter.

The terms "target site", "target sequence", "target DNA", "target locus", "genomic target site", "genomic target sequence", and "genomic target locus" are used interchangeably herein and refer to a polynucleotide sequence in the genome (including chloroplastic and mitochondrial DNA)

of a cell at which a double-strand break is induced in the cell genome by a Cas endonuclease. The target site can be an endogenous site in the genome of a cell or organism, or alternatively, the target site can be heterologous to the cell or organism and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a cell or organism and is at the endogenous or native position of that target sequence in the genome of a cell or organism. Cells include, but are not limited to animal, bacterial, fungal, insect, yeast, and plant cells as well as plants and seeds produced by the methods described herein.

In one embodiments, the target site, in association with the particular gene editing system that is being used, can be similar to a DNA recognition site or target site that is specifically recognized and/or bound by a double-strand break inducing agent, such as but not limited to a Zinc Finger endonuclease, a meganuclease, or a TALEN endonuclease.

An "artificial target site" or "artificial target sequence" are used interchangeably herein and refer to a target sequence that has been introduced into the genome of a cell or organism, such as but not limiting to a plant or yeast. Such an artificial target sequence can be identical in sequence to an endogenous or native target sequence in the genome of a cell but be located in a different position (i.e., a non-endogenous or non-native position) in the genome of a cell or organism.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for modifying a genomic target site of an organism such as but not limiting to a plant or yeast are disclosed herein.

In one embodiment, a method for modifying a target site in the genome of a cell comprises introducing a guide polynucleotide into a cell having a Cas endonuclease, wherein said guide polynucleotide and Cas endonuclease are capable of forming a complex that enables the Cas endonuclease to introduce a double strand break at said target site. This method can further identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii). This method can also further comprise introducing a donor DNA to said cell, wherein said donor DNA comprises a polynucleotide of interest.

Further provided is a method for modifying a target site in the genome of a cell, the method comprising introducing a guide polynucleotide and a Cas endonuclease into a cell, wherein said guide polynucleotide and Cas endonuclease are capable of forming a complex that enables the Cas endonuclease to introduce a double strand break at said target site. This method can further comprise identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii). This method can also further comprise introducing a donor DNA to said cell, wherein said donor DNA comprises a polynucleotide of interest.

Further provided is a method for modifying a target site in the genome of a cell, the method comprising: a) introducing into a cell a crNucleotide, a first recombinant DNA construct capable of expressing a tracrRNA, and a second recombinant DNA capable of expressing a Cas endonuclease, wherein said crNucleotide is a deoxyribonucleotide sequence or a combination of a deoxyribonucleotide and ribonucleotide sequence, wherein said crNucleotide, said tracrRNA and said Cas endonuclease are capable of forming a complex that enables the Cas endonuclease to introduce a double strand break at said target site; and, b) identifying at least one cell that has a modification at said target site, wherein the modification is selected from the group consisting of (i) a replacement of at least one nucleotide, (ii) a deletion of at least one nucleotide, (iii) an insertion of at least one nucleotide, and (iv) any combination of (i)-(iii).

Further provided is a method for method for modifying a target site in the genome of a cell, the method comprising: a) introducing into a cell a tracrNucleotide, a first recombinant DNA construct capable of expressing a crRNA and a second recombinant DNA capable of expressing a Cas endonuclease, wherein said tracrNucleotide is selected a deoxyribonucleotide sequence or a combination of a deoxyribonucleotide and ribonucleotide sequence, wherein said tracrNucleotide, said crRNA and said Cas endonuclease are capable of forming a complex that enables the Cas endonuclease to introduce a double strand break at said target site; and, b) identifying at least one cell that has a modification at said target site, wherein the modification is selected from the group consisting of (i) a replacement of at least one nucleotide, (ii) a deletion of at least one nucleotide, (iii) an insertion of at least one nucleotide, and (iv) any combination of (i)-(iii).

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

Active variants of genomic target sites can also be used. Such active variants can comprise at least 50%, 55%, 60%, 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the cell in a donor DNA construct. As used herein, "donor DNA" is a DNA construct that comprises a polynucleotide of Interest to be inserted into the target site of a Cas endonuclease. Optionally, the donor DNA construct can further comprise a first and a second region of homology that flank the polynucleotide of Interest. The first and second regions of homology of the donor DNA share homology to a first and a second genomic region, respectively, present in or flanking the target site of the plant genome. By "homology" is meant DNA sequences that are similar. For example, a "region of homology to a genomic region" that is found on the donor DNA is a region of DNA that has a similar sequence to a given "genomic region" in the plant genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc); and, Tijssen (1993) Laboratory Techniques in Biochemistry and Molecular Biology—Hybridization with Nucleic Acid Probes, (Elsevier, New York).

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" refers to the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) Genetics 147:689-99). Using FLP-mediated DNA integration at a target FRT in *Drosophila*, Golic et al., showed integration was approximately 10-fold more efficient when the donor and target shared 4.1 kb of homology as compared to 1.1 kb of homology (Golic et al., (1997) Nucleic Acids Res 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) Proc. Natl. Acad. Sci. USA 90:1262-6; Keeler and Gloor, (1997) Mol. Cell Biol. 17:627-34).

Homologous recombination has also been accomplished in other organisms. For example, at least 150-200 bp of homology was required for homologous recombination in the parasitic protozoan *Leishmania* (Papadopoulou and Dumas, (1997) Nucleic Acids Res 25:4278-86). In the filamentous fungus *Aspergillus nidulans*, gene replacement has been accomplished with as little as 50 bp flanking homology (Chaveroche et al., (2000) Nucleic Acids Res 28:e97). Targeted gene replacement has also been demonstrated in the ciliate *Tetrahymena thermophila* (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically offspring. By interbreeding siblings, homozygous mice carrying the selected genes can be obtained. An overview of the process is provided in Watson et al., (1992) Recombinant DNA, 2nd Ed., (Scientific American Books distributed by WH Freeman & Co.); Capecchi, (1989) Trends Genet 5:70-6; and Bronson, (1994) J. Biol. Chem. 269:27155-8. Homologous recombination in mammals other than mouse has been limited by the lack of stem cells capable of being transplanted to oocytes or developing embryos. However, McCreath et al., Nature 405:1066-9 (2000) reported successful homologous recombination in sheep by transformation and selection in primary embryo fibroblast cells.

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9). The two ends of one double-strand break are the most prevalent substrates of NHEJ (Kirik et al., (2000) EMBO J 19:5562-6), however if two different double-strand breaks occur, the free ends from different breaks can be ligated and result in chromosomal deletions (Siebert and Puchta, (2002) Plant Cell 14:1121-31), or chromosomal translocations between different chromosomes (Pacher et al., (2007) Genetics 175:21-9).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152: 1173-81).

Alternatively, the double-strand break can be repaired by homologous recombination between homologous DNA sequences. DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

In some embodiments, the methods provided herein comprise contacting a cell with a donor DNA and a Cas endonuclease. Once a double-strand break is introduced in the target site by the Cas endonuclease, the first and second regions of homology of the donor DNA can undergo homologous recombination with their corresponding genomic regions of homology resulting in exchange of DNA between the donor and the genome.

As such, the provided methods result in the integration of the polynucleotide of interest of the donor DNA into the double-strand break in the target site in the genome of a cell or organism, thereby altering the original target site and producing an altered genomic target site.

In one embodiment of the disclosure, the method comprises a method for introducing a polynucleotide of interest into a target site in the genome of a cell, the method comprising: a) introducing a guide polynucleotide, a donor DNA and a Cas endonuclease into a cell, wherein said guide polynucleotide and Cas endonuclease are capable of forming a complex that enables the Cas endonuclease to introduce a double strand break at said target site; b) contacting the cell of (a) with a donor DNA comprising a polynucleotide of interest; and, c) identifying at least one cell from (b) comprising in its genome the polynucleotide of interest integrated at said target. The guide polynucleotide, Cas endonuclease and donor DNA can be introduced by any means known in the art. These means include, but are not limited to direct delivery of each component via particle bombardment, delivery through one or more recombinant DNA expression cassettes, or any combination thereof.

In some embodiment of the disclosure, the method comprises a method for introducing a polynucleotide of interest into a target site in the genome of a cell, wherein the donor DNA and Cas endonuclease are introduced into said cell using at least one recombinant DNA construct capable of expressing the donor DNA and/or the Cas endonuclease; and/or, wherein the guide polynucleotide is introduced directly by particle bombardment.

The donor DNA may be introduced by any means known in the art. For example, a cell or organism, such as but not limiting to a plant or yeast having a target site is provided. The donor DNA may be provided by any transformation method known in the art including, for example, Agrobacterium-mediated transformation or biolistic particle bombardment. The donor DNA may be present transiently in the cell or it could be introduced via a viral replicon. In the presence of the Cas endonuclease and the target site, the donor DNA is inserted into the transformed genome.

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould et al., (2006) J Mol Biol 355:443-58; Ashworth et al., (2006) Nature 441:656-9; Doyon et al., (2006) J Am Chem Soc 128:2477-84; Rosen et al., (2006) Nucleic Acids Res 34:4791-800; and Smith et al., (2006) Nucleic Acids Res 34:e149; Lyznik et al., (2009) U.S. Patent Application Publication No. 20090133152A1; Smith et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang et al., (2009) Plant Mol Biol 70:669-79). More practically, the maize liguleless locus was targeted using an engineered single-chain endonuclease designed based on the I-CreI meganuclease sequence. Mutations of the selected liguleless locus recognition sequence were detected in 3% of the TO transgenic plants when the designed homing nuclease was introduced by Agrobacterium-mediated transformation of immature embryos (Gao et al., (2010) Plant J 61:176-87).

Polynucleotides of interest are further described herein and are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

Genome Editing Using the Guide Polynucleotide/Cas Endonuclease System.

As described herein, the guide polynucleotide/Cas endonuclease system can be used in combination with a co-delivered polynucleotide modification template to allow for editing of a genomic nucleotide sequence of interest. While numerous double-strand break-making systems exist, their practical applications for gene editing may be restricted due to the relatively low frequency of induced double-strand breaks (DSBs). To date, many genome modification methods rely on the homologous recombination system. Homologous recombination (HR) can provide molecular means for finding genomic DNA sequences of interest and modifying them according to the experimental specifications. Homologous recombination takes place in plant somatic cells at low frequency. The process can be enhanced to a practical level for genome engineering by introducing double-strand breaks (DSBs) at selected endonuclease target sites. The challenge has been to efficiently make DSBs at genomic sites of interest since there is a bias in the directionality of information transfer between two interacting DNA molecules (the broken one acts as an acceptor of genetic information). Described herein is the use of a guide polynucleotide/Cas system which provides flexible genome cleavage specificity and results in a high frequency of double-strand breaks at a DNA target site, thereby enabling efficient gene editing (gene modification) in a nucleotide sequence of interest, wherein the nucleotide sequence of interest to be edited can be located within or outside the target site recognized and cleaved by a Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for editing a nucleotide sequence of interest and compositions, such as but not limited to an enolpyruvylshikimate-3-phosphate synthase (EPSPS) nucleotide sequence in a plant genome are disclosed herein.

In one embodiment of the disclosure, the method comprises a method of A method for producing an enolpyruvyl-shikimate-3-phosphate synthase (EPSPS) mutant plant, the method comprising: a) obtaining a plant or a seed thereof, wherein the plant or the seed comprises a modification in an endogenous EPSPS gene, the modification generated by a Cas endonuclease, a guide RNA and a polynucleotide modification template, wherein the plant or the seed is resistant to glyphosate; and, b) producing a progeny plant that is void of said guide RNA and Cas endonuclease.

In one embodiment, the composition comprises a glyphosate resistant maize plant, wherein the maize plant comprises an endogenous EPSPS polynucleotide sequence encoding a glyphosate resistant EPSPS polypeptide and wherein the maize plant does not express a glyphosate sensitive EPSPS polypeptide.

In one embodiment, the composition comprises a glyphosate resistant maize plant cell, wherein the maize plant cell comprises an endogenous EPSPS polynucleotide sequence encoding a glyphosate resistant EPSPS polypeptide and wherein the endogenous EPSPS polynucleotide sequence is present in the same chromosomal location as compared to a corresponding wild-type control.

The term "polynucleotide modification template" refers to a polynucleotide that comprises at least one nucleotide modification when compared to the nucleotide sequence to be edited. A nucleotide modification can be at least one nucleotide substitution, addition or deletion, or any combination thereof. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure describes a method for editing a nucleotide sequence in the genome of a cell, the method comprising providing a guide polynucleotide, a polynucleotide modification template and at least one Cas endonuclease to a cell, wherein the Cas endonuclease introduces a double-strand break at a target site in the genome of said cell, wherein said polynucleotide modification template comprises at least one nucleotide modification of said nucleotide sequence. Cells include, but are not limited to, animal, bacterial, fungal, insect, yeast, and plant cells as well as plants and seeds produced by the methods described herein. The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In one embodiment, the disclosure describes a method for editing a nucleotide sequence in the genome of a plant cell, the method comprising providing a guide RNA, a polynucleotide modification template, and at least one maize optimized Cas9 endonuclease to a plant cell, wherein the maize optimized Cas9 endonuclease is capable of providing a double-strand break at a moCas9 target sequence in the plant genome, wherein said polynucleotide modification template includes at least one nucleotide modification of said nucleotide sequence.

In one embodiment, the disclosure describes a method for editing an enolpyruvylshikimate-3-phosphate synthase (EPSPS) nucleotide sequence in a cell, the method comprising providing a guide RNA, a polynucleotide modification template, and a Cas endonuclease to said cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence.

In one embodiment, the disclosure describes a method for producing an enolpyruvylshikimate-3-phosphate synthase (EPSPS) mutant cell, the method comprising: a) providing into a cell comprising an EPSPS nucleotide sequence, a guide RNA, a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence; and, b) identifying at least one cell of (a) that has at least one nucleotide modification at said EPSPS nucleotide sequence, wherein the modification includes at least one deletion, insertion or substitution of one or more nucleotides in said EPSPS nucleotide sequence.

In one embodiment, the disclosure describes a method for producing an enolpyruvylshikimate-3-phosphate synthase (EPSPS) mutant cell, the method comprising: a) providing into a cell comprising a Cas endonuclease and an EPSPS nucleotide sequence, a guide RNA and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence; and, b) identifying at least one cell of (a) that has at least one nucleotide modification at said EPSPS nucleotide sequence, wherein the modification includes at least one deletion, insertion or substitution of one or more nucleotides in said EPSPS nucleotide sequence.

In one embodiment, the disclosure describes a method for producing an enolpyruvylshikimate-3-phosphate synthase (EPSPS) mutant cell, the method comprising: a) providing to a cell comprising an EPSPS nucleotide sequence, a first recombinant DNA construct capable of expressing a guide RNA, a second recombinant DNA construct capable of expressing a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence; and, b) identifying at least one cell of (a) that has at least one nucleotide modification at said EPSPS nucleotide sequence, wherein the modification includes at least one deletion, insertion or substitution of one or more nucleotides in said EPSPS nucleotide sequence.

In some embodiments, the polynucleotide modification template (EPSPS polynucleotide modification template) can include a partial fragment of the EPSPS gene (and therefore does not encode a fully functional EPSPS polypeptide by itself).

In one embodiment, the EPSPS polynucleotide modification template contained three point mutations that were responsible for the creation of a T102I/P106S (TIPS) mutation. Transgenic plants expressing a TIPS-EPSPS double mutant transgene exhibit glyphosate tolerance (Funke, T et al., J. Biol. Chem. 2009, 284:9854-9860). As defined herein "Glyphosate" refers to any herbicidally effective form of N-phosphonomethylglycine (including any salt thereof), other forms which result in the production of the glyphosate anion in plants and any other herbicides of the phosphonomethlyglycine family.

In one embodiment, the disclosure describes a method for producing an enolpyruvylshikimate-3-phosphate synthase (EPSPS) mutant plant, the method comprising: a) providing a guide RNA, a polynucleotide modification template, and a Cas endonuclease to a plant cell comprising a EPSPS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said EPSPS nucleotide sequence; b) obtaining a plant from the plant cell of (a); c) evaluating the plant of (b) for the presence of said at least one nucleotide modification; d) selecting a progeny plant that shows resistance to glyphosate.

In one embodiment, the disclosure describes a method for producing an enolpyruvylshikimate-3-phosphate synthase (EPSPS) mutant plant, the method comprising: a) providing a guide RNA, a polynucleotide modification template, and a Cas endonuclease to a plant cell comprising a EPSPS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said EPSPS nucleotide sequence; b) obtaining a plant from the plant cell of (a); c) evaluating the plant of (b) for the presence of said at least one nucleotide modification; and, d) screening a progeny plant of (c) that is void of said guide RNA and Cas endonuclease.

Increased resistance to a herbicide is demonstrated when plants which display the increased resistance to a herbicide are subjected to the herbicide and a dose/response curve is shifted to the right when compared with that provided by an appropriate control plant. Such dose/response curves have "dose" plotted on the x-axis and "percentage injury", "herbicidal effect" etc. plotted on the y-axis.

Plants which are substantially resistant to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field. The terms resistance and tolerance may be used interchangeably in the present disclosure.

FIG. 4 shows a schematic representation of components used in the genome editing procedure. A maize optimized Cas endonuclease, a guide RNA and a polynucleotide modification template were provided to a plant cell. For example, as shown in FIG. 4, the polynucleotide modification template included three nucleotide modifications (indicated by arrows) when compared to the EPSPS genomic sequence to be edited. These three nucleotide modifications are referred to as TIPS mutations as these nucleotide modifications result in the amino acid changes T-102 to I-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon ATC, the third point mutation results from the substitution of the first C nucleotide in the codon sequence CCA with a T nucleotide in order to form a serine codon TCA (FIG. 4).

The nucleotide sequence to be edited can be a sequence that is endogenous, artificial, pre-existing, or transgenic to the cell that is being edited. For example, the nucleotide sequence in the genome of a cell can be a native gene, a mutated gene, a non-native gene, a foreign gene, or a transgene that is stably incorporated into the genome of a cell. Editing of such nucleotide may result in a further desired phenotype or genotype.

Regulatory Sequence Modifications Using the Guide Polynucleotide/Cas Endonuclease System In one embodiment the nucleotide sequence to be modified can be a regulatory sequence such as a promoter wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers (U.S. Pat. No. 5,837,850 issued Nov. 17, 1998), a mutation of DNA binding elements and/or a deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

In one embodiment the nucleotide sequence to be modified can be a promoter wherein the editing of the promoter comprises replacing a native EPSPS1 promoter from with a plant ubiquitin promoter.

In another embodiment, the guide polynucleotide/Cas endonuclease system can be used in combination with a co-delivered polynucleotide modification template or donor DNA sequence to allow for the insertion of a promoter or promoter element into a genomic nucleotide sequence of interest, wherein the promoter insertion (or promoter element insertion) results in any one of the following or any one combination of the following: an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression a mutation of DNA binding elements and/or an addition of DNA binding elements. Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or SulphonylUrea (Su) repressor/operator/inducer elements. The dehydration-responsive element (DRE) was first identified as a cis-acting promoter element in the promoter of the drought-responsive gene rd29A, which contains a 9 bp conserved core sequence, TACCGACAT (Yamaguchi-Shinozaki, K., and Shinozaki, K. (1994) Plant Cell 6, 251-264). Insertion of DRE into an endogenous promoter may confer a drought inducible expression of the downstream gene. Another example is ABA-responsive elements (ABREs) which contain a (C/T)ACGTGGC consensus sequence found to be present in numerous ABA and/or stress-regulated genes (Busk P. K., Pages M. (1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

In one embodiment the nucleotide sequence to be modified can be a promoter wherein the editing of the promoter comprises duplicating a native EPSPS1 promoter using the guide polynucleotide/Cas endonuclease system described herein.

In another embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements and/or an addition of DNA binding elements. Promoter elements to be deleted can be, but are not limited to, promoter core elements, promoter enhancer elements or 35 S enhancer elements. The promoter or promoter fragment to be deleted can be endogenous, artificial, pre-existing, or transgenic to the cell that is being edited.

Terminator Modifications Using the Guide Polynucleotide/Cas Endonuclease System

In one embodiment the nucleotide sequence to be modified can be a terminator wherein the editing of the terminator comprises replacing the terminator (also referred to as a "terminator swap" or "terminator replacement") or terminator fragment with a different terminator (also referred to as replacement terminator) or terminator fragment (also referred to as replacement terminator fragment), wherein the terminator replacement results in any one of the following or any one combination of the following: an increased terminator activity, an increased terminator tissue specificity, a decreased terminator activity, a decreased terminator tissue specificity, a mutation of DNA binding elements and/or a deletion or addition of DNA binding elements." The terminator (or terminator fragment) to be modified can be a terminator (or terminator fragment) that is endogenous, artificial, pre-existing, or transgenic to the cell that is being edited. The replacement terminator (or replacement terminator fragment) can be a terminator (or terminator fragment) that is endogenous, artificial, pre-existing, or transgenic to the cell that is being edited.

In one embodiment, the guide polynucleotide/Cas endonuclease system can be used in combination with a co-delivered polynucleotide modification template or donor DNA sequence to allow for the insertion of a terminator or terminator element into a genomic nucleotide sequence of interest, wherein the terminator insertion (or terminator element insertion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements.

The terminator (or terminator element) to be inserted can be a terminator (or terminator element) that is endogenous, artificial, pre-existing, or transgenic to the cell that is being edited.

In another embodiment, the guide polynucleotide/Cas endonuclease system can be used to allow for the deletion of a terminator or terminator element, wherein the terminator deletion (or terminator element deletion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements. The terminator or terminator fragment to be deleted can be endogenous, artificial, pre-existing, or transgenic to the cell that is being edited.

Additional Regulatory Sequence Modifications Using the Guide Polynucleotide/Cas Endonuclease System In one embodiment, the guide polynucleotide/Cas endonuclease system can be used to modify or replace a regulatory sequence in the genome of a cell. A regulatory sequence is a segment of a nucleic acid molecule which is capable of increasing or decreasing the expression of specific genes within an organism and/or is capable of altering tissue specific expression of genes within an organism. Examples of regulatory sequences include, but are not limited to, 3' UTR (untranslated region) region, 5' UTR region, transcription activators, transcriptional enhancers transcriptions repressors, translational repressors, splicing factors, miRNAs, siRNA, artificial miRNAs, promoter elements, CAMV 35 S enhancer, MMV enhancer elements (PCT/US14/23451 filed Mar. 11, 2013), SECIS elements, polyadenylation signals, and polyubiquitination sites. In some embodiments the editing (modification) or replacement of a regulatory element results in altered protein translation, RNA cleavage, RNA splicing, transcriptional termination or post translational modification. In one embodiment, regulatory elements can be identified within a promoter and these regulatory elements can be edited or modified do to optimize these regulatory elements for up or down regulation of the promoter.

In one embodiment, the genomic sequence of interest to be modified is a polyubiquitination site, wherein the modification of the polyubiquitination sites results in a modified rate of protein degradation. The ubiquitin tag condemns proteins to be degraded by proteasomes or autophagy. Proteasome inhibitors are known to cause a protein overproduction. Modifications made to a DNA sequence encoding a protein of interest can result in at least one amino acid modification of the protein of interest, wherein said modification allows for the polyubiquitination of the protein (a post translational modification) resulting in a modification of the protein degradation In one embodiment, the genomic sequence of interest to be modified is a polyubiquitination site on a maize EPSPS gene, wherein the polyubiquitination site is modified using a guide polynucleotide/Cas endonuclease system described herein, resulting in an increased protein content due to a slower rate of EPSPS protein degradation.

In one embodiment, the genomic sequence of interest to be modified is an intron site, wherein the modification consists of inserting an intron enhancing motif into the intron, using a guide polynucleotide/Cas endonuclease system described herein, which results in modulation of the transcriptional activity of the gene comprising said intron.

In one embodiment, the genomic sequence of interest to be modified is a an intron site, wherein the modification consist of replacing a soybean EPSP1 intron with a soybean ubiquitin intron 1 as described herein.

Modifications of Splicing Sites and/or Introducing Alternate Splicing Sites Using the Guide Polynucleotide/Cas Endonuclease System Protein synthesis utilizes mRNA molecules that emerge from pre-mRNA molecules subjected to the maturation process. The pre-mRNA molecules are capped, spliced and stabilized by addition of polyA tails. Eukaryotic cells developed a complex process of splicing that result in alternative variants of the original pre-mRNA molecules. Some of them may not produce functional templates for protein synthesis. In maize cells, the splicing process is affected by splicing sites at the exon-intron junction sites. An example of a canonical splice site is AGGT. Gene coding sequences can contains a number of alternate splicing sites that may affect the overall efficiency of the pre-mRNA maturation process and as such may limit the protein accumulation in cells. The guide polynucleotide/Cas endonuclease system can be used in combination with a co-delivered polynucleotide modification template to edit a gene of interest to introduce a canonical splice site at a described junction or any variant of a splicing site that changes the splicing pattern of pre-mRNA molecules.

In one embodiment, the nucleotide sequence of interest to be modified is a maize EPSPS gene, wherein the modification of the gene consists of modifying alternative splicing sites, using a guide polynucleotide/Cas endonuclease system described herein, resulting in enhanced production of the functional gene transcripts and gene products (proteins).

In one embodiment, the nucleotide sequence of interest to be modified is a gene, wherein the modification of the gene consists of editing the intron borders of alternatively spliced genes to alter the accumulation of splice variants.

Modifications of Nucleotide Sequences Encoding a Protein of Interest Using the Guide Polynucleotide/Cas Endonuclease System In one embodiment, the guide polynucleotide/Cas endonuclease system can be used to modify or replace a coding sequence in the genome of a cell, wherein the modification or replacement results in any one of the following, or any one combination of the following: an increased protein (enzyme) activity, an increased protein functionality, a decreased protein activity, a decreased protein functionality, a site specific mutation, a protein domain swap, a protein knock-out, a new protein functionality, a modified protein functionality.

In one embodiment the protein knockout is due to the introduction of a stop codon into the coding sequence of interest.

In one embodiment the protein knockout is due to the deletion of a start codon into the coding sequence of interest.

Amino Acid and/or Protein Fusions Using the Guide Polynucleotide/Cas Endonuclease System In one embodiment, the guide polynucleotide/Cas endonuclease system can be used with or without a co-delivered polynucleotide sequence to fuse a first coding sequence encoding a first protein to a second coding sequence encoding a second protein in the genome of a cell, wherein the protein fusion results in any one of the following or any one combination of the following: an increased protein (enzyme) activity, an increased protein functionality, a decreased protein activity, a decreased protein functionality, a new protein functionality, a modified protein functionality, a new protein localization, a new timing of protein expression, a modified protein expression pattern, a chimeric protein, or a modified protein with dominant phenotype functionality.

In one embodiment, the guide polynucleotide/Cas endonuclease system can be used with or without a co-delivered polynucleotide sequence to fuse a first coding sequence encoding a chloroplast localization signal (e.g., a chloroplast transit peptide) to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding to a second coding sequence, wherein the protein fusion results in a modified protein with dominant phenotype functionality.

Methods for editing a nucleotide sequence of interest and compositions such as, but not limited to, an enolpyruvylshikimate-3-phosphate synthase (EPSPS) nucleotide sequence in a plant genome are disclosed herein. Methods for producing a mutant EPSPS gene and/or enolpyruvylshikimate-3-phosphate synthase (EPSPS) mutant plant cells or plants are described herein and may include editing of the EPSPS codon region, producing variant plant EPSPS, duplication of the native EPSPS gene, regulatory sequence modifications, editing of the EPSPS gene polyubiquitination sites, editing intron elements, editing splicing sites, terminator modifications, additional regulatory sequence modifications, modifications of splicing sites and/or introducing alternate splicing sites, modifications of nucleotide sequences encoding a protein of interest, amino acid and/or protein fusions as described herein, or any one combination thereof. For example, one can combine gene modification of the EPSPS gene (through methods described herein such as but not limiting to editing of the EPSPS codon region, editing or modification of splicing sites etc.), while simultaneously modifying the promoter driving the EPSPS gene.

Methods for Identifying at Least One Plant Cell Comprising in its Genome a Polynucleotide of Interest Integrated at the Target Site.

Further provided, are methods for identifying at least one plant cell comprising in its genome a polynucleotide of Interest integrated at the target site. A variety of methods are available for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein.

The method also comprises recovering a plant from the plant cell comprising a polynucleotide of Interest integrated into its genome. The plant may be sterile or fertile. It is recognized that any polynucleotide of interest can be provided, integrated into the plant genome at the target site, and expressed in a plant.

Polynucleotides/polypeptides of interest include, but are not limited to, herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with glyphosate resistance described herein.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) J. Bacteriol. 170:5837-5847) facilitate expression of polyhydroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) Gene 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) Nature 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

These polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male fertility genes such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676). Maize plants (*Zea mays* L.) can be bred by both self-pollination and cross-pollination techniques. Maize has male flowers, located on the tassel, and female flowers, located on the ear, on the same plant. It can self-pollinate ("selfing") or cross pollinate. Natural pollination occurs in maize when wind blows pollen from the tassels to the silks that protrude from the tops of the incipient ears. Pollination may be readily controlled by techniques known to those of skill in the art. The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated F1. The F1 hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid (F1) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used as a hybrid parent. Mutations that cause male sterility in maize have been produced by a variety of methods such as X-rays or UV-irradiations, chemical treatments, or transposable element insertions (ms23, ms25, ms26, ms32) (Chaubal et al. (2000) Am J Bot 87:1193-1201). Conditional regulation of fertility genes through fertility/sterility "molecular switches" could enhance the options for designing new male-sterility systems for crop improvement (Unger et al. (2002) Transgenic Res 11:455-465).

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) Proc. Natl. Acad. Sci. USA 89:6314-8; Yao et al., (1992) Cell 71:63-72; Reznikoff, (1992) Mol Microbiol 6:2419-22; Hu et al., (1987) Cell 48:555-66; Brown et al., (1987) Cell 49:603-12; Figge et al., (1988) Cell 52:713-22; Deuschle et al., (1989) Proc. Natl. Acad. Sci. USA 86:5400-4; Fuerst et al., (1989) Proc. Natl. Acad. Sci. USA 86:2549-53; Deuschle et al., (1990) Science 248:480-3; Gossen, (1993) Ph.D. Thesis, University of Heidelberg; Reines et al., (1993) Proc. Natl. Acad. Sci. USA 90:1917-21; Labow et al., (1990) Mol Cell Biol 10:3343-56; Zambretti et al., (1992) Proc. Natl. Acad. Sci. USA 89:3952-6; Baim et al., (1991) Proc. Natl. Acad. Sci. USA 88:5072-6; Wyborski et al., (1991) Nucleic Acids Res 19:4647-53; Hillen and Wissman, (1989) Topics Mol Struc Biol 10:143-62; Degenkolb et al., (1991) Antimicrob Agents Chemother 35:1591-5; Kleinschnidt et al., (1988) Biochemistry 27:1094-104; Bonin, (1993) Ph. D. Thesis, University of Heidelberg; Gossen et al., (1992) Proc. Natl. Acad. Sci. USA 89:5547-51; Oliva et al., (1992) Antimicrob Agents Chemother 36:913-9; Hlavka et al., (1985) Handbook of Experimental Pharmacology, Vol. 78 (Springer-Verlag, Berlin); Gill et al., (1988) Nature 334:721-4. Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

"Open reading frame" is abbreviated ORF.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. Genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1 SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) CABIOS 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) CABIOS 5:151-153; Higgins et al., (1992) *Comput Appl Biosci* 8:189-191) and found in the MegAlign™ v 6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" refers to a nucleic acid fragment that generally expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the invention, the mutated gene comprises an alteration that results from a guide polynucleotide/Cas endonuclease system as disclosed herein. A mutated plant is a plant comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

In one embodiment, the targeted mutation is the result of a guide polynucleotide/Cas endonuclease induced gene editing as described herein. The guide polynucleotide/Cas endonuclease induced targeted mutation can occur in a nucleotide sequence that is located within or outside a genomic target site that is recognized and cleaved by a Cas endonuclease.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage.

Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present invention comprises one or more of such sequence modifications.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) Plant Cell 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript-pre mRNA. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target m RNA.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, N.Y. (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) Mol Gen Genetics 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA, guide polynucleotide, or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different genes of interest.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to a 1 average recombination frequency between the two linked genes, markers, target sites, loci, or any pair thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

A variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300, 543), meristem transformation (U.S. Pat. No. 5,736,369), electroporation (Riggs et al., (1986) Proc. Natl. Acad. Sci. USA 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995)

"Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in *The Experimental Manipulation of Ovule Tissues*, ed. Chapman et al., (Longman, N.Y.), pp. 197-209 (pollen); Kaeppler et al., (1990) *Plant Cell Rep* 9:415-8 and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) Nat *Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" or "crossing" in the context of this invention means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, modified (mutated or edited) native allele, or a selected allele of a marker or QTL.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

The present invention further provides expression constructs for expressing in a yeast or plant, plant cell, or plant part a guide polynucleotide/Cas system that is capable of binding to and creating a double strand break in a target site. In one embodiment, the expression constructs of the invention comprise a promoter operably linked to a nucleotide sequence encoding a Cas gene and a promoter operably linked to a guide polynucleotide of the present invention. The promoter is capable of driving expression of an operably linked nucleotide sequence in a plant cell.

A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1, 3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

A modified (mutated or edited) native DNA sequence such as EPSPS can comprise one or more genes of interest. Such genes of interest can encode, for example, a protein that provides agronomic advantage to the plant.

Marker Assisted Selection and Breeding of Plants

A primary motivation for development of molecular markers in crop species is the potential for increased efficiency in plant breeding through marker assisted selection (MAS). Genetic marker alleles, or alternatively, quantitative trait loci (QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. It will be appreciated that for the purposes of MAS, the term marker can encompass both marker and QTL loci.

After a desired phenotype and a polymorphic chromosomal locus, e.g., a marker locus or QTL, are determined to segregate together, it is possible to use those polymorphic loci to select for alleles corresponding to the desired phenotype—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, southern blot analysis, northern blot analysis, in situ hybridization, hybridization of primers followed by PCR amplification of a region of the marker or the like. A variety of procedures for detecting markers are well known in the art. After the presence (or absence) of a particular marker in the biological sample is verified, the plant is selected, i.e., used to make progeny plants by selective breeding.

Plant breeders need to combine traits of interest with genes for high yield and other desirable traits to develop improved plant varieties. Screening for large numbers of samples can be expensive, time consuming, and unreliable. Use of markers, and/or genetically-linked nucleic acids is an effective method for selecting plant having the desired traits in breeding programs. For example, one advantage of marker-assisted selection over field evaluations is that MAS can be done at any time of year regardless of the growing season. Moreover, environmental effects are irrelevant to marker-assisted selection.

When a population is segregating for multiple loci affecting one or multiple traits, the efficiency of MAS compared to phenotypic screening becomes even greater because all the loci can be processed in the lab together from a single sample of DNA.

The DNA repair mechanisms of cells are the basis to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be routinely used in gene targeting or editing until it has been found that the process can be stimulated by DNA double-strand breaks (Bibikova et al., (2001) Mol. Cell Biol. 21:289-297; Puchta and Baltimore, (2003) Science 300:763; Wright et al., (2005) Plant J. 44:693-705).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Non-limiting examples of compositions and methods disclosed herein are as follows:

1. A method for producing an enolpyruvylshikimate-3-phosphate synthase (EPSPS) mutant plant, the method comprising:
    a) providing a guide RNA, a polynucleotide modification template, and a Cas endonuclease to a plant cell comprising a EPSPS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said EPSPS nucleotide sequence;
    b) obtaining a plant from the plant cell of (a);
    c) evaluating the plant of (b) for the presence of said at least one nucleotide modification; and,
    d) selecting a progeny plant that shows resistance to glyphosate.

2. A method for producing an enolpyruvylshikimate-3-phosphate synthase (EPSPS) mutant plant, the method comprising:
    a) providing a guide RNA and a polynucleotide modification template to a plant cell comprising a Cas endonuclease and a EPSPS nucleotide sequence, wherein said Cas endonuclease introduces a double strand break at a target site in the genome of said plant cell, wherein said polynucleotide modification template comprises at least one nucleotide modification of said EPSPS nucleotide sequence;
    b) obtaining a plant from the plant cell of (a);
    c) evaluating the plant of (b) for the presence of said at least one nucleotide modification; and,
    d) selecting a progeny plant that shows resistance to glyphosate.

3. The method of any of embodiments 1-2, wherein said polynucleotide modification template comprises a non-functional or partial fragment of the EPSPS nucleotide sequence.

4. The method of any of embodiments 1-2, wherein the target site is located within the EPSPS nucleotide sequence.

5. The method of any of embodiments 1-2, further comprising selecting a progeny plant that is void of said guide RNA and Cas endonuclease.

6. A method for producing an enolpyruvylshikimate-3-phosphate synthase (EPSPS) mutant plant, the method comprising:
 a) obtaining a plant or a seed thereof, wherein the plant or the seed comprises a modification in an endogenous EPSPS gene, the modification generated by a Cas endonuclease, a guide RNA and a polynucleotide modification template, wherein the plant or the seed is resistant to glyphosate; and,
 b) producing a progeny plant that is void of said guide RNA and Cas endonuclease.

7. The method of embodiment 6 further comprising selecting a plant that shows resistance to glyphosate.

8. The method of any one embodiments of 1-7, wherein the mutant plant comprises a TIPS edited EPSPS gene.

9. The method of any one embodiments of 1-7, wherein the mutant plant comprises a K90R and TIPS edited EPSPS gene.

10. The method of any one embodiments of 1-7, wherein the mutant plant comprises an IME and TIPS edited EPSPS gene.

11. The method of any one embodiments of 1-7, wherein the mutant plant comprises a Tspliced and TIPS edited EPSPS gene.

12. The method of any one of embodiments 1-11, wherein the plant is a monocot or a dicot.

13. The method of embodiment 12, wherein the monocot is selected from the group consisting of maize, rice, sorghum, rye, barley, wheat, millet, oats, sugarcane, turfgrass, or switchgrass.

14. The method of embodiment 12, wherein the dicot is selected from the group consisting of soybean, canola, alfalfa, sunflower, cotton, tobacco, peanut, potato, tobacco, *Arabidopsis*, or safflower.

15. The method of any one of embodiments 1-12, wherein the guide RNA is provided directly by particle bombardment.

16. The method of any one of embodiments 1, 3-12 wherein Cas endonuclease is provided directly to the cell.

17. The method of any one of embodiments 1-12, wherein the guide RNA is provided via particle bombardment or *Agrobacterium* transformation of a recombinant DNA construct comprising the corresponding guide DNA operably linked to a plant U6 polymerase III promoter.

18. The method of any one of embodiments 1-17, wherein the Cas endonuclease gene is selected from the group of a Cas9 endonuclease or a plant optimized Cas9 endonuclease.

19. The method of embodiment 18, wherein the plant optimized Cas9 endonuclease is selected from the group of a maize optimized Cas9 endonuclease and a soybean optimized Cas9 endonuclease.

20. The method of any one of the preceding embodiments wherein the Cas9 endonuclease is encoded by any one of SEQ ID NOs: 105-110, or any functional fragment or variant thereof.

21. A method of generating a glyphosate resistant maize plant, the method comprising providing a maize plant cell wherein its endogenous chromosomal EPSPS gene by has been modified through a guide RNA/Cas endonuclease system to produce a glyphosate resistant EPSPS protein and growing a maize plant from said maize plant cell, wherein said plant is resistant to glyphosate.

22. The method of embodiment 21, wherein the maize plant is resistant to a 1× glyphosate application.

23. The method of embodiment 22, wherein the endogenous chromosomal EPSPS gene is a preexisting recombinant DNA.

24. A plant produced by the method of any one of embodiments 1-23.

25. A seed produced by the plant of embodiment 24.

26. The plant of embodiment 24 wherein the plant is resistant to a 1× glyphosate application 27. A guide RNA wherein the variable targeting domain targets a fragment of a plant EPSPS nucleotide sequence.

28. The guide RNA of embodiment 27, wherein the variable targeting domain targets a plant target site selected from the group consisting of SEQ ID NOs: 12, 13, 14, 60, 61, 83, 84, 96, 97

29. The guide RNA of embodiment 27, wherein DNA sequence corresponding to the guide RNA is SEQ ID NO: 24.

30. A method for producing an enolpyruvylshikimate-3-phosphate synthase (EPSPS) mutant plant cell, the method comprising:
 a) providing to a cell comprising an EPSPS nucleotide sequence, a guide RNA, a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said EPSPS nucleotide sequence; and,
 b) obtaining at least one plant cell of (a) that has at least one nucleotide modification at said EPSPS nucleotide sequence, wherein the modification includes at least one deletion, insertion or substitution of one or more nucleotides in said EPSPS nucleotide sequence.

31. A method for producing an enolpyruvylshikimate-3-phosphate synthase (EPSPS) mutant plant cell, the method comprising:
 a) providing a guide RNA and a polynucleotide modification template to a plant cell comprising a Cas endonuclease and a EPSPS nucleotide sequence, wherein said Cas endonuclease introduces a double strand break at a target site in the genome of said plant cell, wherein said polynucleotide modification template comprises at least one nucleotide modification of said EPSPS nucleotide sequence; and,
 b) identifying at least one plant cell of (a) that has at least one nucleotide modification at said EPSPS nucleotide sequence, wherein the modification includes at least one deletion, insertion or substitution of one or more nucleotides in said EPSPS nucleotide sequence.

32. A method for producing an enolpyruvylshikimate-3-phosphate synthase (EPSPS) mutant cell, the method comprising:
 a) providing to a cell comprising an EPSPS nucleotide sequence, a first recombinant DNA construct capable of expressing a guide RNA, a second recombinant DNA construct capable of expressing a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises a non-functional fragment of the EPSPS gene and at least one nucleotide modification of said EPSPS nucleotide sequence; and,
   b) identifying at least one cell of (a) that has at least one nucleotide modification at said EPSPS nucleotide sequence, wherein the modification includes at least one deletion, insertion or substitution of one or more nucleotides in said EPSPS nucleotide sequence.
33. The method of any of embodiments 30-32, wherein said polynucleotide modification template comprises a non-functional or partial fragment of the EPSPS nucleotide sequence.
34. The method of any of embodiments 30-32, wherein the target site is located within the EPSPS nucleotide sequence.
35. A method for duplicating an enolpyruvylshikimate-3-phosphate synthase (EPSPS) gene fragment in a cell, the method comprising providing a guide RNA, a polynucleotide modification template, and a Cas endonuclease to said cell, wherein said guide RNA and Cas endonuclease are capable of forming a complex that enables the Cas endonuclease to introduce a double strand break at a target site in the genome of said cell, wherein said polynucleotide modification template comprises at least one copy of an EPSPS gene fragment.
36. A method for replacing a first enolpyruvylshikimate-3-phosphate synthase (EPSPS) promoter sequence in a cell, the method comprising providing a guide RNA, a polynucleotide modification template, and a Cas endonuclease to said cell, wherein said guide RNA and Cas endonuclease are capable of forming a complex that enables the Cas endonuclease to introduce a double strand break at a target site in the genome of said cell, wherein said polynucleotide modification template comprises a second promoter or second promoter fragment that is different from said first EPSPS promoter sequence.
37. The method of embodiment 36, wherein the replacement of the first EPSPS promoter sequence results in any one of the following, or any one combination of the following: an increased promoter activity, an increased promoter tissue specificity, a decreased promoter activity, a decreased promoter tissue specificity, a new promoter activity, an inducible promoter activity, an extended window of gene expression, or a modification of the timing or developmental progress of gene expression in a cell layer.
38. The method of embodiment 36, wherein the second promoter or second promoter fragment is a maize ubiquitin promoter.
39. A method for inserting a regulatory element in an enolpyruvylshikimate-3-phosphate synthase (EPSPS) nucleotide sequence in a cell, the method comprising providing a guide RNA, a polynucleotide modification template, and a Cas endonuclease to said cell, wherein said guide RNA and Cas endonuclease are capable of forming a complex that enables the Cas endonuclease to introduce a double strand break at a target site in the genome of said cell, wherein said polynucleotide modification template comprises a regulatory element to be inserted into said EPSPS nucleotide sequence.
40. The method of embodiment 39, wherein the insertion of the regulatory element results in any one of the following, or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements, or an addition of DNA binding elements.
41. The method of any of embodiments 30-32, wherein said polynucleotide modification template comprises at least one intron mediated enhancer motif.
42. The method of any of embodiments 30-32, wherein said polynucleotide modification template comprises at least one splice site different from the native EPSPS coding sequence.
43. A method for inserting an intron in an enolpyruvylshikimate-3-phosphate synthase (EPSPS) nucleotide sequence in a cell, the method comprising providing a guide RNA, a polynucleotide modification template, and a Cas endonuclease to said cell, wherein said guide RNA and Cas endonuclease are capable of forming a complex that enables the Cas endonuclease to introduce a double strand break at a target site in the genome of said cell, wherein said polynucleotide modification template comprises an intron sequence.
44. The method of any of embodiments 30-32, wherein the EPSPS nucleotide sequence is selected from the group consisting of a partial fragment of the native EPSPS gene sequence, an EPSPS promoter sequence, an EPSPS terminator sequence, an EPSPS regulatory sequence, and a EPSPS coding sequence, an EPSPS splice sequence, an EPSPS polyubiquitination sequence and an EPSPS intron sequence.
45. The method of any of embodiments 30-32, wherein said at least one nucleotide modification of said EPSPS nucleotide sequence is located outside the target site of said Cas endonuclease.
46. The method of any of embodiments 30-32, wherein said at least one nucleotide modification of said EPSPS nucleotide sequence is located within the target site of said Cas endonuclease.
47. The method of any one of embodiments 30-47, wherein the cell is a plant cell.
48. The method of embodiment 47, wherein the plant cell is selected from the group consisting of a monocot and dicot cell.
49. The method of embodiment 48, wherein the plant cell is selected from the group consisting of a maize, rice, sorghum, rye, barley, wheat, millet, oats, sugarcane, turfgrass, switchgrass, soybean, canola, alfalfa, sunflower, cotton, tobacco, peanut, potato, tobacco, *Arabidopsis*, and safflower cell.
50. A plant cell produced by the method of any one of embodiments 30-32.
51. A plant or progeny plant produced from plant cell of embodiment 50, wherein said plant or progeny plant shows resistance to glyphosate.
52. A glyphosate resistant maize plant, wherein the maize plant comprises an endogenous EPSPS polynucleotide sequence encoding a glyphosate resistant EPSPS polypeptide and wherein the maize plant does not express a glyphosate sensitive EPSPS polypeptide.
53. A glyphosate resistant maize plant cell, wherein the maize plant cell comprises an endogenous EPSPS polynucleotide sequence encoding a glyphosate resistant EPSPS polypeptide and wherein the endogenous EPSPS polynucleotide sequence is present in the same chromosomal location as compared to a corresponding wild-type control.
54. A method for producing an enolpyruvylshikimate-3-phosphate synthase (EPSPS) mutant plant cell, the method comprising:

a) editing of the EPSPS codon region; or,
b) duplication of the native EPSPS gene; or,
c) regulatory sequence modifications; or
d) editing of the EPSPS gene polyubiquitination sites; or,
e) editing intron elements; or,
f) editing or modifying splicing sites; or,
g) terminator modifications, or,
h) introducing alternate splicing sites; or,
i) amino acid and/or protein fusions; or,
j) any one combination of (a)-(j);
  wherein said method comprises providing at least one guide RNA, at least one Cas endonuclease, and optionally a polynucleotide modification template or a donor DNA, to a plant cell comprising an EPSPS nucleotide sequence, wherein said at least one guide RNA and at least one Cas endonuclease are capable of forming a complex that enables the Cas endonuclease to recognize, bind to and optionally cleave at least one target site in the genome of said plant cell, wherein said polynucleotide modification template comprises at least one nucleotide modification of said EPSPS nucleotide sequence;
b) obtaining a plant from the plant cell of (a);
c) evaluating the plant of (b) for the presence of said at least one nucleotide modification; and,
d) selecting a progeny plant that shows resistance to glyphosate.
55. The method of embodiment 54, further comprising obtaining a plant from said plant cell, evaluating said plant for the presence of said at least one nucleotide modification, and selecting a progeny plant that shows resistance to glyphosate.

EXAMPLES

In the following Examples, unless otherwise stated, in which parts and percentages are by weight and degrees are Celsius. It should be understood that these Examples, while indicating embodiments of the invention, are given by way of illustration only. From the above discussion and these Examples, one skilled in the art, can make various changes and modifications of the invention to adapt it to various usages and conditions. Such modifications are also intended to fall within the scope of the appended embodiments.

Example 1

Expression Cassettes for Guide RNA/Cas Endonuclease Based Genome Modification in Maize Plants Described herein is a guide RNA/Cas endonuclease system that is based on the type II CRISPR/Cas system and includes a Cas endonuclease and a guide RNA (or duplexed crRNA and tracrRNA) that together can form a complex that recognizes a genomic target site in a plant and introduces a double-strand-break into said target site (U.S. patent application 61/868,706, filed Aug. 22, 2013).

Figure 2A:
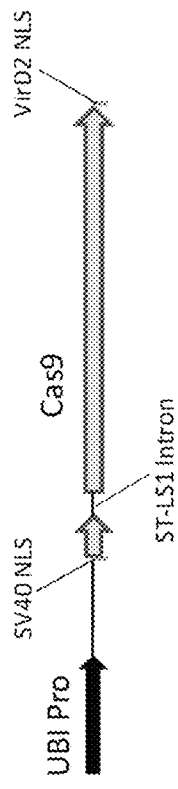
Figure 2B:
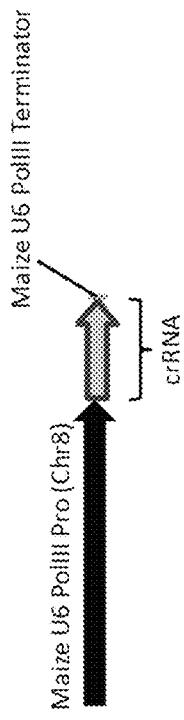
Figure 2C:
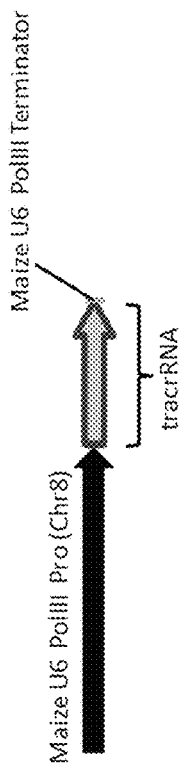

To test the guide RNA/Cas endonuclease system in maize, the Cas9 gene from *Streptococcus pyogenes* M1 GAS (SF370) (SEQ ID NO: 1) was maize codon optimized per standard techniques known in the art and the potato ST-LS1 intron (SEQ ID NO: 2) was introduced in order to eliminate its expression in *E. coli* and *Agrobacterium* (FIG. 1 A). To facilitate nuclear localization of the Cas9 protein in maize cells, *Simian virus* 40 (SV40) monopartite amino terminal nuclear localization signal (MAPKKKRKV, SEQ ID NO: 3) and *Agrobacterium tumefaciens* bipartite VirD2 T-DNA border endonuclease carboxyl terminal nuclear localization signal (KRPRDRHDGELGGRKRAR, SEQ ID NO: 4) were incorporated at the amino and carboxyl-termini of the Cas9 open reading frame (FIG. 2A), respectively. The maize optimized Cas9 gene was operably linked to a maize constitutive or regulated promoter by standard molecular biological techniques. An example of the maize optimized Cas9 expression cassette (SEQ ID NO: 5) is illustrated in FIG. 2 A. FIG. 2A shows a maize optimized Cas9 gene containing the ST-LS1 intron, SV40 amino terminal nuclear localization signal (NLS) and VirD2 carboxyl terminal NLS driven by a plant Ubiquitin promoter.

Figure 2D:
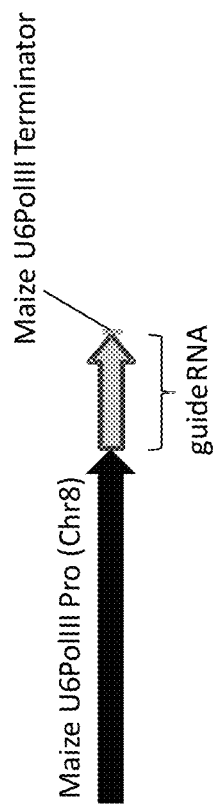
Figure 2E:
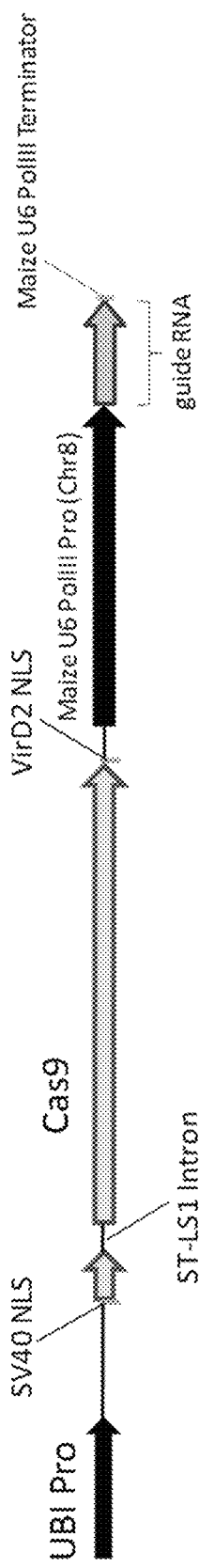

The second component necessary to form a functional guide RNA/Cas endonuclease system for genome engineering applications is a duplex of the crRNA and tracrRNA molecules (FIG. 1A) or a fusing of the crRNA and tracrRNA molecules, referred to as a single guide RNA (FIG. 1B). To confer efficient guide RNA expression (or expression of the duplexed crRNA and tracrRNA) in maize, the maize U6 polymerase III promoter (SEQ ID NO: 9) and maize U6 polymerase III terminator (first 8 bases of SEQ ID NO: 10) residing on chromosome 8 were isolated and operably fused to the termini of a guide RNA (FIG. 2 D) using standard molecular biology techniques. An example expression cassette is shown in FIG. 2D which illustrates a maize U6 polymerase III promoter driving expression of a single guide RNA terminated with a U6 polymerase III terminator.

As shown in FIG. 3A, the guide RNA (or crRNA molecule) also contains a region complementary to one strand of the double strand DNA target (referred to as the variable targeting domain) that is approximately 12-30 nucleotides in length and upstream of a PAM sequence (5'NGG3' on antisense strand of FIG. 3A, corresponding to 5'CCN3' on sense strand of FIG. 3A) for target site recognition and cleavage (Gasiunas et al. (2012) *Proc. Natl. Acad. Sci. USA* 109:E2579-86, Jinek et al. (2012) *Science* 337:816-21, Mali et al. (2013) *Science* 339:823-26, and Cong et al. (2013) *Science* 339:819-23). To facilitate the rapid introduction of maize genomic DNA target sequences into the crRNA or single guide RNA expression constructs, two Type IIS BbsI restriction endonuclease target sites were introduced in an inverted tandem orientation with cleavage orientated in an outward direction as described in Cong et al. (2013) *Science* 339:819-23. Upon cleavage, the Type IIS restriction endonuclease excises its target sites from the crRNA or single guide RNA expression plasmid, generating overhangs allowing for the in-frame directional cloning of duplexed oligos containing the desired maize genomic DNA target site into the variable targeting domain. In this example, only target sequences starting with a G nucleotide were used to promote favorable polymerase III expression of the single guide RNA or crRNA.

Expression of both the Cas endonuclease gene and the single guide RNA then allows for the formation of the guide RNA/Cas complex depicted in FIG. 3A, which is capable of introducing a double strand break into a Cas endonuclease target site.

Alternatively, expression of the Cas endonucleases gene (FIG. 2A), crRNA FIG. 3B), and tracrRNA (FIG. 3C) allow for the formation of the crRNA/tracrRNA/Cas complex capable of introducing a double strand break into a Cas endonuclease target site.

Example 2

The Guide RNA/Cas Endonuclease System Cleaves Chromosomal DNA in Maize and Introduces Mutations by Non-Homologous End-Joining To test whether the maize optimized guide RNA/Cas endonuclease described in example 1 could recognize, cleave, and mutate a maize EPSPS gene through non-homologous end-joining (NHEJ) repair pathways, three different genomic target sequences in the maize epsps locus were targeted for cleavage (see Table 1) and examined by deep sequencing for the presence of NHEJ mutations.

TABLE 1

Maize genomic target sites targeted by a single guide RNA/Cas endonuclease system.

| Locus | Target Site Location | Target Site Designation | Maize Genomic Target Site Sequence | PAM Sequence | SEQ ID NO: |
|---|---|---|---|---|---|
| EPSPS | Chr. 9: 69.43 cM | EPSPSCas-1 | GGAATGCTGGAACTGCAATG | CGG | 12 |
|  |  | EPSPSCas-2 | GCAGCTCTTCTTGGGGAATGC | TGG | 13 |
|  |  | EPSPSCas-3 | GCAGTAACAGCTGCTGTCAA | TGG | 14 |

EPSPS = Enolpyruvylshikimate Phosphate Synthase Gene

The maize optimized Cas9 endonuclease and single guide RNA expression cassettes containing the specific maize variable targeting domains were co-delivered to 60-90 Hi-II immature maize embryos by particle-mediated delivery (see Example 14) in the presence of BBM and WUS2 genes (U.S. patent application Ser. No. 13/800,447, filed Mar. 13, 2013).

After 7 days, the 20-30 most uniformly transformed embryos were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 2 and the primers used in the secondary PCR reaction were AATGATACGGCGACCACCGAGATCTA-CACTCTTTCCCTACACG (forward, SEQ ID NO: 15) and CAAGCAGAAGACGGCATA (reverse, SEQ ID NO: 16).

TABLE 2

PCR primer sequences

| Target Site | Primer Orientation | Primary PCR Primer Sequence | SEQ ID NO: |
|---|---|---|---|
| EPSPSCas-1 | Forward | CTACACTCTTTCCCTACACGACGCTCTTCCGATCTGGAAGAGGAAACATACGTTGCATTTCCA | 17 |
| EPSPSCas-1 | Reverse | CAAGCAGAAGACGGCATACGAGCTCTTCCGATCTGGTGGAAAGTTCCCAGTTGAGGA | 18 |
| EPSPSCas-2 | Forward | CTACACTCTTTCCCTACACGACGCTCTTCCGATCTAAGCGGTGGAAAGTTCCCAGTTGAGGA | 19 |
| EPSPSCas-2 | Reverse | CAAGCAGAAGACGGCATACGAGCTCTTCCGATCTGAGGAAACATACGTTGCATTTCCA | 20 |
| EPSPSCas-3 | Forward | CTACACTCTTTCCCTACACGACGCTCTTCCGATCTCCTTGAGGAAACATACGTTGCATTTCCA | 21 |
| EPSPSCas-3 | Reverse | CAAGCAGAAGACGGCATACGAGCTCTTCCGATCTGGTGGAAAGTTCCCAGTTGAGGA | 18 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the % mutant reads based on the total number of reads of an appropriate length containing a perfect match to the barcode and forward primer.

The frequency of NHEJ mutations recovered by deep sequencing for the guide RNA/Cas endonuclease system targeting the three EPSPS targets (SEQ ID NOS: 12, 13, 14) compared to the cas9 only control is shown in Table 3. This data indicates that the guide RNA/Cas9 endonuclease system described herein can be used to introduce a double strand break at genomic sites of interest. Editing the EPSPS target can result in the production of plants that are tolerant and/or resistant against glyphosate based herbicides.

TABLE 3

Percent (%) mutant reads at maize Enolpyruvylshikimate Phosphate Synthase target loci produced by the guide RNA/Cas system.

| System | Total Number of Reads | Number of Mutant Reads | % Mutant Reads |
| --- | --- | --- | --- |
| Cas9 Only Control (EPSPS) | 1,347,086 | 6 | 0.00% |
| EPSPSCas-1 guide/Cas9 | 1,420,274 | 13,051 | 0.92% |
| EPSPSCas-2 guide/Cas9 | 1,225,082 | 26,340 | 2.15% |
| EPSPSCas-3 guide/Cas9 | 1,406,905 | 53,603 | 3.81% |

Taken together, our data indicate that the maize optimized guide RNA/Cas endonuclease system described herein using a single guide RNA expression cassette cleaves maize chromosomal DNA and generates NHEJ mutations Example 3

Figure 5:
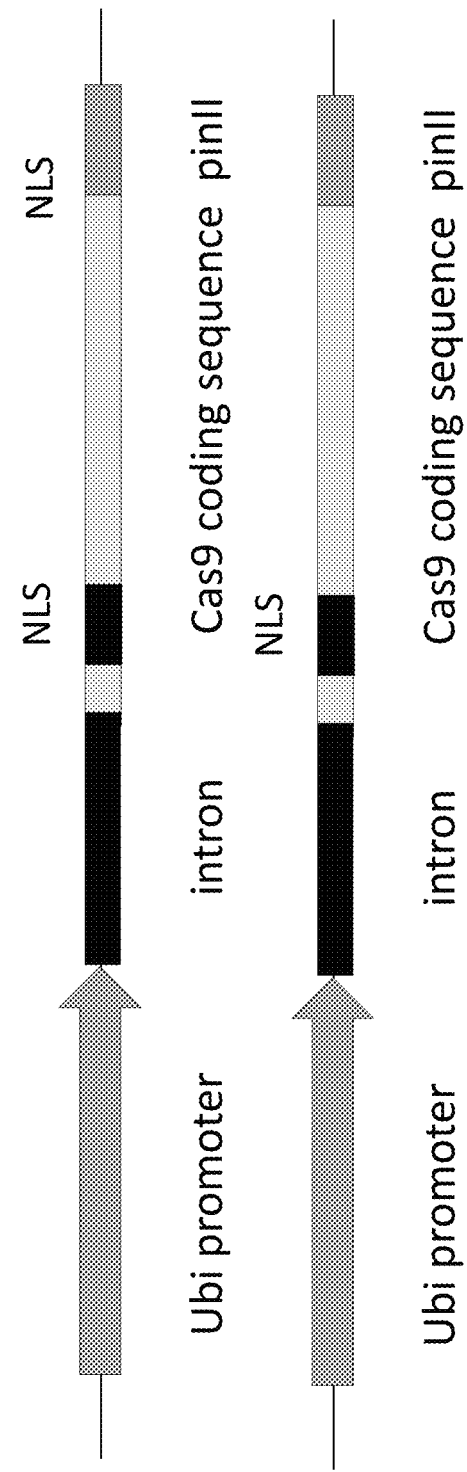

The Guide RNA/Cas Endonuclease System Delivers Double-Strand Breaks (DBSs) to the Maize Epsps Locus Resulting in Desired Point Mutations Two maize optimized Cas9 endonucleases were developed and evaluated for their ability to introduce a double-strand break at a genomic target sequence. A first Cas9 endonuclease was as described in FIG. 2A (Example 1 and expression cassette SEQ ID NO:5). A second maize optimized Cas9 endonuclease (moCas9 endonuclease; SEQ ID NO:22 (protein) and 23 (DNA)) was supplemented with the SV40 nuclear localization signal by adding it to the 5' end of the moCas9 coding sequence (FIG. 5). The plant moCas9 expression cassette was subsequently modified by the insertion of the ST-LS1 intron into the moCas9 coding sequence in order to enhance its expression in maize cells and to eliminate its expression in E. coli and Agrobacterium. The maize ubiquitin promoter and the potato proteinase inhibitor II gene terminator sequences complemented the moCas9 endonuclease gene designs. The structural elements of the moCas9 expression cassette are shown in FIG. 5 and its amino acid and nucleotide sequences are listed as SEQ ID NOs: 22 and 23.

A single guide RNA (sgRNA) expression cassette was essentially as described in Example 1 and shown in FIG. 2D. It consists of the U6 polymerase III maize promoter (SEQ ID NO: 9) and its cognate U6 polymerase III termination sequences (TTTTTTTT). The guide RNA (SEQ ID NO: 24) comprised a 20 nucleotide variable targeting domain (nucleotide)-20 of SEQ ID NO: 24) followed by a RNA sequence capable of interacting with the double strand break inducing endonuclease.

A maize optimized Cas9 endonuclease target sequence (moCas9 target sequence) within the EPSPS codon sequence was complementary to the 20 nucleotide variable sequence of the guide sgRNA, which determined the site of the Cas9 endonuclease cleavage within the EPSPS coding sequence.

The moCAS9 target sequence (nucleotides 25-44 of SEQ ID NO:39) was synthesized and cloned into the guide RNA-Cas9 expression vector designed for delivery of the components of the guide RNA-Cas9 system to the BMS (Black Mexican Sweet) cells through Agrobacterium-mediated transformation. Agrobacterium T-DNA delivered also the yeast FLP site-specific recombinase and the WDV (wheat dwarf virus) replication-associated protein (replicase). Since the moCas9 target sequences were flanked by the FLP recombination targets (FRT), they were excised by FLP in maize cells forming episomal (chromosome-like) structures. Such circular DNA fragments were replicated by the WDV replicase (the origin of replication was embedded into the WDV promoter) allowing their recovery in E. coli cells. If the maize optimized Cas9 endonuclease made a double-strand break at the moCas9 target sequence, its repair might produce mutations. The procedure is described in detail in: Lyznik, L. A., Djukanovic, V., Yang, M. and Jones, S. (2012) Double-strand break-induced targeted mutagenesis in plants. In: *Transgenic plants: Methods and Protocols* (Dunwell, J. M. and Wetten, A. C. eds). New York Heidelberg Dordrecht London: Springer, pp. 399-416.

The guide RNA/Cas9 endonuclease systems using either one of the maize optimized Cas9 endonucleases described herein, generated double-strand breaks in the moCas9 target sequence (Table 4). Table 4 shows the percent of the moCas9 target sequences mutagenized in the maize BMS cells using the moCas9 endonuclease of SEQ ID NO: 23 or the maize optimized Cas9 endonuclease of SEQ ID NO:5. Both guide RNA/Cas endonuclease systems generated double-strand breaks (as judged by the number of targeted mutagenesis events) ranging from 67 to 84% of the moCas9 target sequences available on episomal DNA molecules and recovered from maize BMS cells. A sample of mutagenized EPSPS target sequences are shown in FIG. 6. This observation indicates that the maize optimized Cas9 endonuclease described herein is functional in maize cells and efficiently generates double-strand breaks at the moCas9 target sequence.

TABLE 4

Percent of the moCas9 target sequences mutagenized in the maize BMS cells by maize optimized Cas9 endonucleases.

| Cas9 endonuclease version | # of moCas9 target sequences analyzed | # of intact moCas9 target sequences recovered | # of mutagenized moCas9 target sequences found | Percent mutagenesis (%) |
|---|---|---|---|---|
| SEQ ID NO: 23 (FIG. 13) | 81 | 13 | 68 | 84% |
| SEQ ID NO: 5 (FIG. 1A) | 93 | 31 | 62 | 67% |

In order to accomplish targeted genome editing of the maize chromosomal EPSPS gene, in an aspect, a polynucleotide modification template which provided genetic information for editing the EPSPS coding sequence was created (SEQ ID NO:25) and co-delivered with the guide RNA/Cas9 system components.

As shown in FIG. 4, the polynucleotide modification template comprised three nucleotide modifications (indicated by arrows) when compared to the native EPSPS genomic sequence to be edited. These three nucleotide modifications are referred to as TIPS mutations as these nucleotide modifications result in the amino acid changes T-102 to 1-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon (ATC), the third point mutation results from the substitution of the first C nucleotide in the codon sequence CCA with a T nucleotide in order to form a serine codon, TCA (FIG. 4). Both codon sequences were located within 9 nucleotides of each other as shown in SEQ ID NO: 26: atcgcaatgcggtca. The three nucleotide modifications are shown in bold. The nucleotides between the two codons were homologous to the non-edited, native EPSPS gene at the epsps locus. The polynucleotide modification template further comprised DNA fragments of maize EPSPS genomic sequence that were used as homologous sequence for the EPSPS gene editing. The short arm of homologous sequence (HR1—FIG. 4) was 810 base pairs long and the long arm of homologous sequence (HR2—FIG. 4 was 2,883 base pairs long (SEQ ID NO: 25). None of the EPSPS template sequence used encoded a functional EPSPS protein.

In this example, the EPSPS polynucleotide modification template was co-delivered using particle gun bombardment as a plasmid-(see template vector 1, FIG. 7) together with the guide sgRNA expression cassette and a maize optimized-Cas9 endonuclease expression vector which contained the maize optimized Cas9 endonuclease expression cassette described in Example 1, SEQ ID NO:5) and also contained a moPAT selectable marker gene. Ten to eleven day-old immature embryos were placed, embryo-axis down, onto plates containing the N6 medium (Table 5) and incubated at 28° C. for 4-6 hours before bombardment. The plates were placed on the third shelf from the bottom in the PDS-1000 apparatus and bombarded at 200 psi. Post-bombardment, embryos were incubated in the dark overnight at 28° C. and then transferred to plates containing the N6-2 media for 6-8 days at 28° C. The embryos were then transferred to plates containing the N6-3 media for three weeks, followed by transferring the responding callus to plates containing the N6-4 media for an additional three-week selection. After six total weeks of selection at 28° C., a small amount of selected tissue was transferred onto the MS regeneration medium and incubated for three weeks in the dark at 28° C.

TABLE 5

Composition of Culture Media.

| Culture medium | Composition |
|---|---|
| N6 | 4.0 g/L $N_6$ Basal Salts (Sigma C-1416; Sigma-Aldrich Co., St. Louis, MO, USA), 1.0 ml/L Ericksson's Vitamin Mix (Sigma E-1511), 0.5 mg/L thiamine HCl, 190 g/L sucrose, 1.0 mg/L 2,4-dichlorophenoxyacetic acid (2,4-D), 2.88 g/L L-proline, 8.5 mg/L silver nitrate, 25 mg/L cefotaxime, and 6.36 g/L Sigma agar at pH 5.8 |
| N6-2 | 4.0 g/L $N_6$ Basal Salts (Sigma C-1416), 1.0 ml/L Ericksson's Vitamin Mix (Sigma E-1511), 0.5 mg/L thiamine HCl, 20 g/L sucrose, 1.0 mg/L 2,4-D, 2.88 g/L L-proline, 8.5 mg/L silver nitrate, 25 mg/L cefotaxime, and 8.5 g/L Sigma agar at pH 5.8 |
| N6-3 | 4.0 g/L $N_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L 2-(N-morpholino)ethanesulphonic acid (MES) buffer, 0.85 mg/L silver nitrate, 5 mg/L glufosinate $NH_4$, and 8.0 g/L Sigma agar at pH 5.8 |
| N6-4 | 4.0 g/L $N_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L MES buffer, 0.85 mg/L silver nitrate, 3 mg/L bialophos, and 8.0 g/L Sigma agar at pH 5.8 |
| MS | 4.3 g/L Murashige and Skoog (MS) salts (Gibco 11117; Gibco, Grand Island, NY), 5.0 ml/L MS Vitamins Stock Solution (Sigma M3900), 100 mg/L myo-inositol, 0.1 μmol abscisic acid (ABA), 1 mg/L indoleacetic acid (IAA), 0.5 mg/L zeatin, 60.0 g/L sucrose, 3.0 mg/L Bialaphos, and 8.0 g/L Sigma agar at pH 5.6 |

DNA was extracted by placing callus cell samples, two stainless-steel beads, and 450 ul of extraction buffer (250 mM NaCl, 200 mM Tris-HCl pH 7.4, 25 mM EDTA, 4.2 M Guanidine HCl) into each tube of a Mega titer rack. The rack was shaken in the Genogrinder at 1650 r.p.m. for 60 seconds and centrifuged at 3000×g for 20 min at 4° C. Three hundred μl of supernatant was transferred to the wells of the Unifilter 96-well DNA Binding GF/F Microplate (770-2810, Whatman, GE Healthcare). The plate was placed on the top of a Multi-well plate vacuum manifold (5017, Pall Life Sciences). A vacuum pressure was applied until the wells were completely dried. The vacuum filtration procedure was repeated one time with 100 ul extraction buffer and two times with 250 ul washing buffer (50 mM Tris-HCl pH 7.4, 200 mM NaCl, 70% ethanol). The residual ethanol was removed by placing the GF/F filter plate on an empty waste collection plate and centrifuged for 10 min at 3000×g. The DNA was eluted in 100 ul Elution Buffer (10 mM Tris-Hcl, pH 8.3) and centrifuged at 3000×g for 1 min. For each sample, four different PCR reactions were run (F-E2, F-T, H-T, and F-E3). They included approximately 40 ng genomic DNA, 10 ul REDExtract-N-Amp PCR ReadyMix (R4775, Sigma-Aldrich Co.), and 5 picomoles of each primer in a total volume of 20 ul. Primer combinations for each PCR reaction are listed in the Table 6.

TABLE 6

Primer combinations for PCR reactions.

| PCR reaction | Primer sequence | SEQ ID NO: | PCR product |
|---|---|---|---|
| F-E2 | CCGAGGAGATCGTGCTGCA | 27 | Template randomly integrated or gene editing event |
|  | CAATGGCCGCATTGCAGTTC | 28 |  |
| F-T | CCGAGGAGATCGTGCTGCA | 29 | Wild-type EPSPS allele |
|  | TGACCGCATTGCGATTCCAG | 30 |  |
| H-T | TCCAAGTCGCTTTCCAACAGGATC | 31 | TIPS editing event |
|  | TGACCGCATTGCGATTCCAG | 32 |  |
| F-E3 | CCGAGGAGATCGTGCTGCA | 33 | A partial fragment of the epsps locus for cloning and sequencing |
|  | ACCAAGCTGCTTCAATCCGACAAC | 34 |  |

The same PCR reactions were done on five samples of genomic DNA obtained from untransformed maize inbred plantlets. After an initial denaturation at 95° C. for 5 minutes, each PCR amplification was carried out over 35 cycles using DNA Engine Tetrad2 Thermal Cycler (BioRad Laboratories, Hercules, Calif.) at 94° C. for 30 sec denaturation, 68° C. for 30 sec annealing, and 72° C. for 1 min extension. PCR products F-E2, F-T and H-T were separated in 1% agarose gel at 100 Volts for 45 minutes, with 100 bp DNA Ladder (N0467S, NewEngland Biolabs). For sequencing, the F-E3 PCR amplified fragments from selected calli were cloned into pCR 2.1-TOPO vectors using the TOPO TA Cloning Kit (Invitrogen Corp, Carlsbad, Calif.). DNA sequencing was done with BigDye Terminator chemistry on ABI 3700 capillary sequencing machines (Applied Biosystems, Foster City, Calif.). Each sample contained about 0.5 ug Topo plasmid DNA and 6.4 pmole primer E3-EPex3 Rev (ACCAAGCTGCTTCAATCCGACAAC, SEQ ID N0:34). Sequences were analyzed using the Sequencher program.

Figure 9:
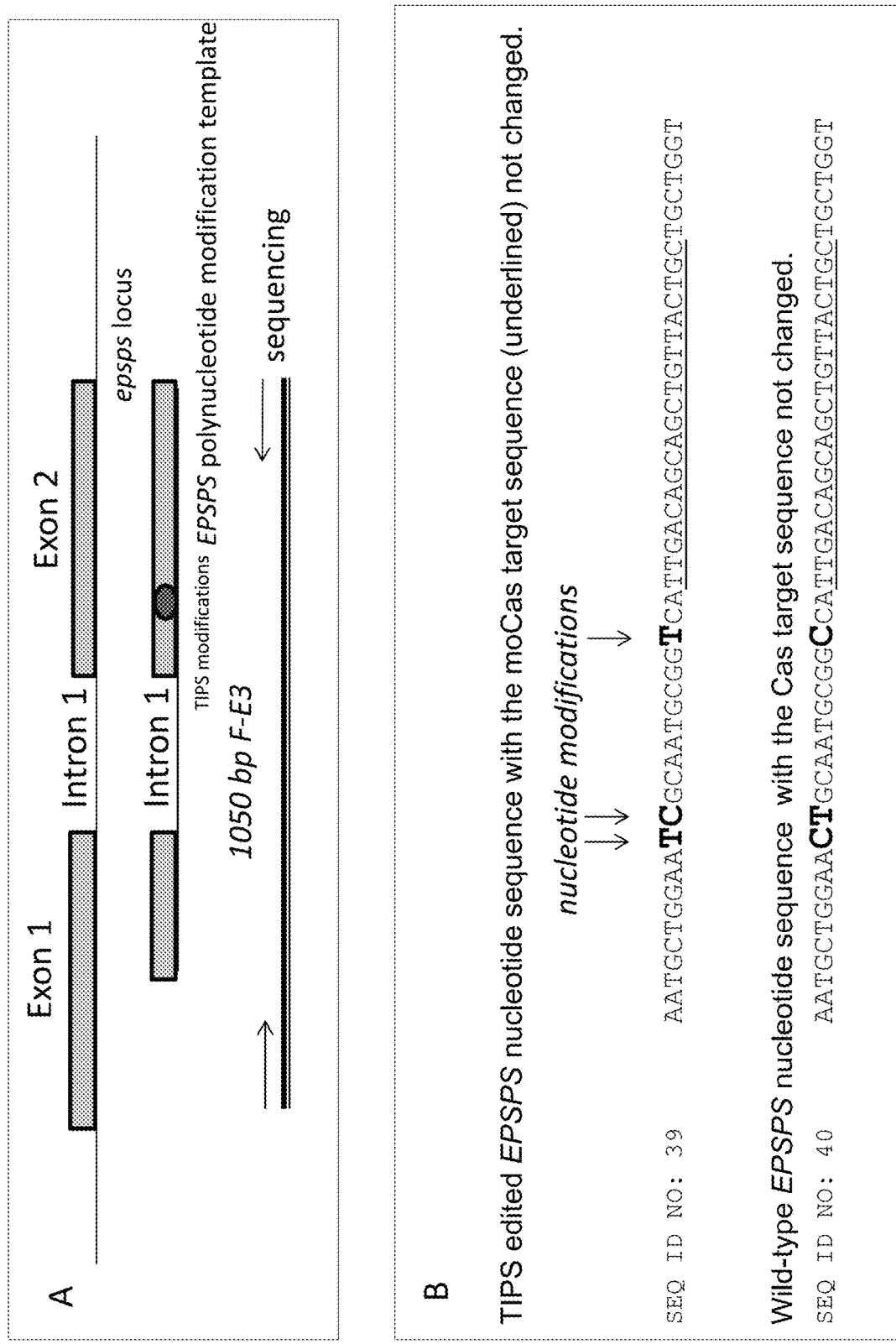

A sample of thirty one callus events selected on media containing bialophos (the moPAT selectable marker gene was part of the guide RNA-moCas9 expression vector) were screened for the presence of the TIPS point mutations. Twenty four events contained the TIPS point mutations integrated into genomic DNA (FIG. 8, the F-E2 treatment). Among them, six events showed the PCR amplification product of the chromosomal EPSPS gene with TIPS mutations (FIG. 8, the H-T treatment). The pair of PCR primers (one that can hybridize to the genomic epsps sequence not present in the EPSPS polynucleotide modification template and the other one binding to the edited EPSPS sequence present in the EPSPS polynucleotide modification template) distinguished the epsps-TIPS editing products from the wild-type EPSPS alleles or random insertions of the TIPS mutations. If one EPSPS allele was edited to contain the TIPS substitutions, it should be detected as a DNA fragment originating from the genomic epsps locus, regardless whether the TIPS substitutions were selected for during the PCR amplification process. The TIPS primer was replaced with the wild-type EPSPS primer (Table 6, the F-E3 pair of primers) and the PCR amplification products were cloned into the TOPO cloning vectors and sequenced. The sequencing data represented a random sample of the genomic epsps locus sequences in one of the selected events (FIG. 9, callus A12 3360.92). FIG. 9 shows that the method disclosed herein resulted in the successful nucleotide editing of three nucleotides (FIG. 9 bold) responsible for the TIPS mutations without altering any of the other epsps nucleotides, while the moCas9 target sequence (the site of guide RNA binding underlined in FIG. 9) was not mutagenized.

Also, the other EPSPS allele was not edited indicating that only one EPSPS allele was edited in this particular event (FIG. 9B).

Example 4

The Guide RNA/Cas Endonuclease System Delivers Double-Strand Breaks to the Maize Epsps Locus Resulting in Maize Plants Containing an Epsps-TIPS Edited Gene The EPSPS gene edited events were produced and selected as described in Example 3. In summary, the EPSPS polynucleotide modification template was co-delivered using particle gun bombardment as a plasmid (see template vector 1, FIG. 7) together with the guide RNA expression cassette and a maize optimized Cas9 endonuclease expression vector which contained the maize optimized Cas9 endonuclease expression cassette described in Example 1 (SEQ ID NO:5) and also contained a moPAT selectable marker gene.

After six weeks of selection at 28° C., a small amount of selected tissue was transferred onto the MS regeneration medium and incubated for three weeks in the dark at 28° C. After the three week incubation visible shoots were transferred to plates containing the MS-1 medium and incubated at 26° C. in the light for 1-2 weeks until they were ready to be sent to a greenhouse and transferred into soil flats. The Ms-1 medium contained: 4.3 g/L MS salts (Gibco 11117), 5.0 ml/L MS Vitamins Stock Solution (Sigma M3900), 100 mg/L myo-inositol, 40.0 g/L sucrose, and 6.0 g/L Bacto-Agar at pH 5.6.

Using the procedures described above, 390 T0 maize plants were produced originating from 3282 embryos, resulting in an overall transformation efficiency of 12%, further indicating that the guideRNA/Cas system used herein results in low or no toxicity (Table 7).

TABLE 7

Transformation efficiency of the EPSPS editing.

| Treatment | # Embryos | # Calli selected | Selection efficiency | T0 plants to GH | Overall Efficiency |
|---|---|---|---|---|---|
| Particle bombardment | 3282 | 489 | 15% | 390 | 12% |

DNA was extracted from each T0 plantlet 7-10 days after transfer to the greenhouse and PCR procedures were conducted as described in the Example 3 to screen the T0 plants for mutations at the epsps locus.

Seventy two percent of analyzed T0 plants (270/375, Table 8) contained mutagenized EPSPS alleles as determined by the end-point PCR procedure described in the Example 3. Most of the mutations (230/375 or 89%) were produced as a result of error-prone non-homologous end joining (NHEJ), while fourty T0 plants (40/375 or 11%) contained the TIPS edited epsps alleles indicating the involvement of a templated double-strand break repair mechanism (Table 8).

TABLE 8

Mutations at the epsps locus.

| Transformation | T0 Plants Analyzed | Mutations at the epsps locus | Mutation rate | TIPS editing | Gene Editing Rate (TIPS) |
|---|---|---|---|---|---|
| Particle bombardment | 375 | 270 | 72% | 40 | 11% |

A pair of primers (Table 6, the F-E3 pair of primers) was used to amplify a native, endogenous fragment of the epsps locus containing the moCas6 target sequence and the EPSPS editing site from the genomic DNA of selected T0 plants. The PCR amplification products were cloned into the TOPO cloning vectors and sequenced as described in Example 3. The sequencing data represent a random sample of the genomic epsps locus sequences from a particular T0 plant (Table 9) and indicate the genotype of the selected T0 plants. The list of the epsps-TIPS allele-containing T0 plants transferred to the pots is presented in Table 9 (a selected set of T0 plants from the original 40 TIPS-containing events).

TABLE 9

The epsps locus genotypes observed in T0 plants. TIPS refers to a clone comprising the TIPS edited epsps sequence. NHEJ refers to the presence of a NHEJ mutation and WT refers to the presence of a wild-type EPSPS sequence amplified from the native epsps locus.

| Event (T0 plant) | Observed Sequences found at the epsps locus |
|---|---|
| E1 | 16 TIPS, 13 NHEJ |
| E2 | 28 TIPS, 0 NHEJ |
| E3 | 2 TIPS, 20 WT |
| E4 | 1 TIPS, 28 NHEJ |
| E5 | 2 TIPS, 2 NHEJ, 9 WT |
| E6 | 10 TIPS, 17 NHEJ |
| E7 | 12 TIPS, 17 NHEJ |
| E8 | 11 TIPS, 15 NHEJ |
| E9 | 17 TIPS, 10 NHEJ |

As presented in Table 9, the selected plants of E1 and E3 to E9 contained the epsps-TIPS edited version of the EPSPS gene either accompanied by a wild-type EPSPS allele (WT) or a NHEJ mutagenized epsps allele (NHEJ). The numbers before TIPS, WT, NHEJ in Table 9 indicate the frequency at which a particular version of the EPSPS allele was identified. If all clones contained the TIPS-edited EPSPS sequence, the analyzed plant was likely to be homozygous for the epsps-TIPS allele (see for example E2). If only about 50% of clones contained a TIPS-edited epsps sequence, the analyzed plant was likely to be hemizygous for the epsps-TIPS allele (see for example E1). Other plants, such as E3 or E4, were likely to be chimeric for TIPS. In one event, E2, the T0 plant contained only TIPS-edited sequence at the epsps locus indicating that the guide RNA/Cas endonuclease system disclosed herein resulted in the successful nucleotide editing of three nucleotides (FIG. 9B bold) responsible for the two epsps-TIPS alleles at the epsps locus in maize plants.

A qPCR analysis was performed on the selected T0 plants to estimate the copy number of the wild-type EPSPS genes and the moCas9 endonuclease sequences. Multiplex qPCR amplifications of the maize EPSPS gene and the ADH housekeeping gene were carried out on the DNA samples from T0 plants. The primers and probes used in the PCR reaction are shown in Table 10.

TABLE 10

Primers used in qPCR analysis of T0 plants.

| Primer/probe | Primary PCR Primer Sequence | SEQ ID NO: |
|---|---|---|
| primer qADH F | 5'-CAAGTCGCGGTTTTCAATCA-3 | SEQ ID NO: 41 |
| Primer qADH R | 5'-TGAAGGTGGAAGTCCCAACAA-3' | SEQ ID NO: 42 |
| probe ADH-VIC | VIC-TGGGAAGCCTATCTACCAC | SEQ ID NO: 43 |
| Probe wtEPSPS | 6FAM-CGGCCATTGACAGCA-MGB-NFQ | SEQ ID NO: 44 |
| Forward primer qEPSPS F | 5'-TCTTGGGGAATGCTGGAACT-3' | ,SEQ ID NO: 45 |
| reverse primer qEPSPSR | 5'-CACCAGCAGCAGTAACAGCTG-3' | SEQ ID NO: 46 |
| FAM-wtEPSPS R probe | 6FAM-TGCTGTCAATGGCCGCA | SEQ ID NO: 47 |

TABLE 10-continued

Primers used in qPCR analysis of T0 plants.

| Primer/probe | Primary PCR Primer Sequence | SEQ ID NO: |
|---|---|---|
| forward primer qEPSPS F | 5'-TCTTGGGGAATGCTGGAACT-3' | SEQ ID NO: 48 |
| reverse primer q wtEPSPS RA | 5'-CCACCAGCAGCAGTAACAGC-3 | SEQ ID NO: 49 |

All analyses were conducted using the LightCycler 480 Real-Time PCR System (Roche Diagnostics). A threshold value for the wtEPSPS genotype was set at 1.76. Every sample showing less than 1.76 copies of EPSPS, with the end-point florescence measurements up to two times lower than the wild-type control, was categorized as the One Allele EPSPS genotype (hemizygous for the wild-type EPSPS allele).

A qPCR method was used to estimate the TIPS sequence copy number. The primers and probes used in the qPCR reaction are shown in Table 11.

TABLE 11

Primers used in qPCR analysis to estimate the TIPS sequence copy number.

| Primer/probe | Primary PCR Primer Sequence | SEQ ID NO: |
|---|---|---|
| forward primer q epTIPS F | 5'-GGAAGTGCAGCTCTTCTTGGG-3' | SEQ ID NO: 50 |
| reverse primer q epTIPS R | 5'-AGCTGCTGTCAATGACCGC-3' | SEQ ID NO: 51 |
| TIPS probe | 6FAM-AATGCTGGAATCGCA | SEQ ID NO: 52 |

A comparative Ct method with Delta Ct values normalized to the average Delta Ct from the bi-allelic TIPS genotypes provided a copy number estimation for the TIPS sequence detected in the analyzed plant samples.

TABLE 12 qPCR genotyping and copy number of selected T0 plants.

| Event name | TIPS EPSPS allele | Wild-type EPSPS allele # | TIPS copy # | moCas9 coding sequence |
|---|---|---|---|---|
| E1 | positive | Null | 5 | positive |
| E2 | positive | Null | 2 | positive |
| E7 | positive | Null | 6 | positive |
| E8 | positive | Null | 1 | positive |
| E9 | positive | Null | 3 | positive |

The qPCR genotyping indicated that no wild-type EPSPS alleles were detected in the selected T0 plants of Events E1, E2, E7, E8 and E9 (Wild-type EPSPS allele #, Table 12). Both, the TIPS template sequences and the moCas9 coding sequence were found in the selected T0 plants, presumably, as a result of random insertions associated with the transformation process (Table 12: for the TIPS template sequences E1, E7, and E9 T0 plants). Both genetic elements (the randomly inserted TIPS templates and the moCas9 expression cassette) can be segregated out by standard breeding procedures in the T1 progeny generation, if not linked to the edited epsps-TIPS gene.

T0 plants grew well in the greenhouse and were fertile. A sample of T0 plants was sprayed with a 1× dose of glyphosate at V3 growth stage using the spray booth setting of 20 gallons per acre. The 1× dose of glyphosate was prepared as follow: 2.55 ml Powermax in 300 ml water (active ingredient: glyphosate, N-(phosphonomethyl) glycine, in the form of its potassium salt at 48.7%). Seven days after glyphosate application, no leaf tissue damage was observed in some of the T0 plants. These plantlets were hemizygous for the epsps-TIPS alleles, while other plantlets were severely damaged. One plant showing no damage to the leaf tissue 14 days after herbicide application contained 21 epsps-TIPS alleles among 44 genomic clones of the epsps locus (cloned and sequenced as described in the Example 3). This T0 plant was designated as hemizygous at the epsps locus.

These data indicate that a guide RNA/Cas system was used to create a TIPS-edited EPSPS allele in maize. Maize plants homozygous at the epsps locus (two epsps-TIPS alleles) with no additional insertion of the TIPS template (plant E2) were also obtained. Furthermore, some epsps-TIPS edited maize T0 plants did show some level of tolerance against a 1× dose of glyphosate.

Example 5

Characterization of F1 Progeny of Maize Plants Containing an Epsps-TIPS Edited Gene Two T0 plants (E1 and E2) produced and characterized as described in the Example 3 and 4 containing one or two epsps-TIPS alleles were cross pollinated to wild-type maize parental plants. The seeds were collected, dried and planted. The emerging seedlings were genotyped for the presence of wt-EPSPS, modified EPSPS, Cas9, and moPAT sequences (Table 13). "Genomic-TIPS" represents the TIPS edited allele of the EPSPS gene (neg=is the TIPS modification not present, positive=theTIPS modification present at the epsps locus), "Cas9 CDS" represent a diagnostic fragment of the Cas9 coding sequence, "moPAT CDS—a diagnostic DNA fragment of the selectable marker gene, "TIPS sequence"—a total number of DNA fragments containing the TIPS edited sequence, "Wt EPSPS Allele"—a number of the wild-type EPSPS alleles that were not edited or modified. "Neg" means that no foreign DNA fragment was amplified by PCR.

TABLE 13

A list of the F1 progeny maize plants segregating out genetic elements of the vector DNA used for transformation

| Plant | Genomic-TIPS | Cas9 CDS | moPAT CDS | TIPS Sequence Copy # estimation | Wt EPSPS Allele Copy # estimation |
|---|---|---|---|---|---|
| 1 | neg | neg | neg | NULL | One Allele |
| 2 | neg | POSITIVE | POSITIVE | 4.5 | NULL |
| 3 | POSITIVE | neg | neg | 0.8 | One Allele |
| 4 | neg | neg | neg | NULL | One Allele |
| 5 | neg | neg | neg | NULL | One Allele |
| 6 | POSITIVE | POSITIVE | POSITIVE | 4.5 | NULL |

The F1 progeny plants such as the plant #3 in Table 13 containing one wild-type EPSPS allele and one epsps-TIPS allele (hemizygous at the espsp locus) were selected, grown and self pollinated. The F2 seeds were collected. The F2 population contained segregating EPSPS alleles that produced wild-type, hemizygous, and homozygous F2 plants at the epsps locus.

Example 6

Embryo Rescue of F2 Progeny from Selected F1 Plants

A random sample of the F1 plants progeny of the E1 and E2 parental plants) was sprayed with 2.55 ml Powermax (glyphosate solution) in 300 ml water at the setting of 20 gallons per acre at the V3 stage of growth. The F1 plants containing the epsps-TIPS edited allele survived the glyphosate application, while other F1 plants that did not contain the epsps-TIPS allele showed severe leaf tissue damage (dry, brown leaves). The growth of the epsps-TIPS-containing plants was slowed down and the plants developed bleached sectors of the leaf tissue on newly emerging leaves over time.

For embryo rescue of the F2 progeny seedlings from selfed F1 plants, ears were harvested 18 days after pollination and sterilized in 20:80 bleach/water mix. Embryos were excised and placed on rooting media (272V—4.3 g/L Murashige and Skoog basal salt mixture, 5.0 ml/L MS vitamins stock solution, 100 mg/L mio-inositol, 40 g/L sucrose, 6 g/L Bacto Agar) with or without glyphosate at 0.1 mM, 0.5 mM, 1 mM, 3 mM concentration. They were transferred to a light room at 26° C. and allowed to germinate for 7 days. Embryos containing the wild-type EPSPS alleles, hemizygous and homozygous for the epsps-TIPS allele germinated on media without glyphosate. At the 0.1 mM concentration of glyphosate in the media, only embryos containing the epsps-TIPS alleles produced green seedlings. The presence of the epsps-TIPS allele in the analyzed seedlings is indicated as "positive" or "negative", while the wild-type EPSPS allele copy number is indicated in the columns to the right (Table 14)

TABLE 14

Genotype of the F2 seedlings germinating on media containing 0.1, 0.3, 0.5, 1.0, and 3.0 mM glyphosate.

| Position | Sample Name | Glyphosate | Genomic TIPS PCR | wtEPSPS Allele Genotype | wtEPSPS copy # by DDCt method |
|---|---|---|---|---|---|
| A1 | 0-01 | 272 V | Positive | One Allele | 1.0 |
| A2 | 0-02 | 272 V | Positive | One Allele | 1.1 |
| A3 | 0-03 | 272 V | negative | WT | 2.0 |
| A4 | 0-04 | 272 V | negative | WT | 1.9 |
| A5 | 0-05 | 272 V | negative | WT | 2.3 |
| A6 | 0-06 | 272 V | Positive | One Allele | 1.0 |
| A7 | 0-07 | 272 V | Positive | One Allele | 1.1 |
| A8 | 0-08 | 272 V | negative | WT | 1.9 |
| A9 | 0-09 | 272 V | Positive | NULL | NULL |
| A10 | 0-10 | 272 V | Positive | One Allele | 1.1 |
| A11 | 0-11 | 272 V | negative | WT | 2.2 |
| A12 | 0-12 | 272 V | negative | WT | 2.2 |
| B1 | 0.1-13 | 0.1 mM | Positive | One Allele | 1.5 |
| B2 | 0.1-14 | 0.1 mM | Positive | NULL | NULL |
| B3 | 0.1-15 | 0.1 mM | Positive | One Allele | 1.1 |
| B4 | 0.1-16 | 0.1 mM | Positive | One Allele | 1.0 |
| B5 | 0.1-17 | 0.1 mM | Positive | NULL | NULL |
| B6 | 0.3-18 | 0.3 mM | Positive | One Allele | 0.7 |
| B7 | 0.3-19 | 0.3 mM | Positive | NULL | NULL |
| B8 | 0.3-20 | 0.3 mM | Positive | NULL | NULL |
| B9 | 0.3-21 | 0.3 mM | Positive | One Allele | 1.1 |
| B10 | 0.3-22 | 0.3 mM | Positive | One Allele | 1.1 |
| B11 | 0.3-23 | 0.3 mM | Positive | NULL | NULL |
| B12 | 0.5-24 | 0.5 mM | Positive | One Allele | 1.0 |
| C1 | 0.5-25 | 0.5 mM | Positive | One Allele | 1.3 |
| C2 | 0.5-26 | 0.5 mM | Positive | One Allele | 1.1 |
| C3 | 0.5-27 | 0.5 mM | Positive | One Allele | 1.0 |
| C4 | 0.5-28 | 0.5 mM | Positive | One Allele | 1.2 |
| C5 | 0.5-29 | 0.5 mM | Positive | One Allele | 1.2 |
| C6 | 1-30 | 1 mM | Positive | One Allele | 1.2 |
| C7 | 1-31 | 1 mM | Positive | NULL | NULL |
| C8 | 1-32 | 1 mM | Positive | One Allele | 1.1 |
| C9 | 1-33 | 1 mM | Positive | NULL | NULL |
| C10 | 1-34 | 1 mM | Positive | One Allele | 1.3 |
| C11 | 1-35 | 1 mM | Positive | NULL | NULL |
| C12 | 3-35 | 3 mM | Positive | NULL | NULL |

No wild-type seedlings were detected among germinating embryos on media containing 0.1 mM glyphosate or any other concentration of glyphosate up to 3 mM (Table 14). In addition, embryos homozygous for the epsps-TIPS allele at the epsps locus produced green seedlings at the 1.0 mM concentration of glyphosate, while the hemizygous embryos did not. The level of glyphosate tolerance among germinating embryos was correlated to the presence of the edited epsps-TIPS alleles and their dose (one or two alleles).

Example 7

Editing of the Maize EPSPS Gene Using the Guide RNA/Cas9 System

An EPSPS polynucleotide modification template can be used to introduce amino acid substitutions in the maize epsps locus. The EPSPS-polynucleotide modification template can be synthesized and inserted into the template vector described in FIG. 7 using the corresponding SphI and SpeI restriction sites. The EPSPS polynucleotide modification template can be co-delivered as plasmid DNA together with a guide RNA expression cassette and a maize optimizedCas9 endonuclease expression vector using particle gun bombardment.

Plants can be developed and analyzed for the presence of the amino acid mutations as described in Examples 3, 4, and 5.

Example 8

Variants of Maize EPSPS

EPSPS mutations, other than the TIPS mutation described in Example 3, that reduce sensitivity to glyphosate are known in the art (U.S. Pat. No. 8,436,159) and can also be introduced, (in combination with TIPS or not), into the maize EPSPS gene as described in Example 3. Also, novel EPSPS mutations can be identified by methods known to those skilled in the art. The guide polynucleotide/Cas endonuclease system described herein can be used to introduce any one of these mutations, or any combination of these mutations, in the EPSPS gene and the activity of the resulting maize EPSPS variants can be evaluated for herbicide resistance.

Example 9

Duplication of the Native EPSPS Gene Using the Guide RNA/Cas9 Endonuclease System There is one native EPSPS gene in maize. The F1 progeny plants described in the Example 5 were hemizygous at the epsps-TIPS locus. Maize plants with two functional copies of the EPSPS gene accumulated twice as much EPSPS protein as compared to plants with one functional EPSPS gene copy (Table 15). The amount of the EPSPS peptide in the leaf samples of the wild-type ETX plants was doubled as compared to the hemizygous (one EPSPS allele knocked out) at the epsps locus maize plants.

TABLE 15

Peak areas of the signature EPSPS peptides identified in the leaf samples of the wild-type and mutant EPSPS maize plants.

| Signature peptide | Wild-type ETX | Mutant plants |
|---|---|---|
| ERPIGDLVVGLK | 11.36 ± 2.02 | 6.97 ± 1.25 |
| TLGLSVEADK | 10.45 ± 2.55 | 4.64 ± 1.85 |

Figure 11:
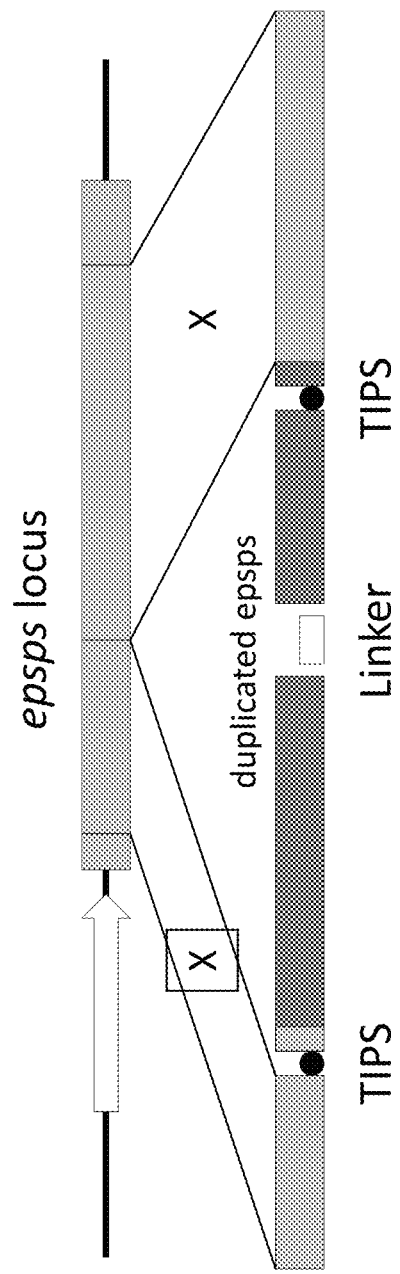

The native EPSPS gene can be duplicated using the guide RNA/Cas9 endonuclease gene editing procedure described herein, for example by using the EPSPS polynucleotide duplication template listed as SEQ ID NO: 54. The genetic elements of this polynucleotide modification template are shown in FIG. 11. The procedure as described in the Examples 3 and 4 introduces the TIPS substitutions into two copies of the EPSPS genes and the duplicated fragments of the native EPSPS gene are copied from the editing DNA template (FIG. 11). The EPSPS-duplication polynucleotide modification template is co-delivered using particle gun bombardment as plasmid DNA together with the guideRNA expression cassette and a maize optimizedCas9 endonuclease expression vector which contains the maize optimized Cas9 endonuclease expression cassette described herein, and also contains a moPAT selectable marker gene. The resulting F2 maize plants homozygous at the edited epsps locus contain four epsps-TIPS coding sequences and these plants can be evaluated for the elevated EPSPS-TIPS protein level in their plant tissues.

Example 10

Promoter Modification of Maize EPSPS Native Gene

Figure 12:
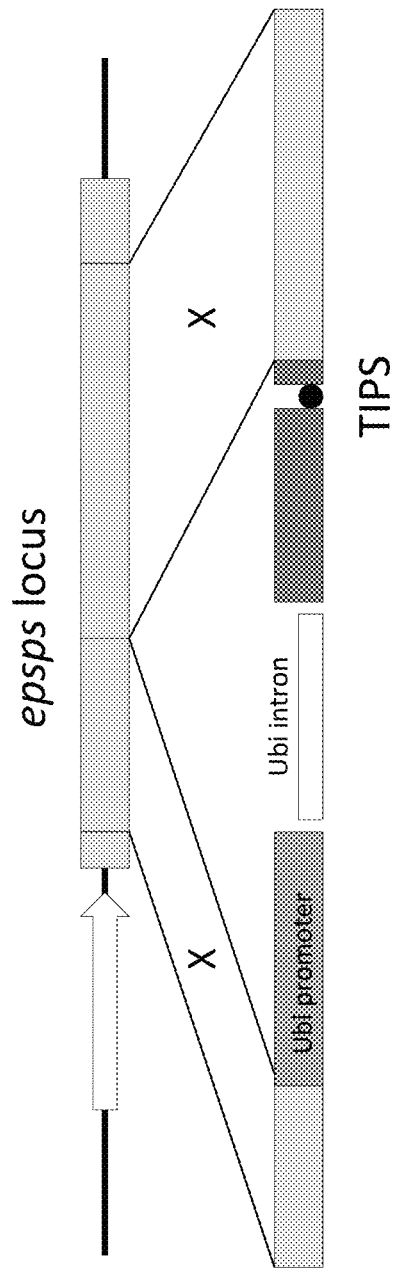

Protein accumulation in maize cells is a function of transcriptional activity of protein-encoding genes. The EPSPS promoter is a weak transcription-controlling genetic element, while the ubiquitin promoters originating from a diverse set of plants are known to be highly active and strong. An EPSPS polynucleotide maize ubiquitin promoter template such as SEQ ID NO: 55 can be designed that allows for editing of the epsps locus to contain the maize ubiquitin promoter placed in the front of the epsps-TIPS coding sequence (epsps-ubiTIPS) (FIG. 12). The EPSPS-polynucleotide maize ubiquitin promoter template is co-delivered using particle gun bombardment as a plasmid together with the guide sgRNA expression cassette and a maize optimized-Cas9 endonuclease expression vector which contain the maize optimized Cas9 endonuclease expression cassette and also contained a moPAT selectable marker gene. Maize plants are edited using the procedures described in Examples 3 and 4. The expression level of the epsps-ubiTIPS allele and the EPSPS-TIPS protein accumulation can be evaluated in maize tissues of the T0 plants and their progeny as compared to the epsps-TIPS allele (and protein accumulation) driven by the native EPSPS gene promoter.

Promoter modifications such as the one described for maize, are not limited to maize and can also be provided to any plant by the methods described herein. DNA recognition sites of the EPSPS gene repressors can be identified and introduced in their natural locations in a plant genome using the gene editing techniques described herein. For example, a gene edited plant can be produced by eliminating or changing repressing elements within the promoter of an EPSPS gene (or any EPSPS repressor sequence in the genome of a plant), wherein the plant shows higher EPSPS activity under different environmental conditions, delivers higher yield and provides an enhanced resistance to glyphosate. Increased EPSPS activity can also be achieved by swapping the native EPSPS promoter with another promoter, such as but not limited to, a constitutive promoter, a tissue specific promoter, an artificial promoter, a chimeric promoter, an edited promoter resulting in a plant having higher yield and enhanced resistance to glyphosate. Promoter regulatory elements can also be added or modified to provide positive regulatory elements enhancing the promoter activity and leading to increased EPSPS activity. Any one of the above described alterations can be provided by themselves or in combination with one another, such as for example combining the eliminating or alteration of repressing elements together with the addition or modification of positive regulatory elements to result in an enhanced the promoter activity and leading to increased EPSPS activity and enhanced resistance to glyphosate.

Example 11

Editing of the EPSPS Gene Polyubiquitination Sites Using the Guide RNA/Cas9 Endonuclease System There are defined ubiquitination sites on proteins to be degraded and they were found within the maize EPSPS protein by using dedicated computer programs (for example, the CKSAAP_UbSite (Ziding Zhang's Laboratory of Protein Bioinformatics College of Biological Sciences, China Agricultural University, 100193 Beijing, China). One of the selected polyubiquitination site within the maize EPSPS coding sequence is shown in FIG. 13A and its amino acid signature sequence is compared to the equivalent EPSPS sites from the other plants (FIG. 13A). The lysine amino acid (K) at position 90 (highly conserved in other plant species) was selected as a potential site of the EPSPS protein polyubiquitination. The polynucleotide modification template (referred to as the EPSPS polynucleotide maize K90R template) used to edit the epsps locus is listed as SEQ ID No: 56. This template allowed for editing the epsps locus to contain the lysine (K) to arginine (R) substitution at position 90 (K90R) and two additional TIPS substitutions at positions 102 and 106 (FIGS. 13B and 13C). Maize genomic DNA was edited using the guideRNA/Cas9 endonuclease system described herein and TO plants were produced as described herein. The TO plants that contained the nucleotide modifications, as specified by the information provided on the K90R template (FIG. 13C), were selected by the genotyping methods described herein. The F1 epsps-K90RTIPS plants can be selected for elevated protein content due to a slower rate of the EPSPS protein degradation.

Example 12

Editing Intron Elements to Introduce Intron Mediated Enhancer Elements (IMEs)

Transcriptional activity of the native EPSPS gene can be modulated by transcriptional enhancers positioned in the vicinity of other transcription controlling elements. Introns are known to contain enhancer elements affecting the overall rate of transcription from native promoters including the EPSPS promoter. For example, the first intron of the maize ubiquitin 5'UTR confers a high level of expression in monocot plants as specified in the WO 2011/156535 A1 patent application. An intron enhancing motif CATATCTG (FIG. 14 A), also referred to as a intron-mediated enhancer element, IME) was identified by proprietary analysis (WO2011/156535 A1, published on Dec. 15, 2011) and appropriate nucleotide sites at the 5' end of the EPSPS first intron were selected for editing in order to introduce the intron-mediated enhancer elements (IMEs) (FIG. 14B-14C). The polynucleotide modification template (referred to as EPSPS polynucleotide maize IME template) is listed as SEQ ID No: 57. The polynucleotide modification template allows for editing of the epsps locus to contain three IMEs (two on one strand of the DNA, one on the reverse strand) in the first EPSPS intron and the TIPS substitutions at positions 102 and 106. The genomic DNA of maize plants was edited using the guideRNA/Cas9 endonuclease system described herein. Maize plants containing the IMETIPS edited EPSPS coding sequence can be selected by genotyping the TO plants and can be further evaluated for elevated EPSPS-TIPS protein content due to the enhanced transcription rate of the edited EPSPS gene and for glyphosate resistance.

Example 13

Editing of Splicing Sites and/or Introducing Alternate Splicing Sites Using the Guide RNA/Cas9 Endonuclease System In maize cells, the splicing process is affected by splicing sites at the exon-intron junction sites as illustrated in the EPSPS mRNA production (FIG. 15A-15B). FIG. 15A shows analysis of EPSPS amplified pre-mRNA (cDNA panel on left). Lane 14 in FIG. 15A shows amplification of the EPSPS pre-mRNA containing the 3$^{rd}$ intron unspliced, resulting in a 804 bp diagnostic fragment indicative of an alternate splicing event. Lanes E3 and F8 show the EPSPS PCR amplified fragments resulting from regularly spliced introns. Diagnostic fragments such as the 804 bp fragment of lane 14 are not amplified unless cDNA is synthesized (as is evident by the absence of bands in lanes E3, 14, and F8 comprising total RNA (shown in the total RNA panel on right of FIG. 15A). The canonical splice site in the maize EPSPS gene and genes from other species is AGGT, while other (alterative) variants of the splice sites may lead to the aberrant processing of pre-mRNA molecules. The EPSPS coding sequence contains a number of alternate splicing sites that may affect the overall efficiency of the pre-mRNA maturation process and as such may limit the EPSPS protein accumulation in maize cells.

Figure 16:
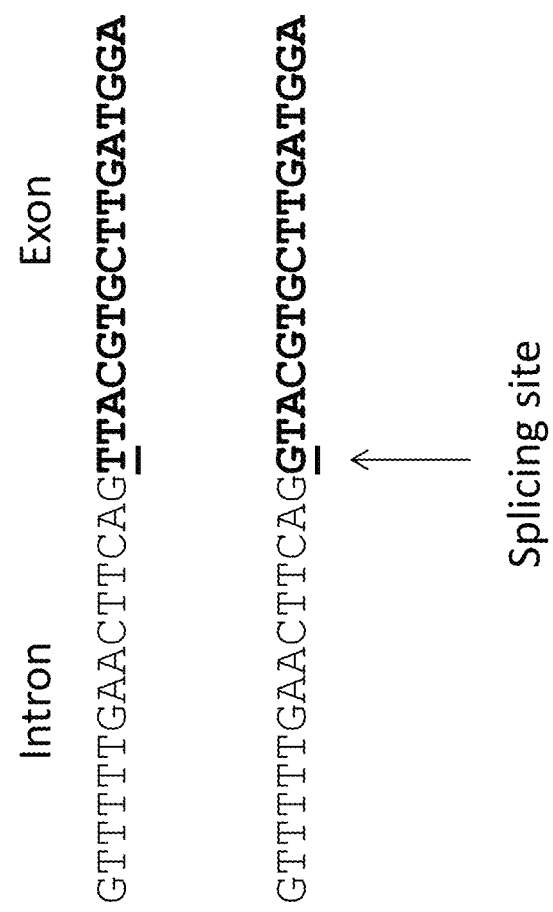

In order to limit the occurrence of alternate splicing events during EPSPS gene expression, a guideRNA/Cas9 endonuclease system as described herein can be used to edit splicing sites. The splicing site at the junction of the second native EPSPS intron and the third exon is AGTT and can be edited in order to introduce the canonical AGGT splice site at this junction (FIG. 16). The T>G substitution does not affect the native EPSPS open reading frame and it does not change the EPSPS amino acid sequence. The polynucleotide modification template (referred to as EPSPS polynucleotide maize Tspliced template) is listed as SEQ ID NO: 58. This polynucleotide modification template allows for editing of the epsps locus to contain the canonical AGGT splice site at the 2$^{nd}$ intron-3$^{rd}$ exon junction site and the TIPS substitutions at positions 102 and 106. Maize plants are edited using the procedures described herein. The F1 epsps-TsplicedTIPS maize plants can be evaluated for glyphosate resistance and increased protein content due to the enhanced production of functional EPSPS mRNA messages.

Example 14

Enhancing the Gene Activity of Native EPSPS Gene by Editing its Coding Sequence

There are several elements in maize genes that are associated with enhanced transcript levels and as such they may lead to the enhanced protein synthesis. They are not restricted to a particular sequence of a coding region but instead they contribute to a global architecture of the coding sequence of a gene of interest. Among them are rare maize codons that may slow down the translation process (examples may include S79-AGT>AGC, V106—GTA>GTT, V155—GTA>GTG, R189—CGT>CGC, L196—CTA>CTT), out-of-frame open reading frames that may result in aberrant termination of protein synthesis, mRNA destabilizing sites that may contribute to the pre-mature degradation of mRNA templates, cryptic introns that may affect the pre-mRNA splicing process, transposon insertion sites and others. A number of such elements were identified in the maize EPSPS coding sequence. These elements can be eliminated or modified using an EPSPS polynucleotide maize template such as SEQ ID NO: 59. Maize plants can be edited using the procedures described in Examples 3 and 4. The EPSPS-TIPS protein content can be increased in the selected F1 EPSPS-synthetic plants due to the enhanced production of functional EPSPS mRNA messages, their stabilization and utilization for protein synthesis. Edited plants can be evaluated for glyphosate resistance.

Example 15

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560L (Initiation medium) and placed in the dark at temperatures ranging from 26° C. to 37° C. for 8 to 24 hours prior to placing on 560Y for 4 hours at 26° C. prior to bombardment as described above.

Plasmids containing the double strand brake inducing agent and donor DNA are constructed using standard molecular biology techniques and co-bombarded with plasmids containing the developmental genes ODP2 (AP2 domain transcription factor ODP2 (Ovule development protein 2); US20090328252 A1) and Wushel (US2011/0167516).

The plasmids and DNA of interest are precipitated onto 0.6 μm (average diameter) gold pellets using a water-soluble cationic lipid Tfx™-50 (Cat # E1811, Promega, Madison, Wis., USA) as follows. DNA solution is prepared on ice using 1 μg of plasmid DNA and optionally other constructs for co-bombardment such as 50 ng (0.5 μl) of each plasmid containing the developmental genes ODP2 (AP2 domain transcription factor ODP2 (Ovule development protein 2); US20090328252 A1) and Wushel. To the pre-mixed DNA, 20 μl of prepared gold particles (15 mg/ml) and 5 μl Tfx-50 is added in water and mixed carefully. Gold particles are pelleted in a microfuge at 10,000 rpm for 1 min and supernatant is removed. The resulting pellet is carefully rinsed with 100 ml of 100% EtOH without resuspending the pellet and the EtOH rinse is carefully removed. 105 μl of 100% EtOH is added and the particles are resuspended by brief sonication. Then, 10 μl is spotted onto the center of each macrocarrier and allowed to dry about 2 minutes before bombardment.

Alternatively, the plasmids and DNA of interest are precipitated onto 1.1 μm (average diameter) tungsten pellets using a calcium chloride ($CaCl_2$) precipitation procedure by mixing 100 μl prepared tungsten particles in water, 10 μl (1 μg) DNA in Tris EDTA buffer (1 μg total DNA), 100 μl 2.5 M CaCl2, and 10 μl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 μl 100% ethanol is added to the final tungsten particle pellet. For particle gun bombardment, the tungsten/DNA particles are briefly sonicated. 10 μl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) Plant Biotech J 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 µM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 16

Gene Editing of the Soybean EPSPS1 Gene Using the Guide RNA/Cas Endonuclease System A. guideRNA/Cas9 Endonuclease Target Site Design on the Soybean EPSPS Genes.

Two guideRNA/Cas9 endonuclease target sites (soy EPSPS-CR1 and soy EPSPS-CR2) were identified in the Exon2 of the soybean EPSPS1 gene Glyma01g33660 (Table 16).

TABLE 16

Guide RNA/Cas9 endonuclease target sites on soybean EPSPS1 gene

| Name of gRNA-Cas9 endonuclease target site | Cas endonuclease target sequence (SEQ ID NO:) | Physical location |
|---|---|---|
| soy EPSPS-CR1 | 60 | Gm01: 45865337 . . . 45865315 |
| soy EPSPS-CR2 | 61 | Gm01: 45865311 . . . 45865333 |

B. Guide-RNA Expression Cassettes, Cas9 Endonuclease Expression Cassettes and Polynucleotide Modification Templates for Introduction of Specific Amino Acid Changes in the Soybean EPSPS1 Gene The soybean U6 small nuclear RNA promoter, GM-U6-13.1 (SEQ ID. NO: 62), was used to express guide RNAs to direct Cas9 nuclease to designated genomic target sites (Table 17). A soybean codon optimized Cas9 endonuclease (SEQ ID NO:82) expression cassette and a guide RNA expression cassette were linked in a first plasmid that was co-delivered with a polynucleotide modification template. The polynucleotide modification template contained specific nucleotide changes that encoded for amino acid changes in the EPSPS1 polypeptide (Glyma01g33660), such as the T183I and P187S (TIPS) in the Exon2. Other amino acid changes in the EPSPS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 17

Guide RNA/Cas9 expression cassettes and polynucleotide modification templates used in soybean stable transformation for the specific amino acid modifications of the EPSPS1 gene.

| Experiment | Guide RNA/Cas9 (plasmid name) | SEQ ID NO: | polynucleotide modification template | SEQ ID NO: |
|---|---|---|---|---|
| soy EPSPS-CR1 | U6-13.1: EPSPS CR1 + EF1A2: CAS9 (QC878) | 63 | RTW1013A | 65 |
| soy EPSPS-CR2 | U6-13.1: EPSPS CR2 + EF1A2: CAS9 (QC879) | 64 | RTW1012A | 66 |

C. Detection of Site-Specific Non-Homologous-End-Joining (NHEJ) Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, Calif.) with target site-specific primers and FAM-labeled fluorescence probe to check copy number changes of the double strand break target sites. The qPCR analysis was done in duplex reactions with a syringolide induced protein (SIP) as the endogenous controls and a wild type 93686 genomic DNA sample that contains one copy of the target site with 2 alleles, as the single copy calibrator. The presence or absence of the guide RNA-Cas9 expression cassette in the transgenic events was also analyzed with the qPCR primer/probes for guideRNA/Cas9 (SEQ IDs: 70-72) and for PinII (SEQ ID: 73-75). The qPCR primers/probes are listed in Table 18.

TABLE 18

Primers/Probes used in qPCR analyses of transgenic soybean events

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGAAATCA | 67 |
| | Soy1-R2 | CCTGCAGCAACCACAGCTGCTGTC | 68 |
| | Soy1-T1 (FAM-MGB) | CTGCAATGCGTCCTT | 69 |
| gRNA/CAS9 | Cas9-F | CCTTCTTCCACCGCCTTGA | 70 |
| | Cas9-R | TGGGTGTCTCTCGTGCTTTTT | 71 |
| | Cas9-T (FAM-MGB) | AATCATTCCTGGTGGAGGA | 72 |
| pINII | pINII-99F | TGATGCCCACATTATAGTGATTAGC | 73 |
| | pINII-13R | CATCTTCTGGATTGGCCAACTT | 74 |
| | pINII-69T (FAM-MGB) | ACTATGTGTGCATCCTT | 75 |
| SIP | SIP-130F | TTCAAGTTGGGCTTTTTCAGAAG | 76 |
| | SIP-198R | TCTCCTTGGTGCTCTCATCACA | 77 |
| | SIP-170T (VIC-MGB) | CTGCAGCAGAACCAA | 78 |

The endogenous control probe SIP-T was labeled with VIC and the gene-specific probes for all the target sites were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93686 genomic DNA with two alleles of the double strand break target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). As shown in Table 19, both guideRNA/Cas endonuclease systems targeting the soy EPSPS-CR1 and EPSPS-CR2 sites can introduce efficient Double Strand Break (DSB) efficiency at their designed target sites. Both NHEJ-Hemi and NHEJ-Null were detected in the 93686 genotype. NHEJ (Non-Homologous-End-Joining) mutations mediated by the guide RNA/Cas9 system at the specific Cas9 target sites were confirmed by PCR/topo cloning/sequencing.

TABLE 19

Target Site Double Strand Break Rate Mutations Induced by the Guide RNA/Cas9 system on soybean EPSPS1 gene. Numbers indicate no. of events (numbers in parentheses are %).

| Project | Total event | Wt-Homo (%) | NHEJ-Hemi (%) | NHEJ-Null (%) |
|---|---|---|---|---|
| U6-13.1 EPSPS-CR1 | 168 | 63 (38%) | 66 (39%) | 39 (23%) |
| U6-13.1 EPSPS-CR2 | 111 | 50 (45%) | 21 (19%) | 40 (36%) |

D. Detection of the TIPS Mutation in the Soybean EPSPS Gene

In order to edit specific amino acids at the native EPSPS gene (such as those resulting in a TIPS modification), a polynucleotide modification template, such as RTW1013A or RTW1012A (Table 17), was co-delivered with the guideRNA/Cas9 expression cassettes into soybean cells.

Figure 17:
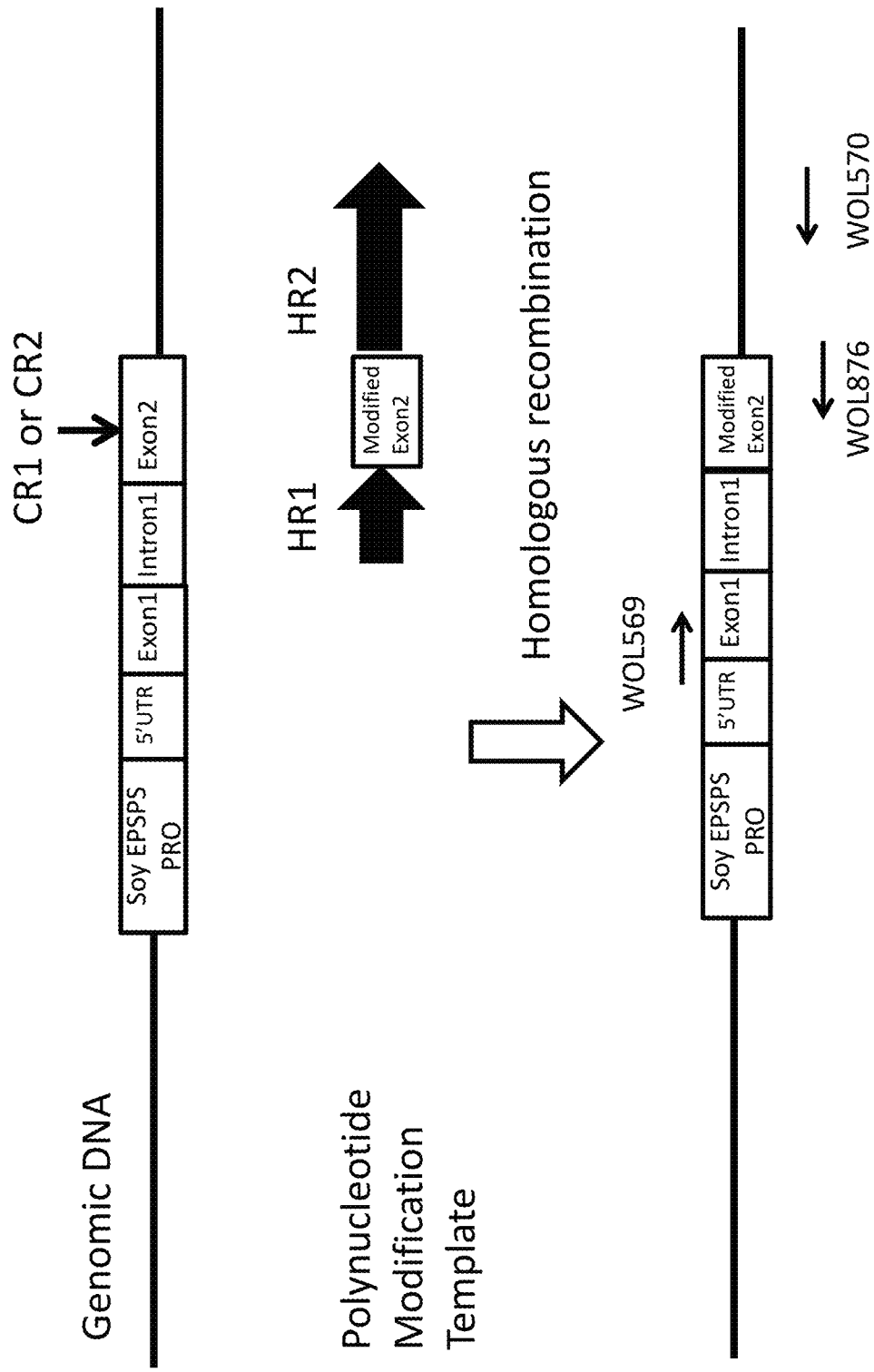
FIG. 17 illustrates an experimental design to edit the amino acid sequences in the native soybean EPSPS1 gene.

The modification of the native EPSPS1 gene via guide RNA/Cas9 system mediated DNA homologous recombination was determined by specific PCR analysis as shown in FIG. 17. A specific PCR assay with primer pair WOL569 (SEQ ID NO: 79) and WOL876 (SEQ ID NO: 80) was used to detect perfect TIPS modification at the native EPSPS1 gene. A second primer pair WOL569 (SEQ ID NO: 79) and WOL570 (SEQ ID NO: 81) was used to amplify both TIPS modified EPSPS1 allele and WT (wild type)/NHEJ mutated allele. Topo cloning/sequencing was used to verify the sequences. With the EPSPS-CR2, seven TO plants were generated with the TIPS editing in the EPSP1 gene. For the EPSPS1 gene in this event, one allele was edited as TIPS and the $2^{nd}$ allele was repaired with non-homologous end-joining (NHEJ) as a 2 bp deletion.

Example 17

Intron Replacement of Soybean Genes Using the GuideRNA/Cas Endonuclease System

A. guideRNA/Cas9 Endonuclease Target Site Design.

Four guideRNA/Cas9 endonuclease target sites were identified in the soybean EPSPS1 gene Glyma01g33660 (Table 20). Two of the target sites (soy EPSPS-CR1 and soy EPSPS-CR2) were identified to target the Exon2 of the soybean EPSPS gene as described in Example 16. Another two target sites (soy EPSPS-CR4 and soy EPSPS-CR5) were designed near the 5' end of the intron1 of the soybean EPSPS gene.

TABLE 20

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 60 | Gm01: 45865337 . . . 45865315 |
| soy EPSPS-CR2 | 61 | Gm01: 45865311 . . . 45865333 |

TABLE 20-continued

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR4 | 83 | Gm01: 45866302 ... 45866280 |
| soy EPSPS-CR5 | 84 | Gm01: 45866295 ... 45866274 |

B. Guide RNA/Cas9 Endonuclease Expression Cassettes and Polynucleotide Modification Templates Used in Soybean Stable Transformation for the Replacement of the Intron1 of the Soybean EPSPS1 Gene with the Soybean Ubiquitin (UBQ) Intron1

The soybean U6 small nuclear RNA promoter GM-U6-13.1 (SEQ ID. NO: 62) was used to express two guide RNAs (soy-EPSPS-CR1 and soy-EPSPS-CR4, or soy-EPSPS-CR1 and soy-EPSPS-CR5) to direct Cas9 endonuclease to designated genomic target sites (Table 21). One of the target sites (soy-EPSPS-CR1) was located in the exon2, as described in Example 16, and a second target site (soy-EPSPS-CR4 or soy-EPSPS-CR5) was located near the 5' end of intron1 of the native EPSPS1 gene. A soybean codon optimized Cas9 endonuclease expression cassette and a guide RNA expression cassette were linked in the expression plasmids QC878/RTW1199 (SEQ ID NO:63/85) or QC878/RTW1200 (SEQ ID NO:63/86) that was co-delivered with a polynucleotide modification template. The polynucleotide modification template, RTW1190A (SEQ ID NO:87), contained 532 bp intron1 of the soybean UBQ gene and the TIPS modified Exon2. Soybean EPSPS1 intron 1 replacement with the soybean UBQ intron1 can be achieved with the guide RNA/Cas system by homologous recombination between the genomic DNA and the polynucleotide modification template, resulting in enhancement of the native or modified soy EPSPS1 gene expression.

TABLE 21

Guide RNA/Cas9 endonuclease expression cassettes and polynucleotide modification templates used in soybean stable transformation for the replacement of the Intron1 of the soybean EPSPS1 gene with the soybean ubiquitin (UBQ) intron1

| Experiment | Guide RNA/Cas9 | SEQ ID NO: | polynucleotide modification template | SEQ ID NO: |
|---|---|---|---|---|
| soy EPSPS-CR1 and soy EPSPS-CR4 | U6-13.1: EPSPS CR1 + CR4+ EF1A2: CAS9 (QC878/RTW1199) | 63/85 | RTW1190A | 87 |
| soy EPSPS-CR1 and soy EPSPS-CR5 | U6-13.1: EPSPS CR1 + CR5+ EF1A2: CAS9 (QC878/RTW1200) | 63/86 | RTW1190A | 87 |

C. Detection of Site-Specific NHEJ Mediated by the Guide RNA/Cas9 System in Stably Transformed Soybean Site-specific NHEJ was detected as described in Example 16C, using the qPCR primers/probes listed in Table 22.

TABLE 22

Primers/Probes used in qPCR analyses of transgenic soybean events

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGAAATCA | 67 |
| | Soy1-R2 | CCTGCAGCAACCACAGCTGCTGTC | 68 |
| | Soy1-T1 (FAM-MGB) | CTGCAATGCGTCCTT | 69 |
| EPSPS-CR4 | Soy1-F3 | GTTTGTTTGTTGTTGGGTGTGGG | 88 |
| | Soy1-R3 | GACATGATGCTTCATTTTCACAGAA | 89 |
| | Soy-T2 (FAM-MGB) | TGTGTAGAGTGGATTTTG | 90 |
| EPSPS-CR5 | Soy1-F2 | TGTTGTTGGGTGTGGGAATAGG | 91 |
| | Soy1-R3 | GACATGATGCTTCATTTTCACAGAA | 89 |
| | Soy1-T2 (FAM-MGB) | TGTGTAGAGTGGATTTTG | 90 |
| gRNA/CAS9 | Cas9-F | CCTTCTTCCACCGCCTTGA | 70 |
| | Cas9-R | TGGGTGTCTCTCGTGCTTTTT | 71 |
| | Cas9-T (FAM-MGB) | AATCATTCCTGGTGGAGGA | 72 |
| pINII | pINII-99F | TGATGCCCACATTATAGTGATTAGC | 73 |
| | pINII-13R | CATCTTCTGGATTGGCCAACTT | 74 |
| | pINII-69T (FAM-MGB) | ACTATGTGTGCATCCTT | 75 |
| SIP | SIP-130F | TTCAAGTTGGGCTTTTTCAGAAG | 76 |
| | SIP-198R | TCTCCTTGGTGCTCTCATCACA | 77 |
| | SIP-170T (VIC-MGB) | CTGCAGCAGAACCAA | 78 |

D. Detection of the Replacement of the Soybean EPSPS1 Intron1 with the Soybean UBQ Intron1 Using the Guide RNA/Cas9 Endonuclease System.

Figure 18:
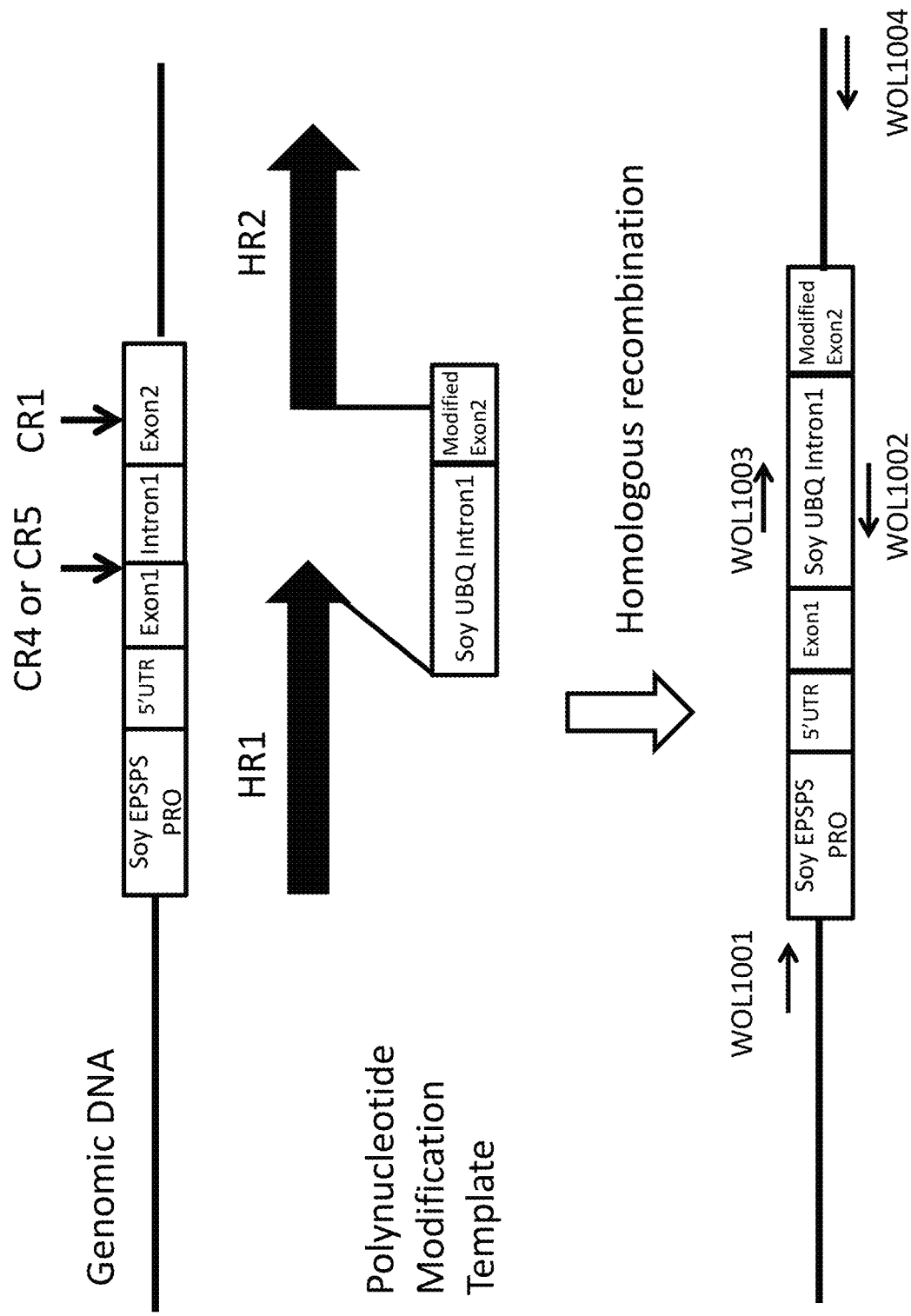
FIG. 18 illustrate an experimental design to replace the EPSPS1 intron1 with the soybean ubiquitin (UBQ) intron1.

In order to replace the soybean EPSPS1 intron1 with the soybean UBQ intron1 at the native EPSPS1 gene, two guideRNA expression vectors were used as shown in Table 22 and FIG. 18. The QC878 vector (SEQ ID NO: 63) was targeting the exon2 and the RTW1199 (SEQ ID NO:85) or RTW1200 (SEQ ID NO:86) was targeting the 5' end of the intron1. The double cleavage of soybean EPSPS gene with the two guide RNA/Cas systems resulted in the removal of the native EPSPS1 intron1/partial Exon2 fragment. At the same time, a polynucleotide modification template RTW1190A (SEQ ID NO:87) was co-delivered into soybean cells and homologous recombination between the polynucleotide modification template and the genomic DNA resulted in the replacement of EPSPS1 intron1 with the soybean UBQ intron1 and the desired amino acid modifications in exon2 as evidenced by PCR analysis. PCR assays with primer WOL1001/WOL1002 pair (SEQ ID NO: 92 and 93) and WOL1003/WOL1004 pair (SEQ ID NO: 94 and 95) were used to detect the intron replacement events.

Example 18

Promoter Replacement (Promoter Swap) of Soybean Genes Using the guideRNA/Cas Endonuclease System
A. guideRNA/Cas9 Endonuclease Target Site Design.

Four guideRNA/Cas9 endonuclease target sites were identified in the soybean EPSPS1 gene Glyma01g33660 (Table 23). Two of the target sites (soy EPSPS-CR1 and soy EPSPS-CR2) were identified to target the Exon2 of the soybean EPSPS gene as described in Example 16. The soy EPSPS-CR6 and soy EPSPS-CR7 were identified near the 5' end of the −798 bp of the native EPSPS promoter.

TABLE 23

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 60 | Gm01: 45865337 ... 45865315 |
| soy EPSPS-CR2 | 61 | Gm01: 45865311 ... 45865333 |
| soy EPSPS-CR6 | 96 | Gm01: 45867471 ... 45867493 |
| soy EPSPS-CR7 | 97 | Gm01: 45867459 ... 45867481 |

B. Guide RNA/Cas9 Endonuclease Expression Cassettes and Polynucleotide Modification Templates Used in Soybean Stable Transformation for the Replacement of the −798 bp Soybean EPSPS1 Promoter with the Soybean UBQ Promoter.

The soybean U6 small nuclear RNA promoter GM-U6-13.1 (SEQ ID. NO: 62) was used to express two guide RNAs (soyEPSPS-CR1 and soyEPSPS-CR6, or soyEPSPS-CR1 and soyEPSPS-CR7) to direct Cas9 nuclease to designated genomic target sites (Table 24). One of the target sites (soy-EPSPS-CR1) was located in the exon2 as described in Example 16 and a second target site (soy-EPSPS-CR6 or soy-EPSPS-CR7) was located near 5' end of the −798 bp of the native EPSPS1 promoter. A soybean codon optimized Cas9 endonuclease expression cassette and a guide RNA expression cassette were linked in the expression plasmids QC878/RTW1201 (SEQ ID NO:63/98) or QC878/RTW1202 (SEQ ID NO:63/99) that was co-delivered with a polynucleotide modification template, RTW1192A (SEQ ID NO:100). The polynucleotide modification template contained 1369 bp of the soybean UBQ gene promoter, 47 bp 5UTR and 532 bp UBQ intron1. Specific soybean EPSPS1 promoter replacement with the soybean UBQ promoter can be achieved with the guide RNA/Cas system by homologous recombination between the genomic DNA and the polynucleotide modification template, resulting enhancement of the native or modified soy EPSPS1 gene expression

TABLE 24

Guide RNA/Cas9 endonuclease expression cassettes and polynucleotide modification templates used in soybean stable transformation for the replacement of the −798 bp soybean EPSPS1 promoter with the soybean UBQ promoter

| Experiment | Guide RNA/Cas9 | SEQ ID NO: | polynucleotide modification template | SEQ ID NO: |
|---|---|---|---|---|
| soy EPSPS-CR1 and soy EPSPS-CR6 | U6-13.1: EPSPS CR1 + CR6+ EF1A2: CAS9 (QC878/RTW1201) | 63, 98 | RTW1192A | 100 |
| soy EPSPS-CR1 and soy EPSPS-CR7 | U6-13.1: EPSPS CR1 + CR7+ EF1A2: CAS9 (QC878/RTW1202) | 63, 99 | RTW1192A | 100 |

C. Detection of Site-Specific NHEJ Mediated by the Guide RNA/Cas9 System in Stably Transformed Soybean Site-specific NHEJ was detected as described in Example 16C, using the qPCR primers/probes listed in Table 25.

TABLE 25

Primers/Probes used in qPCR analyses of transgenic soybean events

| Target Site | Primer/Probe Name | Sequences | SEQ ID NOs: |
|---|---|---|---|
| EPSPS-CR1 & EPSPS-CR12 | Soy1-F1 | CCACTAGTAAGGAATCTAAAGATGAAATCA | 67 |
|  | Soy1-R2 | CCTGCAGCAACCACAGCTGCTGTC | 68 |
|  | Soy1-T1 (FAM-MGB) | CTGCAATGCGTCCTT | 69 |
| EPSPS-CR6 & EPSPS-CR7 | Soy1-F4 | TCAATAATACTACTCTCTTAGACACCAAACAA | 101 |
|  | Soy1-R4 | CAAGGAAAATGAATGATGGCTTT | 102 |
|  | Soy1-T3 (FAM-MGB) | CCTTCCCAAACTATAATC | 103 |
| gRNA/CAS9 | Cas9-F | CCTTCTTCCACCGCCTTGA | 70 |
|  | Cas9-R | TGGGTGTCTCTCGTGCTTTTT | 71 |
|  | Cas9-T (FAM-MGB) | AATCATTCCTGGTGGAGGA | 72 |
| pINII | pINII-99F | TGATGCCCACATTATAGTGATTAGC | 73 |
|  | pINII-13R | CATCTTCTGGATTGGCCAACTT | 74 |
|  | pINII-69T (FAM-MGB) | ACTATGTGTGCATCCTT | 75 |

TABLE 25-continued

Primers/Probes used in qPCR analyses of transgenic soybean events

| Target Site | Primer/Probe Name | Sequences | SEQ ID NOs: |
|---|---|---|---|
| SIP | SIP-130F | TTCAAGTTGGGCTTTTTCAGAAG | 78 |
| | SIP-198R | TCTCCTTGGTGCTCTCATCACA | 79 |
| | SIP-170T (VIC-MGB) | CTGCAGCAGAACCAA | 80 |

D. Detection of the Promoter Replacement of the Soybean EPSPS1 Promoter with the Soybean UBQ Promoter Using the Guide RNA/Cas9 Endonuclease System.

Figure 10:
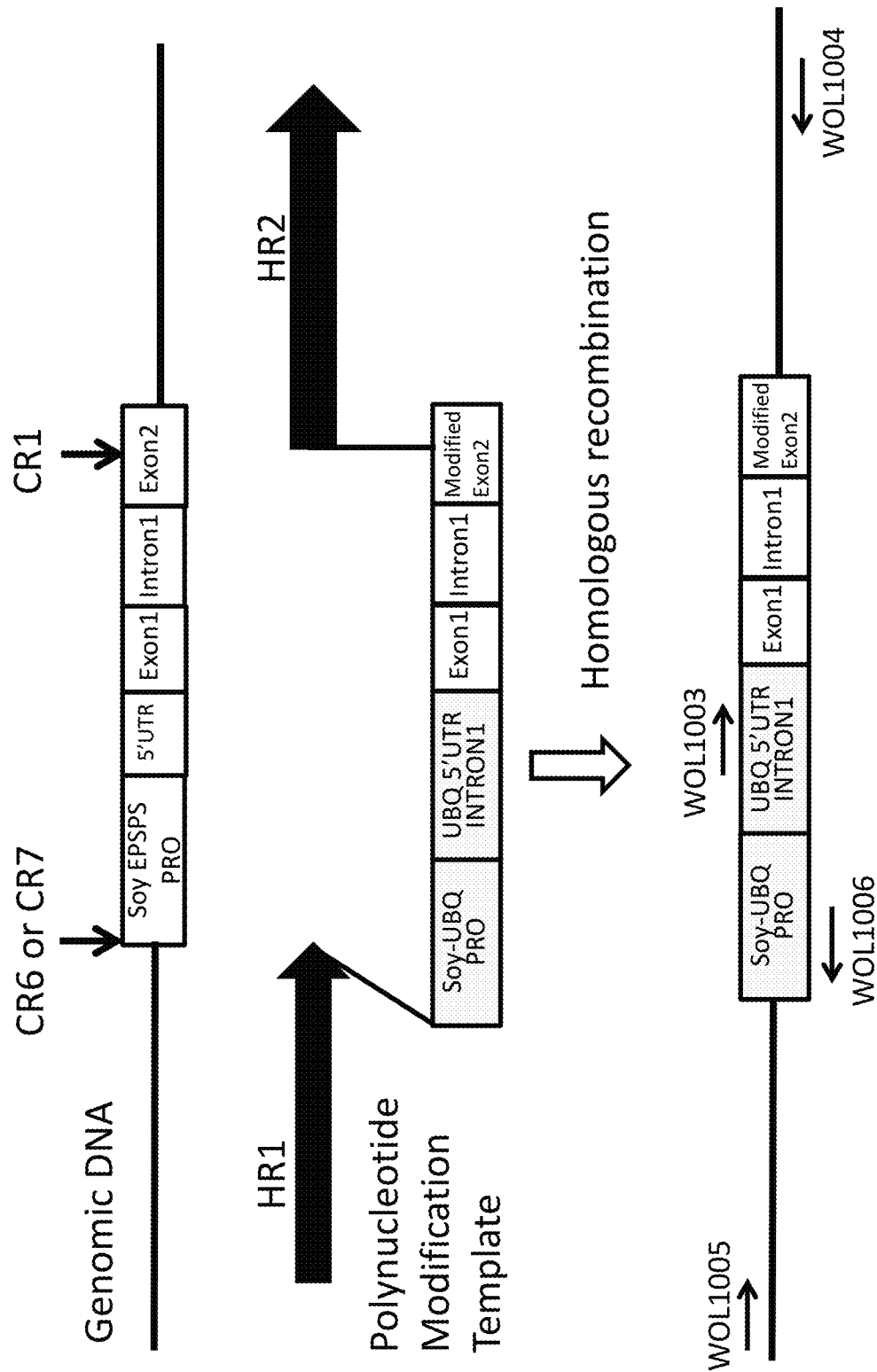

In order to replace the soybean EPSPS1 promoter with the soybean UBQ promoter at the native EPSPS1 gene, two guideRNA expression vectors were used in each soybean transformation experiment as shown in Table 24 and FIG. 10. The QC878 (SEQ ID NO: 63) was targeting the exon2 and the RTW1201(SEQ ID NO: 98) or RTW1202 (SEQ ID NO: 99) was targeting the 5' end of the soybean −798 bp promoter. The double cleavage of the soybean EPSPS1 gene with the two guide RNA/Cas systems resulted in removal of the native EPSPS1 promoter/5'UTR-Exon1/Intron1/partial Exon2 fragment at the native EPSPS gene. At the same time, a polynucleotide modification template RTW1192A (SEQ ID NO: 100) was co-delivered into soybean cells. This RTW1192A DNA contained 1369 bp soybean UBQ promoter, its 47 bp 5-UTR and 532 bp UBQ intron1 in front of the EPSPS1 exon1-Intron1-modified Exon2. Homologous recombination between the polynucleotide modification template and the genomic DNA resulted in the replacement of EPSPS1 promoter/5'UTR with the soybean UBQ promoter/5'UTR/Intron1 and the desired amino acid modifications evidenced by PCR analysis. PCR assays with primer WOL1005/WOL1006 pair (SEQ ID NO: 104 and 105) and WOL1003/WOL1004 pair (SEQ ID NO: 94 and 95) were used to detect the promoter replacement events.

Example 19

Variants of Plant EPSPS

EPSPS mutations, other than the TIPS mutation described in Example 3, that reduce sensitivity to glyphosate are known in the art (U.S. Pat. No. 8,436,159) and can also be introduced (in combination with TIPS or not) into a plant EPSPS gene as described in Example 3 and Example 8.

Also, novel EPSPS mutations can be identified by methods known to those skilled in the art. The guide polynucleotide/Cas endonuclease system described herein can be used to introduce any one of these mutations, or any combination of these mutations, in the EPSPS gene and the activity of the resulting maize EPSPS variants can be evaluated for herbicide resistance. Table 26 lists some EPSPS mutations that can be provided using the methods described herein.

TABLE 26

EPSPS mutations that can be provided using the methods described herein.

| Mutation | Reference & Remarks |
|---|---|
| G102A and T103I | SEQ ID NO: 7 disclosed in US20040148650 |
| P106L | Rice EPSPS; Zhou et al., (2006) Plant Physiol. 140(1): 184-195. |
| P106S | Goosegrass; Baerson et al., (2002) Plant Physiol. 129(3): 1265-75 (EMBL AJ417033) |
| T102I, P106T, P106A, P106L, P106G, P106C | Maize; U.S. Pat. No. 8,436,159 |
| GNAGTAMRPL mutated to GNAGIAMRSL | Brassica napus; SEQ ID NOs: 66 and 67 of U.S. Pat. No. 7,169,970 |

That which is claimed:

1. A method for producing an enolpyruvylshikimate-3-phosphate synthase (EPSPS) mutant plant, the method comprising:
   a) providing to a plant cell comprising an EPSPS nucleotide sequence operably linked to a heterologous regulatory element a guide RNA, a polynucleotide modification template comprising at least one nucleotide modification of the EPSPS nucleotide sequence, and a Cas endonuclease, wherein said guide RNA and Cas endonuclease are capable of forming a complex that enables the Cas endonuclease to introduce a double strand break at a target site in the genome of said plant cell, and wherein the at least one nucleotide modification comprises a TIPS modification;
   b) obtaining a plant from the plant cell of (a);
   c) evaluating the plant of (b) for the presence of said at least one nucleotide modification; and,
   d) selecting a progeny plant that shows resistance to glyphosate.

2. A method for producing an enolpyruvylshikimate-3-phosphate synthase (EPSPS) mutant plant, the method comprising:
   a) providing to a plant cell comprising an EPSPS nucleotide sequence a guide RNA, a polynucleotide modification template comprising at least one nucleotide modification of the EPSPS nucleotide sequence, and a Cas endonuclease, wherein said guide RNA and Cas endonuclease are capable of forming a complex that enables the Cas endonuclease to introduce a double strand break at a target site in the genome of said plant cell, and wherein the at least one nucleotide modification comprises a TIPS modification and a promoter replacement;
   b) obtaining a plant from the plant cell of (a);
   c) evaluating the plant of (b) for the presence of said at least one nucleotide modification; and,
   d) selecting a progeny plant that shows resistance to glyphosate.

3. The method of claim 1, wherein the at least one nucleotide modification further comprises a modification selected from the group consisting of (i) a nucleotide modification resulting in a lysine to arginine substitution (K90R) at the amino acid position corresponding to residue 90 of the maize EPSPS amino acid sequence, (ii) insertion of an intron mediated enhancer element (IME), or combinations thereof.

4. The method of claim 2, wherein the at least one nucleotide modification further comprises a modification selected from the group consisting of (i) a nucleotide modification resulting in a lysine to arginine substitution (K90R) at the amino acid position corresponding to residue 90 of the maize EPSPS amino acid sequence, (ii) insertion of an intron mediated enhancer element (IME), or combinations thereof.

5. A method for producing an enolpyruvylshikimate-3-phosphate synthase (EPSPS) mutant plant, the method comprising:
   a) providing to a plant cell comprising an EPSPS nucleotide sequence comprising a TIPS modification a guide RNA, a polynucleotide modification template comprising at least one nucleotide modification of the EPSPS nucleotide sequence, and a Cas endonuclease, wherein said guide RNA and Cas endonuclease are capable of forming a complex that enables the Cas endonuclease to introduce a double strand break at a target site in the genome of said plant cell, and wherein the at least one nucleotide modification comprises a promoter replacement;

b) obtaining a plant from the plant cell of (a);

c) evaluating the plant of (b) for the presence of said at least one nucleotide modification; and, d) selecting a progeny plant that shows resistance to glyphosate.

6. The method of claim 5, wherein the at least one nucleotide modification further comprises a modification selected from the group consisting of (i) a nucleotide modification resulting in a lysine to arginine substitution (K90R) at the amino acid position corresponding to residue 90 of the maize EPSPS amino acid sequence, (ii) insertion of an intron mediated enhancer element (IME), or combinations thereof.

7. The method of claim 1, wherein the plant is soybean or maize.

8. The method of claim 2, wherein the plant is soybean or maize.

9. The method of claim 5, wherein the plant is soybean or maize.

* * * * *

SEQUENCE LISTING

<160> NUMBER OF SEQ ID NOS: 122

<210> SEQ ID NO 1
<211> LENGTH: 4107
<212> TYPE: DNA
<213> ORGANISM: Streptococcus pyogenes M1 GAS (SF370)

<400> SEQUENCE: 1

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggct cttttatttg acagtggaga gacagcggaa     180
```

-continued

```
gcgactcgtc tcaaacggac agctcgtaga aggtatacac gtcggaagaa tcgtatttgt    240
tatctacagg agatttttc aaatgagatg gcgaaagtag atgatagttt ctttcatcga     300
cttgaagagt cttttttggt ggaagaagac aagaagcatg aacgtcatcc tattttgga    360 aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca ttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aatttttaaaa caattttga tttggcagaa    780 gatgctaaat tacagcttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga    1020
caacaacttc cagaaaagta taaagaaatc ttttttgatc aatcaaaaaa cggatatgca    1080
ggttatattg atgggggagc tagccaagaa gaatttata aatttatcaa accaattta    1140 gaaaaaatgg atggtactga ggaattattg gtgaaactaa atcgtgaaga tttgctgcgc    1200
aagcaacgga cctttgacaa cggctctat cccccatcaaa ttcacttggg tgagctgcat    1260
gctattttga aagacaaga agactttat ccattttaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta cccccatggaa ttttgaagaa    1440 gttgtcgata aggtgcttc agctcaatca tttattgaac gcatgacaaa ctttgataaa    1500
aatcttccaa atgaaaaagt actaccaaaa catagttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaaatgaag atatcttaga ggatattgtt    1860
ttaacattga ccttatttga agatagggag atgattgagg aaagacttaa acatatgct    1920 cacctctttg atgataaggt gatgaaacag cttaaacgtc gccgttatac tggttgggga    1980
cgtttgtctc gaaaattgat taatggtatt agggataagc aatctggcaa aacaatatta    2040
gattttttga aatcagatgg ttttgccaat cgcaatttta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaaggtat tttacagact    2220
gtaaaagttg ttgatgaatt ggtcaaagta atgggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct taaagacgat tcaatagaca ataaggtctt aacgcgttct    2580
```

```
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac cttaaaatct     2880 aaattagttt ctgacttccg aaaagatttc caattctata agtacgtga gattaacaat     2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aagggaaat cgaagaagtt aaaatccgtt     3480
aaagagttac tagggatcac aattatgaaa agaagttcct ttgaaaaaaa tccgattgac    3540
tttttagaag ctaaaggata taggaagtt aaaaaagact taatcattaa actacctaaa     3600
tatagtcttt ttgagttaga aaacggtcgt aacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aatattatt catttattta cgttgacgaa tcttggagct     3960
cccgctgctt ttaaatattt tgatacaaca attgatcgta acgatatac gtctacaaaa     4020 gaagtttag atgccactct tatccatcaa tccatcactg gtctttatga aacacgcatt     4080
gatttgagtc agctaggagg tgactga                                         4107
```

<210> SEQ ID NO 2
<211> LENGTH: 189
<212> TYPE: DNA
<213> ORGANISM: Solanum tuberosum

<400> SEQUENCE: 2

```
gtaagtttct gcttctacct ttgatatata tataataatt atcattaatt agtagtaata     60
taatatttca atattttttt tcaaaataaa agaatgtagt atatagcaat tgcttttctg    120
tagtttataa gtgtgtatat tttaattat aacttttcta atatatgacc aaaacatggt    180
gatgtgcag                                                            189
```

<210> SEQ ID NO 3
<211> LENGTH: 9
<212> TYPE: PRT
<213> ORGANISM: Simian virus 40

<400> SEQUENCE: 3

```
Met Ala Pro Lys Lys Lys Arg Lys Val
1               5
```

```
<210> SEQ ID NO 4
<211> LENGTH: 18
<212> TYPE: PRT
<213> ORGANISM: Agrobacterium tumefaciens

<400> SEQUENCE: 4

Lys Arg Pro Arg Asp Arg His Asp Gly Glu Leu Gly Gly Arg Lys Arg
1               5                   10                  15

Ala Arg

<210> SEQ ID NO 5
<211> LENGTH: 6717
<212> TYPE: DNA
<213> ORGANISM: Artificial Sequence
<220> FEATURE:
<223> OTHER INFORMATION: Maize optimized Cas9 expression cassette

<400> SEQUENCE: 5
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg     300 caaatagctt cacctatata atacttcatc cattttatta gtacatccat ttagggttta    360
gggttaatgg ttttttatag ctaattttttt tagtacatct attttattct attttagcct    420
ctaaattaag aaaactaaaa ctctatttta gttttttttat ttaataattt agatataaaa    480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattccttttc ccaccgctcc    840 ttcgcttttcc cttcctcgcc cgccgtaata aatagacacc cctccacac cctcttttccc    900 caacctcgtg ttgttcggag cgcacacaca cacaaccaga tctcccccaa atccaccccgt    960 cggcacctcc gcttcaaggt acgccgctcg tcctcccccc ccccctctc taccttctct   1020 agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gcccttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttgttcg    1560 cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
```

```
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgttttct tttgtcgatg ctcaccctgt tgtttggtgt    1980
tacttctgca ggtcgactct agaggatcca tggcaccgaa gaagaagcgc aaggtgatgg    2040
acaagaagta cagcatcggc ctcgacatcg gcaccaactc ggtgggctgg gccgtcatca    2100
cggacgaata taaggtcccg tcgaagaagt tcaaggtcct cggcaataca gaccgccaca    2160
gcatcaagaa aaacttgatc ggcgccctcc tgttcgatag cggcgagacc gcggaggcga    2220
ccaggctcaa gaggaccgcc aggagacggt acactaggcg caagaacagg atctgctacc    2280
tgcaggagat cttcagcaac gagatggcga aggtggacga ctccttcttc caccgcctgg    2340
aggaatcatt cctggtggag gaggacaaga agcatgagcg gcacccaatc ttcggcaaca    2400
tcgtcgacga ggtaagtttc tgcttctacc tttgatatat atataataat tatcattaat    2460
tagtagtaat ataatatttc aaatattttt ttcaaaataa aagaatgtag tatatagcaa    2520
ttgcttttct gtagtttata agtgtgtata ttttaattta taacttttct aatatatgac    2580
caaaacatgg tgatgtgcag gtggcctacc acgagaagta cccgacaatc taccacctcc    2640
ggaagaaact ggtggacagc acagacaagg cggacctccg gctcatctac cttgccctcg    2700
cgcatatgat caagttccgc ggccacttcc tcatcgaggg cgacctgaac ccggacaact    2760
ccgacgtgga caagctgttc atccagctcg tgcagacgta caatcaactg ttcgaggaga    2820
accccataaa cgctagcggc gtggacgcca aggccatcct ctcggccagg ctctcgaaat    2880
caagaaggct ggagaacctt atcgcgcagt gccaggcga aaagaagaac ggcctcttcg    2940
gcaaccttat tgcgctcagc ctcggcctga cgccgaactt caaatcaaac ttcgacctcg    3000
cggaggacgc caagctccag ctctcaaagg acacctacga cgacgacctc gacaacctcc    3060
tggcccagat aggagaccag tacgcggacc tcttcctcgc cgccaagaac ctctccgacg    3120
ctatcctgct cagcgacatc cttcgggtca acaccgaaat taccaaggca ccgctgtccg    3180
ccagcatgat taaacgctac gacgagcacc atcaggacct cacgctgctc aaggcactcg    3240
tccgccagca gctccccgag aagtacaagg agatcttctt cgaccaatca aaaaacggct    3300
acgcgggata tatcgacggc ggtgccagcc aggaagagtt ctacaagttc atcaaaccaa    3360
tcctggagaa gatggacggc accgaggagt tgctggtcaa gctcaacagg gaggacctcc    3420
tcaggaagca gaggaccttc gacaacggct ccatcccgca tcagatccac ctgggcgaac    3480
tgcatgccat cctgcggcgc caggaggact ctacccgtt cctgaaggat aaccgggaga    3540
agatcgagaa gatcttgacg ttccgcatcc catactacgt gggcccgctg ctcgcggca    3600 actccggtt cgcctggatg acccggaagt cggaggagac catcacaccc tggaactttg    3660
aggaggtggt cgataagggc gctagcgctc agagcttcat cgagcgcatg accaacttcg    3720
ataaaaacct gcccaatgaa aaagtcctcc ccaagcactc gctgctctac gagtacttca    3780
ccgtgtacaa cgagctcacc aaggtcaat acgtcaccga gggcatgcgg aagccggcgt    3840
tcctgagcgg cgagcagaag aaggcgatag tggacctcct cttcaagacc aacaggaagg    3900
tgaccgtgaa gcaattaaaa gaggactact tcaagaaaat agagtgcttc gactccgtgg    3960
agatctcggg cgtggaggat cggttcaacg cctcactcgg cacgtatcac gacctcctca    4020
```

```
agatcattaa agacaaggac ttcctcgaca acgaggagaa cgaggacatc ctcgaggaca   4080
tcgtcctcac cctgaccctg ttcgaggacc gcgaaatgat cgaggagagg ctgaagacct   4140
acgcgcacct gttcgacgac aaggtcatga acagctcaa gaggcgccgc tacactggtt    4200
ggggaaggct gtcccgcaag ctcattaatg gcatcaggga caagcagagc ggcaagacca   4260
tcctggactt cctcaagtcc gacgggttcg ccaaccgcaa cttcatgcag ctcattcacg   4320
acgactcgct cacgttcaag gaagacatcc agaaggcaca ggtgagcggg cagggtgact   4380
ccctccacga acacatcgcc aacctggccg gctcgccggc cattaaaaag ggcatcctgc   4440
agacggtcaa ggtcgtcgac gagctcgtga aggtgatggg ccggcacaag cccgaaaata   4500
tcgtcataga gatggccagg gagaaccaga ccacccaaaa agggcagaag aactcgcgcg   4560
agcggatgaa acggatcgag gagggcatta agagctcgg gtcccagatc ctgaaggagc    4620
accccgtgga aaatacccag ctccagaatg aaaagctcta cctctactac ctgcagaacg   4680
gccgcgacat gtacgtggac caggagctgg acattaatcg gctatcggac tacgacgtcg   4740
accacatcgt gccgcagtcg ttcctcaagg acgatagcat cgacaacaag gtgctcaccc   4800
ggtcggataa aaatcggggc aagagcgaca acgtgcccag cgaggaggtc gtgaagaaga   4860
tgaaaaacta ctggcgccag ctcctcaacg cgaaactgat cacccagcgc aagttcgaca   4920
acctgacgaa ggcggaacgc ggtggcttga gcgaactcga taaggcgggc ttcataaaaa   4980
ggcagctggt cgagacgcgc cagatcacga agcatgtcgc ccagatcctg acagccgca    5040 tgaatactaa gtacgatgaa acgacaagc tgatccggga ggtgaaggtg atcacgctga    5100
agtccaagct cgtgtcggac ttccgcaagg acttccagtt ctacaaggtc cgcgagatca   5160
acaactacca ccacgcccac gacgcctacc tgaatgcggt ggtcgggacc gccctgatca   5220
agaagtaccc gaagctggag tcggagttcg tgtacggcga ctacaaggtc tacgacgtgc   5280
gcaaaatgat cgccaagtcc gagcaggaga tcggcaaggc cacggcaaaa tacttcttct   5340
actcgaacat catgaacttc ttcaagaccg agatcacccct cgcgaacggc gagatccgca   5400
agcgcccgct catcgaaacc aacggcgaga cgggcgagat cgtctgggat aagggccggg   5460
atttcgcgac ggtccgcaag gtgctctcca tgccgcaagt caatatcgtg aaaaagacgg   5520
aggtccagac gggcgggttc agcaaggagt ccatcctccc gaagcgcaac tccgacaagc   5580
tcatcgcgag gaagaaggat tgggacccga aaaaatatgg cggcttcgac agcccgaccg   5640
tcgcatacag cgtcctcgtc gtggcgaagg tggagaaggg caagtcaaag aagctcaagt   5700
ccgtgaagga gctgctcggg atcacgatta tggagcggtc ctccttcgag aagaacccga   5760
tcgacttcct agaggccaag ggatataagg aggtcaagaa ggacctgatt attaaactgc   5820
cgaagtactc gctcttcgag ctggaaaacg gccgcaagag gatgctcgcc tccgcaggcg   5880
agttgcagaa gggcaacgag ctcgccctcc cgagcaaata cgtcaatttc ctgtacctcg   5940
ctagccacta tgaaaagctc aagggcagcc cggaggacaa cgagcagaag cagctcttcg   6000
tggagcagca caagcattac ctggacgaga tcatcgagca gatcagcgag ttctcgaagc   6060
gggtgatcct cgccgacgcg aacctggaca aggtgctgtc ggcatataac aagcaccgcg   6120
acaaaccaat acgcgagcag gccgaaaata tcatccacct cttcaccctc accaacctcg   6180
gcgctccggc agccttcaag tacttcgaca ccacgattga ccggaagcgg tacacgagca   6240
cgaaggaggt gctcgatgcg acgctgatcc accagagcat cacagggctc tatgaaacac   6300
gcatcgacct gagccagctg ggcggagaca agagaccacg ggaccgccac gatgcgagc    6360 tgggaggccg caagcgggca aggtaggtac cgttaaccta gacttgtcca tcttctggat    6420
```

```
tggccaactt aattaatgta tgaaataaaa ggatgcacac atagtgacat gctaatcact    6480
ataatgtggg catcaaagtt gtgtgttatg tgtaattact agttatctga ataaaagaga    6540
aagagatcat ccatatttct tatcctaaat gaatgtcacg tgtctttata attctttgat    6600
gaaccagatg catttcatta accaaatcca tatacatata aatattaatc atatataatt    6660
aatatcaatt gggttagcaa aacaaatcta gtctaggtgt gttttgcgaa tgcggcc      6717
```

```
<210> SEQ ID NO 6
<211> LENGTH: 39
<212> TYPE: RNA
<213> ORGANISM: Artificial Sequence
<220> FEATURE:
<223> OTHER INFORMATION: crRNA targeting the LIGCas-3 target sequence

<400> SEQUENCE: 6
gcguacgcgu acgugugguu uuagagcuau gcuguuuug                          39

<210> SEQ ID NO 7
<211> LENGTH: 86
<212> TYPE: RNA
<213> ORGANISM: Streptococcus pyogenes M1 GAS (SF370)

<400> SEQUENCE: 7
ggaaccauuc aaaacagcau agcaaguuaa aauaaggcua guccguuauc aacuugaaaa    60
aguggcaccg agucggugcu uuuuuu                                        86

<210> SEQ ID NO 8
<211> LENGTH: 94
<212> TYPE: RNA
<213> ORGANISM: Artificial Sequence
<220> FEATURE:
<223> OTHER INFORMATION: single guide RNA targeting the LIGCas-3 target
      sequence

<400> SEQUENCE: 8
gcguacgcgu acgugugguu uuagagcuag aaauagcaag uuaaaauaag gcuaguccgu    60
uaucaacuug aaaaaguggc accgagucgg ugcu                               94

<210> SEQ ID NO 9
<211> LENGTH: 1000
<212> TYPE: DNA
<213> ORGANISM: Zea mays

<400> SEQUENCE: 9
tgagagtaca atgatgaacc tagattaatc aatgccaaag tctgaaaaat gcaccctcag    60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga gggggcatca    480
aagatctggc tgtgttttcca gctgtttttg ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaaatgct    660
```

```
attcgaattt ctactagcag taagtcgtgt ttagaaatta ttttttttata tacctttttt      720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt                           1000

<210> SEQ ID NO 10
<211> LENGTH: 16
<212> TYPE: DNA
<213> ORGANISM: Zea mays

<400> SEQUENCE: 10
tttttttttt tttttt                                                       16

<210> SEQ ID NO 11
<211> LENGTH: 1102
<212> TYPE: DNA
<213> ORGANISM: Artificial Sequence
<220> FEATURE:
<223> OTHER INFORMATION: Maize optimized single long guide RNA
      expression cassette targeting the LIGCas-3 target sequence

<400> SEQUENCE: 11
tgagagtaca atgatgaacc tagattaatc aatgccaaag tctgaaaaat gcaccctcag       60
tctatgatcc agaaaatcaa gattgcttga ggccctgttc ggttgttccg gattagagcc      120
ccggattaat tcctagccgg attacttctc taatttatat agattttgat gagctggaat      180
gaatcctggc ttattccggt acaaccgaac aggccctgaa ggataccagt aatcgctgag      240
ctaaattggc atgctgtcag agtgtcagta ttgcagcaag gtagtgagat aaccggcatc      300
atggtgccag tttgatggca ccattagggt tagagatggt ggccatgggc gcatgtcctg      360
gccaactttg tatgatatat ggcagggtga ataggaaagt aaaattgtat tgtaaaaagg      420
gatttcttct gtttgttagc gcatgtacaa ggaatgcaag ttttgagcga gggggcatca      480
aagatctggc tgtgtttcca gctgttttg ttagccccat cgaatccttg acataatgat       540
cccgcttaaa taagcaacct cgcttgtata gttccttgtg ctctaacaca cgatgatgat      600
aagtcgtaaa atagtggtgt ccaaagaatt tccaggccca gttgtaaaag ctaaaatgct      660
attcgaattt ctactagcag taagtcgtgt ttagaaatta ttttttttata tacctttttt     720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt gcgtacgcgt acgtgtggtt     1020
ttagagctag aaatagcaag ttaaaataag ctagtccgt tatcaacttg aaaaagtggc      1080
accgagtcgg tgcttttttt tt                                              1102

<210> SEQ ID NO 12
<211> LENGTH: 23
<212> TYPE: DNA
<213> ORGANISM: Zea mays

<400> SEQUENCE: 12
```
ggaatgctgg aactgcaatg cgg                                          23

<210> SEQ ID NO 13
<211> LENGTH: 24
<212> TYPE: DNA
<213> ORGANISM: Zea mays

<400> SEQUENCE: 13
gcagctcttc ttggggaatg ctgg                                         24

<210> SEQ ID NO 14
<211> LENGTH: 23
<212> TYPE: DNA
<213> ORGANISM: Zea mays

<400> SEQUENCE: 14
gcagtaacag ctgctgtcaa tgg                                          23

<210> SEQ ID NO 15
<211> LENGTH: 43
<212> TYPE: DNA
<213> ORGANISM: Artificial Sequence
<220> FEATURE:
<223> OTHER INFORMATION: Forward primer for secondary PCR

<400> SEQUENCE: 15
aatgatacgg cgaccaccga gatctacact ctttccctac acg                    43

<210> SEQ ID NO 16
<211> LENGTH: 18
<212> TYPE: DNA
<213> ORGANISM: Artificial Sequence
<220> FEATURE:
<223> OTHER INFORMATION: Reverse primer for secondary PCR

<400> SEQUENCE: 16
caagcagaag acggcata                                                18

<210> SEQ ID NO 17
<211> LENGTH: 63
<212> TYPE: DNA
<213> ORGANISM: Artificial Sequence
<220> FEATURE:
<223> OTHER INFORMATION: EPSPSCas-1 forward primer for primary PCR

<400> SEQUENCE: 17
ctacactctt tccctacacg acgctcttcc gatctggaag aggaaacata cgttgcattt   60
cca                                                                63

<210> SEQ ID NO 18
<211> LENGTH: 57
<212> TYPE: DNA
<213> ORGANISM: Artificial Sequence
<220> FEATURE:
<223> OTHER INFORMATION: EPSPSCas-1 and EPSPSCas-3 reverse primer for
      primary PCR

<400> SEQUENCE: 18
caagcagaag acggcatacg agctcttccg atctggtgga agttcccag ttgagga       57

<210> SEQ ID NO 19
<211> LENGTH: 62
<212> TYPE: DNA
<213> ORGANISM: Artificial Sequence

```
<220> FEATURE:
<223> OTHER INFORMATION: EPSPSCas-2 forward primer for primary PCR

<400> SEQUENCE: 19
ctacactctt tccctacacg acgctcttcc gatctaagcg gtggaaagtt cccagttgag    60
ga                                                                  62

<210> SEQ ID NO 20
<211> LENGTH: 58
<212> TYPE: DNA
<213> ORGANISM: Artificial Sequence
<220> FEATURE:
<223> OTHER INFORMATION: EPSPSCas-2 reverse primer for primary PCR

<400> SEQUENCE: 20
caagcagaag acggcatacg agctcttccg atctgaggaa acatacgttg catttcca     58

<210> SEQ ID NO 21
<211> LENGTH: 63
<212> TYPE: DNA
<213> ORGANISM: Artificial Sequence
<220> FEATURE:
<223> OTHER INFORMATION: EPSPSCas-3 forward primer for primary PCR

<400> SEQUENCE: 21
ctacactctt tccctacacg acgctcttcc gatctccttg aggaaacata cgttgcattt    60
cca                                                                 63

<210> SEQ ID NO 22
<211> LENGTH: 1377
<212> TYPE: PRT
<213> ORGANISM: Artificial sequence
<220> FEATURE:
<223> OTHER INFORMATION: maize optimized moCAS9 endonuclease

<400> SEQUENCE: 22

Met Ala Pro Lys Lys Arg Lys Val Met Asp Lys Lys Tyr Ser Ile
1               5                  10                  15

Gly Leu Asp Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
```

```
            180                 185                 190
Leu Phe Ile Gln Leu Val Gln Thr Tyr Asn Gln Leu Phe Glu Glu Asn
            195                 200                 205
Pro Ile Asn Ala Ser Gly Val Asp Ala Lys Ala Ile Leu Ser Ala Arg
210                 215                 220
Leu Ser Lys Ser Arg Arg Leu Glu Asn Leu Ile Ala Gln Leu Pro Gly
225                 230                 235                 240
Glu Lys Lys Asn Gly Leu Phe Gly Asn Leu Ile Ala Leu Ser Leu Gly
            245                 250                 255
Leu Thr Pro Asn Phe Lys Ser Asn Phe Asp Leu Ala Glu Asp Ala Lys
            260                 265                 270
Leu Gln Leu Ser Lys Asp Thr Tyr Asp Asp Leu Asp Asn Leu Leu
            275                 280                 285
Ala Gln Ile Gly Asp Gln Tyr Ala Asp Leu Phe Leu Ala Ala Lys Asn
            290                 295                 300
Leu Ser Asp Ala Ile Leu Leu Ser Asp Ile Leu Arg Val Asn Thr Glu
305                 310                 315                 320
Ile Thr Lys Ala Pro Leu Ser Ala Ser Met Ile Lys Arg Tyr Asp Glu
            325                 330                 335
His His Gln Asp Leu Thr Leu Leu Lys Ala Leu Val Arg Gln Gln Leu
            340                 345                 350
Pro Glu Lys Tyr Lys Glu Ile Phe Phe Asp Gln Ser Lys Asn Gly Tyr
            355                 360                 365
Ala Gly Tyr Ile Asp Gly Gly Ala Ser Gln Glu Glu Phe Tyr Lys Phe
            370                 375                 380
Ile Lys Pro Ile Leu Glu Lys Met Asp Gly Thr Glu Glu Leu Leu Val
385                 390                 395                 400
Lys Leu Asn Arg Glu Asp Leu Leu Arg Lys Gln Arg Thr Phe Asp Asn
            405                 410                 415
Gly Ser Ile Pro His Gln Ile His Leu Gly Glu Leu His Ala Ile Leu
            420                 425                 430
Arg Arg Gln Glu Asp Phe Tyr Pro Phe Leu Lys Asp Asn Arg Glu Lys
            435                 440                 445
Ile Glu Lys Ile Leu Thr Phe Arg Ile Pro Tyr Tyr Val Gly Pro Leu
450                 455                 460
Ala Arg Gly Asn Ser Arg Phe Ala Trp Met Thr Arg Lys Ser Glu Glu
465                 470                 475                 480
Thr Ile Thr Pro Trp Asn Phe Glu Glu Val Val Asp Lys Gly Ala Ser
            485                 490                 495
Ala Gln Ser Phe Ile Glu Arg Met Thr Asn Phe Asp Lys Asn Leu Pro
            500                 505                 510
Asn Glu Lys Val Leu Pro Lys His Ser Leu Leu Tyr Glu Tyr Phe Thr
            515                 520                 525
Val Tyr Asn Glu Leu Thr Lys Val Lys Tyr Val Thr Glu Gly Met Arg
            530                 535                 540
Lys Pro Ala Phe Leu Ser Gly Glu Gln Lys Lys Ala Ile Val Asp Leu
545                 550                 555                 560
Leu Phe Lys Thr Asn Arg Lys Val Thr Val Lys Gln Leu Lys Glu Asp
            565                 570                 575
Tyr Phe Lys Lys Ile Glu Cys Phe Asp Ser Val Glu Ile Ser Gly Val
            580                 585                 590
Glu Asp Arg Phe Asn Ala Ser Leu Gly Thr Tyr His Asp Leu Leu Lys
            595                 600                 605
```

```
Ile Ile Lys Asp Lys Asp Phe Leu Asp Asn Glu Glu Asn Glu Asp Ile
610                 615                 620

Leu Glu Asp Ile Val Leu Thr Leu Thr Leu Phe Glu Asp Arg Glu Met
625                 630                 635                 640

Ile Glu Glu Arg Leu Lys Thr Tyr Ala His Leu Phe Asp Lys Val
            645                 650                 655

Met Lys Gln Leu Lys Arg Arg Tyr Thr Gly Trp Gly Arg Leu Ser
            660                 665                 670

Arg Lys Leu Ile Asn Gly Ile Arg Asp Lys Gln Ser Gly Lys Thr Ile
            675                 680                 685

Leu Asp Phe Leu Lys Ser Asp Gly Phe Ala Asn Arg Asn Phe Met Gln
            690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
            725                 730                 735

Ala Gly Ser Pro Ala Ile Lys Lys Gly Ile Leu Gln Thr Val Lys Val
            740                 745                 750

Val Asp Glu Leu Val Lys Val Met Gly Arg His Lys Pro Glu Asn Ile
            755                 760                 765

Val Ile Glu Met Ala Arg Glu Asn Gln Thr Thr Gln Lys Gly Gln Lys
770                 775                 780

Asn Ser Arg Glu Arg Met Lys Arg Ile Glu Glu Gly Ile Lys Glu Leu
785                 790                 795                 800

Gly Ser Gln Ile Leu Lys Glu His Pro Val Glu Asn Thr Gln Leu Gln
            805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
            835                 840                 845

His Ile Val Pro Gln Ser Phe Leu Lys Asp Asp Ser Ile Asp Asn Lys
850                 855                 860

Val Leu Thr Arg Ser Asp Lys Asn Arg Gly Lys Ser Asp Asn Val Pro
865                 870                 875                 880

Ser Glu Glu Val Val Lys Lys Met Lys Asn Tyr Trp Arg Gln Leu Leu
            885                 890                 895

Asn Ala Lys Leu Ile Thr Gln Arg Lys Phe Asp Asn Leu Thr Lys Ala
            900                 905                 910

Glu Arg Gly Gly Leu Ser Glu Leu Asp Lys Ala Gly Phe Ile Lys Arg
            915                 920                 925

Gln Leu Val Glu Thr Arg Gln Ile Thr Lys His Val Ala Gln Ile Leu
930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
            965                 970                 975

Lys Asp Phe Gln Phe Tyr Lys Val Arg Glu Ile Asn Asn Tyr His His
            980                 985                 990

Ala His Asp Ala Tyr Leu Asn Ala Val Val Gly Thr Ala Leu Ile Lys
            995                 1000                1005

Lys Tyr Pro Lys Leu Glu Ser Glu Phe Val Tyr Gly Asp Tyr Lys
    1010                1015                1020
```

Val Tyr Asp Val Arg Lys Met Ile Ala Lys Ser Glu Gln Glu Ile
1025              1030              1035

Gly Lys Ala Thr Ala Lys Tyr Phe Phe Tyr Ser Asn Ile Met Asn
1040              1045              1050

Phe Phe Lys Thr Glu Ile Thr Leu Ala Asn Gly Glu Ile Arg Lys
1055              1060              1065

Arg Pro Leu Ile Glu Thr Asn Gly Glu Thr Gly Glu Ile Val Trp
1070              1075              1080

Asp Lys Gly Arg Asp Phe Ala Thr Val Arg Lys Val Leu Ser Met
1085              1090              1095

Pro Gln Val Asn Ile Val Lys Lys Thr Glu Val Gln Thr Gly Gly
1100              1105              1110

Phe Ser Lys Glu Ser Ile Leu Pro Lys Arg Asn Ser Asp Lys Leu
1115              1120              1125

Ile Ala Arg Lys Lys Asp Trp Asp Pro Lys Lys Tyr Gly Gly Phe
1130              1135              1140

Asp Ser Pro Thr Val Ala Tyr Ser Val Leu Val Val Ala Lys Val
1145              1150              1155

Glu Lys Gly Lys Ser Lys Lys Leu Lys Ser Val Lys Glu Leu Leu
1160              1165              1170

Gly Ile Thr Ile Met Glu Arg Ser Ser Phe Glu Lys Asn Pro Ile
1175              1180              1185

Asp Phe Leu Glu Ala Lys Gly Tyr Lys Glu Val Lys Lys Asp Leu
1190              1195              1200

Ile Ile Lys Leu Pro Lys Tyr Ser Leu Phe Glu Leu Glu Asn Gly
1205              1210              1215

Arg Lys Arg Met Leu Ala Ser Ala Gly Glu Leu Gln Lys Gly Asn
1220              1225              1230

Glu Leu Ala Leu Pro Ser Lys Tyr Val Asn Phe Leu Tyr Leu Ala
1235              1240              1245

Ser His Tyr Glu Lys Leu Lys Gly Ser Pro Glu Asp Asn Glu Gln
1250              1255              1260

Lys Gln Leu Phe Val Glu Gln His Lys His Tyr Leu Asp Glu Ile
1265              1270              1275

Ile Glu Gln Ile Ser Glu Phe Ser Lys Arg Val Ile Leu Ala Asp
1280              1285              1290

Ala Asn Leu Asp Lys Val Leu Ser Ala Tyr Asn Lys His Arg Asp
1295              1300              1305

Lys Pro Ile Arg Glu Gln Ala Glu Asn Ile Ile His Leu Phe Thr
1310              1315              1320

Leu Thr Asn Leu Gly Ala Pro Ala Ala Phe Lys Tyr Phe Asp Thr
1325              1330              1335

Thr Ile Asp Arg Lys Arg Tyr Thr Ser Thr Lys Glu Val Leu Asp
1340              1345              1350

Ala Thr Leu Ile His Gln Ser Ile Thr Gly Leu Tyr Glu Thr Arg
1355              1360              1365

Ile Asp Leu Ser Gln Leu Gly Gly Asp
1370              1375

<210> SEQ ID NO 23
<211> LENGTH: 6677
<212> TYPE: DNA
<213> ORGANISM: Artificial sequence
<220> FEATURE:
<223> OTHER INFORMATION: maize optimized moCAS9 endonuclease

<400> SEQUENCE: 23

```
ctgcagtgca gcgtgacccg gtcgtgcccc tctctagaga taatgagcat tgcatgtcta      60
agttataaaa aattaccaca tatttttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga     240
gtattttgac aacaggactc tacagtttta tcttttagt gtgcatgtgt tctccttttt      300
ttttgcaaat agcttcacct atataatact tcatccattt tattagtaca tccatttagg     360
gtttagggtt aatggttttt atagactaat tttttagta catctatttt attctatttt      420
agcctctaaa ttaagaaaac taaaactcta tttagtttt tttatttaat aatttagata      480
taaaatagaa taaaataaag tgactaaaaa ttaaacaaat acccttaag aaattaaaaa       540
aactaaggaa acattttct tgtttcgagt agataatgcc agcctgttaa acgccgtcga      600
cgagtctaac ggacaccaac cagcgaacca gcagcgtcgc gtcgggccaa gcgaagcaga     660
cggcacggca tctctgtcgc tgcctctgga cccctctcga gagttccgct ccaccgttgg     720
acttgctccg ctgtcggcat ccagaaattg cgtggcggag cggcagacgt gagccggcac     780
ggcaggcggc ctcctcctcc tctcacggca cggcagctac gggggattcc tttcccaccg     840
ctccttcgct ttcccttcct cgcccgccgt aataaataga cacccctcc acaccctctt      900
tccccaacct cgtgttgttc ggagcgcaca cacacacaac cagatctccc ccaaatccac     960
ccgtcggcac ctccgcttca aggtacgccg ctcgtcctcc cccccccccc tctctacctt    1020
ctctagatcg gcgttccggt ccatgcatgg ttagggcccg gtagttctac ttctgttcat    1080
gtttgtgtta gatccgtgtt tgtgttagat ccgtgctgct agcgttcgta cacggatgcg    1140
acctgtacgt cagacacgtt ctgattgcta acttgccagt gtttctcttt ggggaatcct    1200
gggatggctc tagccgttcc gcagacggga tcgatttcat gatttttttt gtttcgttgc    1260
ataggggtttg gtttgccctt ttcctttatt tcaatatatg ccgtgcactt gtttgtcggg   1320
tcatcttttc atgcttttt ttgtcttggt tgtgatgatg tggtctggtt gggcggtcgt     1380
tctagatcgg agtagaattc tgtttcaaac tacctggtgg atttattaat tttggatctg    1440
tatgtgtgtg ccatacatat tcatagttac gaattgaaga tgatggatgg aaatatcgat    1500
ctaggatagg tatacatgtt gatgcgggtt ttactgatgc atatacagag atgctttttg    1560
ttcgcttggt tgtgatgatg tggtgtggtt gggcggtcgt tcattcgttc tagatcggag    1620
tagaatactg tttcaaacta cctggtgtat ttattaattt tggaactgta tgtgtgtgtc    1680
atacatcttc atagttacga gtttaagatg gatggaaata tcgatctagg ataggtatac    1740
atgttgatgt gggttttact gatgcatata catgatggca tatgcagcat ctattcatat    1800
gctctaacct tgagtaccta tctattataa taaacaagta tgttttataa ttattttgat    1860
cttgatatac ttggatgatg gcatatgcag cagctatatg tggattttt tagccctgcc     1920
ttcatacgct atttatttgc ttggtactgt ttcttttgtc gatgctcacc ctgttgtttg    1980
gtgttacttc tgcaggtcga ctctagagga tccccatggc cccgaagaag aagaggaagg    2040
tgcacatgga taagaagtac agcatcggcc tcgacatcgg gaccaacagc gtcggctggg    2100
ccgtcatcac cgacgaatat aaggtgccca gcaagaagtt caaggtgctc gggaatacag    2160
accgccacag catcaagaag aacctgatcg gcgccctcct gttcgactcg ggcgagaccg    2220
ctgaggccac cagactaaag aggaccgctc gccgccgcta cacccgccgc aagaaccgca    2280
```

```
tatgctacct ccaggagatc ttcagcaacg agatggccaa ggtggacgac agcttcttcc    2340
accgccttga ggagtcgttc ctcgtggagg aggacaagaa gcatgagagg cacccgatct    2400
tcgggaacat cgtggacgag gtaagtttct gcttctacct ttgatatata tataataatt    2460
atcattaatt agtagtaata taatatttca aatattttt tcaaaataaa agaatgtagt     2520
atatagcaat tgcttttctg tagtttataa gtgtgtatat tttaatttat aacttttcta    2580
atatatgacc aaaacatggt gatgtgcagg tggcgtacca cgagaagtac ccgacgatct    2640
accacctccg caagaagctg gtcgactcca cagacaaggc cgacctcaga ctgatctacc    2700
tggccctcgc gcacatgatc aagttccgcg gcacttcct catcgagggc gacctgaacc     2760
cggacaactc cgacgtcgac aagctcttca tccagctggt ccagacctac aatcaactgt    2820
tcgaggagaa cccgatcaac gcgtccgcg tggacgcgaa ggccatcctc agcgcgaggc     2880
tcagcaaatc aagacggctg gagaacctga tcgcccagct cccaggcgag aagaaaaacg    2940
gcttgttcgg caacctgatc gcgctctcgc tcggcctcac gcccaacttc aaatcaaact    3000
tcgacctggc cgaggacgcg aaactgcagc tgtccaagga cacttacgac gacgacctcg    3060
acaacctgct ggcgcaaatc ggtgaccagt acgcagacct cttcctggcc gccaagaacc    3120
tctcggacgc catcctgctg tccgatatcc tgagagtgaa tacggagatc accaaggcgc    3180
cgctcagcgc ctccatgatt aaaaggtacg acgagcacca ccaggacctg acgctgctca    3240
aggccctggt gcgccagcag ctccccgaga gtacaagga tcttcttc gaccaatcaa       3300 aaaacggcta cgccggctac atcgacgggg cgcctccca ggaggagttc tacaagttca     3360
tcaaaccaat tctcgagaag atggacggca cggaggagct tctcgtgaag ctcaaccggg    3420
aggacctcct gaggaagcag aggacgttcg acaacggctc gataccgcat cagatccacc    3480
tgggcgagct ccacgccatc ctgcgccggc aggaggattt ctatccgttc tcaaggaca    3540 acagggagaa gatcgagaaa attctgacgt tccgcatccc gtactacgtg ggccctctcg    3600
cgcgcgggaa cagccggttc gcctggatga ctcggaagtc ggaggagacg atcacgccgt    3660
ggaacttcga ggaggtggtg gacaagggcg cctccgccca gtcgttcatc gagcgcatga    3720
cgaacttcga taaaaatctg cccaatgaaa aagtgctccc gaagcacagc ctcctctacg    3780
agtacttcac ggtgtacaac gagctcacga aggtgaagta cgtgaccgag ggtatgcgga    3840
agccggcgtt cctgagcggc gagcagaaga aggccatcgt ggacctcctc ttcaagacga    3900
accggaaagt caccgtgaag caattaaagg aggactactt caagaaaata gagtgcttcg    3960
acagcgtcga gatctcgggc gtcgaggaca ggttcaacgc gtcgctgggc acataccacg    4020
acctcctcaa gatcattaaa gacaaggact cctggacaa cgaggagaac gaggacatcc     4080
tcgaggacat cgtgctgacc ctcacccctgt ttgaggaccg ggagatgatc gaggagcgcc   4140
tcaagacgta cgctcacctt ttcgacgaca aggtgatgaa acagctgaag cggcgccgct    4200
acaccggatg gggccggctc tcccgcaagc tcattaatgg gatcagggac aagcagtccg    4260
gcaagaccat actcgatttc ctgaagagcg acggcttcgc caaccggaac ttcatgcagc    4320
tcatccacga cgactccctc actttcaagg aggacatcca gaaggcccag gtcagcggac    4380
agggcgactc gctccacgaa cacatcgcca acctggccgg gtcgcctgcg attaaaaagg    4440
gaatccttca gaccgtcaag gtcgtggacg agctggtgaa ggtgatgggc aggcacaagc    4500
ccgaaaatat cgtcattgag atggcccggg agaaccagac cacgcagaaa ggccagaaga    4560
acagccggga gcgcatgaaa cggatcgagg agggtatcaa ggagctgggc tcgcagatcc    4620
tcaaggagca ccctgtggaa aatacccagc tgcagaatga aaagctctac ctctactacc    4680
```

```
tccagaacgg ccgcgacatg tacgtggacc aggagctgga cattaatcgc ctctcggact    4740
acgacgtcga ccacatcgtc ccgcagtcct tcctgaagga cgacagcatc gacaacaagg    4800
tcttgacccg ctccgataaa aatcgcggga agtccgacaa cgtgccgtcg gaggaggtgg    4860
tcaagaagat gaaaaactac tggcgccagc tgctcaacgc caagctaatc acgcagcgca    4920
agttcgacaa cctcaccaag gccgaacgcg gcggtctctc cgagcttgat aaggctgggt    4980
tcatcaagag acagctggtg gagacccggc agatcaccaa gcatgtcgcc cagatcctgg    5040
actcgcgcat gaatactaag tacgatgaaa acgacaagct catccgcgag gtgaaggtga    5100
tcaccctgaa gagcaagctg gtctcggact tccggaagga cttccagttc tacaaggtcc    5160
gggagatcaa caactaccac cacgcgcacg acgcctacct gaacgcggtg gtgggcacag    5220
cccttataaa gaagtaccct aagctcgagt ccgagttcgt gtacggcgac tacaaggtgt    5280
acgacgtccg caagatgatc gcgaagagcg agcaggagat cgggaaggcc accgcaaaat    5340
acttcttcta ctccaacatc atgaacttct tcaagaccga gatcacccctg ccaacgggg    5400
agatccgcaa gcgcccgctg attgagacga acggagagac aggcgagata gtctgggaca    5460
agggcagggt cttcgccacc gtgcgcaagg ttctgtccat gccgcaggtg aacatcgtga    5520
agaagactga ggtgcagaca ggcggcttct cgaaggagtc catcctgccc aagcggaaca    5580
gcgacaagct catccgcgcg aagaaggact gggaccctaa aaaatatggc gggttcgact    5640
cgcccaccgt ggcttactcg gtcctcgtgg tggccaaggt cgagaagggc aaaagcaaga    5700
agctgaagag cgtcaaggag ctcctcggca tcaccatcat ggagcggtcc agcttcgaga    5760
agaacccgat cgacttcctc gaggcgaagg gatataagga ggtgaagaag gacctcatca    5820
ttaaactgcc gaagtactcg ctattcgaac tggagaatgg tcgcaagagg atgctcgcga    5880
gcgctggcga gctgcagaaa gggaacgagc tggctctccc gagcaagtac gtcaacttcc    5940
tctacctggc ctcccactat gaaaagctca agggctcgcc ggaggacaac gagcagaagc    6000
agctgttcgt cgagcagcac aagcattacc tcgacgagat catcgagcag atctcggagt    6060
tcagcaagcg cgtgatcctg gccgacgcca acctcgacaa ggtgctgtcc gcatataaca    6120
agcaccgcga caaaccaata cgggagcagg ccgaaaatat catccacctg ttcaccctca    6180
cgaacctggg cgccccccgcc gcgttcaagt acttcgacac aaccatcgac cgcaagcggt    6240
acacgagcac gaaggaggtg ctggacgcca cgttgattca ccagtccatc acgggcctgt    6300
atgaaacaag gatcgatctc agccagctcg gcggcgacta ggtaccacat ggttaaccta    6360
gacttgtcca tcttctggat tggccaactt aattaatgta tgaaataaaa ggatgcacac    6420
atagtgacat gctaatcact ataatgtggg catcaaagtt gtgtgttatg tgtaattact    6480
agttatctga ataaaagaga aagagatcat ccatatttct tatcctaaat gaatgtcacg    6540
tgtctttata attctttgat gaaccagatg catttcatta accaaatcca tatacatata    6600
aatattaatc atatataatt aatatcaatt gggttagcaa aacaaatcta gtctaggtgt    6660
gttttgcgaa ttgcggc                                                  6677
```

```
<210> SEQ ID NO 24
<211> LENGTH: 100
<212> TYPE: DNA
<213> ORGANISM: Artificial sequence
<220> FEATURE:
<223> OTHER INFORMATION: DNA version of guide RNA (EPSPS sgRNA)

<400> SEQUENCE: 24
```
gcagtaacag ctgctgtcaa gttttagagc tagaaatagc aagttaaaat aaggctagtc    60
cgttatcaac ttgaaaaagt ggcaccgagt cggtgctttt    100

<210> SEQ ID NO 25
<211> LENGTH: 3708
<212> TYPE: DNA
<213> ORGANISM: Artificial sequence
<220> FEATURE:
<223> OTHER INFORMATION: EPSPS polynucleotide template

<400> SEQUENCE: 25
ctgcagccca tcaaggagat ctccggcacc gtcaagctgc cggggtccaa gtcgctttcc    60
aacaggatcc tcctgctcgc cgccctgtcc gaggtgagcg atttggtgc ttgctgcgct    120 gccctgtctc actgctacct aaatgtttg cctgtcgaat accatggatt ctcggtgtaa    180
tccatctcac gatcagatgc accgcatgtc gcatgcctag ctctctctaa tttgtctagt    240
agtttgtata cggattaaga ttgataaatc ggtaccgcaa aagctaggtg taaataaaca    300
ctacaaaatt ggatgttccc ctatcggcct gtactcggct actcgttctt gtgatggcat    360
gttatttctt cttggtgttt ggtgaactcc cttatgaaat tgggcgcaa agaaatcgcc    420 ctcaagggtt gatcttatgc catcgtcatg ataaacagtg aagcacggat gatcctttac    480
gttgttttta acaaactttg tcagaaaact agcaatgtta acttcttaat gatgatttca    540
caacaaaaaa ggtaaccttg ctactaacat aacaaaagac ttgttgctta ttaattatat    600 gttttttaa tctttgatca ggggacaaca gtggttgata acctgttgaa cagtgaggat    660
gtccactaca tgctcggggc cttgaggact cttggtctct ctgtcgaagc ggacaaagct    720
gccaaaagag ctgtagttgt tggctgtggt ggaaagttcc cagttgagga tgctaaagag    780
gaagtgcagc tcttcttggg gaatgctgga atcgcaatgc ggtcattgac agcagctgtt    840
actgctgctg gtggaaatgc aacgtatgtt cctctctctct ctctacaata cttgttggag    900
ttagtatgaa acccatgtgt atgtctagtg gcttatggtg tattggtttt tgaacttcag    960
ttacgtgctt gatggagtac caagaatgag ggagagaccc attggcgact tggttgtcgg    1020
attgaagcag cttggtgcag atgttgattg tttccttggc actgactgcc cacctgttcg    1080
tgtcaatgga atcggagggc tacctggtgg caaggttagt tactaagggc cacatgttac    1140
attcttctgt aaatggtaca actattgtcg agcttttgca tttgtaagga aaacattgat    1200
tgatctgaat ttgatgctac accacaaaat atctacaaat ggtcatccct aactagcaaa    1260
ccatgtctcc attaagctca atgaagtaat acttggcatg tgtttatcaa cttaatttcc    1320
atcttctggg gtattgcctg ttttctagtc taatagcatt tgttttaga attagctctt    1380 acaactgtta tgttctacag gtcaagctgt ctggctccat cagcagtcag tacttgagtg    1440
ccttgctgat ggctgctcct ttggctcttg gggatgtgga gattgaaatc attgataaat    1500
taatctccat tccctacgtc gaaatgacat tgagattgat ggagcgtttt ggtgtgaaag    1560
cagagcattc tgatagctgg gacagattct acattaaggg aggtcaaaaa tacaagtaag    1620
ctctgtaatg tatttcacta ctttgatgcc aatgtttcag ttttcagttt tccaaacagt    1680
cgcatcaata tttgaataga tgcactgtag aaaaaaatca ttgcagggaa aaactagtac    1740
tgagtatttt gactgtaaat tatttaacca gtcggaatat agtcagtcta ttggagtcaa    1800
gagcgtgaac cgaaatagcc agttaattat cccattatac agaggacaac catgtatact    1860
attgaaactt ggtttaagag aatctaggta gctggactcg tagctgcttg gcatggatac    1920
cttcttatct ttaggaaaag acacttgatt tttttctgt ggccctctat gatgtgtgaa    1980

```
cctgcttctc tattgcttta gaaggatata tctatgtcgt tatgcaacat gcttccctta    2040
gtcatttgta ctgaaatcag tttcataagt tcgttagtgg ttccctaaac gaaaccttgt    2100
ttttctttgc aatcaacagg tcccctaaaa atgcctatgt tgaaggtgat gcctcaagcg    2160
caagctattt cttggctggt gctgcaatta ctggagggac tgtgactgtg aaggttgtg     2220 gcaccaccag tttgcaggta aagatttctt ggctggtgct acgataactg cttttgtctt    2280
tttggtttca gcattgttct cagagtcact aaataacatt atcatctgca aacgtcaaat    2340
agacatactt aggtgaatgg atattcatgt aaccgtttcc ttacaaattt gctgaaacct    2400
cagggtgatg tgaagtttgc tgaggtactg gagatgatgg gagcgaaggt tacatggacc    2460
gagactagcg taactgttac tggcccaccg cgggagccat tgggaggaa acacctcaag     2520 gcgattgatg tcaacatgaa caagatgcct gatgtcgcca tgactcttgc tgtggttgcc    2580
ctctttgccg atggcccgac agccatcaga gacggtaaaa cattctcagc cctacaacca    2640
tgcctcttct acatcactac ttgacaagac taaaaactat tggctcgttg gcagtggctt    2700
cctggagagt aaaggagacc gagaggatgg ttgcgatccg gacggagcta accaaggtaa    2760
ggctacatac ttcacatgtc tcacgtcgtc tttccatagc tcgctgcctc ttagcggctt    2820
gcctgcggtc gctccatcct cggttgctgt ctgtgttttc cacagctggg agcatctgtt    2880
gaggaagggc cggactactg catcatcacg ccgccgagaa agctgaacgt gacggcgatc    2940
gacacgtacg acgaccacag gatggccatg gccttctccc ttgccgcctg tgccgaggtc    3000
cccgtgacca tccgggaccc tgggtgcacc cggaagacct tccccgacta cttcgatgtg    3060
ctgagcactt tcgtcaagaa ttaataaagc gtgcgatact accacgcagc ttgattgaag    3120
tgataggctt gtgctgagga aatacatttc ttttgttctg ttttttctct ttcacgggat    3180
taagttttga gtctgtaacg ttagttgttt gtagcaagtt tctatttcgg atcttaagtt    3240
tgtgcactgt aagccaaatt tcatttcaag agtggttcgt tggaataata agaataataa    3300
attacgtttc agtggctgtc aagcctgctg ctacgttta ggagatggca ttagacattc     3360
atcatcaaca acaataaaac cttttagcct caaacaataa tagtgaagtt attttttagt    3420
cctaaacaag ttgcattagg atatagttaa aacacaaaag aagctaaagt tagggtttag    3480
acatgtggat attgttttcc atgtatagta tgttctttct ttgagtctca tttaactacc    3540
tctacacata ccaactttag tttttttct acctcttcat gttactatgg tgccttctta     3600
tcccactgag cattggtata tttagaggtt tttgttgaac atgcctaaat catctcaatc    3660
aacgatggac aatcttttct tcgattgagc tgaggtacgt catctaga               3708
```

<210> SEQ ID NO 26
<211> LENGTH: 15
<212> TYPE: DNA
<213> ORGANISM: Artificial sequence
<220> FEATURE:
<223> OTHER INFORMATION: TIPS nucleotide modifications

<400> SEQUENCE: 26
atcgcaatgc ggtca    15

<210> SEQ ID NO 27
<211> LENGTH: 19
<212> TYPE: DNA
<213> ORGANISM: Artificial sequence
<220> FEATURE:
<223> OTHER INFORMATION: Primer Seqeunce-1 F-E2

```
<400> SEQUENCE: 27
ccgaggagat cgtgctgca                                                 19

<210> SEQ ID NO 28
<211> LENGTH: 20
<212> TYPE: DNA
<213> ORGANISM: Artificial sequence
<220> FEATURE:
<223> OTHER INFORMATION: Primer Seqeunce-2 F-E2

<400> SEQUENCE: 28
caatggccgc attgcagttc                                                20

<210> SEQ ID NO 29
<211> LENGTH: 19
<212> TYPE: DNA
<213> ORGANISM: Artificial sequence
<220> FEATURE:
<223> OTHER INFORMATION: Primer Seqeunce-1 F-T

<400> SEQUENCE: 29
ccgaggagat cgtgctgca                                                 19

<210> SEQ ID NO 30
<211> LENGTH: 20
<212> TYPE: DNA
<213> ORGANISM: Artificial sequence
<220> FEATURE:
<223> OTHER INFORMATION: Primer Seqeunce-2 F-T

<400> SEQUENCE: 30
tgaccgcatt gcgattccag                                                20

<210> SEQ ID NO 31
<211> LENGTH: 24
<212> TYPE: DNA
<213> ORGANISM: Artificial sequence
<220> FEATURE:
<223> OTHER INFORMATION: Primer Seqeunce-1 H-T

<400> SEQUENCE: 31
tccaagtcgc tttccaacag gatc                                           24

<210> SEQ ID NO 32
<211> LENGTH: 20
<212> TYPE: DNA
<213> ORGANISM: Artificial sequence
<220> FEATURE:
<223> OTHER INFORMATION: Primer Seqeunce-2 H-T

<400> SEQUENCE: 32
tgaccgcatt gcgattccag                                                20

<210> SEQ ID NO 33
<211> LENGTH: 19
<212> TYPE: DNA
<213> ORGANISM: Artificial sequence
<220> FEATURE:
<223> OTHER INFORMATION: Primer Seqeunce-1 F-E3

<400> SEQUENCE: 33
ccgaggagat cgtgctgca                                                 19

<210> SEQ ID NO 34
<211> LENGTH: 24
```

```
<212> TYPE: DNA
<213> ORGANISM: Artificial sequence
<220> FEATURE:
<223> OTHER INFORMATION: Primer Seqeunce-2 F-E3

<400> SEQUENCE: 34
accaagctgc ttcaatccga caac                                           24

<210> SEQ ID NO 35
<211> LENGTH: 63
<212> TYPE: DNA
<213> ORGANISM: Artificial sequence
<220> FEATURE:
<223> OTHER INFORMATION: DNA fragment with intact Cas target sequence

<400> SEQUENCE: 35
ggggaatgct ggaactgcaa tgcggccatt gacagcagct gttactgctg ctggtggaaa   60
tgc                                                                  63

<210> SEQ ID NO 36
<211> LENGTH: 60
<212> TYPE: DNA
<213> ORGANISM: Artificial sequence
<220> FEATURE:
<223> OTHER INFORMATION: DNA fragment with mutated Cas target sequence

<400> SEQUENCE: 36
ggggaatgct ggaactgcaa tgcggccatt ggcagctgtt actgctgctg gtggaaatgc   60

<210> SEQ ID NO 37
<211> LENGTH: 50
<212> TYPE: DNA
<213> ORGANISM: Artificial sequence
<220> FEATURE:
<223> OTHER INFORMATION: DNA fragment with mutated Cas target sequence

<400> SEQUENCE: 37
ggggaatgct ggaactgcac agcagctgtt actgctgctg gtggaaatgc               50

<210> SEQ ID NO 38
<211> LENGTH: 33
<212> TYPE: DNA
<213> ORGANISM: Artificial sequence
<220> FEATURE:
<223> OTHER INFORMATION: DNA fragment with mutated Cas target sequence

<400> SEQUENCE: 38
ggggaatgct gttactgctg ctggtggaaa tgc                                 33

<210> SEQ ID NO 39
<211> LENGTH: 51
<212> TYPE: DNA
<213> ORGANISM: Artificial sequence
<220> FEATURE:
<223> OTHER INFORMATION: TIPS edited EPSPS nucleotide sequence fragment

<400> SEQUENCE: 39
aatgctggaa tcgcaatgcg gtcattgaca gcagctgtta ctgctgctgg t             51

<210> SEQ ID NO 40
<211> LENGTH: 51
<212> TYPE: DNA
<213> ORGANISM: Artificial sequence
<220> FEATURE:
<223> OTHER INFORMATION: Wild-type epsps nucleotide sequence  fragment
```

```
<400> SEQUENCE: 40
aatgctggaa ctgcaatgcg gccattgaca gcagctgtta ctgctgctgg t          51

<210> SEQ ID NO 41
<211> LENGTH: 20
<212> TYPE: DNA
<213> ORGANISM: Artificial sequence
<220> FEATURE:
<223> OTHER INFORMATION: Mprimer qADH-F

<400> SEQUENCE: 41
caagtcgcgg ttttcaatca                                             20

<210> SEQ ID NO 42
<211> LENGTH: 21
<212> TYPE: DNA
<213> ORGANISM: Artificial sequence
<220> FEATURE:
<223> OTHER INFORMATION: Primer qADH-R

<400> SEQUENCE: 42
tgaaggtgga agtcccaaca a                                           21

<210> SEQ ID NO 43
<211> LENGTH: 19
<212> TYPE: DNA
<213> ORGANISM: Artificial sequence
<220> FEATURE:
<223> OTHER INFORMATION: probe ADH-VIC

<400> SEQUENCE: 43
tgggaagcct atctaccac                                              19

<210> SEQ ID NO 44
<211> LENGTH: 15
<212> TYPE: DNA
<213> ORGANISM: Artificial sequence
<220> FEATURE:
<223> OTHER INFORMATION: Probe wtEPSPS

<400> SEQUENCE: 44
cggccattga cagca                                                  15

<210> SEQ ID NO 45
<211> LENGTH: 20
<212> TYPE: DNA
<213> ORGANISM: Artificial sequence
<220> FEATURE:
<223> OTHER INFORMATION: Forward primer qEPSPS-F

<400> SEQUENCE: 45
tcttggggaa tgctggaact                                             20

<210> SEQ ID NO 46
<211> LENGTH: 21
<212> TYPE: DNA
<213> ORGANISM: Artificial sequence
<220> FEATURE:
<223> OTHER INFORMATION: reverse primer qEPSPSR

<400> SEQUENCE: 46
caccagcagc agtaacagct g                                           21

<210> SEQ ID NO 47
<211> LENGTH: 17
```

```
<212> TYPE: DNA
<213> ORGANISM: Artificial sequence
<220> FEATURE:
<223> OTHER INFORMATION: FAM-wtEPSPS R probe

<400> SEQUENCE: 47
tgctgtcaat ggccgca                                                  17

<210> SEQ ID NO 48
<211> LENGTH: 20
<212> TYPE: DNA
<213> ORGANISM: Artificial sequence
<220> FEATURE:
<223> OTHER INFORMATION: forward primer qEPSPS-F

<400> SEQUENCE: 48
tcttggggaa tgctggaact                                               20

<210> SEQ ID NO 49
<211> LENGTH: 20
<212> TYPE: DNA
<213> ORGANISM: Artificial sequence
<220> FEATURE:
<223> OTHER INFORMATION: reverse primer q wtEPSPS RA

<400> SEQUENCE: 49
ccaccagcag cagtaacagc                                               20

<210> SEQ ID NO 50
<211> LENGTH: 21
<212> TYPE: DNA
<213> ORGANISM: Artificial sequence
<220> FEATURE:
<223> OTHER INFORMATION: forward primer q epTIPS F

<400> SEQUENCE: 50
ggaagtgcag ctcttcttgg g                                             21

<210> SEQ ID NO 51
<211> LENGTH: 19
<212> TYPE: DNA
<213> ORGANISM: Artificial sequence
<220> FEATURE:
<223> OTHER INFORMATION: reverse primer q epTIPS R

<400> SEQUENCE: 51
agctgctgtc aatgaccgc                                                19

<210> SEQ ID NO 52
<211> LENGTH: 15
<212> TYPE: DNA
<213> ORGANISM: Artificial sequence
<220> FEATURE:
<223> OTHER INFORMATION: TIPS probe

<400> SEQUENCE: 52
aatgctggaa tcgca                                                    15

<210> SEQ ID NO 53
<211> LENGTH: 28
<212> TYPE: DNA
<213> ORGANISM: Artificial sequence
<220> FEATURE:
<223> OTHER INFORMATION: WOL1006, Reverse_primer

<400> SEQUENCE: 53
```

```
attatttttc cgtacatgat gtaaccgc                                          28
```

<210> SEQ ID NO 54
<211> LENGTH: 6274
<212> TYPE: DNA
<213> ORGANISM: Zea mays, L.
<220> FEATURE:
<221> NAME/KEY: misc_feature
<222> LOCATION: (1)..(6274)
<223> OTHER INFORMATION: EPSPS-duplication template

<400> SEQUENCE: 54

```
gatctccggc accgtcaagc tgccggggtc caagtcgctt ccaacagga tcctcctgct        60
cgccgccctg tccgaggtga gcgattttgg tgcttgctgc gctgccctgt ctcactgcta       120
cctaaatgtt ttgcctgtcg aataccatgg attctcggtg taatccatct cacgatcaga       180
tgcaccgcat gtcgcatgcc tagctctctc taatttgtct agtagtttgt atacggatta       240
agattgataa atcggtaccg caaaagctag gtgtaaataa acactacaaa attggatgtt       300
cccctatcgg cctgtactcg gctactcgtt cttgtgatgg catgttattt cttcttggtg       360
tttggtgaac tcccttatga aatttgggcg caaagaaatc gccctcaagg gttgatctta       420
tgccatcgtc atgataaaca gtgaagcacg gatgatcctt tacgttgttt ttaacaaact       480
ttgtcagaaa actagcaatg ttaacttctt aatgatgatt tcacaacaaa aaaggtaacc       540
ttgctactaa cataacaaaa gacttgttgc ttattaatta tatgtttttt taatctttga       600
tcaggggaca acagtggttg ataacctgtt gaacagtgag gatgtccact acatgctcgg       660
ggccttgagg actcttggtc tctctgtcga agcggacaaa gctgccaaaa gagctgtagt       720
tgttggctgt ggtggaaagt tcccagttga ggatgctaaa gaggaagtgc agctcttctt       780
ggggaatgct ggaatcgcaa tgcggtcatt gacagcagct gttactgctg ctggtggaaa       840
tgcaacgtat gtttcctctc tctctctaca atacttgttg gagttagtat gaaacccatg       900
tgtatgtcta gtggcttatg gtgtattggt ttttgaactt cagttacgtg cttgatggag       960
taccaagaat gagggagaga cccattggcg acttggttgt cggattgaag cagcttggtg      1020
cagatgttga ttgtttcctt ggcactgact gcccacctgt tcgtgtcaat ggaatcggag      1080
ggctacctgg tggcaaggtt agttactaag ggccacatgt tatattcttc tgtaaatggt      1140
acaactattg tcgagctttt gcatttgtaa ggaaaacatt gaatgatctg aatttgatgc      1200
tacaccacaa aatatctaca aatggtcatc cctaactagc aaaccatgtc tccattaagc      1260
tcaatgaagt aacacttggc atgtgtttat caacttaatt tccatcttct ggggtattgc      1320
ctgttttcta gtctaatagc atttgttttt agcatgaatt agctcttaca actgttatgt      1380
tctacaggtc aagctgtctg ctccatcag cagtcagtac ttgagtgcct tgctgatggc       1440
tgctcctttg gctcttgggg atgtggagat tgaaatcatt gataaattaa tctccattcc      1500
gtacgtcgaa atgacattga gattgatgga gcgttttggt gtgaaagcag agcattctga      1560
tagctgggac agattctaca ttaagggagg tcaaaaatac aagtaagctc tgtaatgtat      1620
ttcactactt tgatgccaat gtttcagttt tcagttttcc aaacagtcgc atcaatattt      1680
gaatagatgc actgtagaaa aaaaatcatt gcagggaaaa aaactagcac tgagtatttt      1740
gactgtaaat tatttaacca gtcggaatat agtcagtcta ttggagtcaa gagcgtgaac      1800
cgaaataacc agttaattat cccattatac agaggacaac catgtatact attgaaactt      1860
ggtttataag agaatctagg tagctggact cgtagctgct tggcatggat accttcttat      1920
cttcaggaaa agacacttga tttttttttct gtggccctct atgatgtgtg aacctgcttc      1980
```

```
tctattgctt tagaaggata tatccatgtt gttatgcaac atgcttccct tagtcatttg    2040
tactgaaatc agtttcataa gttcgttagt ggttccctaa acgaaacctt gtttttcttt    2100
gcaatcaaca ggtcccctaa aaatgcctat gttgaaggtg atgcctcaag cgcaagctat    2160
ttcttggctg gtgctgcaat tactggaggg actgtgactg tggaaggttg tggcaccacc    2220
agtttgcagg taaagatttc ttggctggtg ctacaataac tgcttttgtc ttttggttt     2280 cagcattgtt ctcagagtca ctaaataaca ttatcatctg caaatgtcaa atagacatac    2340
ttaggtgaat ggatattcat gtaaccgttt ccttacaaat ttgctgaaac ctcagggtga    2400
tgtgaagttt gctgaggtac tggagatgat gggagcgaag gttacatgga ccagactag     2460 cgtaactgtt actggcccac cgcgggagcc atttggggagg aaacacctca aggcgattga   2520
tgtcaacatg aacaagatgc ctgatgtcgc catgactctt gctgtggttg ccctctttgc    2580
cgatggcccg acagccatca gagacggtaa acattctca  gccctacaac catgcctctt    2640
ctacatcact acttgacaag actaaaaact attggctcgt tggcagtggc ttcctggaga    2700
gtaaaggaga ccgagaggat ggttgcgatc cggacggagc taaccaaggt aaggctacat    2760
acttcacatg tctcacgtcg tctttccata gctcgctgcc tcttagcggc ttgcctgcgg    2820
tcgctccatc ctcggttgct gtctgtgttt tccacagctg ggagcatctg ttgaggaagg    2880
gccggactac tgcatcatca cgccgccgga gaagctgaac gtgacggcga tcgacacgta    2940
cgacgaccac aggatggcca tggccttctc ccttgccgcc tgtgccgagg tccccgtcac    3000
catccgggac cctgggtgca cccggaagac cttccccgac tacttcgatg tgctgagcac    3060
tttcgtcaag aatggcggcg gtagcggcgg tggctctggc ggtggctcgg atccaacaat    3120
ggcggccatg gcgaccaagg ccgcgcgggg caccgtgtcg ctggacctcg ccgcgccgtc    3180
gcgccgccac caccgcccga gctcggcgcg cccgcccttc cgccccgccg tccgcgggct    3240
gcgggcgcct gggcgccgcg tgatcgccgc gccgccggcg gcggcagcgg cggcggcggt    3300
gcaggcgggt gccgaggaga tcgtgctgca gcccatcaag gagatctccg gcaccgtcaa    3360
gctgccgggg tccaagtcgc tttccaaccg gatcctccta ctcgccgccc tgtccgaggt    3420
gagcgatttt ggtgcttgct gcgctgccct gtctcactgc tacctaaatg ttttgcctgt    3480
cgaataccat gtattctcgg tgtaatccat ctcacgatca gatgcaccgc atatcgcatg    3540
ccctagctct ctctaattg tctagtagtt tgtatacgga ttaatattga taaatcggta    3600
ccgcaaaagc tagctgtaaa taaacactag aaaattggat gttcccctat cggcctgtac    3660
tcggctactc gttcttgtga tggcatgctg tctcttcttg gtgtttggtg aactccctta    3720
tgaaatttgg gcgcaaagaa ctcgccctca agggttgatc ttatgccatc gtcatgataa    3780
acagtgaagc actgatgatc ctttacgttg tttttaacaa actttgtcag aaaactagca    3840
ttgttaactt cttaatgatg atttcacaac aaaaaaggca accttgctac taacataaca    3900
aaagacttgt tgcttattaa ttatatgttt ttttaatctt tgatcagggg acaacagtgg    3960
ttgataacct gctgaacagt gaggatgtcc actacatgct cggggccttg aggactcttg    4020
gtctctctgt cgaagcggac aaagctgcca aaagagctgt agttgttggc tgtggtggaa    4080
agttcccagt tgaggatgct aaagaggaag tgcagctctt cttggggaat gctggaatcg    4140
caatgcggtc attgacagca gctgttactg ctgctggtgg aaatgcaacg tatgtttcct    4200
ctctctctac aatacttgtt ggagttagta tgaaacccat gtgtatgtct agtggcttat    4260
ggtgtattgg tttttgaact tcagttacgt gcttgatgga gtaccaagaa tgagggagag    4320
```

| | |
|---|---|
| acccattggc gacttggttg tcggattgaa gcagcttggt gcagatgttg attgtttcct | 4380 |
| tggcactgac tgcccacctg ttcgtgtcaa tggaatcgga gggctacctg gtggcaaggt | 4440 |
| tagttactaa gggccacatg ttacattctt ctgtaaatgg tacaactatt gtcgagcttt | 4500 |
| tgcatttgta aggaaaacat tgattgatct gaatttgatg ctacaccaca aaatatctac | 4560 |
| aaatggtcat ccctaactag caaaccatgt ctccattaag ctcaatgaag taatacttgg | 4620 |
| catgtgttta tcaacttaat ttccatcttc tggggtattg cctgttttct agtctaatag | 4680 |
| catttgtttt tagaattagc tcttacaact gttatgttct acaggtcaag ctgtctggct | 4740 |
| ccatcagcag tcagtacttg agtgccttgc tgatggctgc tcctttggct cttggggatg | 4800 |
| tggagattga atcattgat aaattaatct ccattcccta cgtcgaaatg acattgagat | 4860 |
| tgatggagcg ttttggtgtg aaagcagagc attctgatag ctgggacaga ttctacatta | 4920 |
| agggaggtca aaaatacaag taagctctgt aatgtatttc actactttga tgccaatgtt | 4980 |
| tcagttttca gttttccaaa cagtcgcatc aatatttgaa tagatgcact gtagaaaaaa | 5040 |
| atcattgcag ggaaaaacta gtactgagta ttttgactgt aaattattta accagtcgga | 5100 |
| atatagtcag tctattggag tcaagagcgt gaaccgaaat agccagttaa ttatcccatt | 5160 |
| atacagagga caaccatgta tactattgaa acttggttta agagaatcta ggtagctgga | 5220 |
| ctcgtagctg cttggcatgg ataccttctt atctttagga aaagacactt gattttttt | 5280 |
| ctgtggccct ctatgatgtg tgaacctgct tctctattgc tttagaagga tatatctatg | 5340 |
| tcgttatgca acatgcttcc cttagtcatt tgtactgaaa tcagtttcat aagttcgtta | 5400 |
| gtggttccct aaacgaaacc ttgttttct ttgcaatcaa caggtcccct aaaaatgcct | 5460 |
| atgttgaagg tgatgcctca agcgcaagct atttcttggc tggtgctgca attactggag | 5520 |
| ggactgtgac tgtggaaggt tgtggcacca ccagtttgca ggtaaagatt tcttggctgg | 5580 |
| tgctacgata actgcttttg tcttttggt ttcagcattg ttctcagagt cactaaataa | 5640 |
| cattatcatc tgcaaacgtc aaatagacat acttaggtga atggatattc atgtaaccgt | 5700 |
| ttccttacaa atttgctgaa acctcagggt gatgtgaagt ttgctgaggt actggagatg | 5760 |
| atgggagcga aggttacatg gaccgagact agcgtaactg ttactggccc accgcgggag | 5820 |
| ccatttggga ggaaacacct caaggcgatt gatgtcaaca tgaacaagat gcctgatgtc | 5880 |
| gccatgactc ttgctgtggt tgccctcttt gccgatggcc cgacagccat cagagacggt | 5940 |
| aaaacattct cagccctaca accatgcctc ttctacatca ctacttgaca agactaaaaa | 6000 |
| ctattggctc gttggcagtg gcttcctgga gagtaaagga gaccgagagg atggttgcga | 6060 |
| tccggacgga gctaaccaag gtaaggctac atacttcaca tgtctcacgt cgtctttcca | 6120 |
| tagctcgctg cctcttagcg gcttgcctgc ggtcgctcca tcctcggttg ctgtctgtgt | 6180 |
| tttccacagc tgggagcatc tgttgaggaa gggccggact actgcatcat cacgccgccg | 6240 |
| gagaagctga acgtgacggc gatcgacacg tacc | 6274 |

<210> SEQ ID NO 55
<211> LENGTH: 6038
<212> TYPE: DNA
<213> ORGANISM: Zea mays, L.
<220> FEATURE:
<221> NAME/KEY: misc_feature
<222> LOCATION: (1)..(6038)
<223> OTHER INFORMATION: EPSPS-maize ubiquitin promoter template

<400> SEQUENCE: 55

| | |
|---|---|
| gatctccggc accgtcaagc tgccggggtc caagtcgctt ccaacagga tcctcctgct | 60 |

-continued

```
cgccgccctg tccgaggtga gcgattttgg tgcttgctgc gctgccctgt ctcactgcta    120
cctaaatgtt ttgcctgtcg aataccatgg attctcggtg taatccatct cacgatcaga    180
tgcaccgcat gtcgcatgcc tagctctctc taatttgtct agtagtttgt atacggatta    240
agattgataa atcggtaccg caaaagctag gtgtaaataa acactacaaa attggatgtt    300
cccctatcgg cctgtactcg gctactcgtt cttgtgatgg catgttattt cttcttggtg    360
tttggtgaac tccctatga aatttgggcg caaagaaatc gccctcaagg ttgatctta     420
tgccatcgtc atgataaaca gtgaagcacg gatgatcctt tacgttgttt ttaacaaact    480
ttgtcagaaa actagcaatg ttaacttctt aatgatgatt tcacaacaaa aaaggtaacc    540
ttgctactaa cataacaaaa gacttgttgc ttattaatta tatgtttttt taatctttga    600
tcagggaca acagtggttg ataacctgtt gaacagtgag gatgtccact acatgctcgg     660
ggccttgagg actcttggtc tctctgtcga agcggacaaa gctgccaaaa gagctgtagt    720
tgttggctgt ggtggaaagt tcccagttga ggatgctaaa gaggaagtgc agctcttctt    780
ggggaatgct ggaatcgcaa tgcggtcatt gacagcagct gttactgctg ctggtggaaa    840
tgcaacgtat gtttcctctc tctctctctg cagtgcagcg tgacccggtc gtgcccctct    900
ctagagataa tgagcattgc atgtctaagt tataaaaaat taccacatat tttttttgtc    960
acacttgttt gaagtgcagt ttatctatct ttatacatat atttaaactt tactctacga   1020
ataatataat ctatagtact acaataatat cagtgtttta gagaatcata taaatgaaca   1080
gttagacatg gtctaaagga caattgagta ttttgacaac aggactctac agttttatct   1140
ttttagtgtg catgtgttct cctttttttt tgcaaatagc ttcacctata taatacttca   1200
tccattttat tagtacatcc atttagggtt tagggttaat ggttttttata gactaatttt   1260
tttagtacat ctattttatt ctattttagc ctctaaatta agaaaactaa aactctatt     1320
tagttttttt atttaataat ttagatataa aatagaataa aataaagtga ctaaaaatta   1380
aacaaatacc ctttaagaaa ttaaaaaaac taaggaaaca ttttttcttgt ttcgagtaga   1440
taatgccagc ctgttaaacg ccgtcgacga gtctaacgga caccaaccag cgaaccagca   1500
gcgtcgcgtc gggccaagcg aagcagacgg cacggcatct ctgtcgctgc ctctggaccc   1560
ctctcgagag ttccgctcca ccgttggact tgctccgctg tcggcatcca gaaattgcgt   1620
ggcggagcgg cagacgtgag ccggcacggc aggcggcctc ctcctcctct cacggcacgg   1680
cagctacggg ggattccttt cccaccgctc cttcgctttc ccttcctcgc ccgccgtaat   1740
aaatagacac cccctccaca ccctctttcc ccaacctcgt gttgttcgga gcgcacacac   1800
acacaaccag atctccccca aatccacccg tcggcacctc cgcttcaagg tacgccgctc   1860
gtcctccccc ccccccctct ctaccttctc tagatcggcg ttccggtcca tgcatggtta   1920
gggcccggta gttctacttc tgttcatgtt tgtgttagat ccgtgtttgt gttagatccg   1980
tgctgctagc gttcgtacac ggatgcgacc tgtacgtcag acacgttctg attgctaact   2040
tgccagtgtt tctctttggg gaatcctggg atggctctag ccgttccgca gacgggatcg   2100
atttcatgat ttttttttgtt tcgttgcata gggtttggtt tgcccttttc ctttatttca   2160
atatatgccg tgcacttgtt tgtcgggtca tcttttcatg cttttttttg tcttggttgt   2220
gatgatgtgg tctggttggg cggtcgttct agatcggagt agaattctgt ttcaaactac   2280
ctggtggatt tattaatttt ggatctgtat gtgtgtgcca tacatattca tagttacgaa   2340
ttgaagatga tggatggaaa tatcgatcta ggataggtat acatgttgat gcgggtttta   2400
```

```
ctgatgcata tacagagatg ctttttgttc gcttggttgt gatgatgtgg tgtggttggg    2460
cggtcgttca ttcgttctag atcggagtag aatactgttt caaactacct ggtgtattta    2520
ttaattttgg aactgtatgt gtgtgtcata catcttcata gttacgagtt taagatggat    2580
ggaaatatcg atctaggata ggtatacatg ttgatgtggg ttttactgat gcatatacat    2640
gatggcatat gcagcatcta ttcatatgct ctaaccttga gtacctatct attataataa    2700
acaagtatgt tttataatta ttttgatctt gatatacttg gatgatggca tatgcagcag    2760
ctatatgtgg attttttttag ccctgccttc atacgctatt tatttgcttg gtactgtttc    2820
ttttgtcgat gctcaccctg ttgtttggtg ttacttctgc aggtcgactc tagaggatcc    2880
ccatggcggc catggcgacc aaggccgccg cgggcaccgt gtcgctggac ctcgccgcgc    2940
cgtcgcgccg ccaccaccgc ccgagctcgg cgcgcccgcc cttccgcccc gccgtccgcg    3000
ggctgcgggc gcctgggcgc cgcgtgatcg ccgcgccgcc ggcggcggca gcggcggcgg    3060
cggtgcaggc gggtgccgag gagatcgtgc tgcagcccat caaggagatc tccggcaccg    3120
tcaagctgcc ggggtccaag tcgctttcca accggatcct cctactcgcc gccctgtccg    3180
aggtgagcga ttttggtgct tgctgcgctg ccctgtctca ctgctaccta aatgttttgc    3240
ctgtcgaata ccatgtattc tcggtgtaat ccatctcacg atcagatgca ccgcatatcg    3300
catgccctag ctctctctaa tttgtctagt agtttgtata cggattaata ttgataaatc    3360
ggtaccgcaa aagctagctg taaataaaca ctagaaaatt ggatgttccc ctatcggcct    3420
gtactcggct actcgttctt gtgatggcat gctgtctctt cttggtgttt ggtgaactcc    3480
cttatgaaat ttgggcgcaa agaactcgcc ctcaagggtt gatcttatgc catcgtcatg    3540
ataaacagtg aagcactgat gatcctttac gttgttttta acaaactttg tcagaaaact    3600
agcattgtta acttcttaat gatgatttca caacaaaaaa ggcaaccttg ctactaacat    3660
aacaaaagac ttgttgctta ttaattatat gttttttttaa tctttgatca ggggacaaca    3720
gtggttgata acctgctgaa cagtgaggat gtccactaca tgctcgggggc cttgaggact    3780
cttggtctct ctgtcgaagc ggacaaagct gccaaaagag ctgtagttgt tggctgtggt    3840
ggaaagttcc cagttgagga tgctaaagag gaagtgcagc tcttcttggg gaatgctgga    3900
atcgcaatgc ggtcattgac agcagctgtt actgctgctg gtggaaatgc aacgtatgtt    3960
tcctctctct ctacaatact tgttggagtt agtatgaaac ccatgtgtat gtctagtggc    4020
ttatggtgta ttggttttttg aacttcagtt acgtgcttga tggagtacca agaatgaggg    4080
agagacccat tggcgacttg gttgtcggat tgaagcagct tggtgcagat gttgattgtt    4140
tccttggcac tgactgccca cctgttcgtg tcaatggaat cggagggcta cctggtggca    4200
aggttagtta ctaagggcca catgttacat tcttctgtaa atggtacaac tattgtcgag    4260
cttttgcatt tgtaaggaaa acattgattg atctgaattt gatgctacac cacaaaatat    4320
ctacaaatgg tcatccctaa ctagcaaacc atgtctccat taagctcaat gaagtaatac    4380
ttggcatgtg tttatcaact taatttccat cttctggggt attgcctgtt ttctagtcta    4440
atagcatttg tttttagaat tagctcttac aactgttatg ttctacaggt caagctgtct    4500
ggctccatca gcagtcagta cttgagtgcc ttgctgatgg ctgctccttt ggctcttggg    4560
gatgtggaga ttgaaatcat tgataaatta atctccattc cctacgtcga aatgacattg    4620
agattgatgg agcgttttgg tgtgaaagca gagcattctg atagctggga cagattctac    4680
attaagggag gtcaaaaata caagtaagct ctgtaatgta tttcactact ttgatgccaa    4740
tgtttcagtt ttcagttttc caaacagtcg catcaatatt tgaatagatg cactgtagaa    4800
```

```
aaaaatcatt gcagggaaaa actagtactg agtattttga ctgtaaatta tttaaccagt    4860
cggaatatag tcagtctatt ggagtcaaga gcgtgaaccg aaatagccag ttaattatcc    4920
cattatacag aggacaacca tgtatactat tgaaacttgg tttaagagaa tctaggtagc    4980
tggactcgta gctgcttggc atggatacct tcttatcttt aggaaaagac acttgatttt    5040
ttttctgtgg ccctctatga tgtgtgaacc tgcttctcta ttgctttaga aggatatatc    5100
tatgtcgtta tgcaacatgc ttcccttagt catttgtact gaaatcagtt tcataagttc    5160
gttagtggtt ccctaaacga aaccttgttt ttctttgcaa tcaacaggtc ccctaaaaat    5220
gcctatgttg aaggtgatgc ctcaagcgca agctatttct tggctggtgc tgcaattact    5280
ggagggactg tgactgtgga aggttgtggc accaccagtt tgcaggtaaa gatttcttgg    5340
ctggtgctac gataactgct tttgtctttt tggtttcagc attgttctca gagtcactaa    5400
ataacattat catctgcaaa cgtcaaatag acatacttag gtgaatggat attcatgtaa    5460
ccgtttcctt acaaatttgc tgaaacctca gggtgatgtg aagtttgctg aggtactgga    5520
gatgatggga gcgaaggtta catggaccga gactagcgta actgttactg cccaccgcg    5580 ggagccattt ggaggaaaac acctcaaggc gattgatgtc aacatgaaca agatgcctga    5640
tgtcgccatg actcttgctg tggttgccct cttttgccgat ggcccgacag ccatcagaga    5700
cggtaaaaca ttctcagccc tacaaccatg cctcttctac atcactactt gacaagacta    5760
aaaactattg gctcgttggc agtggcttcc tggagagtaa aggagaccga gaggatggtt    5820
gcgatccgga cggagctaac caaggtaagg ctacatactt cacatgtctc acgtcgtctt    5880
tccatagctc gctgcctctt agcggcttgc ctgcggtcgc tccatcctcg gttgctgtct    5940
gtgttttcca cagctgggag catctgttga ggaagggccg gactactgca tcatcacgcc    6000
gccggagaag ctgaacgtga cggcgatcga cacgtacc                            6038
```

<210> SEQ ID NO 56
<211> LENGTH: 3708
<212> TYPE: DNA
<213> ORGANISM: Zea mays, L.
<220> FEATURE:
<221> NAME/KEY: misc_feature
<222> LOCATION: (1)..(3708)
<223> OTHER INFORMATION: EPSPS-K90R template

<400> SEQUENCE: 56

```
ctgcagccca tcaaggagat ctccggcacc gtcaagctgc cggggtccaa gtcgctttcc      60
aacaggatcc tcctgctcgc cgccctgtcc gaggtgagcg atttttggtgc ttgctgcgct    120 gccctgtctc actgctacct aaatgttttg cctgtcgaat accatggatt ctcggtgtaa    180
tccatctcac gatcagatgc accgcatgtc gcatgcctag ctctctctaa tttgtctagt    240
agtttgtata cggattaaga ttgataaatc ggtaccgcaa aagctaggtg taaataaaca    300
ctacaaaatt ggatgttccc ctatcggcct gtactcggct actcgttctt gtgatggcat    360
gttatttctt cttggtgttt ggtgaactcc cttatgaaat ttgggcgcaa agaaatcgcc    420
ctcaagggtt gatcttatgc catcgtcatg ataaacagtg aagcacggat gatcctttac    480
gttgttttta acaaactttg tcagaaaact agcaatgtta acttcttaat gatgatttca    540
caacaaaaaa ggtaaccttg ctactaacat aacaaaagac ttgttgctta ttaattatat    600 gttttttaa tctttgatca ggggacaaca gtggttgata acctgttgaa cagtgaggat    660
gtccactaca tgctcgggc cttgaggact cttggtctct ctgtcgaagc ggacaaagct    720
```

```
gccaaaagag ctgtagttgt tggctgtggt ggaaagttcc cagttgagga tgctagagag    780
gaagtgcagc tcttcttggg gaatgctgga atcgcaatgc ggtcattgac agcagctgtt    840
actgctgctg gtggaaatgc aacgtatgtt tcctctctct ctctacaata cttgttggag    900
ttagtatgaa acccatgtgt atgtctagtg gcttatggtg tattggtttt tgaacttcag    960
ttacgtgctt gatggagtac caagaatgag ggagagaccc attggcgact tggttgtcgg   1020
attgaagcag cttggtgcag atgttgattg tttccttggc actgactgcc cacctgttcg   1080
tgtcaatgga atcggagggc tacctggtgg caaggttagt tactaagggc cacatgttac   1140
attcttctgt aaatggtaca actattgtcg agcttttgca tttgtaagga aaacattgat   1200
tgatctgaat ttgatgctac accacaaaat atctacaaat ggtcatccct aactagcaaa   1260
ccatgtctcc attaagctca atgaagtaat acttggcatg tgtttatcaa cttaatttcc   1320
atcttctggg gtattgcctg ttttctagtc taatagcatt tgttttaga attagctctt    1380 acaactgtta tgttctacag gtcaagctgt ctggctccat cagcagtcag tacttgagtg   1440
ccttgctgat ggctgctcct ttggctcttg gggatgtgga gattgaaatc attgataaat   1500
taatctccat tccctacgtc gaaatgacat tgagattgat ggagcgtttt ggtgtgaaag   1560
cagagcattc tgatagctgg gacagattct acattaaggg aggtcaaaaa tacaagtaag   1620
ctctgtaatg tatttcacta ctttgatgcc aatgtttcag ttttcagttt tccaaacagt   1680
cgcatcaata tttgaataga tgcactgtag aaaaaaatca ttgcagggaa aaactagtac   1740
tgagtatttt gactgtaaat tatttaacca gtcggaatat agtcagtcta ttggagtcaa   1800
gagcgtgaac cgaaatagcc agttaattat cccattatac agaggacaac catgtatact   1860
attgaaactt ggtttaagag aatctaggta gctggactcg tagctgcttg gcatggatac   1920
cttcttatct ttaggaaaag acacttgatt ttttttctgt ggccctctat gatgtgtgaa   1980
cctgcttctc tattgcttta gaaggatata tctatgtcgt tatgcaacat gcttccctta   2040
gtcatttgta ctgaaatcag tttcataagt tcgttagtgg ttccctaaac gaaaccttgt   2100
ttttctttgc aatcaacagg tcccctaaaa atgcctatgt tgaaggtgat gcctcaagcg   2160
caagctattt cttggctggt gctgcaatta ctggagggac tgtgactgtg aaggttgtg    2220 gcaccaccag tttgcaggta agatttctt ggctggtgct acgataactg cttttgtctt    2280
tttggtttca gcattgttct cagagtcact aaataacatt atcatctgca aacgtcaaat   2340
agacatactt aggtgaatgg atattcatgt aaccgtttcc ttacaaattt gctgaaacct   2400
cagggtgatg tgaagtttgc tgaggtactg gagatgatgg gagcgaaggt tacatggacc   2460
gagactagcg taactgttac tggcccaccg cgggagccat ttgggaggaa acacctcaag   2520
gcgattgatg tcaacatgaa caagatgcct gatgtcgcca tgactcttgc tgtggttgcc   2580
ctctttgccg atggcccgac agccatcaga gacggtaaaa cattctcagc cctacaacca   2640
tgcctcttct acatcactac ttgacaagac taaaaactat tggctcgttg gcagtggctt   2700
cctggagagt aaaggagacc gagaggatgg ttgcgatccg gacggagcta accaaggtaa   2760
ggctacatac ttcacatgtc tcacgtcgtc tttccatagc tcgctgcctc ttagcggctt   2820
gcctgcggtc gctccatcct cggttgctgt ctgtgttttc cacagctggg agcatctgtt   2880
gaggaagggc cggactactg catcatcacg ccgccggaga agctgaacgt gacggcgatc   2940
gacacgtacg acgaccacag gatggccatg gccttctccc ttgccgcctg tgccgaggtc   3000
cccgtgacca tccgggaccc tgggtgcacc cggaagacct tccccgacta cttcgatgtg   3060
ctgagcactt tcgtcaagaa ttaataaagc gtgcgatact accacgcagc ttgattgaag   3120
```

```
tgataggctt gtgctgagga aatacatttc ttttgttctg ttttttctct ttcacgggat    3180
taagttttga gtctgtaacg ttagttgttt gtagcaagtt tctatttcgg atcttaagtt    3240
tgtgcactgt aagccaaatt tcatttcaag agtggttcgt tggaataata agaataataa    3300
attacgtttc agtggctgtc aagcctgctg ctacgtttta ggagatggca ttagacattc    3360
atcatcaaca acaataaaac cttttagcct caaacaataa tagtgaagtt attttttagt    3420
cctaaacaag ttgcattagg atatagttaa aacacaaaag aagctaaagt tagggtttag    3480
acatgtggat attgttttcc atgtatagta tgttctttct ttgagtctca tttaactacc    3540
tctacacata ccaactttag ttttttttct acctcttcat gttactatgg tgccttctta    3600
tcccactgag cattggtata tttagaggtt tttgttgaac atgcctaaat catctcaatc    3660
aacgatggac aatctttttct tcgattgagc tgaggtacgt catctaga              3708
```

<210> SEQ ID NO 57
<211> LENGTH: 3714
<212> TYPE: DNA
<213> ORGANISM: Zea mays, L.
<220> FEATURE:
<221> NAME/KEY: misc_feature
<222> LOCATION: (1)..(3714)
<223> OTHER INFORMATION: EPSPS-IME template

<400> SEQUENCE: 57

```
ctgcagccca tcaaggagat ctccggcacc gtcaagctgc cggggtccaa gtcgctttcc      60
aacaggatcc tcctgctcgc cgccctgtcc gaggtgagcg attttggtgc ttgctgcgct     120
gccctgtctc actgctacct aaatgttttg cctgtcgaat accatggatt ctcggtgtaa     180
tccatatctg cacgatcaga tatgcaccgc atgtcgcata tctgagctct ctctaatttg     240
tctagtagtt tgtatacgga ttaagattga taaatcggta ccgcaaaagc taggtgtaaa     300
taaacactac aaaattggat gttccccctat cggcctgtac tcggctactc gttcttgtga    360
tggcatgtta tttcttcttg gtgtttggtg aactcccctta tgaaatttgg gcgcaaagaa     420
atcgccctca agggttgatc ttatgccatc gtcatgataa acagtgaagc acggatgatc     480
ctttacgttg tttttaacaa actttgtcag aaaactagca atgttaactt cttaatgatg     540
atttcacaac aaaaaaggta accttgctac taacataaca aaagacttgt tgcttattaa     600
ttatatgttt ttttaatctt tgatcagggg acaacagtgg ttgataaccct gttgaacagt    660 gaggatgtcc actacatgct cggggccttg aggactcttg gtctctctgt cgaagcggac    720
aaagctgcca aaagagctgt agttgttggc tgtggtggaa agttcccagt tgaggatgct    780
aaagaggaag tgcagctctt cttggggaat gctggaatcg caatgcggtc attgacagca    840
gctgttactc tgctggtgg aaatgcaacg tatgtttcct ctctctctct acaatacttg     900
ttggagttag tatgaaaccc atgtgtatgt ctagtggctt atggtgtatt ggttttttgaa     960 cttcagttac gtgcttgatg gagtaccaag aatgagggag agacccattg gcgacttggt    1020
tgtcggattg aagcagcttg gtgcagatgt tgattgtttc cttggcactg actgcccacc    1080
tgttcgtgtc aatggaatcg gagggctacc tggtggcaag gttagttact aagggccaca    1140
tgttacattc ttctgtaaat ggtacaacta ttgtcgagct tttgcatttg taaggaaaac    1200
attgattgat ctgaatttga tgctacacca caaaatatct acaaatggtc atccctaact    1260
agcaaaccat gtctccatta agctcaatga agtaatactt ggcatgtgtt tatcaactta    1320
atttccatct tctggggtat tgcctgtttt ctagtctaat agcatttgtt tttagaatta    1380
```

-continued

```
gctcttacaa ctgttatgtt ctacaggtca agctgtctgg ctccatcagc agtcagtact    1440
tgagtgcctt gctgatggct gctcctttgg ctcttgggga tgtggagatt gaaatcattg    1500
ataaattaat ctccattccc tacgtcgaaa tgacattgag attgatggag cgttttggtg    1560
tgaaagcaga gcattctgat agctgggaca gattctacat taagggaggt caaaaataca    1620
agtaagctct gtaatgtatt tcactacttt gatgccaatg tttcagtttt cagttttcca    1680
aacagtcgca tcaatatttg aatagatgca ctgtagaaaa aaatcattgc agggaaaaac    1740
tagtactgag tattttgact gtaaattatt taaccagtcg gaatatagtc agtctattgg    1800
agtcaagagc gtgaaccgaa atagccagtt aattatccca ttatacagag acaaccatg     1860
tatactattg aaacttggtt taagagaatc taggtagctg gactcgtagc tgcttggcat    1920
ggataccttc ttatctttag gaaaagacac ttgatttttt ttctgtggcc ctctatgatg    1980
tgtgaacctg cttctctatt gctttagaag gatatatcta tgtcgttatg caacatgctt    2040
cccttagtca tttgtactga aatcagtttc ataagttcgt tagtggttcc ctaaacgaaa    2100
ccttgttttt ctttgcaatc aacaggtccc ctaaaaatgc ctatgttgaa ggtgatgcct    2160
caagcgcaag ctatttcttg gctggtgctg caattactgg agggactgtg actgtggaag    2220
gttgtggcac caccagtttg caggtaaaga tttcttggct ggtgctacga taactgcttt    2280
tgtcttttg gtttcagcat tgttctcaga gtcactaaat aacattatca tctgcaaacg     2340
tcaaatagac atacttaggt gaatggatat tcatgtaacc gtttccttac aaatttgctg    2400
aaacctcagg gtgatgtgaa gtttgctgag gtactggaga tgatgggagc gaaggttaca    2460
tggaccgaga ctagcgtaac tgttactggc ccaccgcggg agccatttgg gaggaaacac    2520
ctcaaggcga ttgatgtcaa catgaacaag atgcctgatg tcgccatgac tcttgctgtg    2580
gttgccctct ttgccgatgg cccgacagcc atcagagacg gtaaaacatt ctcagcccta    2640
caaccatgcc tcttctacat cactacttga caagactaaa aactattggc tcgttggcag    2700
tggcttcctg gagagtaaag gagaccgaga ggatggttgc gatccggacg gagctaacca    2760
aggtaaggct acatacttca catgtctcac gtcgtctttc catagctcgc tgcctcttag    2820
cggcttgcct gcggtcgctc catcctcggt tgctgtctgt gttttccaca gctgggagca    2880
tctgttgagg aagggccgga ctactgcatc atcacgccgc cggagaagct gaacgtgacg    2940
gcgatcgaca cgtacgacga ccacaggatg gccatggcct ctccccttgc cgcctgtgcc    3000
gaggtccccg tgaccatccg ggaccctggg tgcacccgga agaccttccc cgactacttc    3060
gatgtgctga gcactttcgt caagaattaa taaagcgtgc gatactacca cgcagcttga    3120
ttgaagtgat aggcttgtgc tgaggaaata catttctttt gttctgtttt ttctctttca    3180
cgggattaag ttttgagtct gtaacgttag ttgtttgtag caagtttcta tttcggatct    3240
taagtttgtg cactgtaagc caaatttcat ttcaagagtg gttcgttgga ataataagaa    3300
taataaatta cgtttcagtg gctgtcaagc ctgctgctac gttttaggag atggcattag    3360
acattcatca tcaacaacaa taaaaccttt tagcctcaaa caataatagt gaagttattt    3420
tttagtccta aacaagttgc attaggatat agttaaaaca caaagaagc taaagttagg     3480
gtttagacat gtggatattg ttttccatgt atagtatgtt cttctttga gtctcattta     3540
actacctcta cacataccaa ctttagtttt ttttctacct cttcatgtta ctatggtgcc    3600
ttcttatccc actgagcatt ggtatattta gaggttttg ttgaacatgc ctaaatcatc     3660
tcaatcaacg atggacaatc ttttcttcga ttgagctgag gtacgtcatc taga          3714
```

```
<210> SEQ ID NO 58
<211> LENGTH: 3708
<212> TYPE: DNA
<213> ORGANISM: Zea mays, L.
<220> FEATURE:
<221> NAME/KEY: misc_feature
<222> LOCATION: (1)..(3708)
<223> OTHER INFORMATION: EPSPS-Tspliced template

<400> SEQUENCE: 58
```

| | | | | |
|---|---|---|---|---|
| ctgcagccca | tcaaggagat | ctccggcacc | gtcaagctgc | cggggtccaa gtcgctttcc | 60 |
| aacaggatcc | tcctgctcgc | cgccctgtcc | gaggtgagcg | attttggtgc ttgctgcgct | 120 |
| gccctgtctc | actgctacct | aaatgttttg | cctgtcgaat | accatggatt tcggtgtaa | 180 |
| tccatctcac | gatcagatgc | accgcatgtc | gcatgcctag | ctctctctaa tttgtctagt | 240 |
| agtttgtata | cggattaaga | ttgataaatc | ggtaccgcaa | aagctaggtg taaataaaca | 300 |
| ctacaaaatt | ggatgttccc | ctatcggcct | gtactcggct | actcgttctt gtgatggcat | 360 |
| gttatttctt | cttggtgttt | ggtgaactcc | cttatgaaat | ttgggcgcaa agaaatcgcc | 420 |
| ctcaagggtt | gatcttatgc | catcgtcatg | ataaacagtg | aagcacggat gatcctttac | 480 |
| gttgttttta | acaaactttg | tcagaaaact | agcaatgtta | acttcttaat gatgatttca | 540 |
| caacaaaaaa | ggtaaccttg | ctactaacat | aacaaaagac | ttgttgctta ttaattatat | 600 |
| gttttttaa | tctttgatca | ggggacaaca | gtggttgata | acctgttgaa cagtgaggat | 660 |
| gtccactaca | tgctcggggc | cttgaggact | cttggtctct | ctgtcgaagc ggacaaagct | 720 |
| gccaaaagag | ctgtagttgt | tggctgtggt | ggaaagttcc | cagttgagga tgctagaaag | 780 |
| gaagtgcagc | tcttcttggg | gaatgctgga | atcgcaatgc | ggtcattgac agcagctgtt | 840 |
| actgctgctg | gtggaaatgc | aacgtatgtt | tcctctctct | ctctacaata cttgttggag | 900 |
| ttagtatgaa | acccatgtgt | atgtctagtg | gcttatggtg | tattggtttt tgaacttcag | 960 |
| gtacgtgctt | gatggagtac | caagaatgag | ggagagaccc | attggcgact tggttgtcgg | 1020 |
| attgaagcag | cttggtgcag | atgttgattg | tttccttggc | actgactgcc cacctgttcg | 1080 |
| tgtcaatgga | atcggagggc | tacctggtgg | caaggttagt | tactaagggc acatgttac | 1140 |
| attcttctgt | aaatggtaca | actattgtcg | agcttttgca | tttgtaagga aaacattgat | 1200 |
| tgatctgaat | ttgatgctac | accacaaaat | atctacaaat | ggtcatccct aactagcaaa | 1260 |
| ccatgtctcc | attaagctca | atgaagtaat | acttggcatg | tgtttatcaa cttaatttcc | 1320 |
| atcttctggg | gtattgcctg | ttttctagtc | taatagcatt | tgttttaga attagctctt | 1380 |
| acaactgtta | tgttctacag | gtcaagctgt | ctggctccat | cagcagtcag tacttgagtg | 1440 |
| ccttgctgat | ggctgctcct | ttggctcttg | gggatgtgga | gattgaaatc attgataaat | 1500 |
| taatctccat | tccctacgtc | gaaatgacat | tgagattgat | ggagcgtttt ggtgtgaaag | 1560 |
| cagagcattc | tgatagctgg | gacagattct | acattaaggg | aggtcaaaaa tacaagtaag | 1620 |
| ctctgtaatg | tatttcacta | ctttgatgcc | aatgtttcag | ttttcagttt tccaaacagt | 1680 |
| cgcatcaata | tttgaataga | tgcactgtag | aaaaaaatca | ttgcagggaa aaactagtac | 1740 |
| tgagtatttt | gactgtaaat | tatttaacca | gtcggaatat | agtcagtcta ttggagtcaa | 1800 |
| gagcgtgaac | cgaaatagcc | agttaattat | cccattatac | agaggacaac catgtatact | 1860 |
| attgaaactt | ggtttaagag | aatctaggta | gctggactcg | tagctgcttg gcatggatac | 1920 |
| cttcttatct | ttaggaaaag | acacttgatt | ttttttctgt | ggccctctat gatgtgtgaa | 1980 |
| cctgcttctc | tattgcttta | gaaggatata | tctatgtcgt | tatgcaacat gcttccctta | 2040 |

-continued

```
gtcatttgta ctgaaatcag tttcataagt tcgttagtgg ttccctaaac gaaaccttgt    2100
ttttctttgc aatcaacagg tcccctaaaa atgcctatgt tgaaggtgat gcctcaagcg    2160
caagctattt cttggctggt gctgcaatta ctggagggac tgtgactgtg aaggttgtg    2220 gcaccaccag tttgcaggta aagatttctt ggctggtgct acgataactg cttttgtctt    2280
tttggtttca gcattgttct cagagtcact aaataacatt atcatctgca aacgtcaaat    2340
agacatactt aggtgaatgg atattcatgt aaccgtttcc ttacaaattt gctgaaacct    2400
cagggtgatg tgaagtttgc tgaggtactg gagatgatgg gagcgaaggt tacatggacc    2460
gagactagcg taactgttac tggcccaccg cgggagccat tgggaggaa acacctcaag    2520 gcgattgatg tcaacatgaa caagatgcct gatgtcgcca tgactcttgc tgtggttgcc    2580
ctctttgccg atggcccgac agccatcaga gacggtaaaa cattctcagc cctacaacca    2640
tgcctcttct acatcactac ttgacaagac taaaaactat tggctcgttg gcagtggctt    2700
cctggagagt aaaggagacc gagaggatgg ttgcgatccg gacggagcta accaaggtaa    2760
ggctacatac ttcacatgtc tcacgtcgtc tttccatagc tcgctgcctc ttagcggctt    2820
gcctgcggtc gctccatcct cggttgctgt ctgtgttttc cacagctggg agcatctgtt    2880
gaggaagggc cggactactg catcatcacg ccgccggaga agctgaacgt gacggcgatc    2940
gacacgtacg acgaccacag gatggccatg gccttctccc ttgccgcctg tgccgaggtc    3000
cccgtgacca tccggaccc tgggtgcacc cggaagacct tccccgacta cttcgatgtg    3060
ctgagcactt tcgtcaagaa ttaataaagc gtgcgatact accacgcagc ttgattgaag    3120
tgataggctt gtgctgagga aatacatttc ttttgttctg tttttctct ttcacgggat    3180 taagttttga gtctgtaacg ttagttgttt gtagcaagtt tctatttcgg atcttaagtt    3240
tgtgcactgt aagccaaatt tcatttcaag agtggttcgt tggaataata agaataataa    3300
attacgtttc agtggctgtc aagcctgctg ctacgtttta ggagatggca ttagacattc    3360
atcatcaaca acaataaaac cttttagcct caaacaataa tagtgaagtt attttttagt    3420
cctaaacaag ttgcattagg atatagttaa aacacaaaag aagctaaagt tagggtttag    3480
acatgtggat attgttttcc atgtatagta tgttctttct ttgagtctca tttaactacc    3540
tctacacata ccaactttag ttttttttct acctcttcat gttactatgg tgccttctta    3600
tcccactgag cattggtata tttagaggtt tttgttgaac atgcctaaat catctcaatc    3660
aacgatggac aatcttttct tcgattgagc tgaggtacgt catctaga              3708
```

<210> SEQ ID NO 59
<211> LENGTH: 3201
<212> TYPE: DNA
<213> ORGANISM: Zea mays, L.
<220> FEATURE:
<221> NAME/KEY: misc_feature
<222> LOCATION: (1)..(3201)
<223> OTHER INFORMATION: EPSPS-synthetic template

<400> SEQUENCE: 59

```
atggcggcca tggcgaccaa ggccgccgcg ggcaccgtgt cgctggacct cgccgcgccg      60
ccggcggcgg cagcggcggc ggcggtgcag gcgggtgccg aggagatcgt gctgcagccc     120
atcaaggaga tctccggcac cgtcaagctg ccggggtcca agtcgctttc caacaggatc     180
ctcctgctcg ccgccctgtc cgaggtgagc gattttggtg cttgctgcgc tgccctgtct     240
cactgctacc taaatgtttt gcctgtcgaa taccatggat tctcggtgta atccatatct     300
gcacgatcag atatgcaccg catgtcgcat atctgagctc tctctaattt gtctagtagt     360
```

```
ttgtatacgg attaagattg ataaatcggt accgcaaaag ctaggtgtaa ataaacacta    420
caaaattgga tgttcccta tcggcctgta ctcggctact cgttcttgtg atggcatgtt    480
atttcttctt ggtgtttggt gaactcccct atgaaatttg ggcgcaaaga aatcgccctc    540
aagggttgat cttatgccat cgtcatgata aacagtgaag cacggatgat cctttacgtt    600 gttttaaca aactttgtca gaaaactagc aatgttaact tcttaatgat gatttcacaa    660 caaaaaggt aaccttgcta ctaacataac aaaagacttg ttgcttatta attatatgtt    720
tttttaatct ttgatcaggg acaacagtg gttgataacc tgttgaacag cgaggatgtc    780
cactacatgc tcggggcctt gaggactctt ggtctctctg tcgaagcgga caaagctgcc    840
aaaagagctg ttgttgttgg ctgtggtgga agttcccag ttgaggatgc taaagaggaa    900
gtgcagctct tcttggggaa tgctggaatt gcaatgcggt cattgacagc agctgttact    960
gctgctggtg aaatgcaac gtatgtttcc tctctctctc tacaatactt gttggagtta    1020
gtatgaaacc catgtgtatg tctagtggct tatggtgtat tggttttga acttcagtta    1080 cgtgcttgat ggagtgccaa gaatgaggga gagacccatt ggcgacttgg ttgtcggatt    1140
gaagcagctt ggtgcagatg ttgattgttt ccttggcact gactgcccac ctgttcgcgt    1200
caatggaatc ggagggcttc ctggtggcaa ggttagttac taagggccac atgttacatt    1260
cttctgtaaa tggtacaact attgtcgagc ttttgcattt gtaaggaaaa cattgattga    1320
tctgaatttg atgctacacc acaaaatatc tacaaatggt catccctaac tagcaaacca    1380
tgtctccatt aagctcaatg aagtaatact tggcatgtgt ttatcaactt aatttccatc    1440 ttctgggta ttgcctgttt tctagtctaa tagcatttgt ttttagaatt agctcttaca    1500
actgttatgt tctacaggtc aagctgtctg gctccatcag cagccagtac ttgagcgcct    1560
tgctgatggc tgctcctttg gctcttgggg atgtggagat tgaaatcatt gataaattaa    1620
tctccattcc ctacgtcgaa atgacattga gattgatgga gcgctttggt gtgaaagcag    1680
agcattctga tagctgggac agattctaca ttaagggagg tcaaaaatac aagtaagctc    1740
tgtaatgtat ttcactactt tgatgccaat gtttcagttt tcagttttcc aaacagtcgc    1800
atcaatattt gaatagatgc actgtagaaa aaaatcattg cagggaaaaa ctagtactga    1860
gtattttgac tgtaaattat ttaaccagtc ggaatatagt cagtctattg gagtcaagag    1920
cgtgaaccga aatagccagt taattatccc attatacaga ggacaaccat gtatactatt    1980
gaaacttggt ttaagagaat ctaggtagct ggactcgtag ctgcttggca tggatacctt    2040
cttatcttta ggaaaagaca cttgattttt tttctgtggc cctctatgat gtgtgaacct    2100
gcttctctat tgctttagaa ggatatatct atgtcgttat gcaacatgct tcccttagtc    2160
atttgtactg aaatcagttt cataagttcg ttagtggttc cctaaacgaa accttgtttt    2220 tcttttgcaat caacaggtcc cctaaaaatg cctatgttga aggtgatgcc tcaagcgcaa    2280
gctatttctt ggctggtgct gcaattactg gagggactgt gactgtggaa ggttgtggca    2340
ccaccagctt gcaggtaaag atttcttggc tggtgctacg ataactgctt ttgtcttttt    2400
ggtttcagca ttgttctcag agtcactaaa taacattatc atctgcaaac gtcaaataga    2460
catacttagg tgaatggata ttcatgtaac cgtttcctta caaatttgct gaaacctcag    2520
ggtgatgtga agtttgctga ggttctggag atgatgggag cgaaggttac atggaccgag    2580
actagcgtta ctgttactgg cccaccgcgg gagccatttg ggaggaaaca cctcaaggcg    2640
attgatgtca acatgaacaa gatgcctgat gtcgccatga ctcttgctgt ggttgccctc    2700
```

-continued

```
tttgccgatg gcccgacagc catcagagac ggtaaaacat tctcagccct acaaccatgc    2760
ctcttctaca tcactacttg acaagactaa aaactattgg ctcgttggca gtggcttcct    2820
ggagagttaa ggagaccgag aggatggttg cgatccggac ggagctaacc aaggtaaggc    2880
tacatacttc acatgtctca cgtcgtcttt ccatagctcg ctgcctctta gcggcttgcc    2940
tgcggtcgct ccatcctcgg ttgctgtctg tgttttccac agctgggagc atctgttgag    3000
gaagggccgg actactgcat catcacgccg ccggagaagc tgaacgtgac ggcgatcgac    3060
acgtacgacg accacaggat ggccatggcc ttctcccttg ccgcctgtgc cgaggtcccc    3120
gtgaccatcc gggaccctgg gtgcacccgg aagaccttcc ccgactactt cgatgtgctg    3180
agcactttcg tcaagaatta a                                              3201
```

<210> SEQ ID NO 60
<211> LENGTH: 23
<212> TYPE: DNA
<213> ORGANISM: Glycine max
<220> FEATURE:
<221> NAME/KEY: misc_feature
<222> LOCATION: (1)..(23)
<223> OTHER INFORMATION: soy EPSPS-CR1, Cas9 target sequence

<400> SEQUENCE: 60

```
gcgtcctttg acagcagctg tgg                                              23
```

<210> SEQ ID NO 61
<211> LENGTH: 23
<212> TYPE: DNA
<213> ORGANISM: Glycine max
<220> FEATURE:
<221> NAME/KEY: misc_feature
<222> LOCATION: (1)..(23)
<223> OTHER INFORMATION: soy EPSPS-CR2, Cas9 target sequence

<400> SEQUENCE: 61

```
gcaaccacag ctgctgtcaa agg                                              23
```

<210> SEQ ID NO 62
<211> LENGTH: 434
<212> TYPE: DNA
<213> ORGANISM: Glycine max
<220> FEATURE:
<221> NAME/KEY: misc_feature
<222> LOCATION: (1)..(434)
<223> OTHER INFORMATION: GM-U6-13.1 PRO

<400> SEQUENCE: 62

```
ccgggtgtga tttagtataa agtgaagtaa tggtcaaaag aaaaagtgta aaacgaagta     60
cctagtaata agtaatattg aacaaaataa atggtaaagt gtcagatata taaataggc     120 tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaa                                                      434
```

<210> SEQ ID NO 63
<211> LENGTH: 9093
<212> TYPE: DNA
<213> ORGANISM: Artificial sequence

```
<220> FEATURE:
<223> OTHER INFORMATION: QC878

<400> SEQUENCE: 63
ccgggtgtga tttagtataa agtgaagtaa tggtcaaaag aaaaagtgta aaacgaagta      60
cctagtaata agtaatattg aacaaaataa atggtaaagt gtcagatata taaaataggc     120
tttaataaaa ggaagaaaaa aaacaaacaa aaaataggtt gcaatggggc agagcagagt     180
catcatgaag ctagaaaggc taccgataga taaactatag ttaattaaat acattaaaaa     240
atacttggat ctttctctta ccctgtttat attgagacct gaaacttgag agagatacac     300
taatcttgcc ttgttgtttc attccctaac ttacaggact cagcgcatgt catgtggtct     360
cgttccccat ttaagtccca caccgtctaa acttattaaa ttattaatgt ttataactag     420
atgcacaaca acaaagcttg cgtcctttga cagcagctgg ttttagagct agaaatagca     480
agttaaaata aggctagtcc gttatcaact tgaaaaagtg gcaccgagtc ggtgcttttt     540
tttgcggccg caattggatc gggtttactt attttgtggg tatctatact tttattagat     600
ttttaatcag gctcctgatt ctttttatt tcgattgaat tcctgaactt gtattattca     660
gtagatcgaa taaattataa aaagataaaa tcataaaata atattttatc ctatcaatca     720
tattaaagca atgaatatgt aaaattaatc ttatctttat tttaaaaaat catataggtt     780
tagtatttttt ttaaaaataa agataggatt agttttacta ttcactgctt attacttttta     840
aaaaaatcat aaaggtttag tattttttta aaataaatat aggaatagtt ttactattca     900
ctgctttaat agaaaaatag tttaaaattt aagatagttt taatcccagc atttgccacg     960
tttgaacgtg agccgaaacg atgtcgttac attatcttaa cctagctgaa acgatgtcgt    1020
cataatatcg ccaaatgcca actggactac gtcgaaccca caaatcccac aaagcgcgtg    1080
aaatcaaatc gctcaaacca caaaaaagaa caacgcgttt gttacacgct caatcccacg    1140
cgagtagagc acagtaacct tcaaataagc gaatggggca taatcagaaa tccgaaataa    1200
acctaggggc attatcggaa atgaaaagta gctcactcaa tataaaaatc taggaaccct    1260
agttttcgtt atcactctgt gctccctcgc tctatttctc agtctctgtg tttgcggctg    1320
aggattccga acgagtgacc ttcttcgttt ctcgcaaagg taacagcctc tgctcttgtc    1380
tcttcgattc gatctatgcc tgtctcttat ttacgatgat gtttcttcgg ttatgttttt    1440
ttatttatgc tttatgctgt tgatgttcgg ttgtttgttt cgctttgttt ttgtggttca    1500
gttttttagg attcttttgg tttttgaatc gattaatcgg aagagatttt cgagttattt    1560
ggtgtgttgg aggtgaatct ttttttttgag gtcatagatc tgttgtattt gtgttataaa    1620
catgcgactt tgtatgattt tttacgaggt tatgatgttc tggttgtttt attatgaatc    1680
tgttgagaca gaaccatgat ttttgttgat gttcgtttac actattaaag gtttgtttta    1740
acaggattaa aagttttttta agcatgttga aggagtcttg tagatatgta accgtcgata    1800
gttttttgt gggtttgttc acatgttatc aagcttaatc ttttactatg tatgcgacca    1860
tatctggatc cagcaaaggc gattttttaa ttccttgtga aacttttgta atatgaagtt    1920
gaaattttgt tattggtaaa ctataaatgt gtgaagttgg agtataccctt taccttctta    1980
tttggctttg tgatagttta atttatatgt attttgagtt ctgacttgta tttctttgaa    2040
ttgattctag tttaagtaat ccatggacaa aaagtactca ataggggctcg acatagggac    2100
taactccgtt ggatgggccg tcatcaccga cgagtacaag gtgccctcca agaagttcaa    2160
ggtgttggga aacaccgaca ggcacagcat aaagaagaat ttgatcggtg ccctcctctt    2220
```

```
cgactccgga gagaccgctg aggctaccag gctcaagagg accgctagaa ggcgctacac    2280
cagaaggaag aacagaatct gctacctgca ggagatcttc tccaacgaga tggccaaggt    2340
ggacgactcc ttcttccacc gccttgagga atcattcctg gtggaggagg ataaaaagca    2400
cgagagacac ccaatcttcg ggaacatcgt cgacgaggtg gcctaccatg aaaagtaccc    2460
taccatctac cacctgagga agaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640
ccagcttttc gaggagaacc caatcaacgc cagtggagtt gacgccaagg ctatcctctc    2700
tgctcgtctg tcaaagtcca ggaggcttga gaacttgatt gcccagctgc ctggcgaaaa    2760
gaagaacgga ctgttcggaa acttgatcgc tctctccctg ggattgactc ccaacttcaa    2820
gtccaacttc gacctcgccg aggacgctaa gttgcagttg tctaaagaca cctacgacga    2880
tgacctcgac aacttgctgg cccagatagg cgaccaatac gccgatctct tcctcgccgc    2940
taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga cacagcagct gcccgagaag tacaaggaga tcttttttcga    3120 ccagtccaag aacggctacg ccggatacat tgacggaggc gcctcccagg aagagttcta    3180
caagttcatc aagcccatcc ttgagaagat ggacggtacc gaggagctgt tggtgaagtt    3240
gaacagagag gacctgttga ggaagcagag aaccttcgac aacggaagca tccctcacca    3300
aatccacctg ggagagctcc acgccatctt gaggaggcag gaggatttct atcccttcct    3360
gaaggacaac cgcgagaaga ttgagaagat cttgaccttc agaattcctt actacgtcgg    3420
gccactcgcc agaggaaact ctaggttcgc ctggatgacc cgcaaatctg aagagaccat    3480
tactccctgg aacttcgagg aagtcgtgga caagggcgct tccgctcagt ctttcatcga    3540
gaggatgacc aacttcgata aaaatctgcc caacgagaag gtgctgccca agcactccct    3600
gttgtacgag tatttcacag tgtacaacga gctcaccaag gtgaagtacg tcacagaggg    3660
aatgaggaag cctgccttct tgtccggaga gcagaagaag gccatcgtcg acctgctctt    3720
caagaccaac aggaaggtga ctgtcaagca gctgaaggag gactacttca gaagatcga    3780 gtgcttcgac tccgtcgaga tctctggtgt cgaggacagg ttcaacgcct cccttgggac    3840
ttaccacgat ctgctcaaga ttattaaaga caaggacttc ctggacaacg aggagaacga    3900
ggacatcctt gaggacatcg tgctcaccct gaccttgttc gaagacaggg aaatgatcga    3960
agagaggctc aagacctacg cccacctctt cgacgacaag gtgatgaaac agctgaagag    4020
acgcagatat accggctggg gaaggctctc ccgcaaattg atcaacggga tcagggacaa    4080
gcagtcaggg aagactatac tcgacttcct gaagtccgac ggattcgcca acaggaactt    4140
catgcagctc attcacgacg actccttgac cttcaaggag gacatccaga aggctcaggt    4200
gtctggacag ggtgactcct tgcatgagca cattgctaac ttggccggct ctcccgctat    4260
taagaagggc atttttgcaga ccgtgaaggt cgttgacgag ctcgtgaagg tgatgggacg    4320
ccacaagcca gagaacatcg ttattgagat ggctcgcgca aaccaaacta cccagaaagg    4380
gcagaagaat tcccgcgaga ggatgaagcg cattgaggag ggcataaaag agcttggctc    4440
tcagatcctc aaggagcacc ccgtcgagaa cactcagctg cagaacgaga agctgtacct    4500
gtactacctc caaaacggaa gggacatgta cgtggaccag gagctggaca tcaacaggtt    4560
gtccgactac gacgtcgacc acatcgtgcc tcagtccttc ctgaaggatg actccatcga    4620
```

```
caataaagtg ctgacacgct ccgataaaaa tagaggcaag tccgacaacg tcccctccga    4680
ggaggtcgtg aagaagatga aaaactactg gagacagctc ttgaacgcca agctcatcac    4740
ccagcgtaag ttcgacaacc tgactaaggc tgagagagga ggattgtccg agctcgataa    4800
ggccggattc atcaagagac agctcgtcga aacccgccaa attaccaagc acgtggccca    4860
aattctggat tcccgcatga acaccaagta cgatgaaaat gacaagctga tccgcgaggt    4920
caaggtgatc accttgaagt ccaagctggt ctccgacttc cgcaaggact tccagttcta    4980
caaggtgagg gagatcaaca actaccacca cgcacacgac gcctacctca acgctgtcgt    5040
tggaaccgcc ctcatcaaaa aatatcctaa gctggagtct gagttcgtct acggcgacta    5100
caaggtgtac gacgtgagga agatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg gagagatcgt    5280
gtgggacaaa gggagggatt tcgctactgt gaggaaggtg ctctccatgc ctcaggtgaa    5340
catcgtcaag aagaccgaag ttcagaccgg aggattctcc aaggagtcca tcctccccaa    5400
gagaaactcc gacaagctga tcgctagaaa gaaagactgg gaccctaaga agtacggagg    5460
cttcgattct cctaccgtgg cctactctgt gctggtcgtg gccaaggtgg agaagggcaa    5520
gtccaagaag ctgaaatccg tcaaggagct cctcgggatt accatcatgg agaggagttc    5580
cttcgagaag aaccctatcg acttcctgga ggccaaggga tataaagagg tgaagaagga    5640
cctcatcatc aagctgccca gtactcccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag ggctctcctg aggacaacga    5820
gcagaagcag ctcttcgtgg agcagcacaa gcactacctg gacgaaatta cgagcagat     5880 ctctgagttc tccaagcgcg tgatattggc cgacgccaac ctcgacaagg tgctgtccgc    5940
ctacaacaag cacagggata gcccattcg cgagcaggct gaaaacatta tccacctgtt     6000
taccctcaca aacttgggag cccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
tccatatttc ttatcctaaa tgaatgtcac gtgtctttat aattctttga tgaaccagat    6420
gcatttcatt aaccaaatcc atatacatat aaatattaat catatataat taatatcaat    6480
tgggttagca aaacaaatct agtctaggtg tgttttgcga attcgatatc aagcttatcg    6540
ataccgtcga ggggggcccc ggtaccgcg cgccgttcta tagtgtcacc taaatcgtat    6600
gtgtatgata cataaggtta tgtattaatt gtagccgcgt tctaacgaca atatgtccat    6660
atggtgcact ctcagtacaa tctgctctga tgccgcatag ttaagccagc ccgacaccc     6720 gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct atttttatag gttaatgtca tgaccaaaat    6900
cccttaacgt gagttttcgt tccactgagc gtcagacccc gtagaaaaga tcaaaggatc    6960
```

```
ttcttgagat cctttttttc tgcgcgtaat ctgctgcttg caaacaaaaa aaccaccgct    7020
accagcggtg gtttgtttgc cggatcaaga gctaccaact cttttttccga aggtaactgg    7080 cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacggggggg ttcgtgcaca cagcccagct tggagcgaac    7320
gacctacacc gaactgagat acctacagcg tgagcattga gaaagcgcca cgcttcccga    7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgatttttgt gatgctcgtc aggggggcgg agcctatgga aaaacgccag    7560
caacgcggcc ttttacggt tcctggcctt ttgctggcct tttgctcaca tgttctttcc    7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860
ataattttgt ttaactttaa gaaggagata tacccatgga aaagcctgaa ctcaccgcga    7920
cgtctgtcga aagtttctg atcgaaaagt tcgacacgcg ctccgacctg atgcagctct    7980
cggagggcga agaatctcgt gctttcagct tcgatgtagg agggcgtgga tatgtcctgc    8040
gggtaaatag ctgcgccgat ggtttctaca aagatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacggcaa tttcgatgat gcagcttggg    8760
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
gaaaccgacg ccccagcact cgtccgaggg caaaggaata gtgaggtaca gcttggatcg    8940
atccggctgc taacaaagcc cgaaaggaag ctgagttggc tgctgccacc gctgagcaat    9000
aactagcata accccttggg gcctctaaac gggtcttgag gggttttttg ctgaaaggag    9060
gaactatatc cggatgatcg ggcgcgccgg tac                                 9093
```

<210> SEQ ID NO 64
<211> LENGTH: 9093
<212> TYPE: DNA
<213> ORGANISM: Artificial sequence
<220> FEATURE:
<223> OTHER INFORMATION: QC879

<400> SEQUENCE: 64

```
ccgggtgtga tttagtataa agtgaagtaa tggtcaaaag aaaaagtgta aaacgaagta      60
cctagtaata agtaatattg aacaaaataa atggtaaagt gtcagatata taaataggc     120
tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg caaccacagc tgctgtcaag ttttagagct agaaatagca    480
agttaaaata aggctagtcc gttatcaact tgaaaaagtg gcaccgagtc ggtgcttttt    540
tttgcggccg caattggatc gggtttactt attttgtggg tatctatact tttattagat    600
ttttaatcag gctcctgatt tcttttattt tcgattgaat tcctgaactt gtattattca    660
gtagatcgaa taaattataa aaagataaaa tcataaaata atattttatc ctatcaatca    720
tattaaagca atgaatatgt aaaattaatc ttatctttat tttaaaaaat catataggtt    780
tagtattttt ttaaaaataa agataggatt agttttacta ttcactgctt attactttta    840
aaaaaatcat aaaggtttag tatttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtcgt   1020
cataatatcg ccaaatgcca actggactac gtcgaaccca caaatcccac aaagcgcgtg   1080
aaatcaaatc gctcaaacca caaaaaagaa caacgcgttt gttacacgct caatcccacg   1140
cgagtagagc acagtaacct tcaaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgttttt   1440
ttatttatgc tttatgctgt tgatgttcgg ttgtttgttt cgctttgttt ttgtggttca   1500
gtttttagg attcttttgg tttttgaatc gattaatcgg aagagatttt cgagttattt   1560
ggtgtgttgg aggtgaatct tttttttgag gtcatagatc tgttgtattt gtgttataaa   1620
catgcgactt tgtatgattt tttacgaggt tatgatgttc tggttgtttt attatgaatc   1680
tgttgagaca gaaccatgat ttttgttgat gttcgtttac actattaaag gtttgtttta   1740
acaggattaa aagttttta agcatgttga aggagtcttg tagatatgta accgtcgata   1800
gttttttgt gggtttgttc acatgttatc aagcttaatc ttttactatg tatgcgacca   1860
tatctggatc cagcaaaggc gatttttaa ttccttgtga aacttttgta atatgaagtt   1920
gaaattttgt tattggtaaa ctataaatgt gtgaagttgg agtataccctt taccttctta   1980
tttggctttg tgatagttta atttatatgt attttgagtt ctgacttgta tttctttgaa   2040
ttgattctag tttaagtaat ccatggacaa aaagtactca atagggctcg acataggggac   2100
taactccgtt ggatgggccg tcatcaccga cgagtacaag gtgcctcca agaagttcaa   2160
ggtgttggga aacaccgaca ggcacagcat aaagaagaat tgatcggtg ccctcctctt   2220
cgactccgga gagaccgctg aggctaccag gctcaagagg accgctagaa ggcgctacac   2280
```

```
cagaaggaag aacagaatct gctacctgca ggagatcttc tccaacgaga tggccaaggt    2340
ggacgactcc ttcttccacc gccttgagga atcattcctg gtggaggagg ataaaaagca    2400
cgagagacac ccaatcttcg ggaacatcgt cgacgaggtg gcctaccatg aaaagtaccc    2460
taccatctac cacctgagga agaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640
ccagcttttc gaggagaacc caatcaacgc cagtggagtt gacgccaagg ctatcctctc    2700
tgctcgtctg tcaaagtcca ggaggcttga aacttgatt gcccagctgc ctggcgaaaa     2760
gaagaacgga ctgttcggaa acttgatcgc tctctccctg ggattgactc ccaacttcaa    2820
gtccaacttc gacctcgccg aggacgctaa gttgcagttg tctaaagaca cctacgacga    2880
tgacctcgac aacttgctgg cccagatagg cgaccaatac gccgatctct tcctcgccgc    2940
taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga cacagcagct gcccgagaag tacaaggaga tcttttttcga   3120
ccagtccaag aacggctacg ccggatacat tgacggaggc gcctcccagg aagagttcta    3180
caagttcatc aagcccatcc ttgagaagat ggacggtacc gaggagctgt tggtgaagtt    3240
gaacagagag gacctgttga ggaagcagag aaccttcgac aacggaagca tccctcacca    3300
aatccacctg ggagagctcc acgccatctt gaggaggcag gaggatttct atcccttcct    3360
gaaggacaac cgcgagaaga ttgagaagat cttgaccttc agaattcctt actacgtcgg    3420
gccactcgcc agaggaaact ctaggttcgc ctggatgacc cgcaaatctg aagagaccat    3480
tactccctgg aacttcgagg aagtcgtgga caagggcgct tccgctcagt ctttcatcga    3540
gaggatgacc aacttcgata aaaatctgcc caacgagaag gtgctgccca gcactccct     3600
gttgtacgag tatttcacag tgtacaacga gctcaccaag gtgaagtacg tcacagaggg    3660
aatgaggaag cctgccttct gtccggaga gcagaagaag gccatcgtcg acctgctctt     3720
caagaccaac aggaaggtga ctgtcaagca gctgaaggag gactacttca agaagatcga    3780
gtgcttcgac tccgtcgaga tctctggtgt cgaggacagg ttcaacgcct cccttgggac    3840
ttaccacgat ctgctcaaga ttattaaaga caaggacttc ctggacaacg aggagaacga    3900
ggacatcctt gaggacatcg tgctcaccct gaccttgttc gaagacaggg aaatgatcga    3960
agagaggctc aagacctacg cccacctctt cgacgacaag gtgatgaaac agctgaagag    4020
acgcagatat accggctggg gaaggctctc ccgcaaattg atcaacggga tcagggacaa    4080
gcagtcaggg aagactatac tcgacttcct gaagtccgac ggattcgcca caggaactt     4140
catgcagctc attcacgacg actccttgac cttcaaggag gacatccaga aggctcaggt    4200
gtctggacag ggtgactcct tgcatgagca cattgctaac ttggccggct ctcccgctat    4260
taagaagggc attttgcaga ccgtgaaggt cgttgacgag ctcgtgaagg tgatgggacg    4320
ccacaagcca gagaacatcg ttattgagat ggctcgcgag aaccaaacta cccagaaagg    4380
gcagaagaat tcccgcgaga ggatgaagcg cattgaggag ggcataaaag agcttggctc    4440
tcagatcctc aaggagcacc ccgtcgagaa cactcagctg cagaacgaga agctgtacct    4500
gtactacctc caaaacggaa gggacatgta cgtggaccag gagctggaca tcaacaggtt    4560
gtccgactac gacgtcgacc acatcgtgcc tcagtccttc ctgaaggatg actccatcga    4620
caataaagtg ctgacacgct ccgataaaaa tagaggcaag tccgacaacg tccccctcga    4680
```

-continued

```
ggaggtcgtg aagaagatga aaaactactg gagacagctc ttgaacgcca agctcatcac    4740
ccagcgtaag ttcgacaacc tgactaaggc tgagagagga ggattgtccg agctcgataa    4800
ggccggattc atcaagagac agctcgtcga aacccgccaa attaccaagc acgtggccca    4860
aattctggat tcccgcatga acaccaagta cgatgaaaat gacaagctga tccgcgaggt    4920
caaggtgatc accttgaagt ccaagctggt ctccgacttc cgcaaggact tccagttcta    4980
caaggtgagg gagatcaaca actaccacca cgcacacgac gcctacctca acgctgtcgt    5040
tggaaccgcc ctcatcaaaa aatatcctaa gctggagtct gagttcgtct acggcgacta    5100
caaggtgtac gacgtgagga agatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg agagatcgt     5280
gtgggacaaa gggagggatt tcgctactgt gaggaaggtg ctctccatgc ctcaggtgaa    5340
catcgtcaag aagaccgaag ttcagaccgg aggattctcc aaggagtcca tcctccccaa    5400
gagaaactcc gacaagctga tcgctagaaa gaaagactgg gaccctaaga agtacggagg    5460
cttcgattct cctaccgtgg cctactctgt gctggtcgtg gccaaggtgg agaagggcaa    5520
gtccaagaag ctgaaatccg tcaaggagct cctcgggatt accatcatgg agaggagttc    5580
cttcgagaag aaccctatcg acttcctgga ggccaaggga tataaagagg tgaagaagga    5640
cctcatcatc aagctgccca gtactcccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag ggctctcctg aggacaacga    5820
gcagaagcag ctcttcgtgg agcagcacaa gcactacctg gacgaaatta tcgagcagat    5880
ctctgagttc tccaagcgcg tgatattggc cgacgccaac ctcgacaagg tgctgtccgc    5940
ctacaacaag cacagggata gcccattcg cgagcaggct gaaaacatta tccacctgtt     6000
taccctcaca aacttgggag cccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
tccatatttc ttatcctaaa tgaatgtcac gtgtctttat aattctttga tgaaccagat    6420
gcatttcatt aaccaaatcc atatacatat aaatattaat catatataat taatatcaat    6480
tgggttagca aaacaaatct agtctaggtg tgttttgcga attcgatatc aagcttatcg    6540
ataccgtcga ggggggggccc ggtaccggcg cgccgttcta tagtgtcacc taaatcgtat    6600
gtgtatgata cataaggtta tgtattaatt gtagccgcgt tctaacgaca atatgtccat    6660
atggtgcact ctcagtacaa tctgctctga tgccgcatag ttaagccagc cccgacaccc    6720
gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct atttttatag gttaatgtca tgaccaaaat    6900
cccttaacgt gagttttcgt tccactgagc gtcagacccc gtagaaaaga tcaaaggatc    6960
ttcttgagat cctttttttc tgcgcgtaat ctgctgcttg caaacaaaaa aaccaccgct    7020
```

```
accagcggtg gtttgtttgc cggatcaaga gctaccaact cttttttccga aggtaactgg    7080 cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacggggggg ttcgtgcaca cagcccagct tggagcgaac    7320
gacctacacc gaactgagat acctacagcg tgagcattga gaaagcgcca cgcttcccga    7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgattttttgt gatgctcgtc aggggggcgg agcctatgga aaaacgccag    7560
caacgcggcc ttttttacggt tcctggcctt ttgctggcct tttgctcaca tgttctttcc    7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860 ataatttttgt ttaactttaa gaaggagata tacccatgga aaagcctgaa ctcaccgcga    7920
cgtctgtcga gaagtttctg atcgaaaagt tcgacagcgt ctccgacctg atgcagctct    7980
cggagggcga agaatctcgt gctttcagct tcgatgtagg agggcgtgga tatgtcctgc    8040
gggtaaatag ctgcgccgat ggtttctaca agatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacggcaa tttcgatgat gcagcttggg    8760
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
gaaaccgacg ccccagcact cgtccgaggg caaaggaata gtgaggtaca gcttggatcg    8940
atccggctgc taacaaagcc cgaaaggaag ctgagttggc tgctgccacc gctgagcaat    9000
aactagcata accccttggg gcctctaaac gggtcttgag gggttttttg ctgaaaggag    9060
gaactatatc cggatgatcg ggcgcgccgg tac                                 9093
```

<210> SEQ ID NO 65
<211> LENGTH: 1357
<212> TYPE: DNA
<213> ORGANISM: Artificial sequence
<220> FEATURE:
<223> OTHER INFORMATION: RTW1013A

<400> SEQUENCE: 65

```
ctagaagata aaccctcccc caaaacacaa attagaatga catttcaagt tccatgtatg      60
tcactttcat tctattattt ttacaacttt tagttactta acagatgtct tgttcagcat     120
aaattataat ttattctgtt ttttttagg gaacaactgt tgtagacaac ttgttgtata      180
gtgaggatat tcattacatg cttggtgcat taaggaccct tggactgcgt gtggaagatg     240
acaaaacaac caaacaagca attgttgaag gctgtggggg attgtttccc actagtaagg    300
aatctaaaga tgaaatcaat ttattccttg gaaatgctgg tattgcaatg agatctttga    360
cagcagctgt tgttgctgca ggtggaaatg caaggtctgt ttttttttt tttgttcagc     420 ataatctttg aattgttcct cgtataacta atcacaacag agtacgtgtt cttcttcctg    480
ttataatcta aaaatctcat ccagattagt catcctttct tcttaaaagg aacctttaat    540
tatcaatgta tttatttaat atttaaatta gcttgtcaaa gtctagcata tacatatttt    600
gattatattc tgagaaatgc acctgagggt gttcctcatg atctacttca acctctgtta    660
ttattagatt ttctatcatg attactggtt tgagtctcta agtagaccat cttgatgttc    720
aaaatatttc agctacgtac ttgatggggt gccccgaatg agagagaggc caattgggga    780
tttggttgct ggtcttaagc aacttggtgc agatgttgat tgctttcttg gcacaaactg    840
tccacctgtt cgtgtaaatg ggaagggagg acttcctggc ggaaaggtat ggtttggatt    900
tcatttagaa taaggtggag taactttcct ggatcaaaat tctaatttaa gaagcctccc    960
tgttttcctc tctttagaat aagactaagg gtaggtttag gagttgggtt ttggagagaa   1020
atggaaggga gagcaatttt tttcttcttc taataaatat tctttaattt gatacatttt   1080
ttaagtaaaa gaatataaag atagattagc ataacttaat gttttaatct tttatttatt   1140
tttataaata ttatatacct gtctatttaa aaatcaaata tttgtcctcc attcccttttc   1200 ccttcaaaac ctcagttcca aatataccgt agttgaatta tattttggaa ggcctattgg   1260
ttggagactt ttccttttca gagattatcc ctcacccttta ttatagcctt tctattttta   1320
aacttcatat agacgccatt cttggggcgg ccgcgat                              1357
```

<210> SEQ ID NO 66
<211> LENGTH: 1357
<212> TYPE: DNA
<213> ORGANISM: Artificial sequence
<220> FEATURE:
<223> OTHER INFORMATION: RTW1012A

<400> SEQUENCE: 66

```
ctagaagata aaccctcccc caaaacacaa attagaatga catttcaagt tccatgtatg      60
tcactttcat tctattattt ttacaacttt tagttactta acagatgtct tgttcagcat     120
aaattataat ttattctgtt ttttttagg gaacaactgt tgtagacaac ttgttgtata      180
gtgaggatat tcattacatg cttggtgcat taaggaccct tggactgcgt gtggaagatg     240
acaaaacaac caaacaagca attgttgaag gctgtggggg attgtttccc actagtaagg    300
aatctaaaga tgaaatcaat ttattccttg gaaatgctgg tattgcaatg agatctttga    360
cagcagctgt ggttgctgca ggtggaaatg caaggtctgt ttttttttt tttgttcagc     420 ataatctttg aattgttcct cgtataacta atcacaacag agtacgtgtt cttcttcctg    480
ttataatcta aaaatctcat ccagattagt catcctttct tcttaaaagg aacctttaat    540
tatcaatgta tttatttaat atttaaatta gcttgtcaaa gtctagcata tacatatttt    600
gattatattc tgagaaatgc acctgagggt gttcctcatg atctacttca acctctgtta    660
```

```
ttattagatt ttctatcatg attactggtt tgagtctcta agtagaccat cttgatgttc      720
aaaatatttc agctacgtac ttgatggggt gccccgaatg agagagaggc caattgggga      780
tttggttgct ggtcttaagc aacttggtgc agatgttgat tgcttttcttg gcacaaactg     840 tccacctgtt cgtgtaaatg ggaagggagg acttcctggc ggaaaggtat ggtttggatt      900
tcatttagaa taaggtggag taactttcct ggatcaaaat tctaatttaa gaagcctccc      960
tgttttcctc tctttagaat aagactaagg gtaggtttag gagttgggtt ttggagagaa     1020
atggaaggga gagcaatttt tttcttcttc taataaatat tctttaattt gatacatttt     1080
ttaagtaaaa gaatataaag atagattagc ataacttaat gttttaatct tttatttatt    1140
tttataaata ttatatacct gtctatttaa aaatcaaata tttgtcctcc attccctttc    1200
ccttcaaaac ctcagttcca aatataccgt agttgaatta tattttggaa ggcctattgg     1260
ttggagactt ttccttttca gagattatcc ctcacccttta ttatagcctt tctatttta    1320 aacttcatat agacgccatt cttggggcgg ccgcgat                              1357
```

```
<210> SEQ ID NO 67
<211> LENGTH: 30
<212> TYPE: DNA
<213> ORGANISM: Artificial sequence
<220> FEATURE:
<223> OTHER INFORMATION: primer, soy1-F1

<400> SEQUENCE: 67
ccactagtaa ggaatctaaa gatgaaatca                                        30

<210> SEQ ID NO 68
<211> LENGTH: 24
<212> TYPE: DNA
<213> ORGANISM: Artificial sequence
<220> FEATURE:
<223> OTHER INFORMATION: primer, soy1-R2

<400> SEQUENCE: 68
cctgcagcaa ccacagctgc tgtc                                              24

<210> SEQ ID NO 69
<211> LENGTH: 15
<212> TYPE: DNA
<213> ORGANISM: Artificial sequence
<220> FEATURE:
<223> OTHER INFORMATION: probe, soy1-T1(FAM-MGB)

<400> SEQUENCE: 69
ctgcaatgcg tcctt                                                        15

<210> SEQ ID NO 70
<211> LENGTH: 19
<212> TYPE: DNA
<213> ORGANISM: Artificial sequence
<220> FEATURE:
<223> OTHER INFORMATION: primer, cas9-F

<400> SEQUENCE: 70
ccttcttcca ccgccttga                                                    19

<210> SEQ ID NO 71
<211> LENGTH: 21
<212> TYPE: DNA
<213> ORGANISM: Artificial sequence
<220> FEATURE:
<223> OTHER INFORMATION: primer, Cas9-R
```

-continued

```
<400> SEQUENCE: 71
tgggtgtctc tcgtgctttt t                                          21

<210> SEQ ID NO 72
<211> LENGTH: 19
<212> TYPE: DNA
<213> ORGANISM: Artificial sequence
<220> FEATURE:
<223> OTHER INFORMATION: probe, Cas9-T(FAM-MGB

<400> SEQUENCE: 72
aatcattcct ggtggagga                                             19

<210> SEQ ID NO 73
<211> LENGTH: 25
<212> TYPE: DNA
<213> ORGANISM: Artificial sequence
<220> FEATURE:
<223> OTHER INFORMATION: primer, pINII-99F

<400> SEQUENCE: 73
tgatgcccac attatagtga ttagc                                      25

<210> SEQ ID NO 74
<211> LENGTH: 22
<212> TYPE: DNA
<213> ORGANISM: Artificial sequence
<220> FEATURE:
<223> OTHER INFORMATION: primer, pINII-13R

<400> SEQUENCE: 74
catcttctgg attggccaac tt                                         22

<210> SEQ ID NO 75
<211> LENGTH: 17
<212> TYPE: DNA
<213> ORGANISM: Artificial sequence
<220> FEATURE:
<223> OTHER INFORMATION: probe, pINII-69T(FAM-MGB)

<400> SEQUENCE: 75
actatgtgtg catcctt                                               17

<210> SEQ ID NO 76
<211> LENGTH: 23
<212> TYPE: DNA
<213> ORGANISM: Artificial sequence
<220> FEATURE:
<223> OTHER INFORMATION: primer, SIP-130F

<400> SEQUENCE: 76
ttcaagttgg gcttttcag aag                                         23

<210> SEQ ID NO 77
<211> LENGTH: 22
<212> TYPE: DNA
<213> ORGANISM: Artificial sequence
<220> FEATURE:
<223> OTHER INFORMATION: primer, SIP-198R

<400> SEQUENCE: 77
tctccttggt gctctcatca ca                                         22

<210> SEQ ID NO 78
```

-continued

```
<211> LENGTH: 15
<212> TYPE: DNA
<213> ORGANISM: Artificial sequence
<220> FEATURE:
<223> OTHER INFORMATION: probe, SIP-170T(VIC-MGB)

<400> SEQUENCE: 78
ctgcagcaga accaa                                                         15

<210> SEQ ID NO 79
<211> LENGTH: 24
<212> TYPE: DNA
<213> ORGANISM: Artificial
<220> FEATURE:
<223> OTHER INFORMATION: WOL569, Forward_primer

<400> SEQUENCE: 79
ggacccatta ggtgagagcg tggg                                               24

<210> SEQ ID NO 80
<211> LENGTH: 19
<212> TYPE: DNA
<213> ORGANISM: Artificial
<220> FEATURE:
<223> OTHER INFORMATION: WOL876, Reverse_primer;

<400> SEQUENCE: 80
cagctgctgt caaagatct                                                     19

<210> SEQ ID NO 81
<211> LENGTH: 29
<212> TYPE: DNA
<213> ORGANISM: Artificial
<220> FEATURE:
<223> OTHER INFORMATION: WOL570, Reverse_primer

<400> SEQUENCE: 81
tctaataata acagaggttg aagtagatc                                          29

<210> SEQ ID NO 82
<211> LENGTH: 4104
<212> TYPE: DNA
<213> ORGANISM: Artificial sequence
<220> FEATURE:
<223> OTHER INFORMATION: soybean codon optimized Cas9

<400> SEQUENCE: 82
atggacaaaa agtactcaat agggctcgac atagggacta actccgttgg atgggccgtc        60
atcaccgacg agtacaaggt gccctccaag aagttcaagg tgttgggaaa caccgacagg       120
cacagcataa agaagaattt gatcggtgcc ctcctcttcg actccggaga gaccgctgag       180
gctaccaggc tcaagaggac cgctagaagg cgctacacca gaaggaagaa cagaatctgc       240
tacctgcagg agatcttctc caacgagatg gccaaggtgg acgactcctt cttccaccgc       300
cttgaggaat cattcctggt ggaggaggat aaaaagcacg agacacccc aatcttcggg        360 aacatcgtcg acgaggtggc ctaccatgaa agtaccccta ccatctacca cctgaggaag       420
aagctggtcg actctaccga caaggctgac ttgcgcttga tttacctggc tctcgctcac       480
atgataaagt ccgcggaca cttcctcatt gagggagacc tgaacccaga caactccgac       540
gtggacaagc tcttcatcca gctcgttcag acctacaacc agcttttcga ggagaaccca       600
atcaacgcca gtggagttga cgccaaggct atcctctctg ctcgtctgtc aaagtccagg       660
aggcttgaga acttgattgc ccagctgcct ggcgaaaaga gaacggact gttcggaaac        720
```

```
ttgatcgctc tctccctggg attgactccc aacttcaagt ccaacttcga cctcgccgag    780
gacgctaagt tgcagttgtc taaagacacc tacgacgatg acctcgacaa cttgctggcc    840
cagataggcg accaatacgc cgatctcttc ctcgccgcta agaacttgtc cgacgcaatc    900
ctgctgtccg acatcctgag agtcaacact gagattacca agctcctct gtctgcttcc     960
atgattaagc gctacgacga gcaccaccaa gatctgaccc tgctcaaggc cctggtgaga   1020
cagcagctgc ccgagaagta caaggagatc ttttcgacc agtccaagaa cggctacgcc    1080
ggatacattg acggaggcgc ctcccaggaa gagttctaca agttcatcaa gcccatcctt   1140
gagaagatga cggtaccga ggagctgttg gtgaagttga acagagagga cctgttgagg    1200
aagcagagaa ccttcgacaa cggaagcatc cctcaccaaa tccacctggg agagctccac   1260
gccatcttga ggaggcagga ggatttctat cccttcctga aggacaaccg cgagaagatt   1320
gagaagatct tgaccttcag aattccttac tacgtcgggc cactcgccag aggaaactct   1380
aggttcgcct ggatgacccg caaatctgaa gagaccatta ctcccctggaa cttcgaggaa  1440
gtcgtggaca agggcgcttc cgctcagtct ttcatcgaga ggatgaccaa cttcgataaa   1500
aatctgccca cgagaaggt gctgcccaag cactccctgt tgtacgagta tttcacagtg    1560
tacaacgagc tcaccaaggt gaagtacgtc acagagggaa tgaggaagcc tgccttcttg   1620
tccggagagc agaagaaggc catcgtcgac ctgctcttca agaccaacag gaaggtgact   1680
gtcaagcagc tgaaggagga ctacttcaag aagatcgagt gcttcgactc cgtcgagatc   1740
tctggtgtcg aggacaggtt caacgcctcc cttgggactt accacgatct gctcaagatt   1800
attaaagaca aggacttcct ggacaacgag gagaacgagg acatccttga ggacatcgtg   1860
ctcaccctga ccttgttcga agacaggaa atgatcgaag agaggctcaa gacctacgcc    1920
cacctcttcg acgacaaggt gatgaaacag ctgaagagac gcagatatac cggctgggga   1980
aggctctccc gcaaattgat caacgggatc agggacaagc agtcaggaa gactatactc    2040
gacttcctga agtccgacgg attcgccaac aggaacttca tgcagctcat tcacgacgac   2100
tccttgacct tcaaggagga catccagaag gctcaggtgt ctggacaggg tgactccttg   2160
catgagcaca ttgctaactt ggccggctct cccgctatta gaagggcat tttgcagacc    2220
gtgaaggtcg ttgacgagct cgtgaaggtg atgggacgcc acaagccaga gaacatcgtt   2280
attgagatgg ctcgcgagaa ccaaactacc cagaaagggc agaagaattc ccgcgagagg   2340
atgaagcgca ttgaggaggg cataaaagag cttggctctc agatcctcaa ggagcacccc   2400
gtcgagaaca ctcagctgca gaacgagaag ctgtacctgt actacctcca aaacggaagg   2460
gacatgtacg tggaccagga gctggacatc aacaggttgt ccgactacga cgtcgaccac   2520
atcgtgcctc agtccttcct gaaggatgac tccatcgaca taaagtgct gacacgctcc    2580
gataaaaata gaggcaagtc cgacaacgtc ccctccgagg aggtcgtgaa gaagatgaaa   2640
aactactgga gacagctctt gaacgccaag ctcatcaccc agcgtaagtt cgacaacctg   2700
actaaggctg agagaggagg attgtccgag ctcgataagg ccggattcat caagagacag   2760
ctcgtcgaaa cccgccaaat taccaagcac gtggcccaaa ttctggattc ccgcatgaac   2820
accaagtacg atgaaaatga caagctgatc cgcgaggtca aggtgatcac cttgaagtcc   2880
aagctggtct ccgacttccg caaggacttc cagttctaca aggtgaggga gatcaacaac   2940
taccaccacg cacacgacgc ctacctcaac gctgtcgttg gaaccgccct catcaaaaaa   3000
tatcctaagc tggagtctga gttcgtctac ggcgactaca aggtgtacga cgtgaggaag   3060
```

```
atgatcgcta agtctgagca ggagatcggc aaggccaccg ccaagtactt cttctactcc    3120
aacatcatga acttcttcaa gaccgagatc actctcgcca acgtgagat caggaagcgc    3180 ccactgatcg agaccaacgg tgagactgga gagatcgtgt gggacaaagg gagggatttc    3240
gctactgtga ggaaggtgct ctccatgcct caggtgaaca tcgtcaagaa gaccgaagtt    3300
cagaccggag gattctccaa ggagtccatc ctccccaaga gaaactccga caagctgatc    3360
gctagaaaga aagactggga ccctaagaag tacggaggct tcgattctcc taccgtggcc    3420
tactctgtgc tggtcgtggc caaggtggag aagggcaagt ccaagaagct gaaatccgtc    3480
aaggagctcc tcgggattac catcatggag aggagttcct tcgagaagaa ccctatcgac    3540
ttcctggagg ccaagggata taagaggtg aagaaggacc tcatcatcaa gctgcccaag    3600
tactccctct tcgagttgga gaacggaagg aagaggatgc tggcttctgc cggagagttg    3660
cagaagggaa atgagctcgc ccttccctcc aagtacgtga acttcctgta cctcgcctct    3720
cactatgaaa agttgaaggg ctctcctgag gacaacgagc agaagcagct cttcgtggag    3780
cagcacaagc actacctgga cgaaattatc gagcagatct ctgagttctc caagcgcgtg    3840
atattggccg acgccaacct cgacaaggtg ctgtccgcct acaacaagca cagggataag    3900
cccattcgcg agcaggctga aaacattatc cacctgttta ccctcacaaa cttgggagcc    3960
cctgctgcct tcaagtactt cgacaccacc attgacagga agatacac ctccaccaag    4020 gaggtgctcg acgcaacact catccaccaa tccatcaccg gcctctatga aacaaggatt    4080
gacttgtccc agctgggagg cgac                                         4104

<210> SEQ ID NO 83
<211> LENGTH: 23
<212> TYPE: DNA
<213> ORGANISM: Glycine max
<220> FEATURE:
<221> NAME/KEY: misc_feature
<222> LOCATION: (1)..(23)
<223> OTHER INFORMATION: soy EPSPS-CR4, Cas9 target sequence

<400> SEQUENCE: 83
gtttgtttgt tgttgggtgt ggg                                            23

<210> SEQ ID NO 84
<211> LENGTH: 22
<212> TYPE: DNA
<213> ORGANISM: Glycine max
<220> FEATURE:
<221> NAME/KEY: misc_feature
<222> LOCATION: (1)..(23)
<223> OTHER INFORMATION: soy EPSPS-CR5, Cas9 target sequence

<400> SEQUENCE: 84
tgttgttggg tgtgggaata gg                                             22

<210> SEQ ID NO 85
<211> LENGTH: 9174
<212> TYPE: DNA
<213> ORGANISM: Artificial sequence
<220> FEATURE:
<223> OTHER INFORMATION: RTW1199

<400> SEQUENCE: 85
ccgggtgtga tttagtataa agtgaagtaa tggtcaaaag aaaaagtgta aaacgaagta     60
cctagtaata agtaatattg aacaaaataa atggtaaagt gtcagatata taaaataggc    120
tttaataaaa ggaagaaaaa aaacaaacaa aaaataggtt gcaatggggc agagcagagt    180
```

```
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg tttgtttgtt gttgggtgtg ttttagagct agaaatagca    480
agttaaaata aggctagtcc gttatcaact tgaaaaagtg gcaccgagtc ggtgcttttt    540
tttgcggccg caattggatc gggtttactt attttgtggg tatctatact tttattagat    600
ttttaatcag gctcctgatt tcttttttatt tcgattgaat tcctgaactt gtattattca    660
gtagatcgaa taaattataa aaagataaaa tcataaaata atattttatc ctatcaatca    720
tattaaagca atgaatatgt aaaattaatc ttatctttat tttaaaaaat catataggtt    780
tagtattttt ttaaaaataa agataggatt agttttacta ttcactgctt attactttta    840
aaaaaatcat aaaggtttag tattttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtcgt   1020
cataatatcg ccaaatgcca actggactac gtcgaaccca caatcccac aaagcgcgtg    1080 aaatcaaatc gctcaaacca caaaaaagaa caacgcgttt gttacacgct caatcccacg   1140
cgagtagagc acagtaacct tcaaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgttttt   1440
ttatttatgc tttatgctgt tgatgttcgg ttgtttgttt cgctttgttt ttgtggttca   1500
gttttttagg attcttttgg ttttttgaatc gattaatcgg aagagatttt cgagttattt   1560
ggtgtgttgg aggtgaatct ttttttttgag gtcatagatc tgttgtattt gtgttataaa   1620
catgcgactt tgtatgattt tttacgaggt tatgatgttc tggttgtttt attatgaatc   1680
tgttgagaca gaaccatgat ttttgttgat gttcgtttac actattaaag gtttgtttta   1740
acaggattaa aagtttttta agcatgttga aggagtcttg tagatatgta accgtcgata   1800 gttttttttgt gggtttgttc acatgttatc aagcttaatc ttttactatg tatgcgacca   1860
tatctggatc cagcaaaggc gattttttaa ttccttgtga aacttttgta atatgaagtt   1920 gaaatttttgt tattggtaaa ctataaatgt gtgaagttgg agtataccct taccttctta   1980
tttggctttg tgatagttta atttatatgt attttgagtt ctgacttgta tttctttgaa   2040
ttgattctag tttaagtaat ccatggcacc gaagaagaag cgcaaggtga tggacaaaaa   2100
gtactcaata gggctcgaca tagggactaa ctccgttgga tgggccgtca tcaccgacga   2160
gtacaaggtg ccctccaaga agttcaaggt gttgggaaac accgacaggc acagcataaa   2220
gaagaatttg atcggtgccc tcctcttcga ctccggagag accgctgagg ctaccaggct   2280
caagaggacc gctagaaggc gctacaccag aaggaagaac agaatctgct acctgcagga   2340
gatcttctcc aacgagatgg ccaaggtgga cgactccttc ttccaccgcc ttgaggaatc   2400
attcctggtg gaggaggata aaaagcacga gagacaccca atcttcggga acatcgtcga   2460
cgaggtggcc taccatgaaa agtaccctac catctaccac ctgaggaaga gctggtcga   2520
```

-continued

```
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattga    3180 cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcaggaag actatactcg acttcctgaa    4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagag aacatcgtta ttgagatggc    4380
tcgcgagaac caaactaccc agaaagggca gaagaattcc cgcgagagga tgaagcgcat    4440
tgaggagggc ataaaagagc ttggctctca gatcctcaag gagcacccg tcgagaacac    4500 tcagctgcag aacgagaagc tgtacctgta ctacctccaa aacggaaggg acatgtacgt    4560
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
aggcaagtcc gacaacgtcc cctccgagga ggtcgtgaag aagatgaaaa actactggag    4740
acagctcttg aacgccaagc tcatcaccca gcgtaagttc gacaacctga ctaaggctga    4800
gagaggagga ttgtccgagc tcgataaggc cggattcatc aagagacagc tcgtcgaaac    4860
ccgccaaatt accaagcacg tggcccaaat tctggattcc cgcatgaaca ccaagtacga    4920
```

```
tgaaaatgac aagctgatcc gcgaggtcaa ggtgatcacc ttgaagtcca agctggtctc    4980
cgacttccgc aaggacttcc agttctacaa ggtgagggag atcaacaact accaccacgc    5040
acacgacgcc tacctcaacg ctgtcgttgg aaccgccctc atcaaaaaat atcctaagct    5100
ggagtctgag ttcgtctacg gcgactacaa ggtgtacgac gtgaggaaga tgatcgctaa    5160
gtctgagcag gagatcggca aggccaccgc caagtacttc ttctactcca acatcatgaa    5220
cttcttcaag accgagatca ctctcgccaa cggtgagatc aggaagcgcc cactgatcga    5280
gaccaacggt gagactggag agatcgtgtg ggacaaaggg agggatttcg ctactgtgag    5340
gaaggtgctc tccatgcctc aggtgaacat cgtcaagaag accgaagttc agaccggagg    5400
attctccaag gagtccatcc tccccaagag aaactccgac aagctgatcg ctagaaagaa    5460
agactgggac cctaagaagt acggaggctt cgattctcct accgtggcct actctgtgct    5520
ggtcgtggcc aaggtggaga agggcaagtc caagaagctg aaatccgtca aggagctcct    5580
cgggattacc atcatggaga ggagttcctt cgagaagaac cctatcgact tcctggaggc    5640
caagggatat aaagaggtga agaaggacct catcatcaag ctgcccaagt actccctctt    5700
cgagttggag aacggaagga agaggatgct ggcttctgcc ggagagttgc agaagggaaa    5760
tgagctcgcc cttccctcca agtacgtgaa cttcctgtac ctcgcctctc actatgaaaa    5820
gttgaagggc tctcctgagg acaacgagca gaagcagctc ttcgtggagc agcacaagca    5880
ctacctggac gaaattatcg agcagatctc tgagttctcc aagcgcgtga tattggccga    5940
cgccaacctc gacaaggtgc tgtccgccta caacaagcac agggataagc ccattcgcga    6000
gcaggctgaa acattatcc acctgtttac cctcacaaac ttgggagccc ctgctgcctt    6060
caagtacttc gacaccacca ttgacaggaa gagatacacc tccaccaagg aggtgctcga    6120
cgcaacactc atccaccaat ccatcaccgg cctctatgaa acaaggattg acttgtccca    6180
gctgggaggc gactctagag ccgatcccaa gaagaagaga aaggtgaaga ccacgggaa    6240 ccgccacgat ggcgagctgg gaggccgcaa gcgggcaagg taggttaacc tagacttgtc    6300
catcttctgg attggccaac ttaattaatg tatgaaataa aaggatgcac acatagtgac    6360
atgctaatca ctataatgtg ggcatcaaag ttgtgtgtta tgtgtaatta ctagttatct    6420
gaataaaaga gaaagagatc atccatattt cttatcctaa atgaatgtca cgtgtcttta    6480
taattctttg atgaaccaga tgcatttcat taaccaaatc catatacata taatattaa    6540 tcatatataa ttaatatcaa ttgggttagc aaaacaaatc tagtctaggt gtgttttgcg    6600
aattcgatat caagcttatc gataccgtcg aggggggggcc cggtaccggc gcgccgttct    6660
atagtgtcac ctaaatcgta tgtgtatgat acataaggtt atgtattaat tgtagccgcg    6720
ttctaacgac aatatgtcca tatggtgcac tctcagtaca atctgctctg atgccgcata    6780
gttaagccag ccccgacacc cgccaacacc cgctgacgcg ccctgacggg cttgtctgct    6840
cccggcatcc gcttacagac aagctgtgac cgtctccggg agctgcatgt gtcagaggtt    6900
ttcaccgtca tcaccgaaac gcgcgagacg aaagggcctc gtgatacgcc tatttttata    6960
ggttaatgtc atgaccaaaa tcccttaacg tgagttttcg ttccactgag cgtcagaccc    7020
cgtagaaaag atcaaaggat cttcttgaga tccttttttt ctgcgcgtaa tctgctgctt    7080
gcaaacaaaa aaccaccgc taccagcggt ggtttgtttg ccggatcaag agctaccaac    7140 tcttttccg aaggtaactg gcttcagcag agcgcagata ccaaatactg ttcttctagt    7200
gtagccgtag ttaggccacc acttcaagaa ctctgtagca ccgcctacat acctcgctct    7260
```

```
gctaatcctg ttaccagtgg ctgctgccag tggcgataag tcgtgtctta ccgggttgga      7320
ctcaagacga tagttaccgg ataaggcgca gcggtcgggc tgaacggggg gttcgtgcac      7380
acagcccagc ttggagcgaa cgacctacac cgaactgaga tacctacagc gtgagctatg      7440
agaaagcgcc acgcttcccg aagggagaaa ggcggacagg tatccggtaa gcggcagggt      7500
cggaacagga gagcgcacga gggagcttcc agggggaaac gcctggtatc tttatagtcc      7560
tgtcgggttt cgccacctct gacttgagcg tcgatttttg tgatgctcgt caggggggcg      7620
gagcctatgg aaaaacgcca gcaacgcggc cttttracgg ttcctggcct tttgctggcc      7680
ttttgctcac atgttctttc ctgcgttatc ccctgattct gtggataacc gtattaccgc      7740
ctttgagtga gctgataccg ctcgccgcag ccgaacgacc gagcgcagcg agtcagtgag      7800
cgaggaagcg gaagagcgcc caatacgcaa accgcctctc cccgcgcgtt ggccgattca      7860
ttaatgcagg ttgatcagat ctcgatcccg cgaaattaat acgactcact ataggggagac      7920 cacaacggtt tccctctaga aataattttg tttaacttta agaaggagat atacccatgg      7980
aaaagcctga actcaccgcg acgtctgtcg agaagtttct gatcgaaaag ttcgacagcg      8040
tctccgacct gatgcagctc tcggagggcg aagaatctcg tgctttcagc ttcgatgtag      8100
gagggcgtgg atatgtcctg cgggtaaata gctgcgccga tggtttctac aaagatcgtt      8160
atgtttatcg gcactttgca tcggccgcgc tcccgattcc ggaagtgctt gacattgggg      8220
aattcagcga gagcctgacc tattgcatct cccgccgtgc acagggtgtc acgttgcaag      8280
acctgcctga aaccgaactg cccgctgttc tgcagccggt cgcggaggct atggatgcga      8340
tcgctgcggc cgatcttagc cagacgagcg ggttcggccc attcggaccg caaggaatcg      8400
gtcaatacac tacatggcgt gatttcatat gcgcgattgc tgatccccat gtgtatcact      8460
ggcaaactgt gatggacgac accgtcagtg cgtccgtcgc gcaggctctc gatgagctga      8520
tgctttgggc cgaggactgc cccgaagtcc ggcacctcgt gcacgcggat ttcggctcca      8580
acaatgtcct gacggacaat ggccgcataa cagcggtcat tgactggagc gaggcgatgt      8640
tcggggattc ccaatacgag gtcgccaaca tcttcttctg gaggccgtgg ttggcttgta      8700
tggagcagca gacgcgctac ttcgagcgga ggcatccgga gcttgcagga tcgccgcggc      8760
tccgggcgta tatgctccgc attggtcttg accaactcta tcagagcttg gttgacggca      8820
atttcgatga tgcagcttgg gcgcagggtc gatgcgacgc aatcgtccga tccggagccg      8880
ggactgtcgg gcgtacacaa atcgcccgca gaagcgcggc cgtctggacc gatggctgtg      8940
tagaagtact cgccgatagt ggaaaccgac gccccagcac tcgtccgagg gcaaaggaat      9000
agtgaggtac agcttggatc gatccggctg ctaacaaagc ccgaaaggaa gctgagttgg      9060
ctgctgccac cgctgagcaa taactagcat aaccccttgg ggcctctaaa cgggtcttga      9120 ggggttttt gctgaaagga ggaactatat ccggatgctc gggcgcgccg gtac             9174
```

<210> SEQ ID NO 86
<211> LENGTH: 9174
<212> TYPE: DNA
<213> ORGANISM: Artificial sequence
<220> FEATURE:
<223> OTHER INFORMATION: RTW1200

<400> SEQUENCE: 86

```
ccgggtgtga tttagtataa agtgaagtaa tggtcaaaag aaaaagtgta aaacgaagta       60
cctagtaata agtaatattg aacaaaataa atggtaaagt gtcagatata taaaataggc      120
tttaataaaa ggaagaaaaa aaacaaacaa aaaataggtt gcaatggggc agagcagagt      180
```

```
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg tgttgttggg tgtgggaatg ttttagagct agaaatagca    480
agttaaaata aggctagtcc gttatcaact tgaaaaagtg gcaccgagtc ggtgcttttt    540
tttgcggccg caattggatc gggtttactt attttgtggg tatctatact tttattagat    600
ttttaatcag gctcctgatt tcttttttatt tcgattgaat tcctgaactt gtattattca    660
gtagatcgaa taaattataa aaagataaaa tcataaaata atatttttatc ctatcaatca    720
tattaaagca atgaatatgt aaaattaatc ttatctttat tttaaaaaat catataggtt    780
tagtattttt ttaaaaataa agataggatt agttttacta ttcactgctt attacttttta    840
aaaaaatcat aaaggtttag tatttttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtcgt   1020
cataatatcg ccaaatgcca actggactac gtcgaaccca caatcccac aaagcgcgtg    1080
aaatcaaatc gctcaaacca caaaaaagaa caacgcgttt gttacacgct caatcccacg   1140
cgagtagagc acagtaacct tcaaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgttttt   1440
ttatttatgc tttatgctgt tgatgttcgg ttgtttgttt cgctttgttt ttgtggttca   1500
gttttttagg attcttttgg ttttttgaatc gattaatcgg aagagatttt cgagttattt   1560
ggtgtgttgg aggtgaatct tttttttgag gtcatagatc tgttgtattt gtgttataaa   1620
catgcgactt tgtatgattt tttacagggt tatgatgttc tggttgtttt attatgaatc   1680
tgttgagaca gaaccatgat ttttgttgat gttcgtttac actattaaag gtttgtttta   1740
acaggattaa aagttttta agcatgttga aggagtcttg tagatatgta accgtcgata   1800
gttttttttgt gggtttgttc acatgttatc aagcttaatc ttttactatg tatgcgacca   1860
tatctggatc cagcaaaggc gattttttaa ttccttgtga aacttttgta atatgaagtt   1920
gaaattttgt tattggtaaa ctataaatgt gtgaagttgg agtataccct tacctttctta   1980
tttggctttg tgatagttta atttatatgt attttgagtt ctgacttgta tttctttgaa   2040
ttgattctag tttaagtaat ccatggcacc gaagaagaag cgcaaggtga tggacaaaaa   2100
gtactcaata gggctcgaca tagggactaa ctccgttgga tgggccgtca tcaccgacga   2160
gtacaaggtg ccctccaaga gttcaaggt gttgggaaac accgacaggc acagcataaa   2220
gaagaatttg atcggtgccc tcctcttcga ctccggagag accgctgagg ctaccaggct   2280
caagaggacc gctagaaggc gctacaccag aaggaagaac agaatctgct acctgcagga   2340
gatcttctcc aacgagatgg ccaaggtgga cgactccttc ttccaccgcc ttgaggaatc   2400
attcctggtg gaggaggata aaaagcacga gagacaccca atcttcggga acatcgtcga   2460
cgaggtggcc taccatgaaa agtaccctac catctaccac ctgaggaaga agctggtcga   2520
```

```
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattga    3180
cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcaggaagg actatactcg acttcctgaa    4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagag aacatcgtta ttgagatggc    4380
tcgcgagaac caaactaccc agaaagggca gaagaattcc cgcgagagga tgaagcgcat    4440
tgaggagggc ataaaagagc ttggctctca gatcctcaag gagcaccccg tcgagaacac    4500
tcagctgcag aacgagaagc tgtacctgta ctacctccaa aacggaaggg acatgtacgt    4560
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
aggcaagtcc gacaacgtcc cctccgagga ggtcgtgaag aagatgaaaa actactggag    4740
acagctcttg aacgccaagc tcatcaccca gcgtaagttc gacaacctga ctaaggctga    4800
gagaggagga ttgtccgagc tcgataaggc cggattcatc aagagacagc tcgtcgaaac    4860
ccgccaaatt accaagcacg tggcccaaat tctggattcc cgcatgaaca ccaagtacga    4920
```

```
tgaaaatgac aagctgatcc gcgaggtcaa ggtgatcacc ttgaagtcca agctggtctc   4980
cgacttccgc aaggacttcc agttctacaa ggtgagggag atcaacaact accaccacgc   5040
acacgacgcc tacctcaacg ctgtcgttgg aaccgccctc atcaaaaaat atcctaagct   5100
ggagtctgag ttcgtctacg gcgactacaa ggtgtacgac gtgaggaaga tgatcgctaa   5160
gtctgagcag gagatcggca aggccaccgc caagtacttc ttctactcca acatcatgaa   5220
cttcttcaag accgagatca ctctcgccaa cggtgagatc aggaagcgcc cactgatcga   5280
gaccaacggt gagactggag agatcgtgtg ggacaaaggg agggatttcg ctactgtgag   5340
gaaggtgctc tccatgcctc aggtgaacat cgtcaagaag accgaagttc agaccggagg   5400
attctccaag gagtccatcc tccccaagag aaactccgac aagctgatcg ctagaaagaa   5460
agactgggac cctaagaagt acggaggctt cgattctcct accgtggcct actctgtgct   5520
ggtcgtggcc aaggtggaga agggcaagtc caagaagctg aaatccgtca aggagctcct   5580
cgggattacc atcatggaga ggagttcctt cgagaagaac cctatcgact tcctggaggc   5640
caagggatat aaagaggtga agaaggacct catcatcaag ctgcccaagt actccctctt   5700
cgagttggag aacggaagga agaggatgct ggcttctgcc ggagagttgc agaagggaaa   5760
tgagctcgcc cttccctcca gtacgtgaa cttcctgtac ctcgcctctc actatgaaaa   5820
gttgaagggc tctcctgagg acaacgagca gaagcagctc ttcgtggagc agcacaagca   5880
ctacctggac gaaattatcg agcagatctc tgagttctcc aagcgcgtga tattggccga   5940
cgccaacctc gacaaggtgc tgtccgccta acaagcac agggataagc ccattcgcga   6000
gcaggctgaa acattatcc acctgtttac cctcacaaac ttgggagccc ctgctgcctt   6060
caagtacttc gacaccacca ttgacaggaa gagatacacc tccaccaagg aggtgctcga   6120
cgcaacactc atccaccaat ccatcaccgg cctctatgaa acaaggattg acttgtccca   6180
gctgggaggc gactctagag ccgatcccaa gaagaagaga aaggtgaaga ccacgggga   6240
ccgccacgat ggcgagctgg gaggccgcaa gcgggcaagg taggttaacc tagacttgtc   6300
catcttctgg attggccaac ttaattaatg tatgaaataa aaggatgcac acatagtgac   6360
atgctaatca ctataatgtg ggcatcaaag ttgtgtgtta tgtgtaatta ctagttatct   6420
gaataaaaga gaaagagatc atccatattt cttatcctaa atgaatgtca cgtgtcttta   6480
taattctttg atgaaccaga tgcatttcat taaccaaatc catatacata taaatattaa   6540
tcatatataa ttaatatcaa ttgggttagc aaaacaaatc tagtctaggt gtgttttgcg   6600
aattcgatat caagcttatc gataccgtcg aggggggggcc cggtaccggc gcgccgttct   6660
atagtgtcac ctaaatcgta tgtgtatgat acataaggtt atgtattaat tgtagccgcg   6720
ttctaacgac aatatgtcca tatggtgcac tctcagtaca atctgctctg atgccgcata   6780
gttaagccag ccccgacacc cgccaacacc cgctgacgcg ccctgacggg cttgtctgct   6840
cccggcatcc gcttacagac aagctgtgac cgtctccggg agctgcatgt gtcagaggtt   6900
ttcaccgtca tcaccgaaac gcgcgagacg aaagggcctc gtgatacgcc tatttttata   6960
ggttaatgtc atgaccaaaa tcccttaacg tgagttttcg ttccactgag cgtcagaccc   7020
cgtagaaaag atcaaaggat cttcttgaga tccttttttt ctgcgcgtaa tctgctgctt   7080
gcaaacaaaa aaccaccgc taccagcggt ggtttgtttg ccggatcaag agctaccaac   7140
tcttttccg aaggtaactg gcttcagcag agcgcagata ccaaatactg ttcttctagt   7200
gtagccgtag ttaggccacc acttcaagaa ctctgtagca ccgcctacat acctcgctct   7260
```

| | | | | |
|---|---|---|---|---|
| gctaatcctg | ttaccagtgg | ctgctgccag | tggcgataag | tcgtgtctta ccgggttgga | 7320 |
| ctcaagacga | tagttaccgg | ataaggcgca | gcggtcgggc | tgaacggggg gttcgtgcac | 7380 |
| acagcccagc | ttggagcgaa | cgacctacac | cgaactgaga | tacctacagc gtgagctatg | 7440 |
| agaaagcgcc | acgcttcccg | aagggagaaa | ggcggacagg | tatccggtaa gcggcagggt | 7500 |
| cggaacagga | gagcgcacga | gggagcttcc | aggggggaaac | gcctggtatc tttatagtcc | 7560 |
| tgtcgggttt | cgccacctct | gacttgagcg | tcgatttttg | tgatgctcgt caggggggcg | 7620 |
| gagcctatgg | aaaaacgcca | gcaacgcggc | cttttacgg | ttcctggcct tttgctggcc | 7680 |
| ttttgctcac | atgttctttc | ctgcgttatc | ccctgattct | gtggataacc gtattaccgc | 7740 |
| ctttgagtga | gctgataccg | ctcgccgcag | ccgaacgacc | gagcgcagcg agtcagtgag | 7800 |
| cgaggaagcg | gaagagcgcc | caatacgcaa | accgcctctc | cccgcgcgtt ggccgattca | 7860 |
| ttaatgcagg | ttgatcagat | ctcgatcccg | cgaaattaat | acgactcact ataggagac | 7920 |
| cacaacggtt | tccctctaga | aataattttg | tttaacttta | agaaggagat atacccatgg | 7980 |
| aaaagcctga | actcaccgcg | acgtctgtcg | agaagtttct | gatcgaaaag ttcgacagcg | 8040 |
| tctccgacct | gatgcagctc | tcggagggcg | aagaatctcg | tgctttcagc ttcgatgtag | 8100 |
| gagggcgtgg | atatgtcctg | cgggtaaata | gctgcgccga | tggtttctac aaagatcgtt | 8160 |
| atgtttatcg | gcactttgca | tcggccgcgc | tcccgattcc | ggaagtgctt gacattgggg | 8220 |
| aattcagcga | gagcctgacc | tattgcatct | cccgccgtgc | acagggtgtc acgttgcaag | 8280 |
| acctgcctga | aaccgaactg | cccgctgttc | tgcagccggt | cgcggaggct atggatgcga | 8340 |
| tcgctgcggc | cgatcttagc | cagacgagcg | ggttcggccc | attcggaccg caaggaatcg | 8400 |
| gtcaatacac | tacatggcgt | gatttcatat | gcgcgattgc | tgatccccat gtgtatcact | 8460 |
| ggcaaactgt | gatggacgac | accgtcagtg | cgtccgtcgc | gcaggctctc gatgagctga | 8520 |
| tgctttgggc | cgaggactgc | cccgaagtcc | ggcacctcgt | gcacgcggat tcggctcca | 8580 |
| acaatgtcct | gacggacaat | ggccgcataa | cagcggtcat | tgactggagc gaggcgatgt | 8640 |
| tcggggattc | ccaatacgag | gtcgccaaca | tcttcttctg | gaggccgtgg ttggcttgta | 8700 |
| tggagcagca | gacgcgctac | ttcgagcgga | ggcatccgga | gcttgcagga tcgccgcggc | 8760 |
| tccgggcgta | tatgctccgc | attggtcttg | accaactcta | tcagagcttg gttgacggca | 8820 |
| atttcgatga | tgcagcttgg | gcgcagggtc | gatgcgacgc | aatcgtccga tccggagccg | 8880 |
| ggactgtcgg | gcgtacacaa | atcgcccgca | gaagcgcggc | cgtctggacc gatggctgtg | 8940 |
| tagaagtact | cgccgatagt | ggaaaccgac | gccccagcac | tcgtccgagg caaaggaat | 9000 |
| agtgaggtac | agcttggatc | gatccggctg | ctaacaaagc | ccgaaaggaa gctgagttgg | 9060 |
| ctgctgccac | cgctgagcaa | taactagcat | aaccccttgg | ggcctctaaa cgggtcttga | 9120 |
| ggggttttt | gctgaaagga | ggaactatat | ccggatgctc | gggcgcgccg gtac | 9174 |

<210> SEQ ID NO 87
<211> LENGTH: 3175
<212> TYPE: DNA
<213> ORGANISM: Artificial sequence
<220> FEATURE:
<223> OTHER INFORMATION: RTW1190A

<400> SEQUENCE: 87

| | | | | |
|---|---|---|---|---|
| cgaattctac | aggtcactaa | taccatctaa | gtagttggtt | catagtgact gcatatgtaa | 60 |
| aaattatcct | tattttaagg | aaattaaaaa | ttatcatata | tataagtt ttaaattaat | 120 |
| tatcttatat | atgtaccaaa | aagttttaaa | gcaattatta | taaaaattaa taaatttatc | 180 |

```
atataaaata atttataatt aaattttaaa ttatcaattc attaaattaa attatttaaa      240 attttgaat gataatataa taatttatc ctctactaag tcccaacgtt tcctattta        300 ttccactttt agcaataaat tttgtcataa acacttataa caaaaaagt aagtaaaaaa      360 taaaaaaag tttttcaata aagtataaac taatttgtat aaacttttag aaaaaataaa      420
gttatacatt gataatataa atttttaca taattatccg atcaactcat tatatatgat     480
aaatttattg atttttaaa ataattatct taaaataatt taaacaatga tttgcaatta     540
gatgataata taaaattatt ttacacacta catgtattaa actcaaactt ttatatatta    600
gtttttctaa aaactaattt ttaactcaaa aaaaatgtta cttataattt tcttatcttc    660
tttttttata agtatttttt aagaaattta ttgaaacatg accatgcttg ggtcaataat    720
actactctct tagacaccaa acaacccttc ccaaactata atctaatcca aaagccatca    780
ttcattttcc ttggtaggta aagttccaag accttcacca acttttcac tcaattgttt    840 tggtgtaagc aattcgacat gtgttagtgt tagttggcaa ccaaaaatcc ctttatgtga    900
ctcaatccaa caaccactca caccaccaac ccccataacc atttctcaca ataccttca    960 tttacacatt atcatcacca aaataaaata aaaaaaacct ctcattcag agagagagag   1020 agagacttca cagaccaaag tgcagagaac aacaaagttc acaactttaa ggaaaattga   1080
aatggcccaa gtgagcagag tgcacaatct tgctcaaagc actcaaattt ttggccattc   1140
ttccaactcc aacaaactca aatcggtgaa ttcggtttca ttgaggccac gcctttgggg   1200
ggcctcaaaa tctcgcatcc cgatgcataa aaatggaagc tttatgggaa atttaatgt     1260 ggggaaggga aattccggcg tgtttaaggt ttctgcatcg gtcgccgccg cagagaagcc   1320
gtcaacgtcg ccggagatcg tgttggaacc catcaaagac ttctcgggta ccatcacatt    1380
gccagggtcc aagtctctgt ccaatcgaat tttgcttctt gctgctctct ctgaggttcg    1440
tagatttctt ccgttttttt ttcttcttct ttattgtttg ttctacatca gcatgatgtt    1500
gatttgattg tgttttctat cgtttcatcg attataaatt ttcataatca gaagattcag   1560
cttttattaa tgcaagaacg tccttaattg atgattttat aaccgtaaat taggtctaat    1620
tagagttttt ttcataaaga ttttcagatc cgtttacaac aagccttaat tgttgattct    1680
gtagtcgtag attaaggttt ttttcatgaa ctacttcaga tccgttaaac aacagcctta    1740
tttgttgata cttcagtcgt ttttcaagaa attgttcaga tccgttgata aaagccttat    1800
tcgttgattc tgtatggtat ttcaagagat attgctcagg tcctttagca actaccttat    1860
ttgttgattc tgtggccata gattaggatt tttttcacg aaattgcttc ttgaaattac     1920
gtgatggatt ttgattctga tttatcttgt gattgttgac tctacaggga caactgttg    1980 tagacaactt gttgtatagt gaggatattc attacatgct tggtgcatta aggacccttg    2040
gactgcgtgt ggaagatgac aaaacaacca aacaagcaat tgttgaaggc tgtggggat    2100 tgtttcccac tagtaaggaa tctaaagatg aaatcaattt attccttgga aatgctggta   2160
ttgcaatgag atctttgaca gcagctgttg ttgctgcagg tggaaatgca aggtctgttt   2220 ttttttttt tgttcagcat aatctttgaa ttgttcctcg tataactaat cacaacagag    2280
tacgtgttct tcttcctgtt ataatctaaa atctcatcc agattagtca tcctttcttc    2340
ttaaaaggaa cctttaatta tcaatgtatt tatttaatat ttaaattagc ttgtcaaagt    2400
ctagcatata catattttga ttatattctg agaaatgcac ctgagggtgt tcctcatgat   2460
ctacttcaac ctctgttatt attagatttt ctatcatgat tactggtttg agtctctaag   2520
```

| | |
|---|---|
| tagaccatct tgatgttcaa atatttcag ctacgtactt gatggggtgc cccgaatgag | 2580 |
| agagaggcca attggggatt tggttgctgg tcttaagcaa cttggtgcag atgttgattg | 2640 |
| ctttcttggc acaaactgtc cacctgttcg tgtaaatggg aagggaggac ttcctggcgg | 2700 |
| aaaggtatgg tttggatttc atttagaata aggtggagta actttcctgg atcaaaattc | 2760 |
| taatttaaga agcctccctg ttttcctctc tttagaataa gactaagggt aggtttagga | 2820 |
| gttgggtttt ggagagaaat ggaagggaga gcaattttt tcttcttcta ataaatattc | 2880 |
| tttaatttga tacatttttt aagtaaaaga atataaagat agattagcat aacttaatgt | 2940 |
| tttaatcttt tatttatttt tataaatatt atatacctgt ctatttaaaa atcaaatatt | 3000 |
| tgtcctccat tcccttccc ttcaaaacct cagttccaaa tataccgtag ttgaattata | 3060 |
| ttttggaagg cctattggtt ggagactttt ccttttcaga gattatccct cacctttatt | 3120 |
| atagcctttc tatttttaaa cttcatatag acgccattct tggggcggcc gcgat | 3175 |

<210> SEQ ID NO 88
<211> LENGTH: 23
<212> TYPE: DNA
<213> ORGANISM: Artificial sequence
<220> FEATURE:
<223> OTHER INFORMATION: primer, soy1-F3

<400> SEQUENCE: 88
gtttgtttgt tgttgggtgt ggg        23

<210> SEQ ID NO 89
<211> LENGTH: 25
<212> TYPE: DNA
<213> ORGANISM: Artificial sequence
<220> FEATURE:
<223> OTHER INFORMATION: primer, soy1-R3

<400> SEQUENCE: 89
gacatgatgc ttcattttca cagaa        25

<210> SEQ ID NO 90
<211> LENGTH: 18
<212> TYPE: DNA
<213> ORGANISM: Artificial sequence
<220> FEATURE:
<223> OTHER INFORMATION: probe, soy1-T2(FAM-MGB)

<400> SEQUENCE: 90
tgtgtagagt ggattttg        18

<210> SEQ ID NO 91
<211> LENGTH: 22
<212> TYPE: DNA
<213> ORGANISM: Artificial sequence
<220> FEATURE:
<223> OTHER INFORMATION: primer, soy1-F2

<400> SEQUENCE: 91
tgttgttggg tgtgggaata gg        22

<210> SEQ ID NO 92
<211> LENGTH: 31
<212> TYPE: DNA
<213> ORGANISM: Artificial sequence
<220> FEATURE:
<223> OTHER INFORMATION: WOL1001, Forward_primer

<400> SEQUENCE: 92

```
aggtttaatt ttatataatg ttagcataca g                                    31

<210> SEQ ID NO 93
<211> LENGTH: 28
<212> TYPE: DNA
<213> ORGANISM: Artificial sequence
<220> FEATURE:
<223> OTHER INFORMATION: WOL1002, Reverse_primer

<400> SEQUENCE: 93
atcaacatca tgctgatgta gaacaaac                                        28

<210> SEQ ID NO 94
<211> LENGTH: 29
<212> TYPE: DNA
<213> ORGANISM: Artificial sequence
<220> FEATURE:
<223> OTHER INFORMATION: WOL1003, Forward_primer

<400> SEQUENCE: 94
attctgattt atcttgtgat tgttgactc                                       29

<210> SEQ ID NO 95
<211> LENGTH: 27
<212> TYPE: DNA
<213> ORGANISM: Artificial sequence
<220> FEATURE:
<223> OTHER INFORMATION: WOL1004, Reverse_primer

<400> SEQUENCE: 95
atttactttg gagagaataa ggagggg                                         27

<210> SEQ ID NO 96
<211> LENGTH: 23
<212> TYPE: DNA
<213> ORGANISM: Glycine max
<220> FEATURE:
<221> NAME/KEY: misc_feature
<222> LOCATION: (1)..(23)
<223> OTHER INFORMATION: soy EPSPS-CR6, Cas9 target sequence

<400> SEQUENCE: 96
gaaacgttgg gacttagtag agg                                             23

<210> SEQ ID NO 97
<211> LENGTH: 23
<212> TYPE: DNA
<213> ORGANISM: Glycine max
<220> FEATURE:
<221> NAME/KEY: misc_feature
<222> LOCATION: (1)..(23)
<223> OTHER INFORMATION: soy EPSPS-CR7, Cas9 target sequence

<400> SEQUENCE: 97
ggaataaaat aggaaacgtt ggg                                             23

<210> SEQ ID NO 98
<211> LENGTH: 9174
<212> TYPE: DNA
<213> ORGANISM: Artificial sequence
<220> FEATURE:
<223> OTHER INFORMATION: RTW1201

<400> SEQUENCE: 98
ccgggtgtga tttagtataa agtgaagtaa tggtcaaaag aaaaagtgta aaacgaagta     60
```

```
cctagtaata agtaatattg aacaaaataa atggtaaagt gtcagatata taaaataggc    120
tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg aaacgttggg acttagtagg ttttagagct agaaatagca    480
agttaaaata aggctagtcc gttatcaact tgaaaaagtg gcaccgagtc ggtgcttttt    540
tttgcggccg caattggatc gggtttactt attttgtggg tatctatact tttattagat    600
ttttaatcag gctcctgatt tcttttatt tcgattgaat tcctgaactt gtattattca    660
gtagatcgaa taaattataa aaagataaaa tcataaaata atattttatc ctatcaatca    720
tattaaagca atgaatatgt aaaattaatc ttatctttat tttaaaaaat catataggtt    780
tagtattttt ttaaaaataa agataggatt agttttacta ttcactgctt attactttta    840
aaaaaatcat aaaggtttag tattttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtcgt   1020
cataatatcg ccaaatgcca actggactac gtcgaaccca caaatcccac aaagcgcgtg   1080
aaatcaaatc gctcaaacca caaaaagaa caacgcgttt gttacacgct caatcccacg   1140
cgagtagagc acagtaacct tcaaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gttcttcgg ttatgttttt    1440
ttatttatgc tttatgctgt tgatgttcgg ttgtttgttt cgctttgttt ttgtggttca   1500
gttttttagg attcttttgg tttttgaatc gattaatcgg aagagatttt cgagttattt   1560
ggtgtgttgg aggtgaatct tttttttgag gtcatagatc tgttgtattt gtgttataaa   1620
catgcgactt tgtatgattt tttacgaggt tatgatgttc tggttgtttt attatgaatc   1680
tgttgagaca gaaccatgat ttttgttgat gttcgtttac actattaaag gtttgtttta   1740
acaggattaa aagtttttta agcatgttga aggagtcttg tagatatgta accgtcgata   1800
gtttttttgt gggtttgttc acatgttatc aagcttaatc ttttactatg tatgcgacca   1860
tatctggatc cagcaaaggc gatttttaa ttccttgtga aacttttgta atatgaagtt    1920
gaaattttgt tattggtaaa ctataaatgt gtgaagttgg agtataccct taccttctta   1980
tttggctttg tgatagttta atttatatgt attttgagtt ctgacttgta tttctttgaa   2040
ttgattctag tttaagtaat ccatggcacc gaagaagaag cgcaaggtga tggacaaaaa   2100
gtactcaata gggctcgaca tagggactaa ctccgttgga tgggccgtca tcaccgacga   2160
gtacaaggtg ccctccaaga agttcaaggt gttgggaaac accgacaggc acagcataaa   2220
gaagaatttg atcggtgccc tcctcttcga ctccggagag accgctgagg ctaccaggct   2280
caagaggacc gctagaaggc gctacaccag aaggaagaac agaatctgct acctgcagga   2340
gatcttctcc aacgagatgg ccaaggtgga cgactccttc ttccaccgcc ttgaggaatc   2400
attcctggtg gaggaggata aaaagcacga gagacaccca atcttcggga acatcgtcga   2460
```

```
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg gatacattga    3180
cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga gatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcagggaag actatactcg acttcctgaa    4140
gtccgacgga ttcgccaaca ggaacttcat gcagctcatt cacgcgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagag aacatcgtta ttgagatggc    4380
tcgcgagaac caaactaccc agaaagggca gaagaattcc cgcagagga tgaagcgcat    4440
tgaggagggc ataaaagagc ttggctctca gatcctcaag gagcacccg tcgagaacac    4500
tcagctgcag aacgagaagc tgtacctgta ctacctccaa aacggaaggg acatgtacgt    4560
ggaccaggag ctggacatca acaggttgtc cgactacgac gtcgaccaca tcgtgcctca    4620
gtccttcctg aaggatgact ccatcgacaa taagtgctg acacgctccg ataaaatag    4680
aggcaagtcc gacaacgtcc cctccgagga ggtcgtgaag aagatgaaaa actactggag    4740
acagctcttg aacgccaagc tcatcaccca gcgtaagttc gacaacctga ctaaggctga    4800
```

```
gagaggagga ttgtccgagc tcgataaggc cggattcatc aagagacagc tcgtcgaaac    4860
ccgccaaatt accaagcacg tggcccaaat tctggattcc cgcatgaaca ccaagtacga    4920
tgaaaatgac aagctgatcc gcgaggtcaa ggtgatcacc ttgaagtcca agctggtctc    4980
cgacttccgc aaggacttcc agttctacaa ggtgagggag atcaacaact accaccacgc    5040
acacgacgcc tacctcaacg ctgtcgttgg aaccgccctc atcaaaaaat atcctaagct    5100
ggagtctgag ttcgtctacg gcgactacaa ggtgtacgac gtgaggaaga tgatcgctaa    5160
gtctgagcag gagatcggca aggccaccgc caagtacttc ttctactcca acatcatgaa    5220
cttcttcaag accgagatca ctctcgccaa cggtgagatc aggaagcgcc cactgatcga    5280
gaccaacggt gagactggag agatcgtgtg ggacaaaggg agggatttcg ctactgtgag    5340
gaaggtgctc tccatgcctc aggtgaacat cgtcaagaag accgaagttc agaccggagg    5400
attctccaag gagtccatcc tccccaagag aaactccgac aagctgatcg ctagaaagaa    5460
agactgggac cctaagaagt acggaggctt cgattctcct accgtggcct actctgtgct    5520
ggtcgtggcc aaggtggaga agggcaagtc caagaagctg aaatccgtca aggagctcct    5580
cgggattacc atcatggaga ggagttcctt cgagaagaac cctatcgact tcctggaggc    5640
caagggatat aaagaggtga agaaggacct catcatcaag ctgcccaagt actccctctt    5700
cgagttggag aacggaagga agaggatgct ggcttctgcc ggagagttgc agaagggaaa    5760
tgagctcgcc cttccctcca gtacgtgaaa cttcctgtac ctcgcctctc actatgaaaa    5820
gttgaagggc tctcctgagg acaacgagca gaagcagctc ttcgtggagc agcacaagca    5880
ctacctggac gaaattatcg agcagatctc tgagttctcc aagcgcgtga tattggccga    5940
cgccaacctc gacaaggtgc tgtccgccta caacaagcac agggataagc ccattcgcga    6000
gcaggctgaa acattatcc acctgtttac cctcacaaac ttgggagccc ctgctgcctt    6060
caagtacttc gacaccacca ttgacaggaa gagatacacc tccaccaagg aggtgctcga    6120
cgcaacactc atccaccaat ccatcaccgg cctctatgaa acaaggattg acttgtccca    6180
gctgggaggc gactctagag ccgatcccaa gaagaagaga aaggtgaaga gaccacggga    6240
ccgccacgat ggcgagctgg gaggccgcaa gcgggcaagg taggttaacc tagacttgtc    6300
catcttctgg attggccaac ttaattaatg tatgaaataa aaggatgcac acatagtgac    6360
atgctaatca ctataatgtg ggcatcaaag ttgtgtgtta tgtgtaatta ctagttatct    6420
gaataaaaga gaaagagatc atccatattt cttatcctaa atgaatgtca cgtgtcttta    6480
taattctttg atgaaccaga tgcatttcat taaccaaatc catatacata taaatattaa    6540
tcatatataa ttaatatcaa ttgggttagc aaaacaaatc tagtctaggt gtgttttgcg    6600
aattcgatat caagcttatc gataccgtcg aggggggggcc cggtaccggc cgccgttct    6660 atagtgtcac ctaaatcgta tgtgtatgat acataaggtt atgtattaat tgtagccgcg    6720
ttctaacgac aatatgtcca tatggtgcac tctcagtaca atctgctctg atgccgcata    6780
gttaagccag ccccgacacc cgccaacacc cgctgacgcg ccctgacggg cttgtctgct    6840
cccggcatcc gcttacagac aagctgtgac cgtctccggg agctgcatgt gtcagaggtt    6900
ttcaccgtca tcaccgaaac gcgcgagacg aaagggcctc gtgatacgcc tatttttata    6960
ggttaatgtc atgaccaaaa tcccttaacg tgagttttcg ttccactgag cgtcagaccc    7020
cgtagaaaag atcaaaggat cttcttgaga tccttttttt ctgcgcgtaa tctgctgctt    7080
gcaaacaaaa aaaccaccgc taccagcggt ggtttgtttg ccggatcaag agctaccaac    7140
tctttttccg aaggtaactg gcttcagcag agcgcagata ccaaatactg ttcttctagt    7200
```

```
gtagccgtag ttaggccacc acttcaagaa ctctgtagca ccgcctacat acctcgctct   7260
gctaatcctg ttaccagtgg ctgctgccag tggcgataag tcgtgtctta ccgggttgga   7320
ctcaagacga tagttaccgg ataaggcgca gcggtcgggc tgaacggggg gttcgtgcac   7380
acagcccagc ttggagcgaa cgacctacac cgaactgaga tacctacagc gtgagctatg   7440
agaaagcgcc acgcttcccg aagggagaaa ggcggacagg tatccggtaa gcggcagggt   7500
cggaacagga gagcgcacga gggagcttcc agggggaaac gcctggtatc tttatagtcc   7560
tgtcgggttt cgccacctct gacttgagcg tcgattttgt gatgctcgt caggggggcg    7620
gagcctatgg aaaaacgcca gcaacgcggc cttttacgg ttcctggcct tttgctggcc     7680
ttttgctcac atgttctttc ctgcgttatc ccctgattct gtggataacc gtattaccgc   7740
ctttgagtga gctgataccg ctcgccgcag ccgaacgacc gagcgcagcg agtcagtgag   7800
cgaggaagcg gaagagcgcc caatacgcaa accgcctctc cccgcgcgtt ggccgattca   7860
ttaatgcagg ttgatcagat ctcgatcccg cgaaattaat acgactcact atagggagac   7920
cacaacggtt tccctctaga ataattttg tttaacttta agaaggagat atacccatgg    7980
aaaagcctga actcaccgcg acgtctgtcg agaagtttct gatcgaaaag ttcgacagcg   8040
tctccgacct gatgcagctc tcggagggcg aagaatctcg tgctttcagc ttcgatgtag   8100
gagggcgtgg atatgtcctg cgggtaaata gctgcgccga tggtttctac aaagatcgtt   8160
atgtttatcg gcactttgca tcggccgcgc tcccgattcc ggaagtgctt gacattgggg   8220
aattcagcga gagcctgacc tattgcatct cccgccgtgc acagggtgtc acgttgcaag   8280
acctgcctga aaccgaactg cccgctgttc tgcagccggt cgcggaggct atggatgcga   8340
tcgctgcggc cgatcttagc cagacgagcg gttcggccc attcggaccg caaggaatcg    8400
gtcaatacac tacatggcgt gatttcatat gcgcgattgc tgatccccat gtgtatcact   8460
ggcaaactgt gatggacgac accgtcagtg cgtccgtcgc gcaggctctc gatgagctga   8520
tgctttgggc cgaggactgc cccgaagtcc ggcacctcgt gcacgcggat ttcggctcca   8580
acaatgtcct gacggacaat ggccgcataa cagcggtcat tgactggagc gaggcgatgt   8640
tcggggattc ccaatacgag gtcgccaaca tcttcttctg gaggccgtgg ttggcttgta   8700
tggagcagca gacgcgctac ttcgagcgga ggcatccgga gcttgcagga tcgccgcggc   8760
tccgggcgta tatgctccgc attggtcttg accaactcta tcagagcttg gttgacggca   8820
atttcgatga tgcagcttgg gcgcagggtc gatgcgacgc aatcgtccga tccggagccg   8880
ggactgtcgg gcgtacacaa atcgcccgca gaagcgcggc cgtctggacc gatggctgtg   8940
tagaagtact cgccgatagt ggaaaccgac gccccagcac tcgtccgagg gcaaaggaat   9000
agtgaggtac agcttggatc gatccggctg ctaacaaagc ccgaaaggaa gctgagttgg   9060
ctgctgccac cgctgagcaa taactagcat aaccccttgg ggcctctaaa cgggtcttga   9120
gggttttttt gctgaaagga ggaactatat ccggatgctc gggcgcgccg gtac         9174
```

<210> SEQ ID NO 99
<211> LENGTH: 9174
<212> TYPE: DNA
<213> ORGANISM: Artificial sequence
<220> FEATURE:
<223> OTHER INFORMATION: RTW1202

<400> SEQUENCE: 99

```
ccgggtgtga tttagtataa agtgaagtaa tggtcaaaag aaaaagtgta aaacgaagta      60
```

```
cctagtaata agtaatattg aacaaaataa atggtaaagt gtcagatata taaaataggc      120
tttaataaaa ggaagaaaaa aaacaaacaa aaaataggtt gcaatggggc agagcagagt      180
catcatgaag ctagaaaggc taccgataga taaactatag ttaattaaat acattaaaaa      240
atacttggat ctttctctta ccctgtttat attgagacct gaaacttgag agagatacac      300
taatcttgcc ttgttgtttc attccctaac ttacaggact cagcgcatgt catgtggtct      360
cgttccccat ttaagtccca caccgtctaa acttattaaa ttattaatgt ttataactag      420
atgcacaaca acaaagcttg gaataaaata ggaaacgttg ttttagagct agaaatagca      480
agttaaaata aggctagtcc gttatcaact tgaaaagtg gcaccgagtc ggtgcttttt       540
tttgcggccg caattggatc gggtttactt attttgtggg tatctatact tttattagat      600
ttttaatcag gctcctgatt tcttttatt tcgattgaat tcctgaactt gtattattca       660
gtagatcgaa taaattataa aaagataaaa tcataaaata atattttatc ctatcaatca      720
tattaaagca atgaatatgt aaaattaatc ttatctttat tttaaaaaat catataggtt      780
tagtattttt ttaaaaataa agataggatt agttttacta ttcactgctt attacttta       840
aaaaaatcat aaaggtttag tatttttta aataaaatat aggaatagtt ttactattca       900
ctgctttaat agaaaaatag tttaaaattt aagatagttt taatcccagc atttgccacg      960
tttgaacgtg agccgaaacg atgtcgttac attatcttaa cctagctgaa acgatgtcgt     1020
cataatatcg ccaaatgcca actggactac gtcgaaccca caaatcccac aaagcgcgtg     1080
aaatcaaatc gctcaaacca caaaaagaa caacgcgttt gttacacgct caatcccacg      1140
cgagtagagc acagtaacct tcaaataagc gaatggggca taatcagaaa tccgaaataa     1200
acctaggggc attatcggaa atgaaagta gctcactcaa tataaaaatc taggaaccct      1260
agttttcgtt atcactctgt gctccctcgc tctatttctc agtctctgtg tttgcggctg     1320
aggattccga acgagtgacc ttcttcgttt ctcgcaaagg taacagcctc tgctcttgtc     1380
tcttcgattc gatctatgcc tgtctcttat ttacgatgat gttcttcgg ttatgttttt      1440
ttatttatgc tttatgctgt tgatgttcgg ttgtttgttt cgctttgttt ttgtggttca     1500
gttttttagg attcttttgg tttttgaatc gattaatcgg aagagatttt cgagttattt     1560
ggtgtgttgg aggtgaatct ttttttgag gtcatagatc tgttgtattt gtgttataaa      1620
catgcgactt tgtatgattt tttacgaggt tatgatgttc tggttgtttt attatgaatc     1680
tgttgagaca gaaccatgat ttttgttgat gttcgtttac actattaaag gtttgtttta     1740
acaggattaa aagttttta agcatgttga aggagtcttg tagatatgta accgtcgata      1800
gttttttgt gggtttgttc acatgttatc aagcttaatc ttttactatg tatgcgacca     1860
tatctggatc cagcaaaggc gattttttaa ttccttgtga aacttttgta atatgaagtt     1920
gaaattttgt tattggtaaa ctataaatgt gtgaagttgg agtataccttt taccttctta    1980
tttggctttg tgatagttta atttatatgt attttgagtt ctgacttgta tttctttgaa     2040
ttgattctag tttaagtaat ccatggcacc gaagaagaag cgcaaggtga tggacaaaaa     2100
gtactcaata gggctcgaca tagggactaa ctccgttgga tgggccgtca tcaccgacga     2160
gtacaaggtg ccctccaaga agttcaaggt gttgggaaac accgacaggc acagcataaa     2220
gaagaatttg atcggtgccc tcctcttcga ctccggagag accgctgagg ctaccaggct     2280
caagaggacc gctagaaggc gctacaccag aaggaagaac agaatctgct acctgcagga     2340
gatcttctcc aacgagatgg ccaaggtgga cgactccttc ttccaccgcc ttgaggaatc     2400
attcctggtg gaggaggata aaaagcacga gagacaccca atcttcggga acatcgtcga     2460
```

```
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg gatacattga    3180
cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcagggaag actatactcg acttcctgaa    4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagag aacatcgtta ttgagatggc    4380
tcgcgagaac caaactaccc agaaagggca gaagaattcc gcagagagga tgaagcgcat    4440
tgaggagggc ataaaagagc ttggctctca gatcctcaag gagcacccccg tcgagaacac    4500 tcagctgcag aacgagaagc tgtacctgta ctacctccaa aacggaaggg acatgtacgt    4560
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
aggcaagtcc gacaacgtcc cctccgagga ggtcgtgaag aagatgaaaa actactggag    4740
acagctcttg aacgccaagc tcatcaccca gcgtaagttc gacaacctga ctaaggctga    4800
```

```
gagaggagga ttgtccgagc tcgataaggc cggattcatc aagagacagc tcgtcgaaac    4860
ccgccaaatt accaagcacg tggcccaaat tctggattcc cgcatgaaca ccaagtacga    4920
tgaaaatgac aagctgatcc gcgaggtcaa ggtgatcacc ttgaagtcca agctggtctc    4980
cgacttccgc aaggacttcc agttctacaa ggtgagggag atcaacaact accaccacgc    5040
acacgacgcc tacctcaacg ctgtcgttgg aaccgccctc atcaaaaaat atcctaagct    5100
ggagtctgag ttcgtctacg gcgactacaa ggtgtacgac gtgaggaaga tgatcgctaa    5160
gtctgagcag gagatcggca aggccaccgc caagtacttc ttctactcca acatcatgaa    5220
cttcttcaag accgagatca ctctcgccaa cggtgagatc aggaagcgcc cactgatcga    5280
gaccaacggt gagactggag agatcgtgtg ggacaaaggg agggatttcg ctactgtgag    5340
gaaggtgctc tccatgcctc aggtgaacat cgtcaagaag accgaagttc agaccggagg    5400
attctccaag gagtccatcc tccccaagag aaactccgac aagctgatcg ctagaaagaa    5460
agactgggac cctaagaagt acggaggctt cgattctcct accgtggcct actctgtgct    5520
ggtcgtggcc aaggtggaga agggcaagtc caagaagctg aaatccgtca aggagctcct    5580
cgggattacc atcatggaga ggagttcctt cgagaagaac cctatcgact tcctggaggc    5640
caagggatat aaagaggtga agaaggacct catcatcaag ctgcccaagt actccctctt    5700
cgagttggag aacggaagga gaggatgct ggcttctgcc ggagagttgc agaagggaaa    5760
tgagctcgcc cttccctcca agtacgtgaa cttcctgtac ctcgcctctc actatgaaaa    5820
gttgaagggc tctcctgagg acaacgagca gaagcagctc ttcgtggagc agcacaagca    5880
ctacctggac gaaattatcg agcagatctc tgagttctcc aagcgcgtga tattggccga    5940
cgccaacctc gacaaggtgc tgtccgccta caacaagcac agggataagc ccattcgcga    6000
gcaggctgaa acattatcc acctgtttac cctcacaaac ttgggagccc ctgctgcctt    6060
caagtacttc gacaccacca ttgacaggaa gagatacacc tccaccaagg aggtgctcga    6120
cgcaacactc atccaccaat ccatcaccgg cctctatgaa acaaggattg acttgtccca    6180
gctgggaggc gactctagag ccgatcccaa gaagaagaga aaggtgaaga gaccacggga    6240
ccgccacgat ggcgagctgg gaggccgcaa gcgggcaagg taggttaacc tagacttgtc    6300
catcttctgg attggccaac ttaattaatg tatgaaataa aaggatgcac acatagtgac    6360
atgctaatca ctataatgtg ggcatcaaag ttgtgtgtta tgtgtaatta ctagttatct    6420
gaataaaaga gaaagagatc atccatattt cttatcctaa atgaatgtca cgtgtcttta    6480
taattctttg atgaaccaga tgcatttcat taaccaaatc catatacata taaatattaa    6540
tcatatataa ttaatatcaa ttgggttagc aaaacaaatc tagtctaggt gtgttttgcg    6600
aattcgatat caagcttatc gataccgtcg agggggggcc cggtaccggc gcgccgttct    6660
atagtgtcac ctaaatcgta tgtgtatgat acataaggtt atgtattaat tgtagccgcg    6720
ttctaacgac aatatgtcca tatggtgcac tctcagtaca atctgctctg atgccgcata    6780
gttaagccag ccccgacacc cgccaacacc cgctgacgcg ccctgacggg cttgtctgct    6840
cccggcatcc gcttacagac aagctgtgac cgtctccggg agctgcatgt gtcagaggtt    6900
ttcaccgtca tcaccgaaac gcgcgagacg aaagggcctc gtgatacgcc tatttttata    6960
ggttaatgtc atgaccaaaa tcccttaacg tgagttttcg ttccactgag cgtcagaccc    7020
cgtagaaaag atcaaaggat cttcttgaga tcctttttt ctgcgcgtaa tctgctgctt    7080
gcaaacaaaa aaccaccgc taccagcggt ggtttgtttg ccggatcaag agctaccaac    7140 tcttttttccg aaggtaactg gcttcagcag agcgcagata ccaaatactg ttcttctagt    7200
```

```
gtagccgtag ttaggccacc acttcaagaa ctctgtagca ccgcctacat acctcgctct    7260
gctaatcctg ttaccagtgg ctgctgccag tggcgataag tcgtgtctta ccgggttgga    7320
ctcaagacga tagttaccgg ataaggcgca gcggtcgggc tgaacggggg gttcgtgcac    7380
acagcccagc ttggagcgaa cgacctacac cgaactgaga tacctacagc gtgagctatg    7440
agaaagcgcc acgcttcccg aagggagaaa ggcggacagg tatccggtaa gcggcagggt    7500
cggaacagga gagcgcacga gggagcttcc agggggaaac gcctggtatc tttatagtcc    7560
tgtcgggttt cgccacctct gacttgagcg tcgattttgt gatgctcgt caggggggcg     7620 gagcctatgg aaaaacgcca gcaacgcggc ctttttacgg ttcctggcct tttgctggcc    7680
ttttgctcac atgttctttc ctgcgttatc ccctgattct gtggataacc gtattaccgc    7740
ctttgagtga gctgataccg ctcgccgcag ccgaacgacc gagcgcagcg agtcagtgag    7800
cgaggaagcg gaagagcgcc caatacgcaa accgcctctc cccgcgcgtt ggccgattca    7860
ttaatgcagg ttgatcagat ctcgatcccg cgaaattaat acgactcact atagggagac    7920
cacaacggtt tccctctaga ataattttg tttaacttta agaaggagat atacccatgg    7980
aaaagcctga actcaccgcg acgtctgtcg agaagtttct gatcgaaaag ttcgacagcg    8040
tctccgacct gatgcagctc tcggagggcg aagaatctcg tgctttcagc ttcgatgtag    8100
gagggcgtgg atatgtcctg cgggtaaata gctgcgccga tggtttctac aaagatcgtt    8160
atgtttatcg gcactttgca tcggccgcgc tcccgattcc ggaagtgctt gacattgggg    8220
aattcagcga gagcctgacc tattgcatct cccgccgtgc acagggtgtc acgttgcaag    8280
acctgcctga aaccgaactg cccgctgttc tgcagccggt cgcggaggct atggatgcga    8340
tcgctgcggc cgatcttagc cagacgagcg ggttcggccc attcggaccg caaggaatcg    8400
gtcaatacac tacatggcgt gatttcatat gcgcgattgc tgatccccat gtgtatcact    8460
ggcaaactgt gatggacgac accgtcagtg cgtccgtcgc gcaggctctc gatgagctga    8520
tgctttgggc cgaggactgc cccgaagtcc ggcacctcgt gcacgcggat ttcggctcca    8580
acaatgtcct gacggacaat ggccgcataa cagcggtcat tgactggagc gaggcgatgt    8640
tcggggattc ccaatacgag gtcgccaaca tcttcttctg gaggccgtgg ttggcttgta    8700
tggagcagca gacgcgctac ttcgagcgga ggcatccgga gcttgcagga tcgccgcggc    8760
tccgggcgta tatgctccgc attggtcttg accaactcta tcagagcttg gttgacggca    8820
atttcgatga tgcagcttgg gcgcagggtc gatgcgacgc aatcgtccga tccggagccg    8880
ggactgtcgg gcgtacacaa atcgcccgca gaagcgcggc cgtctggacc gatggctgtg    8940
tagaagtact cgccgatagt ggaaaccgac gccccagcac tcgtccgagg gcaaaggaat    9000
agtgaggtac agcttggatc gatccggctg ctaacaaagc ccgaaaggaa gctgagttgg    9060
ctgctgccac cgctgagcaa taactagcat aaccccttgg ggcctctaaa cgggtcttga    9120
ggggtttttt gctgaaagga ggaactatat ccggatgctc gggcgcgccg gtac          9174
```

<210> SEQ ID NO 100
<211> LENGTH: 6113
<212> TYPE: DNA
<213> ORGANISM: Artificial sequence
<220> FEATURE:
<223> OTHER INFORMATION: RTW1192A

<400> SEQUENCE: 100

```
caagtagttc tagtcttaat acaaatgtca aatggcacaa gtgagatttt gaatttctga      60
```

```
tgttgtaaaa atctcaggac atgaatacta ttgggaagca attattcata cttcaccaat    120
ccaaactgac ccaaaattct caaatcacat gaaagcaaaa atgcatataa acgaagaat     180 aagaagaaga ggaactaacc tggggtttcg atgattaaag cgttgttgtt gatgatgaaa    240
acgatgatta tggagagaaa ttgttgttga atggtgaaat tgttatagaa agagaacgaa    300
gatagagaaa aagatatata gattttcaa ggctcaaacc ctaaaatcac catgagagag     360
aacaaagatt gagaaaccta caaccactat gagagagaat gagcagaaca gaagcgtgag    420
atagagaacg agagttaagg tgcgagagga cacgaagaac aaaaggtgtg agagaaagaa    480
caaaggagcc tacggtgtga gatgagagaa tttgaaattc ttaccattta ggtggaattt    540
caattctaca attttattct attaaaatta ttttaaaaaa tgatgtcatt ttaaattctt    600
taaaatctca tatccaacaa ctgaattatg atagaggtat ttcaaattca cttaaaaaaa    660
ttatcttatt taaataccc atccaaacat agcgaaatgt tcatgagaag gatcaagtgg     720
tttggaaaca tagtactaat ggtgtttata cagttcatgg aatccttgat agataattta    780
aaggttgctg gaaattggat gaaggtgtgg agattaaata ttcttccaaa aataaagcgt    840
tttatttgga gagtgttgtg tggttgtctc ccctgtaggc aaaagcttcg atgtaaagga    900
gttcaatgtc caataaccta tgcttctat ccctcgatta ttgaaaatga atgacacatt     960
ttatttggtt gaaatcaaga aataagcatg tggcaagcaa cgggtatttg acaattcata   1020
gaacaaaagg tgaatgcagc aaaagaatta atgaactcct tttcgatcta cttggatcac   1080
tacatggaga tattatcaac aaatttgatg ttactttatg gagcagttgg aattcttgga   1140
atgacaagat atgaaatgaa cataccaacc ctcctcttgt ttctgtttcg gtttctatgc   1200
agtattttgt tgaatggcaa agtgcaaggt aatatgctcc tcaacatcaa ttaacaaatg   1260
ttcatgacat ctcttaccag ctccaacttg gggacgtttg acaaacacca ccgtcaagtt   1320
tccttaaatg caacattaat gttgctcatt tcaaggagga gaatagtttt ggtgtcggca   1380
tgatactcca tcaaggaaga ttcgtcaaag ctcactcacg ttttcgacat gggtcgacat   1440
gggttacctg acccaaaggc tgaggcttag gcttgggttt gcttcaagta ttgatctggg   1500
cccagactat tggtttacat aatatcattt ttgaaaacct aacatctaaa actcaaggtt   1560
gtttagaggt gcgccattcc aaaataagat tatcctattt gtgcatgaat gcgaccaact   1620
atctcctgtt tcagcattat aaagtataaa caacaaactt cttaatcaa gggactaaaa    1680 gatattggac atacaagcta aaagtgatag aatttgagaa aacaaatatt gacaacaata   1740
ttcaagagga cactaaaaca taattctcaa attttttttg tttatttaaa ataaagtggt   1800
tcattaggta gctccgggtg attgcggtta catcatgtac ggaaaaataa ttctaatcct   1860
tgatttaaat ttgaacttga ctatttattt attcttatt tcattttgta aatcatttta    1920
tgtatctcct ggcaagcaat tttatccacc ttgcaccaac accttcgggt tccataatca   1980 aaccaccta acttcacacc atgctgtaac tcacaccgcc cagcatctcc aatgtgaaag    2040
aagctaaaat ttaataaaca atcatacgaa gcagtgacaa ataccagat ggtattaatg    2100 cttcgataaa attaattgga aagtataaa tggtagaaaa taataaatta taattaattt    2160
aagtaagata aaaataatt aaaaactaaa atgttaaat tttaaaaaaa ttatttaa       2220 taatatttaa aaacattaaa aatcatttta aaaaatttat ttatagaaca attaaataaa   2280
tatttcagct aataaaaaac aaaagcttac ctagccttag aagacaactt gtccaacaat   2340
tagatgatac ccattgccct tacgttttct ttaacatcaa ttattgtttt tgtcaacaag   2400
ctatctttta gttttatttt attggtaaaa aatatgtcgc cttcaagttg catcatttaa   2460
```

```
cacatctcgt cattagaaaa ataaaactct tccctaaacg attagtagaa aaaatcattc    2520
gataataaat aagaaagaaa aattagaaaa aaataacttc attttaaaaa aatcattaag    2580
gctatatttt ttaaatgact aattttatat agactgtaac taaaagtata caatttatta    2640
tgctatgtat cttaaagaat tacttataaa aatctacgga agaatatctt acaaagtgaa    2700
aaacaaatga gaaagaattt agtgggatga ttatgatttt atttgaaaat tgaaaaaata    2760
attattaaag actttagtgg agtaagaaag ctttcctatt agtcttttct tatccataaa    2820
aaaaaaaaaa aaaatctagc gtgacagctt ttccatagat tttaataatg taaaatactg    2880
gtagcagccg accgttcagg taatggacac tgtggtccta acttgcaacg ggtgcgggcc    2940
caatttaata acgccgtggt aacggataaa gccaagcgtg aagcggtgaa ggtacatctc    3000
tgactccgtc aagattacga aaccgtcaac tacgaaggac tccccgaaat atcatctgtg    3060
tcataaacac caagtcacac catacatggg cacgcgtcac aatatgattg gagaacggtt    3120
ccaccgcata tgctataaaa tgcccccaca ccctcgacc ctaatcgcac ttcaattgca    3180
atcaaattag ttcattctct tgcgcagtt ccctacctct cctttcaagg ttcgtagatt    3240
tcttccgttt ttttttcttc ttctttattg tttgttctac atcagcatga tgttgatttg    3300
attgtgtttt ctatcgtttc atcgattata aattttcata atcagaagat tcagctttta    3360
ttaatgcaag aacgtcctta attgatgatt ttataaccgt aaattaggtc taattagagt    3420 tttttttcata aagattttca gatccgttta caacaagcct taattgttga ttctgtagtc    3480
gtagattaag gttttttttca tgaactactt cagatccgtt aaacaacagc cttatttgtt    3540
gatacttcag tcgtttttca agaaattgtt cagatccgtt gataaaagcc ttattcgttg    3600
attctgtatg gtatttcaag agatattgct caggtccttt agcaactacc ttatttgttg    3660
attctgtggc catagattag gattttttt cacgaaattg cttcttgaaa ttacgtgatg    3720
gattttgatt ctgatttatc ttgtgattgt tgactctaca gatggcccaa gtgagcagag    3780
tgcacaatct tgctcaaagc actcaaattt ttggccattc ttccaactcc aacaaactca    3840
aatcggtgaa ttcggtttca ttgaggccac gcctttgggg ggcctcaaaa tctcgcatcc    3900
cgatgcataa aaatgaagc tttatgggaa attttaatgt ggggaaggga aattccggcg    3960
tgtttaaggt ttctgcatcg gtcgccgccg cagagaagcc gtcaacgtcg ccggagatcg    4020
tgttggaacc catcaaagac ttctcgggta ccatcacatt gccagggtcc aagtctctgt    4080
ccaatcgaat tttgcttctt gctgctctct ctgaggtgaa gtttatttat ttatttattt    4140
gtttgtttgt tgttgggtgt gggaatagga gtttgatgtg tagagtggat tttgaatatt    4200
tgattttttt ttgtattatt ctgtgaaaat gaagcatcat gtcccatgaa agaaatggac    4260
acgaaattaa gtggcttatg atgtgaaatg aggatagaaa tgtgtgtagg gttttttaat    4320
gggtagcaat aagcatattc aatatctgga ttgatttgga cgtttctgta taaggagta    4380 tgctagcaat gtgttaatgt atggcttgct aaaatactcc taaaaatcaa gtgggagtag    4440
tatacatatc tacagcaaat gtattaggtg aggcatttgg cttctctatt gtaaggaaca    4500
aataatatca gttaatgtga aaatcaatgg ttgatattcc aatacattca tgatgtgtta    4560
tttatatgta cctaatattg actgttgttt ttctccgcaa tgaccaagat tatttatttt    4620
atcctctaaa gtgactaatt gagttgctta ctttagagaa gttggaccca ttaggtgaga    4680
gcgtgggggg aactaatctt gaatatacaa tctgagtctt gattatccaa gtatggttgt    4740
atgaacaatg ttagctctag aagataaacc ctcccccaaa acacaaatta gaatgacatt    4800
```

-continued

| | |
|---|---|
| tcaagttcca tgtatgtcac tttcattcta ttatttttac aacttttagt tacttaacag | 4860 |
| atgtcttgtt cagcataaat tataatttat tctgttttt tttagggaac aactgttgta | 4920 |
| gacaacttgt tgtatagtga ggatattcat tacatgcttg gtgcattaag gacccttgga | 4980 |
| ctgcgtgtgg aagatgacaa aacaaccaaa caagcaattg ttgaaggctg tgggggattg | 5040 |
| tttcccacta gtaaggaatc taaagatgaa atcaatttat tccttggaaa tgctggtatt | 5100 |
| gcaatgagat ctttgacagc agctgttgtt gctgcaggtg gaaatgcaag gtctgttttt | 5160 |
| tttttttttg ttcagcataa tctttgaatt gttcctcgta taactaatca caacagagta | 5220 |
| cgtgttcttc ttcctgttat aatctaaaaa tctcatccag attagtcatc ctttcttctt | 5280 |
| aaaaggaacc tttaattatc aatgtattta tttaatattt aaattagctt gtcaaagtct | 5340 |
| agcatataca tattttgatt atattctgag aaatgcacct gagggtgttc ctcatgatct | 5400 |
| acttcaacct ctgttattat tagattttct atcatgatta ctggtttgag tctctaagta | 5460 |
| gaccatcttg atgttcaaaa tatttcagct acgtacttga tggggtgccc cgaatgagag | 5520 |
| agaggccaat tggggatttg gttgctggtc ttaagcaact tggtgcagat gttgattgct | 5580 |
| ttcttggcac aaactgtcca cctgttcgtg taaatgggaa gggaggactt cctggcggaa | 5640 |
| aggtatggtt tggatttcat ttagaataag gtggagtaac tttcctggat caaaattcta | 5700 |
| atttaagaag cctccctgtt ttcctctctt tagaataaga ctaagggtag gtttaggagt | 5760 |
| tgggttttgg agagaaatgg aagggagagc aatttttttc ttcttctaat aaatattctt | 5820 |
| taatttgata cattttttaa gtaaagaat ataagatag attagcataa cttaatgttt | 5880 |
| taatctttta tttatttta taatattat atacctgtct atttaaaaat caaatatttg | 5940 |
| tcctccattc cctttccctt caaaacctca gttccaaata taccgtagtt gaattatatt | 6000 |
| ttggaaggcc tattggttgg agacttttcc ttttcagaga ttatccctca cctttattat | 6060 |
| agcctttcta ttttaaact tcatatagac gccattcttg gggcggccgc gat | 6113 |

<210> SEQ ID NO 101
<211> LENGTH: 32
<212> TYPE: DNA
<213> ORGANISM: Artificial sequence
<220> FEATURE:
<223> OTHER INFORMATION: primer, soy1-F4

<400> SEQUENCE: 101

| | |
|---|---|
| tcaataatac tactctctta gacaccaaac aa | 32 |

<210> SEQ ID NO 102
<211> LENGTH: 23
<212> TYPE: DNA
<213> ORGANISM: Artificial sequence
<220> FEATURE:
<223> OTHER INFORMATION: primer, soy1-R4

<400> SEQUENCE: 102

| | |
|---|---|
| caaggaaaat gaatgatggc ttt | 23 |

<210> SEQ ID NO 103
<211> LENGTH: 18
<212> TYPE: DNA
<213> ORGANISM: Artificial sequence
<220> FEATURE:
<223> OTHER INFORMATION: probe, soy1-T3(FAM-MGB)

<400> SEQUENCE: 103

| | |
|---|---|
| ccttcccaaa ctataatc | 18 |

<210> SEQ ID NO 104
<211> LENGTH: 27
<212> TYPE: DNA
<213> ORGANISM: Artificial sequence
<220> FEATURE:
<223> OTHER INFORMATION: WOL1005, Forward_primer

<400> SEQUENCE: 104
aaatgttatc agaggaacat gagctgc                                        27

<210> SEQ ID NO 105
<211> LENGTH: 6677
<212> TYPE: DNA
<213> ORGANISM: Artificial sequence
<220> FEATURE:
<223> OTHER INFORMATION: maize optimized moCAS9 endonuclease

<400> SEQUENCE: 105

```
ctgcagtgca gcgtgacccg gtcgtgcccc tctctagaga taatgagcat tgcatgtcta      60
agttataaaa aattaccaca tattttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga     240
gtattttgac aacaggactc tacagtttta tcttttagt gtgcatgtgt tctccttttt     300
ttttgcaaat agcttcacct ataataact tcatccattt tattagtaca tccatttagg     360
gtttaggggtt aatggttttt atagactaat tttttagta catctatttt attctattt      420
agcctctaaa ttaagaaaac taaaactcta ttttagtttt tttatttaat aatttagata     480
taaaatagaa taaaataaag tgactaaaaa ttaaacaaat ccctttaag aaattaaaaa     540
aactaaggaa acatttttct tgtttcgagt agataatgcc agcctgttaa acgccgtcga     600
cgagtctaac ggacaccaac cagcgaacca gcagcgtcgc gtcgggccaa gcgaagcaga     660
cggcacggca tctctgtcgc tgcctctgga cccctctcga gagttccgct ccaccgttgg     720
acttgctccg ctgtcggcat ccagaaattg cgtggcggag cggcagacgt gagccggcac     780
ggcaggcggc ctcctcctcc tctcacggca cggcagctac ggggggattcc tttcccaccg     840
ctccttcgct ttcccttcct cgcccgccgt aataaataga cacccctcc acacctctt     900
tccccaacct cgtgttgttc ggagcgcaca cacacacaac cagatctccc ccaaatccac     960
ccgtcggcac ctccgcttca aggtacgccg ctcgtcctcc cccccccc tctctacctt     1020
ctctagatcg gcgttccggt ccatgcatgg ttagggcccg gtagttctac ttctgttcat    1080
gtttgtgtta gatccgtgtt tgtgttagat ccgtgctgct agcgttcgta cacggatgcg    1140
acctgtacgt cagacacgtt ctgattgcta acttgccagt gtttctcttt ggggaatcct    1200
gggatggctc tagccgttcc gcagacggga tcgatttcat gattttttt gtttcgttgc    1260
atagggtttg gtttgccctt ttcctttatt tcaatatatg ccgtgcactt gtttgtcggg    1320
tcatcttttc atgctttttt ttgtcttggt tgtgatgatg tggtctggtt gggcggtcgt    1380
tctagatcgg agtagaattc tgtttcaaac tacctggtgg atttattaat tttggatctg    1440
tatgtgtgtg ccatacatat tcatagttac gaattgaaga tgatggatgg aaatatcgat    1500
ctaggatagg tatacatgtt gatgcgggtt ttactgatgc atatacagag atgctttttg    1560
ttcgcttggt tgtgatgatg tggtgtggtt gggcggtcgt tcattcgttc tagatcggag    1620
tagaatactg tttcaaacta cctggtgtat ttattaattt tggaactgta tgtgtgtgtc    1680
```

```
atacatcttc atagttacga gtttaagatg gatggaaata tcgatctagg ataggtatac    1740
atgttgatgt gggttttact gatgcatata catgatggca tatgcagcat ctattcatat    1800
gctctaacct tgagtaccta tctattataa taaacaagta tgttttataa ttattttgat    1860
cttgatatac ttggatgatg gcatatgcag cagctatatg tggattttttt tagccctgcc    1920 ttcatacgct atttatttgc ttggtactgt ttcttttgtc gatgctcacc ctgttgtttg    1980
gtgttacttc tgcaggtcga ctctagagga tccccatggc cccgaagaag aagaggaagg    2040
tgcacatgga taagaagtac agcatcggcc tcgacatcgg gaccaacagc gtcggctggg    2100
ccgtcatcac cgacgaatat aaggtgccca gcaagaagtt caaggtgctc gggaatacag    2160
accgccacag catcaagaag aacctgatcg gcgccctcct gttcgactcg ggcgagaccg    2220
ctgaggccac cagactaaag aggaccgctc gccgccgcta cacccgccgc aagaaccgca    2280
tatgctacct ccaggagatc ttcagcaacg agatggccaa ggtggacgac agcttcttcc    2340
accgccttga ggagtcgttc ctcgtggagg aggacaagaa gcatgagagg cacccgatct    2400
tcgggaacat cgtggacgag gtaagtttct gcttctacct ttgatatata tataataatt    2460
atcattaatt agtagtaata taatatttca atatttttt tcaaaataaa agaatgtagt    2520
atatagcaat tgcttttctg tagtttataa gtgtgtatat tttaatttat aacttttcta    2580
atatatgacc aaaacatggt gatgtgcagg tggcgtacca cgagaagtac ccgacgatct    2640
accacctccg caagaagctg gtcgactcca cagacaaggc cgacctcaga ctgatctacc    2700
tggccctcgc gcacatgatc aagttccgcg gcacttcct catcgagggc gacctgaacc    2760
cggacaactc cgacgtcgac aagctcttca tccagctggt ccagacctac aatcaactgt    2820
tcgaggagaa cccgatcaac gcgtccggcg tggacgcgaa ggccatcctc agcgcgaggc    2880
tcagcaaatc aagacggctg gagaacctga tcgcccagct cccaggcgag aagaaaaacg    2940
gcttgttcgg caacctgatc gcgctctcgc tcggcctcac gcccaacttc aaatcaaact    3000
tcgacctggc cgaggacgcg aaactgcagc tgtccaagga cacttacgac gacgacctcg    3060
acaacctgct ggcgcaaatc ggtgaccagt acgcagacct cttcctggcc gccaagaacc    3120
tctcggacgc catcctgctg tccgatatcc tgagagtgaa tacggagatc accaaggcgc    3180
cgctcagcgc ctccatgatt aaaaggtacg acgagcacca ccaggacctg acgctgctca    3240
aggccctggt gcgccagcag ctcccccgaga agtacaagga gatcttcttc gaccaatcaa    3300
aaaacggcta cgccggctac atcgacgggg gcgcctccca ggaggagttc tacaagttca    3360
tcaaaccaat tctcgagaag atggacggca cggaggagct tctcgtgaag ctcaaccggg    3420
aggacctcct gaggaagcag aggacgttcg acaacggctc gataccgcat cagatccacc    3480
tgggcgagct ccacgccatc ctgcgccggc aggaggattt ctatccgttc ctcaaggaca    3540
acagggagaa gatcgagaaa attctgacgt tccgcatccc gtactacgtg ggccctctcg    3600
cgcgcgggaa cagccggttc gcctggatga ctcggaagtc ggaggagacg atcacgccgt    3660
ggaacttcga ggaggtggtg gacaagggcg cctccgccca gtcgttcatc gagcgcatga    3720
cgaacttcga taaaaatctg cccaatgaaa agtgctcccc gaagcacagc ctcctctacg    3780
agtacttcac ggtgtacaac gagctcacga aggtgaagta cgtgaccgag ggtatgcgga    3840
agccggcgtt cctgagcggc gagcagaaga aggccatcgt ggacctcctc ttcaagacga    3900
accggaaagt caccgtgaag caattaaagg aggactactt caagaaaata gagtgcttcg    3960
acagcgtcga gatctcgggc gtcgaggaca ggttcaacgc gtcgctgggc acataccacg    4020
acctcctcaa gatcattaaa gacaaggact tcctggacaa cgaggagaac gaggacatcc    4080
```

```
tcgaggacat cgtgctgacc ctcaccctgt ttgaggaccg ggagatgatc gaggagcgcc   4140
tcaagacgta cgctcacctt ttcgacgaca aggtgatgaa acagctgaag cggcgccgct   4200
acaccggatg gggccggctc tcccgcaagc tcattaatgg gatcagggac aagcagtccg   4260
gcaagaccat actcgatttc ctgaagagcg acggcttcgc caaccggaac ttcatgcagc   4320
tcatccacga cgactccctc actttcaagg aggacatcca aaggcccag gtcagcggac    4380 agggcgactc gctccacgaa cacatcgcca acctggccgg gtcgcctgcg attaaaaagg   4440
gaatccttca gaccgtcaag gtcgtggacg agctggtgaa ggtgatgggc aggcacaagc   4500
ccgaaaatat cgtcattgag atggcccggg agaaccagac cacgcagaaa ggccagaaga   4560
acagccggga gcgcatgaaa cggatcgagg agggtatcaa ggagctgggc tcgcagatcc   4620
tcaaggagca ccctgtggaa aatacccagc tgcagaatga aaagctctac ctctactacc   4680
tccagaacgg ccgcgacatg tacgtggacc aggagctgga cattaatcgc ctctcggact   4740
acgacgtcga ccacatcgtc ccgcagtcct tcctgaagga cgacagcatc gacaacaagg   4800
tcttgacccg ctccgataaa aatcgcggga agtccgacaa cgtgccgtcg gaggaggtgg   4860
tcaagaagat gaaaaactac tggcgccagc tgctcaacgc caagctaatc acgcagcgca   4920
agttcgacaa cctcaccaag gccgaacgcg gcggtctctc cgagcttgat aaggctgggt   4980
tcatcaagag acagctggtg gagacccggc agatcaccaa gcatgtcgcc cagatcctgg   5040
actcgcgcat gaatactaag tacgatgaaa acgacaagct catccgcgag gtgaaggtga   5100
tcaccctgaa gagcaagctg gtctcggact tccggaagga cttccagttc tacaaggtcc   5160
gggagatcaa caactaccac cacgcgcacg acgcctacct gaacgcggtg gtgggcacag   5220
cccttataaa gaagtaccct aagctcgagt ccgagttcgt gtacggcgac tacaaggtgt   5280
acgacgtccg caagatgatc gcgaagagcg agcaggagat cgggaaggcc accgcaaaat   5340
acttcttcta ctccaacatc atgaacttct tcaagaccga gatcacctg gccaacgggg    5400 agatccgcaa gcgcccgctg attgagacga acggagagac aggcgagata gtctgggaca   5460
agggcaggga cttcgccacc gtgcgcaagg ttctgtccat gccgcaggtg aacatcgtga   5520
agaagactga ggtgcagaca ggcggcttct cgaaggagtc catcctgccc aagcggaaca   5580
gcgacaagct catcgcgcgg aagaaggact gggaccctaa aaatatggc gggttcgact    5640 cgcccaccgt ggcttactcg gtcctcgtgg tggccaaggt cgagaagggc aaaagcaaga   5700
agctgaagag cgtcaaggag ctcctcggca tcaccatcat ggagcggtcc agcttcgaga   5760
agaacccgat cgacttcctc gaggcgaagg atataaggag ggtgaagaag gacctcatca   5820
ttaaactgcc gaagtactcg ctattcgaac tggagaatgg tcgcaagagg atgctcgcga   5880
gcgctggcga gctgcagaaa gggaacgagc tggctctccc gagcaagtac gtcaacttcc   5940
tctacctggc ctcccactat gaaaagctca agggctcgcc ggaggacaac gagcagaagc   6000
agctgttcgt cgagcagcac aagcattacc tcgacgagat catcgagcag atctcggagt   6060
tcagcaagcg cgtgatcctg gccgacgcca acctcgacaa ggtgctgtcc gcatataaca   6120
agcaccgcga caaccaata cgggagcagg ccgaaaatat catccacctg ttcaccctca    6180
cgaacctggg cgcccccgcc gcgttcaagt acttcgacac aaccatcgac cgcaagcggt   6240
acacgagcac gaaggaggtg ctggacgcca cgttgattca ccagtccatc acgggcctgt   6300
atgaaacaag gatcgatctc agccagctcg cggcgactag gtaccacat ggttaaccta    6360 gacttgtcca tcttctggat tggccaactt aattaatgta tgaaataaaa ggatgcacac   6420
```

```
atagtgacat gctaatcact ataatgtggg catcaaagtt gtgtgttatg tgtaattact    6480
agttatctga ataaaagaga aagagatcat ccatatttct tatcctaaat gaatgtcacg    6540
tgtctttata attctttgat gaaccagatg catttcatta accaaatcca tatacatata    6600
aatattaatc atatataatt aatatcaatt gggttagcaa aacaaatcta gtctaggtgt    6660
gttttgcgaa ttgcggc                                                  6677

<210> SEQ ID NO 106
<211> LENGTH: 3387
<212> TYPE: DNA
<213> ORGANISM: S. thermophilus

<400> SEQUENCE: 106
atgagtgact tagttttagg acttgatatc ggtataggtt ctgttggtgt aggtatcctt      60
aacaaagtga caggagaaat tatccataaa aactcacgca tcttcccagc agctcaagca     120
gaaaataacc tagtacgtag aacgaatcgt caaggaagac gcttgacacg acgtaaaaaa     180
catcgtatag ttcgtttaaa tcgtctattt gaggaaagtg gattaatcac cgattttacg     240
aagatttcaa ttaatcttaa cccatatcaa ttacgagtta agggcttgac cgatgaattg     300
tctaatgaag aactgtttat cgctcttaaa aatatggtga acaccgtggg gattagttac     360
ctcgatgatg ctagtgatga cggaaattca tcagtaggag actatgcaca aattgttaag     420
gaaaatagta acaattaga aactaagaca ccgggacaga tacagttgga acgctaccaa     480
acatatggtc aattacgtgg tgattttact gttgagaaag atggcaaaaa acatcgcttg     540
attaatgtct ttccaacatc agcttatcgt tcagaagcct taaggatact gcaaactcaa     600
caagaattta atccacagat tacagatgaa tttattaatc gttatctcga aatttaact     660 ggaaaacgga atattatca tggacccgga atgaaaagt cacggactga ttatggtcgt     720
tacagaacga gtggagaaac tttagacaat atttttggaa ttctaattgg gaaatgtaca     780
ttttatccag aagagtttag agcagcaaaa gcttcctaca cggctcaaga attcaatttg     840
ctaaatgatt tgaacaatct aacagttcct actgaaacca aaagttgag caaagaacag     900 aagaatcaaa tcattaatta tgtcaaaaat gaaaaggcaa tggggccagc gaaacttttt     960
aaatatatcg ctaagttact ttcttgtgat gttgcagata tcaagggata ccgtatcgac    1020
aaatcaggta aggctgagat tcatacttc gaagcctatc gaaaatgaa acgcttgaa    1080 accttagata ttgaacaaat ggatagagaa acgcttgata aattagccta tgtcttaaca    1140
ttaaacactg agagggaagg tattcaagaa gccttagaac atgaatttgc tgatggtagc    1200
tttagccaga agcaagttga cgaattggtt caattccgca aagcaaatag ttccattttt    1260
ggaaaaggat ggcataattt ttctgtcaaa ctgatgatgg agttaattcc agaattgtat    1320
gagacgtcag aagagcaaat gactatcctg acacgacttg gaaaacaaaa acgacttcgt    1380
cttcaaataa aacaaatat ttcaaataaa acaaaatata tagatgagaa actattaact    1440
gaagaaatct ataatcctgt tgttgctaag tctgttcgcc aggctataaa aatcgtaaat    1500
gcggcgatta agaatacgg agactttgac aatattgtca tcgaaatggc tcgtgaaaca    1560
aatgaagatg atgaaaagaa agctattcaa aagattcaaa aagccaacaa agatgaaaaa    1620
gatgcagcaa tgcttaaggc tgctaaccaa tataatggaa aggctgaatt accacatagt    1680
gttttccacg gtcataagca attagcgact aaaatccgcc tttggcatca gcaaggagaa    1740
cgttgccttt atactggtaa gacaatctca atccatgatt tgataaataa tcctaatcag    1800
tttgaagtag atcatatttt acctctttct atcacattcg atgatagcct tgcaaataag    1860
```

| | | |
|---|---|---|
| gttttggttt atgcaactgc taaccaagaa aaaggacaac gaacaccttA tcaggcttta | 1920 | |
| gatagtatgg atgatgcgtg gtctttccgt gaattaaaag cttttgtacg tgagtcaaaa | 1980 | |
| acactttcaa acaagaaaaa agaatacctc cttacagaag aagatatttc aaagtttgat | 2040 | |
| gttcgaaaga aatttattga acgaaatctt gtagatacaa gatacgcttc aagagttgtc | 2100 | |
| ctcaatgccc ttcaagaaca ctttagagct cacaagattg atacaaaagt ttccgtggtt | 2160 | |
| cgtggccaat ttacatctca attgagacgc cattggggaa ttgagaagac tcgtgatact | 2220 | |
| tatcatcacc atgctgtcga tgcattgatt attgccgcct caagtcagtt gaatttgtgg | 2280 | |
| aaaaaacaaa agaatacccT tgtaagttat tcagaagaac aactccttga tattgaaaca | 2340 | |
| ggtgaactta ttagtgatga tgagtacaag gaatctgtgt tcaaagcccc ttatcaacat | 2400 | |
| tttgttgata cattgaagag taaagaattt gaagacagta tcttattctc atatcaagtg | 2460 | |
| gattctaagt ttaatcgtaa aatatcagat gccactattt atgcgacaag acaggctaaa | 2520 | |
| gtgggaaaag ataagaagga tgaaacttat gtcttaggga aaatcaaaga tatctatact | 2580 | |
| caggatggtt atgatgcctt tatgaagatt tataagaagg ataagtcaaa attcctcatg | 2640 | |
| tatcgtcacg acccacaaac ctttgagaaa gttatcgagc caattttaga gaactatcct | 2700 | |
| aataagcaaa tgaatgaaaa aggaaaagag gtaccatgta atcctttcct aaaatataaa | 2760 | |
| gaagaacatg gctatattcg taaatatagt aaaaaaggca atggtcctga atcaagagt | 2820 | |
| cttaaatact atgatagtaa gcttttaggt aatcctattg atattactcc agagaatagt | 2880 | |
| aaaaataaag ttgtcttaca gtcattaaaa ccttggagaa cagatgtcta tttcaataag | 2940 | |
| gctactggaa aatacgaaat ccttggatta aaatatgctg atctacaatt tgagaaaggg | 3000 | |
| acaggaacat ataagatttc ccaggaaaaa tacaatgaca ttaagaaaaa agagggtgta | 3060 | |
| gattctgatt cagaattcaa gtttacactt tataaaaatg atttgttact cgttaaagat | 3120 | |
| acagaaacaa agaacaaca gcttttccgt tttctttctc gaactttacc taaacaaaag | 3180 | |
| cattatgttg aattaaaacc ttatgataaa cagaaatttg aaggaggtga ggcgttaatt | 3240 | |
| aaagtgttgg gtaacgttgc taatggtggt caatgcataa aaggactagc aaaatcaaat | 3300 | |
| atttctattt ataaagtaag aacagatgtc ctaggaaatc agcatatcat caaaaatgag | 3360 | |
| ggtgataagc ctaagctaga ttttttaa | 3387 | |

<210> SEQ ID NO 107
<211> LENGTH: 3369
<212> TYPE: DNA
<213> ORGANISM: S. thermophilus

<400> SEQUENCE: 107

| | | |
|---|---|---|
| atgagtgact tagttttagg acttgatatc ggtataggtt ctgttggtgt aggtatcctt | 60 | |
| aacaaagtga caggagaaat tatccataaa aactcacgca tcttcccagc agctcaagca | 120 | |
| gaaaataacc tagtacgtag aacgaatcgt caaggaagac gcttgacacg acgtaaaaaa | 180 | |
| catcgtatag ttcgttaaa tcgtctattt gaggaaagtg gattaatcac cgattttacg | 240 | |
| aagatttcaa ttaatcttaa cccatatcaa ttacgagtta agggcttgac cgatgaattg | 300 | |
| tctaatgaag aactgtttat cgctcttaaa aatatggtga acaccgtggg gattagttac | 360 | |
| ctcgatgatg ctagtgatga cggaaattca tcagtaggag actatgcaca aattgttaag | 420 | |
| gaaaatagta acaattaga aactaagaca ccgggacaga tacagttgga acgctaccaa | 480 | |
| acatatggtc aattacgtgg tgattttact gttgagaaag atggcaaaaa acatcgcttg | 540 | |

-continued

| | |
|---|---|
| attaatgtct ttccaacatc agcttatcgt tcagaagcct taaggatact gcaaactcaa | 600 |
| caagaattta attcacagat tacagatgaa tttattaatc gttatctcga aattttaact | 660 |
| ggaaaacgga aatattatca tggacccgga aatgaaaagt cacggactga ttatggtcgt | 720 |
| tacagaacga atggagaaac tttagacaat attttggaa ttctaattgg gaaatgtaca | 780 |
| ttttatccag acgagtttag agcagcaaaa gcttcctaca cggctcaaga attcaatttg | 840 |
| ctaaatgatt tgaacaatct aacagttcct actgaaacca aaagttgag caaagaacag | 900 |
| aagaatcaaa tcattaatta tgtcaaaaat gaaaaggtaa tggggccagc gaaactttt | 960 |
| aaatatatcg ctaaattact ttcttgtgat gttgcagata tcaagggaca ccgtatcgac | 1020 |
| aaatcaggta aggctgagat tcatactttc gaagcctatc gaaaaatgaa aacgcttgaa | 1080 |
| accttagata ttgagcaaat ggatagagaa acgcttgata aattagccta tgtcttaaca | 1140 |
| ttaaacactg agagggaagg tattcaagaa gctttagaac atgaatttgc tgatggtagc | 1200 |
| tttagccaga agcaagttga cgaattggtt caattccgca agcaaatag ttccatttt | 1260 |
| ggaaaaggat ggcataattt ttctgtcaaa ctgatgatgg agttaattcc agaattgtat | 1320 |
| gagacgtcag aagagcaaat gactatcctg acacgacttg gaaaacaaaa aacaacttcg | 1380 |
| tcttcaaata aaacaaaata tatagatgag aaactattaa ctgaagaaat ctataatcct | 1440 |
| gttgttgcta agtctgttcg ccaggctata aaaatcgtaa atgcggcgat taagaatac | 1500 |
| ggagactttg acaatattgt catcgaaatg gctcgtgaaa caatgaaga tgatgaaaag | 1560 |
| aaagctattc aaaagattca aaaagccaac aaagatgaaa aagatgcagc aatgcttaag | 1620 |
| gctgctaacc aatataatgg aaaggctgaa ttaccacata tgttttcca cggtcataag | 1680 |
| caattagcga ctaaaatccg cctttggcat cagcaaggag aacgttgcct ttatactggt | 1740 |
| aagacaatct caatccatga tttgataaat aatcctaatc agtttgaagt agatcatatt | 1800 |
| ttacctcttt ctatcacatt cgatgatagc cttgcaaata aggttttggt ttatgcaact | 1860 |
| gctaaccaag aaaaggaca acgaacacct tatcaggctt tagatagtat ggatgatgcg | 1920 |
| tggtctttcc gtgaattaaa agcttttgta cgtgagtcaa aaacactttc aaacaagaaa | 1980 |
| aaagaatacc tccttacaga agaagatatt tcaaagtttg atgttcgaaa gaaatttatt | 2040 |
| gaacgaaatc ttgtagatac aagatacgct tcaagagttg tcctcaatgc ccttcaagaa | 2100 |
| cactttagag ctcacaagat tgatacaaaa gtttccgtgg ttcgtggcca atttacatct | 2160 |
| caattgagac gccattgggg aattgagaag actcgtgata cttatcatca ccatgctgtc | 2220 |
| gatgcattga ttattgccgc tcaagtcag ttgaatttgt ggaaaaaaca aaagaatacc | 2280 |
| cttgtaagtt attcagaaga acaactcctt gatattgaaa caggtgaact tattagtgat | 2340 |
| gatgagtaca aggaatctgt gttcaaagcc ccttatcaac attttgttga tacattgaag | 2400 |
| agtaaagaat ttgaagacag tatcttattc tcatatcaag tggattctaa gtttaatcgt | 2460 |
| aaaatatcag atgccactat ttatgcgaca agacaggcta aagtgggaaa agataagaag | 2520 |
| gatgaaactt atgtcttagg gaaaatcaaa gatatctata ctcaggatgg ttatgatgcc | 2580 |
| tttatgaaga tttataagaa ggataagtca aaattcctca tgtatcgtca cgacccacaa | 2640 |
| acctttgaga agttatcga gccaatttta gagaactatc taataagga atgaatgaa | 2700 |
| aaagggaaag aagtaccatg taatcctttc ctaaaatata agaagaaca tggctatatt | 2760 |
| cgtaaatata gtaaaaaagg caatggtcct gaaatcaaga gtcttaaata ctatgatagt | 2820 |
| aagcttttag gtaatcctat tgatattact ccagagaata gtaaaaataa agttgtctta | 2880 |
| cagtcattaa aaccttggag aacagatgtc tatttcaata aaaatactgg taaatatgaa | 2940 |

```
attttaggac tgaaatatgc tgatttacaa tttgaaaaga agacaggaac atataagatt    3000
tcccaggaaa aatacaatgg cattatgaaa gaagagggtg tagattctga ttcagaattc    3060
aagtttacac tttataaaaa tgatttgtta ctcgttaaag atacagaaac aaaagaacaa    3120
cagcttttcc gttttctttc tcgaactatg cctaatgtga aatattatgt agagttaaag    3180
ccttattcaa aagataaatt tgagaagaat gagtcactta ttgaaatttt aggttctgca    3240
gataagtcag gacgatgtat aaaagggcta ggaaaatcaa atatttctat ttataaggta    3300
agaacagatg tcctaggaaa tcagcatatc atcaaaaatg agggtgataa gcctaagcta    3360
gatttttaa                                                           3369
```

<210> SEQ ID NO 108
<211> LENGTH: 4113
<212> TYPE: DNA
<213> ORGANISM: S. agalactiae

<400> SEQUENCE: 108

```
atgaataagc catattcaat aggccttgac atcggtacta attccgtcgg atggagcatt     60
attacagatg attataaagt acctgctaag aagatgagag ttttagggaa cactgataaa    120
gaatatatta agaagaatct cataggtgct ctgcttttg atggcgggaa tactgctgca    180
gatagacgct tgaagcgaac tgctcgtcgt cgttatacac gtcgtagaaa tcgtattcta    240
tatttacaag aaattttgc agaggaaatg agtaaagttg atgatagttt ctttcatcga    300
ttagaggatt cttttctagt tgaggaagat aagagaggga gcaagtatcc tatctttgca    360
acattgcagg aagagaaaga ttatcatgaa aaattttcga caatctatca tttgagaaaa    420
gaattagctg acaagaaaga aaaagcagac cttcgtctta tttatattgc tctagctcat    480
atcattaaat ttagagggca tttcctaatt gaggatgata gctttgatgt caggaataca    540
gacatttcaa aacaatatca agatttttta gaaatcttta atacaacttt tgaaaataat    600
gatttgttat ctcaaaacgt tgacgtagag gcaatactaa cagataagat tagcaagtct    660
gcgaagaaag atcgtatttt agcgcagtat cctaaccaaa aatctactgg catttttgca    720 gaattttga aattgattgt cggaaatcaa gctgacttca gaaatatttt caatttggag    780
gataaaacgc cgcttcaatt cgctaaggat agctacgatg aagatttaga aaatcttctt    840
ggacagattg gtgatgaatt tgcagactta ttctcagcag cgaaaagtt atatgatagt    900 gtccttttgt ctggcattct tacagtaatc gacctcagta ccaaggcgcc acttcagct    960 tctatgattc agcgttatga tgaacataga gaggacttga acagttaaa acaattcgta   1020 aaagcttcat tgccggaaaa atatcaagaa atatttgctg attcatcaaa agatggctac   1080
gctggttata ttgaaggtaa aactaatcaa gaagcttttt ataaatacct gtcaaaattg   1140
ttgaccaagc aagaagatag cgagaatttt cttgaaaaaa tcaagaatga agatttcttg   1200
agaaaacaaa ggacctttga taatggctca attccacacc aagtccattt gacagagctg   1260
aaagctatta tccgccgtca atcagaatac tatcccttct tgaaagagaa tcaagatagg   1320
attgaaaaaa tccttacctt tagaattcct tattatatcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgtatgac caacaatgat   1500
ttttatcttc ctgaagaaaa agttttacca aagcatagtc ttatttatga aaatttacg   1560 gtctataatg agttgactaa ggttagatat aaaaatgagc aaggtgagac ttattttttt   1620
```

-continued

```
gatagcaata ttaaacaaga aatctttgat ggagtattca aggaacatcg taaggtatcc      1680
aagaagaagt tgctagattt tctggctaaa gaatatgagg agtttaggat agtagatgtt      1740
attggtctag ataaagaaaa taaagctttc aacgcctcat tgggaactta ccacgatctc      1800
gaaaaaatac tagacaaaga ttttctagat aatccagata atgagtctat tctggaagat      1860
atcgtccaaa ctctaacatt atttgaagac agagaaatga ttaagaagcg tcttgaaaac      1920
tataaagatc tttttacaga gtcacaacta aaaaaactct atcgtcgtca ctatactggc      1980
tggggacgat tgtctgctaa gttaatcaat ggtattcgag ataagagag tcaaaaaaca       2040 atcttggact atcttattga tgatggtaga tctaatcgca actttatgca gttgataaat      2100
gatgatggtc tatcttttcaa atcaattatc agtaaggcac aggctggtag tcattcagat    2160
aatctaaaag aagttgtagg tgagcttgca ggtagccctg ctattaaaaa gggaattcta      2220
caaagtttga aaattgttga tgagcttgtt aaagtcatgg gatacgaacc tgaacaaatt     2280
gtggttgaga tggcgcgtga gaatcaaaca acaaatcaag gtcgtcgtaa ctctcgacaa      2340
cgctataaac ttcttgatga tggcgttaag aatctagcta gtgacttgaa tggcaatatt     2400
ttgaaagaat atcctacgga taatcaagcg ttgcaaaatg aaagactttt cctttactac     2460
ttacaaaacg gaagagatat gtatacaggg gaagctctag atattgacaa tttaagtcaa     2520
tatgatattg accacattat tcctcaagct ttcataaaag atgattctat tgataatcgt     2580
gttttggtat catctgctaa aaatcgtgga agtcagatg atgttcctag ccttgaaatt       2640 gtaaagatt gtaaagtttt ctggaaaaaa ttacttgatg ctaagttaat gagtcagcgt       2700
aagtatgata atttgactaa ggcagagcgc ggaggcctaa cttccgatga taaggcaaga     2760
tttatccaac gtcagttggt tgagacacga caaattacca agcatgttgc ccgtatcttg     2820
gatgaacgct ttaataatga gcttgatagt aaaggtagaa ggatccgcaa agttaaaatt     2880
gtaaccttga agtcaaattt ggtttcaaat ttccgaaaag aatttggatt ctataaaatt     2940
cgtgaagtta acaattatca ccatgcacat gatgcctatc ttaatgcagt agttgctaaa     3000
gctattctaa ccaaatatcc tcagttagag ccagaatttg tctacggcga ctatccaaaa     3060
tataatagtt acaaaacgcg taaatccgct acagaaaagc tatttttcta ttcaaatatt     3120
atgaacttct ttaaaactaa ggtaactttta gcggatggaa ccgttgttgt aaaagatgat    3180
attgaagtta ataatgatac gggtgaaatt gtttgggata aaagaaaca ctttgcgaca      3240 gttagaaaag tcttgtcata ccctcagaac aatatcgtga agaagacaga gattcagaca    3300
ggtggtttct ctaaggaatc aatcttggcg catggtaact cagataagtt gattccaaga    3360
aaaacgaagg atatttattt agatcctaag aaatatggag gttttgatag tccgatagta     3420
gcttactctg ttttagttgt agctgatatc aaaaagggta aagcacaaaa actaaaaaca     3480
gttacggaac ttttaggaat taccatcatg gagaggtcca gatttgagaa aaatccatca     3540
gctttccttg aatcaaaagg ctatttaaat attagggctg ataaactaat tattttgccc     3600
aagtatagtc tgttcgaatt agaaaatggg cgtcgtcgat tacttgctag tgctggtgaa     3660
ttacaaaaag gtaatgagct agccttacca acacaattta tgaagttctt ataccttgca     3720
agtcgttata tgagtcaaa aggtaaacca gaggagattg agaagaaaca agaatttgta     3780
aatcaacatg tctcttattt tgatgacatc cttcaattaa ttaatgattt ttcaaaacga     3840
gttattctag cagatgctaa tttagagaaa atcaataagc tttaccaaga taataaggaa     3900
aatatatcag tagatgaact tgctaataat attatcaatc tatttacttt taccagtcta    3960
ggagctccag cagcttttaa attttttgat aaaatagttg atagaaaacg ctatacatca     4020
```

```
actaaagaag tacttaattc taccctaatt catcaatcta ttactggact ttatgaaaca    4080
cgtattgatt tgggtaagtt aggagaagat tga                                4113

<210> SEQ ID NO 109
<211> LENGTH: 4134
<212> TYPE: DNA
<213> ORGANISM: S. agalactiae

<400> SEQUENCE: 109
atgaataagc catattcaat aggccttgac atcggtacta attccgtcgg atggagcatt      60
attacagatg attataaagt acctgctaag aagatgagag ttttagggaa cactgataaa     120
gaatatatta agaagaatct cataggtgct ctgcttttg atggcgggaa tactgctgca      180
gatagacgct tgaagcgaac tgctcgtcgt cgttatacac gtcgtagaaa tcgtattcta     240
tatttacaag aaattttgc agaggaaatg agtaaagttg atgatagttt ctttcatcga      300
ttagaggatt cttttctagt tgaggaagat aagagaggta gcaagtatcc tatctttgca     360
acaatgcagg aggagaaata ttatcatgaa aaatttccga caatctatca tttgagaaaa     420
gaattggctg acaagaaaga aaaagcagac cttcgtcttg tttatctggc tctagctcat     480
atcattaaat tcagagggca tttcctaatt gaggatgata gatttgatgt gaggaatacc     540
gatattcaaa acaatatca agcctttta gaaattttg atactacctt tgaaaataat       600
catttgttat ctcaaaatgt agatgtagaa gcaattctaa cagataagat tagcaagtct     660
gcgaagaagg atcgcatctt agcgcagtat cctaaccaaa aatctactgg tatttttgca    720 gaattttga aattgattgt cggaaatcaa gctgacttca gaaacatttt caatttggag     780
gataaaacac cgcttcaatt cgctaaggat agctacgatg aagatttaga aaatcttctt    840
ggacagattg gtgatgaatt tgcagactta ttctcagtag cgaaaaagct atatgatagt    900
gttcttttat ctggcattct tacagtaact gatctcagta ccaaggcgcc actttctgcc    960
tctatgattc agcgttatga tgaacatcat gaggacttaa agcatctaaa acaattcgta    1020
aaagcttcat tacctgaaaa ttatcgggaa gtatttgctg attcatcaaa agatggctac    1080
gctggctata ttgaaggcaa aactaatcaa gaagcttttt ataaatatct gttaaaattg    1140
ttgaccaaac aagaaggtag cgagtatttt cttgagaaaa ttaagaatga agatttttg    1200 agaaaacaga gaacctttga taatggctca atcccgcatc aagtccattt gacagaattg    1260
agggctatta ttcgacgtca atcagaatac tatccattct tgaaagagaa tcaagatagg    1320
attgaaaaaa tccttacctt tagaattcct tattatgtcg ggccactagc acgtgagaag    1380
agtgattttg catggatgac tcgcaaaaca gatgacagta ttcgaccttg gaattttgaa    1440
gacttggttg ataagaaaaa atctgcggaa gcttttatcc atcgcatgac caacaatgac    1500
ctctatcttc cagaagaaaa agttttacca agcatagtc ttatttatga aaaatttact    1560
gtttacaatg aattaacgaa ggttagattt ttggcagaag gctttaaaga tttttcaattt    1620 ttaaatagga agcaaaaaga aactatctttt aacagcttgt ttaaggaaaa acgtaaagta    1680
actgaaaagg atattattag tttttttgaat aaagttgatg gatatgaagg aattgcaatc    1740
aaaggaattg agaaacagtt taacgctagc ctttcaacct atcatgatct taaaaaaata    1800
cttggcaagg atttccttga taatacagat aacgagctta ttttggaaga tatcgtccaa    1860
actctaacct tatttgaaga tagagaaatg attaagaagt gtcttgacat ctataaagat    1920
ttttttacag agtcacagct taaaaagctc tatcgccgtc actatactgg ctggggacga    1980
```

```
ttgtctgcta agctaataaa tggcatccga aataaagaga atcaaaaaac aatcttggac    2040
tatcttattg atgatggaag tgcaaaccga aacttcatgc agttgataaa tgatgatgat    2100
ctatcattta aaccaattat tgacaaggca cgaactggta gtcattcgga taatctgaaa    2160
gaagttgtag gtgaacttgc tggtagccct gctattaaaa aagggattct acaaagtttg    2220
aaaatagttg atgagctggt taaagtcatg ggctatgaac ctgaacaaat cgtggttgaa    2280
atggcacgtg agaaccaaac gacagcaaaa ggattaagtc gttcacgaca acgcttgaca    2340
accttgagag aatctcttgc taatttgaag agtaatattt tggaagagaa aaagcctaag    2400
tatgtgaaag atcaagttga aaatcatcat ttatctgatg accgtctttt cctttactac    2460
ttacaaaacg gaagagatat gtatacaaaa aaggctctgg atattgataa tttaagtcaa    2520
tatgatattg accacattat tcctcaagct ttcataaaag atgattctat tgataatcgt    2580
gttttggtat catctgctaa aaatcgtgga aaatcagatg atgttcctag cattgaaatt    2640
gtaaaagctc gcaaaatgtt ctggaaaaat ttactggatg ctaagttaat gagtcagcgt    2700
aagtatgata atttgactaa ggcagagcgc ggaggcctaa cttccgatga taaggcaaga    2760
tttatccaac gtcagttggt tgagactcga caaattacca agcatgtagc tcgtatcttg    2820
gatgaacgct tcaataatga agttgataat ggtaaaaaga tttgcaaggt taaaattgta    2880
accttgaagt caaatttggt ttcaaatttc cgaaaagaat ttggattcta taaaattcgt    2940
gaagttaatg attatcacca tgcacacgat gcttatctta atgcagtagt tgccaaagct    3000
attctaacca atatccaca gttagagcca gagtttgtct acggaatgta tagacagaaa    3060
aaactttcga aaatcgttca tgaggataag gaagaaaaat atagtgaagc aaccaggaaa    3120
atgtttttct actccaactt gatgaatatg ttcaaaagag ttgtgaggtt agcagatggt    3180
tctattgttg taagaccagt aatagaaact ggtagatata tgagaaaaac tgcatgggat    3240
aaaaagaaac actttgcgac agttagaaaa gtcttgtcat accctcagaa caatatcgtg    3300
aagaagacag agattcagac aggtggtttc tctaaggaat caatcttggc gcatggtaac    3360
tcagataagt tgattccaag aaaaacgaag gatatttatt tagatcctaa gaaatatgga    3420
ggttttgata gtccgatagt agcttactct gttttagttg tagctgatat caaaaaaggt    3480
aaagcacaaa aactaaaaac agttacggaa cttttaggaa ttaccatcat ggagaggtcc    3540
agatttgaga aaaatccatc agctttcctt gaatcaaaag gttatttaaa tattagggac    3600
gataaattaa tgattttacc gaagtatagt ctgttcgaat tagaaaatgg gcgtcgtcga    3660
ttacttgcta gtgctggtga attacaaaaa ggtaacgagc tagccttacc aacacaattt    3720
atgaagttct tataccttgc aagtcgttat aatgagtcaa aaggtaaacc agaggagatt    3780
gagaagaaac aagaatttgt aaatcaacat gtctcttatt ttgatgacat ccttcaatta    3840
attaatgatt tttcaaaacg agttattcta gcagatgcta atttagagaa atcaataag    3900
ctttaccagg ataataagga aaatatacca gtagatgaac ttgctaataa tattatcaat    3960
ctatttactt ttaccagtct aggagctcca gcagctttta aatttttga taaaatagtt    4020
gatagaaaac gctatacatc aactaaagaa gtacttaatt ctactctaat ccatcaatct    4080
attactggac tttatgaaac acgtattgat ttgggtaaat taggagaaga ttga         4134
```

<210> SEQ ID NO 110
<211> LENGTH: 4038
<212> TYPE: DNA
<213> ORGANISM: S. mutans

<400> SEQUENCE: 110

-continued

```
atgaaaaaac cttactctat tggacttgat attggaacca attctgttgg ttgggctgtt     60
gtgacagatg actacaaagt tcctgctaag aagatgaagg ttctgggaaa tacagataaa    120
agtcatatcg agaaaaattt gcttggcgct ttattatttg atagcgggaa tactgcagaa    180
gacagacggt taaagagaac tgctcgccgt cgttacacac gtcgcagaaa tcgtatttta    240
tatttgcaag agattttttc agaagaaatg ggcaaggtag atgatagttt ctttcatcgt    300
ttagaggatt cttttcttgt tactgaggat aaacgaggag agcgccatcc cattttggg     360
aatcttgaag aagaagttaa gtatcatgaa aattttccaa ccatttatca tttgcggcaa    420
tatcttgcgg ataatccaga aaagttgat ttgcgtttag tttatttggc tttggcacat     480
ataattaagt ttagaggtca tttttaatt gaaggaaagt ttgatacacg caataatgat     540
gtacaaagac tgtttcaaga attttagca gtctatgata atacttttga gaatagttcg    600
cttcaggagc aaaatgttca agttgaagaa attctgactg ataaaatcag taaatctgct    660
aagaaagata gagttttgaa acttttttcct aatgaaaagt ctaatggccg ctttgcagaa   720
tttctaaaac taattgttgg taatcaagct gatttttaaaa agcattttga attagaagag   780
aaagcaccat tgcaattttc taaagatact tatgaagaag agttagaagt actattagct   840
caaattggag ataattacgc agagctcttt ttatcagcaa agaaactgta tgatagtatc    900
cttttatcag ggattttaac agttactgat gttggtacca agcgcccttt atctgcttcg    960
atgattcagc gatataatga acatcagatg gatttagctc agcttaaaca attcattcgt   1020
cagaaattat cagataaata taacgaagtt ttttctgatg tttcaaaaga cggctatgcg   1080
ggttatattg atgggaaaac aaatcaagaa gcttttata aataccttaa aggtctatta    1140
aataagattg agggaagtgg ctatttcctt gataaaattg agcgtgaaga ttttctaaga   1200
aagcaacgta cctttgacaa tggctctatt ccacatcaga ttcatcttca gaaatgcgt    1260
gctatcattc gtagacaggc tgaattttat ccgttttag cagacaatca agataggatt    1320
gagaaattat tgactttccg tattccctac tatgttggtc cattagcgcg cggaaaaagt    1380
gattttgctt ggttaagtcg gaaatcggct gataaaatta caccatggaa ttttgatgaa   1440
atcgttgata aagaatcctc tgcagaagct tttatcaatc gtatgacaaa ttatgatttg   1500
tacttgccaa atcaaaaagt tcttcctaaa catagtttat tatacgaaaa atttactgtt   1560
tacaatgaat taacaaggt taaatataaa acagagcaag gaaaaacagc attttttgat    1620
gccaatatga agcaagaaat ctttgatggc gtatttaagg tttatcgaaa agtaactaaa   1680
gataaattaa tggattttcct tgaaaagaa tttgatgaat tcgtattgt tgatttaaca    1740
ggtctggata agaaaataa agtatttaac gcttcttatg gaacttatca tgatttgtgt   1800
aaaattttag ataagagttt tctcgataat tcaaagaatg aaaagatttt agaagatatt   1860
gtgttgacct taacgttatt tgaagataga gaatgatta gaaaacgtct agaaaattac    1920
agtgattat tgaccaaaga acaagtgaaa aagctggaaa gacgtcatta tactggttgg   1980
ggaagattat cagctgagtt aattcatggt attcgcaata agaaagcag aaaaacaatt    2040
cttgattatc tcattgatga tggcaatagc aatcggaact ttatgcaact gattaacgat   2100
gatgctcttt ctttcaaaga agagattgct aaggcacaag ttattggaga acagacaat    2160
ctaaatcaag ttgttagtga tattgctggc agccctgcta ttaaaaaagg aattttacaa   2220
agcttgaaga ttgttgatga gcttgtcaaa attatgggac atcaacctga aaatatcgtc   2280
gtggagatgg cgcgtgaaaa ccagtttacc aatcagggac gacgaaattc acagcaacgt   2340
```

```
ttgaaaggtt tgacagattc tattaaagaa tttggaagtc aaattcttaa agaacatccg    2400
gttgagaatt cacagttaca aaatgataga ttgtttctat attatttaca aaacggcaga    2460
gatatgtata ctggagaaga attggatatt gattatctaa gccagtatga tatagaccat    2520
attatcccgc aagctttat  aaaggataat tctattgata tagagtatt  gactagctca    2580 aaggaaaatc gtggaaaatc ggatgatgta ccaagtaaag atgttgttcg taaaatgaaa    2640
tcctattgga gtaagctact ttcggcaaag cttattacac aacgtaaatt tgataatttg    2700
acaaaagctg aacgaggtgg attgaccgac gatgataaag ctggattcat caagcgtcaa    2760
ttagtagaaa cacgacaaat taccaaacat gtagcacgta ttctggacga acgatttaat    2820
acagaaacag atgaaaacaa caagaaaatt cgtcaagtaa aaattgtgac cttgaaatca    2880
aatcttgttt ccaatttccg taaagagttt gaactctaca aagtgcgtga attaatgac    2940 tatcatcatg cacatgatgc ctatctcaat gctgtaattg aaaggctttt actaggtgtt    3000
tacccacaat tggaacctga atttgtttat ggtgattatc ctcatttttca tggacataaa    3060 gaaaataaag caactgctaa gaaattttc tattcaaata ttatgaactt ctttaaaaaa    3120
gatgatgtcc gtactgataa aaatggtgaa attatctgga aaaagatga gcatatttct    3180 aatattaaaa aagtgctttc ttatccacaa gttaatattg ttaagaaagt agaggagcaa    3240
acgggaggat ttctaaaga atctatcttg ccgaaaggta attctgacaa gcttattcct    3300
cgaaaaacga agaaattta ttgggatacc aagaaatatg gaggatttga tagcccgatt    3360
gttgcttatt ctatttagt tattgctgat attgaaaaag gtaaatctaa aaaattgaaa    3420
acagtcaaag ccttagttgg tgtcactatt atggaaagat gacttttga aagggatcca    3480 gttgctttc ttgagcgaaa aggctatcga atgttcaag aagaaatat tataaagtta     3540 ccaaaatata gttatttaa actagaaaac ggacgaaaaa ggctattggc aagtgctagg    3600
gaacttcaaa agggaaatga aatcgttttg ccaaatcatt taggaaccttt gctttatcac    3660 gctaaaaata ttcataaagt tgatgaacca aagcatttgg actatgttga taaacataaa    3720
gatgaattta aggagttgct agatgttgtg tcaaacttttt ctaaaaaata tactttagca    3780
gaaggaaatt tagaaaaaat caaagaatta tatgcacaaa ataatggtga agatcttaaa    3840
gaattagcaa gttcatttat caacttatta acatttactg ctataggagc accggctact    3900
tttaaattct tgataaaaa tattgatcga aaacgatata cttcaactac tgaaattctc    3960
aacgctaccc tcatccacca atccatcacc ggtctttatg aaacgcggat tgatctcaat    4020
aagttaggag gagactaa                                                  4038
```

<210> SEQ ID NO 111
<211> LENGTH: 8
<212> TYPE: PRT
<213> ORGANISM: Zea mays

<400> SEQUENCE: 111

Val Glu Asp Ala Lys Glu Glu Val
1               5

<210> SEQ ID NO 112
<211> LENGTH: 8
<212> TYPE: PRT
<213> ORGANISM: Petunia sp.

<400> SEQUENCE: 112

Gly Lys Glu Ser Lys Glu Glu Ile
1               5

<210> SEQ ID NO 113
<211> LENGTH: 8
<212> TYPE: PRT
<213> ORGANISM: Solanum lycopersicum L.

<400> SEQUENCE: 113

Gly Lys Lys Ser Glu Glu Glu Ile
1               5

<210> SEQ ID NO 114
<211> LENGTH: 8
<212> TYPE: PRT
<213> ORGANISM: Sorghum bicolor

<400> SEQUENCE: 114

Glu Lys Asp Ala Lys Glu Glu Val
1               5

<210> SEQ ID NO 115
<211> LENGTH: 8
<212> TYPE: PRT
<213> ORGANISM: Oryza sativa

<400> SEQUENCE: 115

Val Glu Asp Ser Lys Glu Glu Val
1               5

<210> SEQ ID NO 116
<211> LENGTH: 8
<212> TYPE: PRT
<213> ORGANISM: Amaranthus sp.

<400> SEQUENCE: 116

Gly Lys Asp Gly Lys Glu Glu Ile
1               5

<210> SEQ ID NO 117
<211> LENGTH: 80
<212> TYPE: DNA
<213> ORGANISM: Artificial
<220> FEATURE:
<223> OTHER INFORMATION: moCas9 target sequence

<400> SEQUENCE: 117
gctaaagagg aagtgcagct cttcttgggg aatgctggaa ctgcaatgcg gccattgaca    60
gcagctgtta ctgctgctgg                                                80

<210> SEQ ID NO 118
<211> LENGTH: 80
<212> TYPE: DNA
<213> ORGANISM: Artificial
<220> FEATURE:
<223> OTHER INFORMATION: moCas9 target sequence

<400> SEQUENCE: 118
gctagagagg aagtgcagct cttcttgggg aatgctggaa tcgcaatgcg gtcattgaca    60
gcagctgtta ctgctgctgg                                                80

<210> SEQ ID NO 119
<211> LENGTH: 37
<212> TYPE: DNA
<213> ORGANISM: Artificial
<220> FEATURE:

```
<223> OTHER INFORMATION: 5prime section of the first intron of the EPSPS
      gene

<400> SEQUENCE: 119
catctcacga tcagatgcac cgcatgtcgc atgccta                                    37

<210> SEQ ID NO 120
<211> LENGTH: 42
<212> TYPE: DNA
<213> ORGANISM: Artificial
<220> FEATURE:
<223> OTHER INFORMATION: edited version conferring three IMEs elements

<400> SEQUENCE: 120
catatctgca cgatcagata tgcaccgcat gtcgcatatc tg                              42

<210> SEQ ID NO 121
<211> LENGTH: 31
<212> TYPE: DNA
<213> ORGANISM: Zea mays

<400> SEQUENCE: 121
gtttttgaac ttcagttacg tgcttgatgg a                                          31

<210> SEQ ID NO 122
<211> LENGTH: 31
<212> TYPE: DNA
<213> ORGANISM: Zea mays

<400> SEQUENCE: 122
gtttttgaac ttcaggtacg tgcttgatgg a                                          31
```